(12) United States Patent
Andreev et al.

(10) Patent No.: US 11,958,910 B2
(45) Date of Patent: Apr. 16, 2024

(54) BISPECIFIC ANTIGEN BINDING MOLECULES THAT BIND HER2, AND METHODS OF USE THEREOF

(71) Applicant: REGENERON PHARMACEUTICALS, INC., Tarrytown, NY (US)

(72) Inventors: Julian Andreev, Sleepy Hollow, NY (US); Andres Perez Bay, New York, NY (US); Christopher Daly, New York, NY (US); Frank Delfino, Poughquag, NY (US); Amy Han, Hockessin, DE (US); Thomas Nittoli, Pearl River, NY (US); William Olson, Yorktown Heights, NY (US); Gavin Thurston, Briarcliff Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 225 days.

(21) Appl. No.: 17/187,511

(22) Filed: Feb. 26, 2021

(65) Prior Publication Data

US 2022/0112306 A1    Apr. 14, 2022

Related U.S. Application Data

(60) Provisional application No. 62/982,989, filed on Feb. 28, 2020.

(51) Int. Cl.
*C07K 16/32* (2006.01)
*A61K 47/68* (2017.01)
*C07K 5/02* (2006.01)

(52) U.S. Cl.
CPC .......... *C07K 16/32* (2013.01); *A61K 47/6803* (2017.08); *C07K 5/021* (2013.01); *C07K 2317/31* (2013.01); *C07K 2317/565* (2013.01); *C07K 2317/94* (2013.01)

(58) Field of Classification Search
CPC .... C07K 16/32; C07K 5/021; C07K 2317/31; A61K 47/6803
See application file for complete search history.

(56) References Cited

U.S. PATENT DOCUMENTS

| | | | |
|---|---|---|---|
| 5,208,020 A | 5/1993 | Chari et al. | |
| 5,714,586 A | 2/1998 | Kunstmann et al. | |
| 7,087,411 B2 | 8/2006 | Daly et al. | |
| 7,534,868 B1 | 4/2009 | Papadopoulos et al. | |
| 7,750,116 B1 | 7/2010 | Doronina et al. | |
| 7,754,681 B2 | 7/2010 | Feng | |
| 8,987,420 B2 | 3/2015 | Thurston et al. | |
| 9,950,076 B2 | 4/2018 | Nittoli et al. | |
| 10,160,812 B2 | 12/2018 | Li et al. | |
| 10,570,151 B2 | 2/2020 | Nittoli | |
| 2007/0258987 A1 | 11/2007 | Francisco et al. | |
| 2007/0280945 A1 | 12/2007 | Stevens et al. | |
| 2008/0305497 A1 | 12/2008 | Kosmeder et al. | |
| 2010/0129314 A1 | 5/2010 | Singh et al. | |
| 2013/0101546 A1 | 4/2013 | Yurkovetskly et al. | |
| 2015/0343058 A1 | 12/2015 | Albanese et al. | |
| 2016/0354482 A1 | 12/2016 | Nittoli et al. | |
| 2016/0375147 A1 | 12/2016 | Nittoli | |
| 2017/0209591 A1 | 7/2017 | Nittoli et al. | |
| 2018/0134794 A1 | 5/2018 | Babb et al. | |
| 2019/0076438 A1 | 3/2019 | Xue et al. | |

FOREIGN PATENT DOCUMENTS

| | | |
|---|---|---|
| WO | 2005089808 | 9/2005 |
| WO | 2008122039 | 10/2008 |
| WO | 2011018611 | 2/2011 |
| WO | 2011130598 | 10/2011 |
| WO | 2012005982 | 1/2012 |
| WO | 2012058592 | 5/2012 |
| WO | 2012166559 | 12/2012 |
| WO | 2013053872 | 4/2013 |
| WO | 2013053873 | 4/2013 |
| WO | 2013055990 | 4/2013 |

(Continued)

OTHER PUBLICATIONS

Almagro & Fransson, Humanization of antibodies, Frontiers in Bioscience 2008; 13: 1619-33 (Year: 2008).*
Rudikoff et al., Single amino acid substitution altering antigen-binding specificity, PNAS, USA, 1982, 79: 1979-1983 (Year: 1982).*
Riemer et al., Matching of trastuzumab (Herceptin®) epitope mimics onto the surface of Her-2/neu—a new method of epitope definition, Mol Immunol, 2005 42(9): 1121-1124 (Year: 2005).*
Agarwal et al. (2013) "A Pictet-Spengler Ligation for Protein Chemical Modification", Proc. Natl. Acad. Sci., USA, 110:46-51.
Ai-Lazikani et al. (1997) "Standard Conformations for the Canonical Structures of Immunoglobulins", J. Mol. Biol., 273:927-948.
Altschul et al. (1990) "Basic Local Alignment Search Tool", J. Mol. Biol. 215:403-410.

(Continued)

*Primary Examiner* — Peter J Reddig
*Assistant Examiner* — Cheng Lu
(74) *Attorney, Agent, or Firm* — FisherBroyles, LLP; Cara L. Crowley-Weber; Kajal Chowdhury

(57) ABSTRACT

Provided herein are bispecific antigen-binding molecules that bind HER2 and methods of use thereof. The bispecific antigen-binding molecules comprise a first and a second antigen-binding domain, wherein the first and second antigen-binding domains bind to two different (preferably non-overlapping) epitopes of the extracellular domain of human HER2. The bispecific antigen-binding molecules cluster on the surface of HER2 IHC2+ and IHC3+ cells, and are internalized into the cellular lysosomes. Also included are antibody-drug conjugates (ADCs) comprising the antibodies or bispecific antigen-binding molecules provided herein linked to a cytotoxic agent, radionuclide, or other moiety, as well as methods of treating cancer in a subject by administering to the subject a bispecific antigen-binding molecule or an ADC thereof.

22 Claims, 18 Drawing Sheets

Specification includes a Sequence Listing.

(56) References Cited

FOREIGN PATENT DOCUMENTS

| WO | 2013055993 | | 4/2013 |
|---|---|---|---|
| WO | 2013068874 | | 5/2013 |
| WO | 2013085925 | | 6/2013 |
| WO | 2014065661 | | 5/2014 |
| WO | 2014145090 | A1 | 9/2014 |
| WO | 2015031396 | A1 | 3/2015 |
| WO | 2015091738 | A1 | 6/2015 |
| WO | 2015157592 | A1 | 10/2015 |
| WO | 2018044540 | | 3/2018 |
| WO | 2018089373 | A2 | 5/2018 |
| WO | 2018182420 | A1 | 10/2018 |
| WO | 2018182422 | A1 | 10/2018 |
| WO | 2019212965 | A1 | 11/2019 |

OTHER PUBLICATIONS

Altschul et al. (1997) "Gapped BLAST and PSI-BLAST: a New Generation of Protein Database Search Programs", Nucleic Acids Res. 25:3389-3402.
Baskin et al. (2007) "Copper-free Click Chemistry for Dynamic in Vivo Imaging", PNAS, 104(43):16793-16797.
Boersma and Pluckthun (2011) "DARPins and Other Repeat Protein Scaffolds: Advances in Engineering and Applications", Curr. Opin. Biotechnol., 22:849-857.
Carrico et al. (2007) "Introducing Genetically Encoded Aldehydes into Proteins", Nat. Chem. Biol., 3:321-322.
Dennler et al. (2014) "Transglutaminase-Based Chemo-Enzymatic Conjugation Approach Yields Homogeneous Antibody-Drug Conjugates", Bioconjugate Chem., 25(3):569-578.
Doronina et al. (2003) "Development of Potent Monoclonal Antibody Auristatin Conjugates for Cancer Therapy", Nature Biotechnology, 21(7):778-942.
Ducry and Stump (2010) "Antibody-Drug Conjugates: Linking Cytotoxic Payloads to Monoclonal Antibodies", Bioconjugate Chem., 21:5-13.
Ehring (1999) "Hydrogen Exchange/Electrospray Ionization Mass Spectrometry Studies of Structural Features of Proteins and Protein/Protein Interactions", Analytical Biochemistry 267(2):252-259.
Engen and Smith (2001) "Peer Reviewed: Investigating Protein Structure and Dynamics by Hydrogen Exchange MS", Anal. Chem., 73:256A-265A.
Faria et al. (2019) "Multiplex LC-MS/MS Assays for Clinical Bioanalysis of MEDI4276, an Antibody-Drug Conjugate of Tubulysin Analogue Attached via Cleavable Linker to a Biparatopic Humanized Antibody against HER-2", Antibodies, 8 (11) doi: 10.3390/antib8010011.
Gonnet et al. (1992) "Exhaustive Matching of the Entire Protein Sequence Database", Science 256: 1443-1445.
Hamblett et al. (2004) "Effects of Drug Loading on the Antitumor Activity of a Monoclonal Antibody Drug Conjugate", Clinical Cancer Research, 10:7063-7070.
Hofer et al. (2008) "An Engineered Selenocysteine Defines a Unique Class of Antibody Derivatives", Proc. Natl. Acad. Sci., USA, 105:12451-12456.
Hollander et al. (2008) "Selection of Reaction Additives Used in the Preparation of Monomeric Antibody-Calicheamicin Conjugates", Bioconjugate Chem., 19:358-361.
Jeger et al. (2010) "Site-Specific and Stoichiometric Modification of Antibodies by Bacterial Transglutaminase" Angew Chem Int Ed Engl. 49(51):9995-9997.
Junghans et al. (1990) "Anti-Tac-H, a Humanized Antibody to the Interleukin 2 Receptor with New Features for Immunotherapy in Malignant and Immune Disorders", Cancer Res., 50:1495-1502.
Kabat, et al. (1991) "Sequences of Proteins of Immunological Interest," National Institutes of Health, Bethesda, Md.
Kazane et al. (2013) "Self-Assembled Antibody Multimers through Peptide Nucleic Acid Conjugation", J. Am. Chem. Soc., 135:340-346 [Epub: Dec. 4, 2012].
Klein et al. (2012) "Progress in Overcoming the Chain Association Issue in Bispecific Heterodimeric IgG Antibodies", mAbs, 4(6):1-11.
Li, John et al., (2016) "A Biparatopic HER2-Targeting Antibody-Drug Conjugate Induces Tumor Regression in Primary Models Refractory to or Ineligible for HER2-Targeted Therapy" Cancer Cell 29: 117-129.
Martin et al. (1989) "Modeling Antibody Hpervariable Loops: a Combined Algorithm", Proc. Natl. Acad. Sci. USA, 86:9268-9272.
NCBI accession No. NP_004439.2.
Ogitani et al. (2016) "DS-8201a, a Novel HER2-Targeting ADC with a Novel DNA Topoisomerase I Inhibitor, Demonstrates a Promising Antitumor Efficacy with Differentiation from T-DM1", Clinical Cancer Research, 22 (20):5097-5106 doi: 10.1158/1078-0432.ccr-15-2822.
Pearson (1994) "Using the FASTA Program to Search Protein and DNA Sequence Databases", Methods Mol. Biol., 24: 307-331.
Pearson (2000) "Flexible Sequence Similarity Searching with the FASTA3 Program Package", Methods in Molecular Biology, 132: 185-219.
Pernas and Tolaney (2019) "HER2-Positive Breast Cancer; New Therapeutic Frontiers and Overcoming Resistance", Therapeutic Advances in Medical Oncology, 11: doi 10.1177/1758835919833519.
Rabuka et al. (2012) "Site-Specific Chemical Protein Conjugations Using Genetically Encoded Aldehyde Tags", Nat. Protocols, 7(6):1052-1067.
Reineke (2004) "Antibody Epitope Mapping Using Arrays of Synthetic Peptides", Methods Mol Biol, 248:443-463.
Ryan et al. (2001) "Polyconal Antibody Production Against Chito-Oligosaccharides", Food & Agriculture Immunol., 13:127-130.
Sapra et al. (2013) "Monoclonal Antibody-Based Therapies in Cancer: Advances and Challenges", Pharmacology & Therapeutics, 138:452-469.
Schumacher et al. (2016) "Current Status: Site-Speciic Antibody Drug Conjugates", J Clin Immunol, 36(Suppl 1): S100-S107.
Shaunak et al. (2006) "Site-Specific PEGylation of Native Disulfide Bonds in Therapeutic Proteins", Nat. Chem. Biol., 2:312-313.
Shield et al. (2002) "Lack of Fucose on Human IgG1 N-Linked Oligosaccharide Improves Binding to Human FcγRIII and Antibody-Dependent Cellular Toxicity", JBC, 277:26733-26740.
Tamura et al. (2019) "Trastuzumab Deruxtecan (DS-8201a) in Patients with Advanced HER2-Positive Breast Cancer Previously Treated with Trastuzumab Emtansine: a Dose-Expansion, Phase 1 Study", The Lancet Oncol., 20 (6):816-826.
Taylor et al. (1992) "A Transgenic Mouse that Expresses a Diversity of Human Sequence Heavy and Light Chain Immunoglobulins", Nucl. Acids Res., 20(23):6287-6295.
Tomer (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis", Protein Science, 9:487-496.
International Search Report and Written Opinion, received for PCT/US2021/020074, dated Jul. 19, 2021, 24 pages.

* cited by examiner

| Her2 epitope regions | Peptide | Charge | 15 sec %D uptake | | | 60 sec %D uptake | | | 600 sec %D uptake | | | 3600 sec %D uptake | | | 6000 sec D uptake | | | Average | |
|---|---|---|---|---|---|---|---|---|---|---|---|---|---|---|---|---|---|---|---|
| | | | HER2-Parental Ab1 | Her2 | Δ%D | HER2-Parental Ab1 | Her2 | Δ%D | HER2-Parental Ab1 | Her2 | Δ%D | HER2-Parental Ab1 | Her2 | Δ%D | HER2-Parental Ab1 | Her2 | Δ%D | Δ%D | ΔD |
| | 133-139 | 2 | 20 | 20 | -0.7 | 25 | 28 | -2.8 | 36 | 38 | -1 | 44 | 44 | 0 | 44.43 | 45.9 | -1.47 | -1.1 | -0.04 |
| | 133-140 | 2 | 16 | 17 | -1.6 | 20 | 21 | | 29 | 31 | -2 | 35 | 36 | -1 | 36 | 37 | -2 | -1.8 | -0.09 |
| | 133-142 | 2 | 14 | 15 | -1.7 | 17 | 21 | -4.8 | 23 | 33 | -10 | 27 | 38 | -11 | 28 | 39 | -11 | -7.6 | -0.53 |
| | 133-142 | 3 | 11 | 14 | -2.6 | 14 | 19 | -5.2 | 21 | 31 | -10 | 25 | 35 | -11 | 26 | 37 | -10 | -7.7 | -0.54 |
| Region I AA141-145 | 133-146 | 2 | 11 | 12 | -0.7 | 12 | 16 | -3.7 | 15 | 24 | -8.8 | 19 | 29 | -11 | 20 | 31 | -11 | -7.0 | -0.77 |
| | 133-146 | 3 | 9.6 | 11 | -1.4 | 12 | 14 | -2.7 | 15 | 22 | -7.4 | 18 | 27 | -9 | 19 | 28 | -10 | -6.0 | -0.66 |
| | 140-146 | 1 | 12 | 12 | -0.1 | 12 | 14 | -1.3 | 12 | 16 | -3.8 | 15 | 23 | -8 | 16 | 24 | -9 | -4.4 | -0.22 |
| | 140-146 | 2 | 10 | 11 | -0.6 | 10.3 | 12 | -1.5 | 11 | 14 | -3.7 | 13 | 21 | -8 | 14 | 22 | -8 | -4.5 | -0.23 |
| | 141-146 | 1 | 11 | 12 | -0.9 | 11 | 13 | -2.3 | 12 | 16 | -4.2 | 14 | 23 | -9 | 15 | 25 | -9 | -5.1 | -0.20 |
| Region II AA166-182 | 160-182 | 5 | 28 | 33 | -5.4 | 29 | 34 | -5.3 | 30 | 35 | -4.4 | 33 | 36 | -2.6 | 33 | 36 | -3.7 | -4.3 | -0.81 |
| | 161-182 | 5 | 26 | 34 | -8.0 | 27 | 34 | -6.8 | 29 | 36 | -7.1 | 33 | 38 | -5.3 | 33 | 39 | -6.3 | -6.7 | -1.21 |

FIG. 14

| Her2 epitope regions | Peptide | Charge | 15 sec %D uptake | | | 60 sec %D uptake | | | 600 sec %D uptake | | | 3600 sec %D uptake | | | 6000 sec D uptake | | | Average | |
|---|---|---|---|---|---|---|---|---|---|---|---|---|---|---|---|---|---|---|---|
| | | | HER2-Parental Ab2 | Her2 | Δ%D | HER2-Parental Ab2 | Her2 | Δ%D | HER2-Parental Ab2 | Her2 | Δ%D | HER2-Parental Ab2 | Her2 | Δ%D | HER2-Parental Ab2 | Her2 | Δ%D | Δ%D | ΔD |
| Region I AA9-23 | 1-21 | 3 | 25 | 32 | -6.7 | 28 | 36 | -7.7 | 33 | 40 | -7.2 | 39 | 42 | -3.4 | 40 | 44 | -4.0 | -5.8 | -0.98 |
| | 1-21 | 4 | 25 | 31 | -6.3 | 28 | 35 | -6.8 | 32 | 38 | -5.5 | 38 | 40 | -2.3 | 38 | 41 | -2.9 | -4.7 | -0.81 |
| | 1-23 | 3 | 28.4 | 34 | -5.3 | 30 | 36 | -6.1 | 32 | 37 | -5.4 | 36 | 38 | -2.4 | 35 | 39 | -4.0 | -4.7 | -0.89 |
| | 1-23 | 4 | 21.7 | 27 | -5.5 | 25 | 31 | -6.4 | 29 | 34 | -5.5 | 34 | 37 | -2.6 | 35 | 38 | -2.7 | -4.5 | -0.86 |
| | 9-21 | 2 | 24.9 | 36 | -11 | 30 | 42 | -12 | 37 | 49 | -11 | 47 | 51 | -4.1 | 47 | 52 | -5.0 | -8.7 | -0.78 |
| | 9-21 | 3 | 24.8 | 36 | -11 | 30 | 42 | -12 | 38 | 48 | -10 | 47 | 51 | -3.8 | 47 | 52 | -4.6 | -8.4 | -0.76 |
| | 9-21 | 4 | 23.7 | 35 | -11 | 29 | 41 | -13 | 37 | 47 | -10 | 45 | 50 | -4.2 | 46 | 51 | -4.4 | -8.5 | -0.77 |
| | 9-23 | 3 | 19.7 | 29 | -8.9 | 24 | 34 | -10 | 30 | 39 | -8.6 | 37 | 41 | -3.6 | 38 | 42 | -4.2 | -7.1 | -0.78 |
| | 9-23 | 4 | 19.4 | 28 | -8.2 | 24 | 34 | -9.8 | 30 | 38 | -8.1 | 37 | 40 | -3.3 | 37 | 41 | -3.9 | -6.7 | -0.73 |
| | 10-19 | 3 | 31.4 | 46 | -15 | 36 | 50 | -15 | 42 | 51 | -9.2 | 50 | 53 | -3.0 | 50 | 54 | -4.0 | -9.1 | -0.54 |
| | 10-21 | 2 | 28 | 39 | -11 | 34 | 45 | -11 | 41 | 47 | -6.7 | 47 | 49 | -2.7 | 46 | 51 | -4.2 | -7.1 | -0.57 |
| | 10-21 | 3 | 28.5 | 40 | -11 | 34 | 46 | -12 | 41 | 48 | -7.1 | 47 | 50 | -3.3 | 47 | 51 | -4.6 | -7.6 | -0.61 |
| | 10-23 | 3 | 21 | 31 | -9.3 | 26 | 35 | -9.2 | 31 | 37 | -5.8 | 36 | 39 | -2.9 | 35 | 39 | -3.9 | -6.2 | -0.62 |
| | 10-23 | 4 | 21 | 29 | -8.5 | 25 | 34 | -9.0 | 30 | 36 | -5.7 | 34 | 37 | -2.9 | 34 | 39 | -4.5 | -6.1 | -0.61 |
| | 11-21 | 3 | 30 | 43 | -12 | 37 | 50 | -14 | 45 | 51 | -6.2 | 51 | 52 | -1.1 | 52 | 52 | -0.8 | -6.8 | -0.47 |
| | 11-23 | 3 | 22 | 31 | -9.5 | 26 | 38 | -11 | 33 | 39 | -6.8 | 37 | 39 | -2.5 | 37 | 40 | -2.5 | -6.5 | -0.59 |
| Region II AA41-51 | 40-51 | 3 | 52 | 60 | -8.1 | 55 | 64 | -9.6 | 61 | 65 | -4.0 | 68 | 69 | -1.3 | 70 | 71 | -0.8 | -4.8 | -0.43 |
| | 40-51 | 3 | 52 | 59 | -7.0 | 55 | 64 | -8.5 | 61 | 65 | -4.2 | 68 | 69 | -0.8 | 68 | 70 | -1.2 | -4.3 | -0.39 |
| | 41-52 | 3 | 52 | 60 | -8.1 | 55 | 64 | -9.6 | 61 | 65 | -4.0 | 68 | 69 | -1.3 | 70 | 71 | -0.8 | -7.4 | -0.43 |
| | 41-52 | 3 | 52 | 59 | -7.0 | 55 | 64 | -8.5 | 61 | 65 | -4.2 | 68 | 69 | -0.8 | 68 | 70 | -1.2 | -6.8 | -0.39 |
| | 41-51 | 2 | 59 | 68 | -9.1 | 64 | 73 | -8.7 | 70 | 74 | -4.4 | 75 | 74 | 0.9 | 74 | 74 | 0.2 | -6.9 | -0.34 |
| | 41-51 | 3 | 57 | 66 | -9.1 | 61 | 71 | -10 | 66 | 70 | -4.1 | 70 | 70 | 0.0 | 70 | 70 | 0.2 | -7.5 | -0.38 |
| | 41-51 | 3 | 59 | 68 | -8.5 | 63 | 73 | -9.8 | 69 | 73 | -4.5 | 73 | 73 | 0.3 | 73 | 73 | 0.3 | -6.0 | -0.35 |
| | 41-51 | 4 | 57 | 65 | -7.7 | 62 | 70 | -8.0 | 65 | 70 | -4.8 | 70 | 70 | 0.0 | 70 | 70 | 0.1 | -4.2 | -0.33 |
| | 41-51 | 3 | 54 | 65 | -11 | 58 | 70 | -12 | 64 | 69 | -5.7 | 68 | 69 | -1.1 | 68 | 70 | -1.8 | -4.7 | -0.50 |
| | 41-50 | 3 | 59 | 70 | -11 | 64 | 75 | -11 | 68 | 75 | -7.1 | 74 | 74 | -0.3 | 74 | 75 | -0.5 | -4.4 | -0.42 |
| | 41-49 | 2 | 59 | 71 | -12 | 63 | 78 | -15 | 71 | 79 | -7.5 | 77 | 80 | -3.5 | 78 | 77 | 0.5 | -6.2 | -0.44 |
| | 41-49 | 3 | 55 | 68 | -13 | 61 | 74 | -13 | 68 | 74 | -6.6 | 74 | 74 | -0.3 | 74 | 74 | -0.7 | -4.1 | -0.41 |
| | 41-49 | 3 | 56 | 68 | -12 | 62 | 76 | -14 | 68 | 75 | -6.8 | 74 | 75 | -1.2 | 75 | 75 | -0.2 | -4.8 | -0.41 |
| | 41-49 | 3 | 52 | 65 | -14 | 56 | 70 | -14 | 64 | 72 | -8.7 | 71 | 72 | -1.2 | 73 | 74 | -0.4 | -4.3 | -0.45 |
| Region III AA64-77 | 61-77 | 3 | 14 | 16 | -1.9 | 16 | 20 | -3.3 | 20 | 26 | -5.6 | 27 | 35 | -8.0 | 28 | 36 | -7.9 | -5.3 | -0.75 |
| | 61-77 | 4 | 15 | 16 | -1.7 | 16 | 20 | -3.4 | 20 | 26 | -5.6 | 27 | 35 | -7.9 | 28 | 36 | -8.2 | -5.4 | -0.75 |
| | 64-77 | 2 | 18 | 19 | -1.8 | 20 | 23 | -3.3 | 25 | 31 | -6.7 | 34 | 43 | -9.3 | 35 | 45 | -9.4 | -6.1 | -0.67 |
| | 64-77 | 3 | 18 | 19 | -1.6 | 20 | 24 | -4.0 | 25 | 32 | -6.8 | 34 | 44 | -10 | 35 | 45 | -11 | -7 | -0.73 |
| | 64-77 | 4 | 16 | 19 | -2.4 | 18 | 22 | -4.1 | 22 | 30 | -7.6 | 31 | 42 | -11 | 32 | 44 | -12 | -7 | -0.81 |
| | 64-85 | 5 | 12 | 14 | -1.5 | 16 | 18 | -2.4 | 19 | 23 | -3.8 | 25 | 30 | -5.2 | 26 | 31 | -5.6 | -3.7 | -0.71 |
| Region IV AA353-359 | 353-374 | 2 | 28 | 32 | -3.8 | 30 | 34 | -3.4 | 33 | 37 | -3.4 | 37 | 42 | -4.8 | 38 | 43 | -5.3 | -4.1 | -0.66 |
| | 353-374 | 3 | 25 | 29 | -3.7 | 27 | 31 | -3.4 | 30 | 33 | -3.2 | 33 | 38 | -4.7 | 34 | 39 | -5.4 | -4.1 | -0.65 |
| | 353-375 | 2 | 26 | 30 | -3.5 | 29 | 32 | -3.3 | 32 | 35 | -3.3 | 36 | 41 | -4.8 | 37 | 42 | -5.6 | -4.1 | -0.70 |
| | 353-375 | 3 | 25 | 28 | -3.4 | 27 | 30 | -3.5 | 29 | 32 | -3.4 | 33 | 38 | -4.7 | 33 | 39 | -5.4 | -4.1 | -0.69 |
| | 353-377 | 2 | 25 | 28 | -3.2 | 29 | 32 | -3.0 | 35 | 38 | -3.1 | 40 | 44 | -4.0 | 41 | 45 | -4.8 | -3.6 | -0.68 |
| | 353-377 | 3 | 24 | 27 | -3.0 | 28 | 31 | -2.8 | 34 | 37 | -2.9 | 38 | 42 | -4.1 | 38 | 43 | -5.0 | -3.6 | -0.68 |
| | 353-377 | 4 | 21 | 24 | -2.8 | 24 | 27 | -2.8 | 27 | 30 | -2.4 | 30 | 34 | -3.8 | 30 | 35 | -4.8 | -3.3 | -0.63 |

FIG. 15

| Her2 epitope regions | Peptide | Charge | 15 sec D uptake | | | 60 sec D uptake | | | 600 sec D uptake | | | 3600 sec D uptake | | | Average |
|---|---|---|---|---|---|---|---|---|---|---|---|---|---|---|---|
| | | | HER2-Parental Ab3 | Her2 | Δ%D | HER2-Parental Ab3 | Her2 | Δ%D | HER2-Parental Ab3 | Her2 | Δ%D | HER2-Parental Ab3 | Her2 | Δ%D | ΔD |
| Region I AA133-148 | 133-142 | 2 | 13 | 16 | -2.4 | 16 | 22 | -5.6 | 22 | 33 | -11 | 26 | 38 | -12 | -0.53 |
| | 133-142 | 3 | 11 | 14 | -2.8 | 14 | 20 | -5.5 | 20 | 31 | -11 | 25 | 35 | -11 | -0.52 |
| | 133-146 | 2 | 9.9 | 11 | -1.4 | 11 | 16 | -4.1 | 13 | 23 | -10 | 16 | 29 | -13 | -0.78 |
| | 133-146 | 3 | 8.8 | 10 | -1.5 | 10 | 14 | -4.2 | 13 | 22 | -8.9 | 15 | 27 | -12 | -0.73 |
| | 140-146 | 1 | 11 | 12 | -0.7 | 12 | 13 | -1.4 | 10 | 16 | -5.3 | 10 | 23 | -12 | -0.25 |
| | 140-146 | 2 | 9.8 | 10 | -0.7 | 9.7 | 12 | -2.1 | 8.9 | 14 | -5.1 | 9.1 | 20 | -11 | -0.24 |
| | 141-146 | 1 | 11 | 12 | -1.0 | 11 | 13 | -1.8 | 10 | 16 | -5.7 | 11 | 23 | -12 | -0.21 |
| | 141-146 | 2 | 11 | 11 | -0.7 | 10 | 11 | -0.9 | 9.2 | 14 | -4.9 | 9.1 | 21 | -12 | -0.18 |
| | 144-151 | 2 | 16 | 22 | -5.9 | 19 | 27 | -7.7 | 21 | 29 | -8.1 | 24 | 29 | -5.0 | -0.40 |
| | 145-151 | 2 | 17 | 23 | -6.3 | 20 | 29 | -8.5 | 21 | 32 | -12 | 26 | 33 | -6.6 | -0.42 |
| Region II AA174-182 | 160-182 | 5 | 27 | 34 | -7.5 | 29 | 36 | -6.3 | 31 | 37 | -6.6 | 34 | 39 | -5.3 | -1.22 |
| | 161-182 | 5 | 25 | 32 | -7.3 | 28 | 34 | -6.2 | 29 | 36 | -6.9 | 32 | 38 | -6.2 | -1.20 |
| | 183-198 | 2 | 24 | 26 | -2.1 | 27 | 31 | -3.9 | 34 | 38 | -4.4 | 38 | 42 | -4.2 | -0.51 |
| Region III AA194-200 | 189-198 | 2 | 26 | 28 | -1.8 | 31 | 37 | -6.5 | 41 | 48 | -7.0 | 49 | 55 | -6.0 | -0.43 |
| | 189-203 | 2 | 32 | 35 | -3.0 | 37 | 41 | -3.9 | 44 | 51 | -6.3 | 50 | 55 | -4.8 | -0.58 |
| | 191-203 | 2 | 35 | 37 | -2.4 | 38 | 43 | -5.4 | 46 | 53 | -6.9 | 50 | 56 | -5.8 | -0.56 |

FIG. 16

| Her2 epitope regions | Peptide | Charge | 15 sec D uptake | | | 60 sec D uptake | | | 600 sec D uptake | | | 3600 sec D uptake | | | Average | |
|---|---|---|---|---|---|---|---|---|---|---|---|---|---|---|---|---|
| | | | Her2-Parental Ab4 | Her2 | Δ%D | Her2-Parental Ab4 | Her2 | Δ%D | Her2-Parental Ab4 | Her2 | Δ%D | Her2-Parental Ab4 | Her2 | Δ%D | Δ%D | ΔD |
| | 147-156 | 3 | 8.4 | 17 | -8.9 | 8.1 | 18 | -10 | 7.3 | 18 | -11 | 8.1 | 18 | -10 | -10 | -0.81 |
| | 147-157 | 2 | 7.0 | 20 | -13 | 7.4 | 20 | -13 | 7.1 | 20 | -13 | 7.3 | 20 | -13 | -13 | -1.17 |
| | 147-157 | 3 | 6.6 | 21 | -15 | 6.6 | 22 | -16 | 6.0 | 22 | -16 | 6.2 | 22 | -16 | -16 | -1.41 |
| | 147-157 | 4 | 6.4 | 22 | -15 | 6.6 | 22 | -16 | 6.2 | 22 | -16 | 6.5 | 22 | -16 | -16 | -1.41 |
| | 147-158 | 2 | 6.9 | 23 | -16 | 6.9 | 26 | -19 | 6.7 | 27 | -20 | 7.9 | 26 | -18 | -18 | -1.82 |
| | 147-158 | 3 | 7.0 | 22 | -15 | 7.2 | 26 | -19 | 6.8 | 27 | -20 | 8.1 | 27 | -19 | -18 | -1.81 |
| Region I AA152-161 | 147-158 | 4 | 6.8 | 22 | -15 | 7.1 | 26 | -19 | 6.7 | 26 | -19 | 7.9 | 26 | -18 | -18 | -1.80 |
| | 147-159 | 2 | 4.5 | 20 | -16 | 4.8 | 24 | -19 | 5.1 | 28 | -23 | 6.5 | 29 | -23 | -20 | -2.23 |
| | 147-159 | 3 | 5.5 | 20 | -15 | 5.8 | 24 | -19 | 5.6 | 29 | -23 | 7.1 | 29 | -22 | -20 | -2.14 |
| | 147-160 | 3 | 7.5 | 25 | -18 | 9.5 | 29 | -20 | 11 | 33 | -22 | 13 | 34 | -21 | -20 | -2.40 |
| | 147-161 | 3 | 7.7 | 23 | -16 | 10 | 27 | -18 | 11 | 31 | -19 | 13 | 31 | -18 | -18 | -2.29 |
| | 147-161 | 4 | 7.8 | 24 | -16 | 9.9 | 28 | -18 | 11 | 31 | -20 | 13 | 32 | -19 | -18 | -2.36 |
| | 152-161 | 2 | 26 | 38 | -13 | 26 | 43 | -17 | 25 | 48 | -23 | 26 | 47 | -21 | -19 | -1.48 |
| | 158-161 | 1 | 10.0 | 26 | -16 | 18 | 27 | -9.0 | 25 | 30 | -4.89 | 26 | 31 | -5.5 | -8.8 | -0.18 |
| | 183-198 | 2 | 23 | 25 | -1.9 | 28 | 31 | -3.1 | 32 | 39 | -6.1 | 37 | 43 | -6.5 | -4.4 | -0.62 |
| Region II AA194-200 | 189-198 | 2 | 27 | 29 | -2.2 | 33 | 39 | -5.4 | 42 | 50 | -8.3 | 48 | 58 | -10 | -7 | -0.52 |
| | 189-203 | 2 | 30 | 34 | -3.2 | 35 | 40 | -4.6 | 43 | 49 | -5.9 | 49 | 54 | -5.1 | -4.7 | -0.61 |
| | 191-203 | 2 | 35 | 37 | -1.7 | 39 | 42 | -3.5 | 47 | 52 | -5.6 | 51 | 57 | -5.9 | -4.2 | -0.46 |
| | 257-269 | 2 | 32 | 32 | -0.1 | 36 | 38 | -2.0 | 38 | 44 | -6.9 | 44 | 55.2 | -11 | -5 | -0.45 |
| | 257-270 | 2 | 35 | 35 | 0.1 | 39 | 40 | -1.7 | 40 | 46 | -6.3 | 46 | 56 | -10 | -5 | -0.45 |
| | 257-272 | 2 | 35 | 35 | -0.4 | 38 | 40 | -2.0 | 40 | 45 | -5.4 | 46 | 55 | -9.0 | -4.2 | -0.50 |
| Region III AA258-273 | 257-272 | 3 | 31 | 32 | -0.8 | 34 | 36 | -1.8 | 35 | 40 | -5.1 | 41 | 49 | -8.2 | -4.0 | -0.48 |
| | 257-273 | 2 | 34 | 34 | -0.3 | 37 | 39 | -1.7 | 39 | 45 | -5.8 | 46 | 54 | -8.5 | -4.1 | -0.53 |
| | 257-273 | 3 | 31 | 31 | 0.0 | 34 | 36 | -2.0 | 36 | 41 | -5.4 | 43 | 51 | -7.3 | -3.7 | -0.48 |
| | 258-270 | 2 | 37 | 38 | -0.3 | 39 | 42 | -2.8 | 42 | 49 | -6.2 | 50 | 60 | -11 | -5 | -0.45 |
| | 258-272 | 2 | 34 | 35 | -0.4 | 38 | 40 | -2.0 | 39 | 45 | -5.6 | 46 | 56 | -9.9 | -4.5 | -0.49 |
| | 258-272 | 3 | 31 | 31 | 0.4 | 34 | 35 | -1.4 | 36 | 40 | -4.4 | 42 | 51 | -9.0 | -3.6 | -0.40 |

FIG. 17

SEQUENCE LISTING

<160> NUMBER OF SEQ ID NOS: 65

<210> SEQ ID NO 1
<211> LENGTH: 360
<212> TYPE: DNA
<213> ORGANISM: Artificial Sequence
<220> FEATURE:
<223> OTHER INFORMATION: Synthetic

<400> SEQUENCE: 1

```
gaggtgcagc tggtggagtc tgggggaggc ttggcacagc ctgggggtc cctgagactc      60 tcctgtgcag cctctggatt ctccatcagt gactacgaaa tacactgggt ccgccaagtt     120
```

```
ccaggaaaag gtctggagtg ggtctctggt attggttctg ctggtaacac atattatcca      180
ggcgccgtga agggccgatt caccatctcc agagaaaatg ccaagaactc cttgtatctt      240
caagtgaaca gcctgacagt cggggacacg gctgtctatt attgtgcaag ggtctggtcc      300
cctctttatt acttcggttt ggacgtctgg ggccaaggga ccacggtcac cgtctcctca      360
```

<210> SEQ ID NO 2
<211> LENGTH: 120
<212> TYPE: PRT
<213> ORGANISM: Artificial Sequence
<220> FEATURE:
<223> OTHER INFORMATION: Synthetic

<400> SEQUENCE: 2

```
Glu Val Gln Leu Val Glu Ser Gly Gly Gly Leu Ala Gln Pro Gly Gly
1               5                   10                  15

Ser Leu Arg Leu Ser Cys Ala Ala Ser Gly Phe Ser Ile Ser Asp Tyr
            20                  25                  30

Glu Ile His Trp Val Arg Gln Val Pro Gly Lys Gly Leu Glu Trp Val
        35                  40                  45

Ser Gly Ile Gly Ser Ala Gly Asn Thr Tyr Tyr Pro Gly Ala Val Lys
    50                  55                  60

Gly Arg Phe Thr Ile Ser Arg Glu Asn Ala Lys Asn Ser Leu Tyr Leu
65                  70                  75                  80

Gln Val Asn Ser Leu Thr Val Gly Asp Thr Ala Val Tyr Tyr Cys Ala
                85                  90                  95

Arg Val Trp Ser Pro Leu Tyr Tyr Phe Gly Leu Asp Val Trp Gly Gln
            100                 105                 110

Gly Thr Thr Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattctcca tcagtgacta cgaa                                              24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Phe Ser Ile Ser Asp Tyr Glu
1               5
```

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5

```
attggttctg ctggtaacac a                                                 21
```

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ile Gly Ser Ala Gly Asn Thr
1               5

<210> SEQ ID NO 7
<211> LENGTH: 42
<212> TYPE: DNA
<213> ORGANISM: Artificial Sequence
<220> FEATURE:
<223> OTHER INFORMATION: Synthetic

<400> SEQUENCE: 7
gcaagggtct ggtcccctct ttattacttc ggtttggacg tc                     42

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Ala Arg Val Trp Ser Pro Leu Tyr Tyr Phe Gly Leu Asp Val
1               5                   10

<210> SEQ ID NO 9
<211> LENGTH: 375
<212> TYPE: DNA
<213> ORGANISM: Artificial Sequence
<220> FEATURE:
<223> OTHER INFORMATION: Synthetic

<400> SEQUENCE: 9
gaagtgcagc tggtggagtc tgggggagac ttggtacagc ctggcaggtc cctgagactc     60
tcctgtgcag cctctggatt cacttttgat gaatatgcca tgcactgggt ccggcaagct    120
ccagggaagg gcctggagtg gtctcacat attagttgga atagtcatca catagcctat    180
gcggactctg tgaagggccg attcaccatc tccagagaca acgccaggaa ctccctatat    240
ctgcaaatga atagtctgag acctgaggac acggccttgt atttctgtgt aaaagattgg    300
ggattgggag caagcggggg ctactactac gttttggacg tctggggcca agggaccacg    360
gtcaccgtct cctca                                                    375

<210> SEQ ID NO 10
<211> LENGTH: 125
<212> TYPE: PRT
<213> ORGANISM: Artificial Sequence
<220> FEATURE:
<223> OTHER INFORMATION: Synthetic

<400> SEQUENCE: 10

Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Asp Glu Tyr
            20                  25                  30

Ala Met His Trp Val Arg Gln Ala Pro Gly Lys Gly Leu Glu Trp Val
         35                  40                  45

Ser His Ile Ser Trp Asn Ser His His Ile Ala Tyr Ala Asp Ser Val
 50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Pro Glu Asp Thr Ala Leu Tyr Phe Cys
                 85                  90                  95

Val Lys Asp Trp Gly Leu Gly Ala Ser Gly Gly Tyr Tyr Tyr Val Leu
            100                 105                 110

Asp Val Trp Gly Gln Gly Thr Thr Val Thr Val Ser Ser
        115                 120                 125

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
ggattcactt ttgatgaata tgcc                                      24

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Gly Phe Thr Phe Asp Glu Tyr Ala
1               5

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
attagttgga atagtcatca cata                                      24

<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Ile Ser Trp Asn Ser His His Ile
1               5

<210> SEQ ID NO 15
<211> LENGTH: 54
<212> TYPE: DNA
<213> ORGANISM: Artificial Sequence
<220> FEATURE:
<223> OTHER INFORMATION: Synthetic

<400> SEQUENCE: 15
gtaaaagatt ggggattggg agcaagcggg ggctactact acgttttgga cgtc      54

<210> SEQ ID NO 16
<211> LENGTH: 18
<212> TYPE: PRT
<213> ORGANISM: Artificial Sequence
<220> FEATURE:
<223> OTHER INFORMATION: Synthetic

<400> SEQUENCE: 16

```
Val Lys Asp Trp Gly Leu Gly Ala Ser Gly Gly Tyr Tyr Tyr Val Leu
1               5                   10                  15

Asp Val
```

<210> SEQ ID NO 17
<211> LENGTH: 324
<212> TYPE: DNA
<213> ORGANISM: Artificial Sequence
<220> FEATURE:
<223> OTHER INFORMATION: Synthetic

<400> SEQUENCE: 17

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                           324
```

<210> SEQ ID NO 18
<211> LENGTH: 108
<212> TYPE: PRT
<213> ORGANISM: Artificial Sequence
<220> FEATURE:
<223> OTHER INFORMATION: Synthetic

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19
cagagcatta gcagctat                                                   18

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Gln Ser Ile Ser Ser Tyr
1               5

<210> SEQ ID NO 21
<211> LENGTH: 9
<212> TYPE: DNA
<213> ORGANISM: Artificial Sequence
<220> FEATURE:
<223> OTHER INFORMATION: Synthetic

<400> SEQUENCE: 21 gctgcatcc                                                              9

<210> SEQ ID NO 22
<211> LENGTH: 3
<212> TYPE: PRT
<213> ORGANISM: Artificial Sequence
<220> FEATURE:
<223> OTHER INFORMATION: Synthetic

<400> SEQUENCE: 22

Ala Ala Ser
1

<210> SEQ ID NO 23
<211> LENGTH: 30
<212> TYPE: DNA
<213> ORGANISM: Artificial Sequence
<220> FEATURE:
<223> OTHER INFORMATION: Synthetic

<400> SEQUENCE: 23
caacagagtt acagtacccc tccgatcacc                                      30

<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24

Gln Gln Ser Tyr Ser Thr Pro Pro Ile Thr
1               5                   10

<210> SEQ ID NO 25
<211> LENGTH: 1344
<212> TYPE: DNA
<213> ORGANISM: Artificial Sequence
<220> FEATURE:
<223> OTHER INFORMATION: Synthetic

<400> SEQUENCE: 25
gaggtgcagc tggtggagtc tggggggaggc ttggcacagc ctggggggtc cctgagactc      60
tcctgtgcag cctctggatt ctccatcagt gactacgaaa tacactgggt ccgccaagtt     120

```
ccaggaaaag gtctggagtg ggtctctggt attggttctg ctggtaacac atattatcca    180
ggcgccgtga agggccgatt caccatctcc agagaaaatg ccaagaactc cttgtatctt    240
caagtgaaca gcctgacagt cggggacacg gctgtctatt attgtgcaag ggtctggtcc    300
cctctttatt acttcggttt ggacgtctgg ggccaaggga ccacggtcac cgtctcctca    360
gccagcacaa aaggtcctag cgttttccca cttgccccat gttcaaggtc aacctccgaa    420
agtaccgccg ctcttggctg tctcgtaaaa gattattttc ccgaacctgt aactgtctcc    480
tggaactccg gcgcactcac ttccggcgta cataccttcc ccgctgtcct ccaatcttcc    540
ggtctctact ccctgtcttc tgttgtcact gttccatcat cctcactcgg cacaaaaaca    600
tatacctgca acgttgatca aagccaagt aataccaaag ttgataagcg cgtcgaatcc    660
aaatacggtc cccctgccc ccatgtccc gctccagagt ttctcggtgg ccctctgtt    720
ttccttttc ccctaaacc caagatacc ctcatgattt ccagaacccc cgaggtcacc    780
tgcgtcgtcg ttgatgtaag ccaagaagat cccgaagtcc agttcaattg gtatgtagac    840
ggtgttgaag tccataatgc aaaaacaaaa cccagagagg aacagtttaa ttcaacctat    900
cgtgtcgtta gcgtactcac cgttcttcat caagactggc tcaatggaaa agaatataaa    960
tgtaaagtta gcaacaaagg tctgcccagt tcaatcgaaa aaacaattag caaagccaaa   1020
ggccaacctc gcgaacccca gtctatacc ttgccccctt ctcaggaaga aatgaccaaa   1080
aaccaagttt cactcacatg cctcgtaaaa ggattctatc catcagacat tgcagtagaa   1140
tgggaatcta acggccaacc tgaaaataat tacaaaacca ctcctcctgt cctcgattct   1200
gacggctctt ttttccttta ctccagattg actgttgata atcccgctg gcaggaaggt   1260
aacgttttt cttgttctgt gatgcacgaa gccctccata acagattcac tcaaaaatct   1320
ctttctctct cccctggcaa ataa                                          1344
```

<210> SEQ ID NO 26
<211> LENGTH: 447
<212> TYPE: PRT
<213> ORGANISM: Artificial Sequence
<220> FEATURE:
<223> OTHER INFORMATION: Synthetic

<400> SEQUENCE: 26

```
Glu Val Gln Leu Val Glu Ser Gly Gly Gly Leu Ala Gln Pro Gly Gly
1               5                   10                  15

Ser Leu Arg Leu Ser Cys Ala Ala Ser Gly Phe Ser Ile Ser Asp Tyr
            20                  25                  30

Glu Ile His Trp Val Arg Gln Val Pro Gly Lys Gly Leu Glu Trp Val
        35                  40                  45

Ser Gly Ile Gly Ser Ala Gly Asn Thr Tyr Tyr Pro Gly Ala Val Lys
    50                  55                  60

Gly Arg Phe Thr Ile Ser Arg Glu Asn Ala Lys Asn Ser Leu Tyr Leu
65                  70                  75                  80

Gln Val Asn Ser Leu Thr Val Gly Asp Thr Ala Val Tyr Tyr Cys Ala
                85                  90                  95

Arg Val Trp Ser Pro Leu Tyr Tyr Phe Gly Leu Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn Arg Phe Thr Gln Lys Ser Leu Ser Leu Ser Pro Gly Lys
        435                 440                 445

<210> SEQ ID NO 27
<211> LENGTH: 1359
<212> TYPE: DNA
<213> ORGANISM: Artificial Sequence
<220> FEATURE:
<223> OTHER INFORMATION: Synthetic

<400> SEQUENCE: 27
gaagtgcagc tggtggagtc tgggggagac ttggtacagc ctggcaggtc cctgagactc      60
tcctgtgcag cctctggatt cacttttgat gaatatgcca tgcactgggt ccggcaagct     120
ccagggaagg gcctggagtg gtctcacat attagttgga atagtcatca catagcctat     180
gcggactctg tgaagggccg attcaccatc tccagagaca acgccaggaa ctccctatat     240
ctgcaaatga atagtctgag acctgaggac acggccttgt atttctgtgt aaaagattgg     300
ggattgggag caagcggggg ctactactac gttttggacg tctggggcca aggaccacg      360
```

-continued

```
gtcaccgtct cctcagcctc caccaagggc ccatcggtct tccccctggc gccctgctcc    420
aggagcacct ccgagagcac agccgccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcacga agacctacac ctgcaacgta gatcacaagc ccagcaacac caaggtggac    660
aagagagttg agtccaaata tggtccccca tgcccaccct gcccagcacc tgagttcctg    720
gggggaccat cagtcttcct gttcccccca aaacccaagg acactctcat gatctcccgg    780
acccctgagg tcacgtgcgt ggtggtggac gtgagccagg aagaccccga ggtccagttc    840
aactggtacg tggatggcgt ggaggtgcat aatgccaaga caaagccgcg ggaggagcag    900
ttcaacagca cgtaccgtgt ggtcagcgtc ctcaccgtcc tgcaccagga ctggctgaac    960
ggcaaggagt acaagtgcaa ggtctccaac aaaggcctcc cgtcctccat cgagaaaacc    1020
atctccaaag ccaaagggca gccccgagag ccacaggtgt acaccctgcc cccatcccag    1080
gaggagatga ccaagaacca ggtcagcctg acctgcctgg tcaaaggctt ctaccccagc    1140
gacatcgccg tggagtggga gagcaatggg cagccggaga acaactacaa gaccacgcct    1200
cccgtgctgg actccgacgg ctccttcttc ctctacagca ggctcaccgt ggacaagagc    1260
aggtggcagg aggggaatgt cttctcatgc tccgtgatgc atgaggctct gcacaaccac    1320
tacacacaga gtccctctcc cctgtctctg ggtaaatga                           1359
```

<210> SEQ ID NO 28
<211> LENGTH: 452
<212> TYPE: PRT
<213> ORGANISM: Artificial Sequence
<220> FEATURE:
<223> OTHER INFORMATION: Synthetic

<400> SEQUENCE: 28

```
Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Asp Glu Tyr
            20                  25                  30

Ala Met His Trp Val Arg Gln Ala Pro Gly Lys Gly Leu Glu Trp Val
        35                  40                  45

Ser His Ile Ser Trp Asn Ser His Ile Ala Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Pro Glu Asp Thr Ala Leu Tyr Phe Cys
                85                  90                  95

Val Lys Asp Trp Gly Leu Gly Ala Ser Gly Gly Tyr Tyr Tyr Val Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

```
Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 29
<211> LENGTH: 648
<212> TYPE: DNA
<213> ORGANISM: Artificial Sequence
<220> FEATURE:
<223> OTHER INFORMATION: Synthetic

<400> SEQUENCE: 29

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
```

```
acgctgagca aagcagacta cgagaaacac aaagtctacg cctgcgaagt cacccatcag    600
ggcctgagct cgcccgtcac aaagagcttc aacaggggag agtgttag                648
```

<210> SEQ ID NO 30
<211> LENGTH: 215
<212> TYPE: PRT
<213> ORGANISM: Artificial Sequence
<220> FEATURE:
<223> OTHER INFORMATION: Synthetic

<400> SEQUENCE: 30

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 31
<211> LENGTH: 381
<212> TYPE: DNA
<213> ORGANISM: Artificial Sequence
<220> FEATURE:
<223> OTHER INFORMATION: Synthetic

<400> SEQUENCE: 31

```
caggtgcagc tggtggagtc tgggggcggc gtggtccagc ctggagggtc cctgagactc    60
tcctgtgaag cctctggctt caccttcagt ggctatgccc tacactgggt ccgccaggct   120
ccaggcaagg ggctggagtg ggtgacagtt atatcatatg atggaagtga taaattctat   180
gcagactccg tgaagggccg attcaccatc tccagagaca attccaagaa cacgctgtac   240
ctgcaaatga acagcctgag aactgaggac acggctctgt attactgtgc gaaagattgg   300
gggacatatc actggaacta cggccactac aattatgtta tggacgtctg gggccaaggg   360
```
accacggtca ccgtctcctc a 381

<210> SEQ ID NO 32
<211> LENGTH: 127
<212> TYPE: PRT
<213> ORGANISM: Artificial Sequence
<220> FEATURE:
<223> OTHER INFORMATION: Synthetic

<400> SEQUENCE: 32

Gln Val Gln Leu Val Glu Ser Gly Gly Val Val Gln Pro Gly Arg
1               5                   10                  15

Ser Leu Arg Leu Ser Cys Glu Ala Ser Gly Phe Thr Phe Ser Gly Tyr
                20                  25                  30

Ala Leu His Trp Val Arg Gln Ala Pro Gly Lys Gly Leu Glu Trp Val
            35                  40                  45

Thr Val Ile Ser Tyr Asp Gly Ser Asp Lys Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Leu Tyr Tyr Cys
                85                  90                  95

Ala Lys Asp Trp Gly Thr Tyr His Trp Asn Tyr Gly His Tyr Asn Tyr
            100                 105                 110

Val Met Asp Val Trp Gly Gln Gly Thr Thr Val Thr Val Ser Ser
        115                 120                 125

<210> SEQ ID NO 33
<211> LENGTH: 24
<212> TYPE: DNA
<213> ORGANISM: Artificial Sequence
<220> FEATURE:
<223> OTHER INFORMATION: Synthetic

<400> SEQUENCE: 33
ggcttcacct tcagtggcta tgcc 24

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Gly Phe Thr Phe Ser Gly Tyr Ala
1               5

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
atatcatatg atggaagtga taaa 24

<210> SEQ ID NO 36
<211> LENGTH: 8
<212> TYPE: PRT
<213> ORGANISM: Artificial Sequence
<220> FEATURE:

<223> OTHER INFORMATION: Synthetic

<400> SEQUENCE: 36

Ile Ser Tyr Asp Gly Ser Asp Lys
1               5

<210> SEQ ID NO 37
<211> LENGTH: 60
<212> TYPE: DNA
<213> ORGANISM: Artificial Sequence
<220> FEATURE:
<223> OTHER INFORMATION: Synthetic

<400> SEQUENCE: 37
gcgaaagatt gggggacata tcactggaac tacggccact acaattatgt tatggacgtc    60

<210> SEQ ID NO 38
<211> LENGTH: 20
<212> TYPE: PRT
<213> ORGANISM: Artificial Sequence
<220> FEATURE:
<223> OTHER INFORMATION: Synthetic

<400> SEQUENCE: 38

Ala Lys Asp Trp Gly Thr Tyr His Trp Asn Tyr Gly His Tyr Asn Tyr
1               5                   10                  15

Val Met Asp Val
            20

<210> SEQ ID NO 39
<211> LENGTH: 366
<212> TYPE: DNA
<213> ORGANISM: Artificial Sequence
<220> FEATURE:
<223> OTHER INFORMATION: Synthetic

<400> SEQUENCE: 39
caggtgcagc tggtggagtc tgggggaggc ttggtcaagc ctggcgggtc cctgagactc    60
tcctgcgcag cctctggatt caccttcagt gactactaca tgagctggat ccgtcaggct   120
ccagggaagg gactggaatg gatttcatac attagcgaca atcgtgatac cgtatactac   180
gcagactctg tgaagggccg attcaccatc tccagggaca acgcccagag tatactatat   240
ttgcaactga aagcctgag agccgaggac acggccatat attattgtgc gagagtggca   300
tacggtgcta attcacggtt ttactttccc tactggggcc agggaaccct ggtcaccgtc   360
tcctca                                                             366

<210> SEQ ID NO 40
<211> LENGTH: 122
<212> TYPE: PRT
<213> ORGANISM: Artificial Sequence
<220> FEATURE:
<223> OTHER INFORMATION: Synthetic

<400> SEQUENCE: 40

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser Tyr Ile Ser Asp Asn Arg Asp Thr Val Tyr Tyr Ala Asp Ser Val

```
            50                  55                  60
Lys Gly Arg Phe Thr Ile Ser Arg Asp Asn Ala Gln Ser Ile Leu Tyr
 65                  70                  75                  80

Leu Gln Leu Arg Ser Leu Arg Ala Glu Asp Thr Ala Ile Tyr Tyr Cys
                 85                  90                  95

Ala Arg Val Ala Tyr Gly Ala Asn Ser Arg Phe Tyr Phe Pro Tyr Trp
            100                 105                 110

Gly Gln Gly Thr Leu Val Thr Val Ser Ser
            115                 120
```

<210> SEQ ID NO 41
<211> LENGTH: 24
<212> TYPE: DNA
<213> ORGANISM: Artificial Sequence
<220> FEATURE:
<223> OTHER INFORMATION: Synthetic

<400> SEQUENCE: 41
ggattcacct tcagtgacta ctac                                    24

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Gly Phe Thr Phe Ser Asp Tyr Tyr
 1               5

<210> SEQ ID NO 43
<211> LENGTH: 24
<212> TYPE: DNA
<213> ORGANISM: Artificial Sequence
<220> FEATURE:
<223> OTHER INFORMATION: G   F   T   F   S   D   Y   Y

<400> SEQUENCE: 43
attagcgaca atcgtgatac cgta                                    24

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Ile Ser Asp Asn Arg Asp Thr Val
 1               5

<210> SEQ ID NO 45
<211> LENGTH: 45
<212> TYPE: DNA
<213> ORGANISM: Artificial Sequence
<220> FEATURE:
<223> OTHER INFORMATION: Synthetic

<400> SEQUENCE: 45
gcgagagtgg catacggtgc taattcacgg ttttactttc cctac              45

<210> SEQ ID NO 46
<211> LENGTH: 15

```
<212> TYPE: PRT
<213> ORGANISM: Artificial Sequence
<220> FEATURE:
<223> OTHER INFORMATION: Synthetic

<400> SEQUENCE: 46

Ala Arg Val Ala Tyr Gly Ala Asn Ser Arg Phe Tyr Phe Pro Tyr
1               5                   10                  15

<210> SEQ ID NO 47
<211> LENGTH: 1365
<212> TYPE: DNA
<213> ORGANISM: Artificial Sequence
<220> FEATURE:
<223> OTHER INFORMATION: Synthetic

<400> SEQUENCE: 47
caggtgcagc tggtggagtc tgggggcggc gtggtccagc ctggggaggtc cctgagactc      60 tcctgtgaag cctctggctt caccttcagt ggctatgccc tacactgggt ccgccaggct     120
ccaggcaagg ggctggagtg ggtgacagtt atatcatatg atggaagtga taaattctat     180
gcagactccg tgaagggccg attcaccatc tccagagaca attccaagaa cacgctgtac     240
ctgcaaatga cagcctgag aactgaggac acggctctgt attactgtgc gaaagattgg     300
gggacatatc actggaacta cggccactac aattatgtta tggacgtctg gggccaaggg     360
accacggtca ccgtctcctc agccagcaca aaaggtccta cgttttttcc acttgcccca     420
tgttcaaggt caacctccga agtaccgcc gctcttggct gtctcgtaaa agattatttt      480
cccgaacctg taactgtctc ctggaactcc ggcgcactca cttccggcgt acataccttc     540
cccgctgtcc tccaatcttc cggtctctac tccctgtctt ctgttgtcac tgttccatca     600
tcctcactcg gcacaaaaac atatacctgc aacgttgatc acaagccaag taataccaaa     660
gttgataagc gcgtcgaatc caaatacggt ccccccctgcc ccccatgtcc cgctccagag     720
tttctcggtg gcccctctgt ttcctttttt cccctaaac ccaaagatac cctcatgatt      780
tccagaaccc ccgaggtcac ctgcgtcgtc gttgatgtaa gccaagaaga tcccgaagtc     840
cagttcaatt ggtatgtaga cggtgttgaa gtccataatg caaaaacaaa acccagagag     900 gaacagtta attcaaccta tcgtgtcgtt agcgtactca ccgttcttca tcaagactgg     960
ctcaatggaa agaatataa atgtaaagtt agcaacaaag gtctgcccag ttcaatcgaa    1020
aaaacaatta gcaaagccaa aggccaacct cgcgaacccc aagtctatac cttgccccct    1080
tctcaggaag aaatgaccaa aaaccaagtt tcactcacat gcctcgtaaa aggattctat    1140
ccatcagaca ttgcagtaga atgggaatct aacggccaac tgaaaataa ttacaaaacc     1200 actcctcctg tcctcgattc tgacggctct ttttcctttt actccagatt gactgttgat    1260
aaatcccgct ggcaggaagg taacgttttt tcttgttctg tgatgcacga agccctccat    1320
aacagattca ctcaaaaatc tctttctctc tcccctggca aataa                    1365

<210> SEQ ID NO 48
<211> LENGTH: 454
<212> TYPE: PRT
<213> ORGANISM: Artificial Sequence
<220> FEATURE:
<223> OTHER INFORMATION: Synthetic

<400> SEQUENCE: 48

Gln Val Gln Leu Val Glu Ser Gly Gly Gly Val Val Gln Pro Gly Arg
1               5                   10                  15
```

-continued

```
Ser Leu Arg Leu Ser Cys Glu Ala Ser Gly Phe Thr Phe Ser Gly Tyr
            20                  25                  30

Ala Leu His Trp Val Arg Gln Ala Pro Gly Lys Gly Leu Glu Trp Val
        35                  40                  45

Thr Val Ile Ser Tyr Asp Gly Ser Asp Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Leu Tyr Tyr Cys
                85                  90                  95

Ala Lys Asp Trp Gly Thr Tyr His Trp Asn Tyr Gly His Tyr Asn Tyr
            100                 105                 110

Val Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn Arg Phe Thr Gln Lys Ser Leu
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic

<400> SEQUENCE: 49

```
caggtgcagc tggtggagtc tgggggaggc ttggtcaagc ctggcgggtc cctgagactc      60
tcctgcgcag cctctggatt caccttcagt gactactaca tgagctggat ccgtcaggct     120
ccagggaagg gactggaatg gatttcatac attagcgaca tcgtgatac  cgtatactac     180
gcagactctg tgaagggccg attcaccatc tccagggaca acgcccagag tatactatat     240
ttgcaactga aagcctgag  agccgaggac acggccatat attattgtgc gagagtggca     300
tacggtgcta attcacggtt ttactttccc tactgggcc  agggaaccct ggtcaccgtc     360
tcctcagcct ccaccaaggg cccatcggtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccaccc tgcccagcac ctgagttcct ggggggacca     720
tcagtcttcc tgttcccccc aaaacccaag gacactctca tgatctcccg gacccctgag     780
gtcacgtgcg tggtggtgga cgtgagccag gaagacccg  aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctacccag  cgacatcgcc    1140
gtggagtggg agagcaatgg gcagccggag aacaactaca agaccacgcc tcccgtgctg    1200
gactccgacg gctccttctt cctctacagc aggctcaccg tggacaagag caggtggcag    1260
gaggggaatg tcttctcatg ctccgtgatg catgaggctc tgcacaacca ctacacacag    1320
aagtccctct ccctgtctct gggtaaatga                                     1350
```

<210> SEQ ID NO 50
<211> LENGTH: 448
<212> TYPE: PRT
<213> ORGANISM: Artificial Sequence
<220> FEATURE:
<223> OTHER INFORMATION: Synthetic

<400> SEQUENCE: 50

```
Val Gln Leu Val Glu Ser Gly Gly Gly Leu Val Lys Pro Gly Gly Ser
 1               5                  10                  15

Leu Arg Leu Ser Cys Ala Ala Ser Gly Phe Thr Phe Ser Asp Tyr Tyr
            20                  25                  30

Met Ser Trp Ile Arg Gln Ala Pro Gly Lys Gly Leu Glu Trp Ile Ser
        35                  40                  45
```

```
Tyr Ile Ser Asp Asn Arg Asp Thr Val Tyr Ala Asp Ser Val Lys
 50                  55                  60

Gly Arg Phe Thr Ile Ser Arg Asp Asn Ala Gln Ser Ile Leu Tyr Leu
 65                  70                  75                  80

Gln Leu Arg Ser Leu Arg Ala Glu Asp Thr Ala Ile Tyr Tyr Cys Ala
                 85                  90                  95

Arg Val Ala Tyr Gly Ala Asn Ser Arg Phe Tyr Phe Pro Tyr Trp Gly
            100                 105                 110

Gln Gly Thr Leu Val Thr Val Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 51
<211> LENGTH: 863
```

```
<212> TYPE: PRT
<213> ORGANISM: Artificial Sequence
<220> FEATURE:
<223> OTHER INFORMATION: Synthetic

<400> SEQUENCE: 51
```

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

-continued

```
Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
            405                 410                 415

Gly Ala Tyr Ser Leu Thr Leu Gln Gly Leu Gly Ile Ser Trp Leu Gly
        420                 425                 430

Leu Arg Ser Leu Arg Glu Leu Gly Ser Gly Leu Ala Leu Ile His His
    435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
            485                 490                 495

His Cys Trp Gly Pro Gly Pro Thr Gln Cys Val Asn Cys Ser Gln Phe
        500                 505                 510

Leu Arg Gly Gln Glu Cys Val Glu Glu Cys Arg Val Leu Gln Gly Leu
    515                 520                 525

Pro Arg Glu Tyr Val Asn Ala Arg His Cys Leu Pro Cys His Pro Glu
530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
            565                 570                 575

Arg Cys Pro Ser Gly Val Lys Pro Asp Leu Ser Tyr Met Pro Ile Trp
        580                 585                 590

Lys Phe Pro Asp Glu Glu Gly Ala Cys Gln Pro Cys Pro Ile Asn Cys
    595                 600                 605

Thr His Ser Cys Val Asp Leu Asp Asp Lys Gly Cys Pro Ala Glu Gln
610                 615                 620

Arg Ala Ser Pro Leu Thr Glu Pro Arg Gly Pro Thr Ile Lys Pro Cys
625                 630                 635                 640

Pro Pro Cys Lys Cys Pro Ala Pro Asn Leu Leu Gly Gly Pro Ser Val
            645                 650                 655

Phe Ile Phe Pro Pro Lys Ile Lys Asp Val Leu Met Ile Ser Leu Ser
        660                 665                 670

Pro Ile Val Thr Cys Val Val Val Asp Val Ser Glu Asp Asp Pro Asp
    675                 680                 685

Val Gln Ile Ser Trp Phe Val Asn Asn Val Glu Val His Thr Ala Gln
690                 695                 700

Thr Gln Thr His Arg Glu Asp Tyr Asn Ser Thr Leu Arg Val Val Ser
705                 710                 715                 720

Ala Leu Pro Ile Gln His Gln Asp Trp Met Ser Gly Lys Glu Phe Lys
            725                 730                 735

Cys Lys Val Asn Asn Lys Asp Leu Pro Ala Pro Ile Glu Arg Thr Ile
        740                 745                 750

Ser Lys Pro Lys Gly Ser Val Arg Ala Pro Gln Val Tyr Val Leu Pro
    755                 760                 765

Pro Pro Glu Glu Glu Met Thr Lys Lys Gln Val Thr Leu Thr Cys Met
770                 775                 780

Val Thr Asp Phe Met Pro Glu Asp Ile Tyr Val Glu Trp Thr Asn Asn
785                 790                 795                 800

Gly Lys Thr Glu Leu Asn Tyr Lys Asn Thr Glu Pro Val Leu Asp Ser
```

```
                    805                 810                 815
Asp Gly Ser Tyr Phe Met Tyr Ser Lys Leu Arg Val Glu Lys Lys Asn
                820                 825                 830

Trp Val Glu Arg Asn Ser Tyr Ser Cys Ser Val Val His Glu Gly Leu
        835                 840                 845

His Asn His His Thr Thr Lys Ser Phe Ser Arg Thr Pro Gly Lys
    850                 855                 860

<210> SEQ ID NO 52
<211> LENGTH: 713
<212> TYPE: PRT
<213> ORGANISM: Artificial Sequence
<220> FEATURE:
<223> OTHER INFORMATION: Synthetic

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Glu Ser Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Gly Gly Gly Gly Ser Glu Val Gln Leu Val Glu Ser Gly Gly Gly
            260                 265                 270

Leu Val Lys Pro Gly Gly Ser Leu Arg Leu Ser Cys Ala Ala Ser Gly
        275                 280                 285

Phe Thr Phe Ser Ser Tyr Ser Met Ser Trp Val Arg Gln Ala Pro Gly
    290                 295                 300

Lys Gly Leu Glu Trp Val Ser Ser Ile Ser Ser Ser Ser Ser Tyr Ile
```

```
              305                 310                 315                 320
Tyr Tyr Ala Asp Ser Val Lys Gly Arg Phe Thr Ile Ser Arg Asp Asn
                325                 330                 335
Ala Lys Asn Ser Leu Tyr Leu Gln Met Asn Ser Leu Arg Ala Glu Asp
                340                 345                 350
Thr Ala Val Tyr Tyr Cys Ala Arg Gly Gly Asp Ala Tyr Asn Tyr Tyr
                355                 360                 365
Tyr Phe Asp Tyr Trp Gly Gln Gly Thr Leu Val Thr Val Ser Ser Ala
            370                 375                 380
Ser Thr Lys Gly Pro Ser Val Phe Pro Leu Ala Pro Ser Ser Lys Ser
385                 390                 395                 400
Thr Ser Gly Gly Thr Ala Ala Leu Gly Cys Leu Val Lys Asp Tyr Phe
                405                 410                 415
Pro Glu Pro Val Thr Val Ser Trp Asn Ser Gly Ala Leu Thr Ser Gly
                420                 425                 430
Val His Thr Phe Pro Ala Val Leu Gln Ser Ser Gly Leu Tyr Ser Leu
                435                 440                 445
Ser Ser Val Val Thr Val Pro Ser Ser Ser Leu Gly Thr Gln Thr Tyr
        450                 455                 460
Ile Cys Asn Val Asn His Lys Pro Ser Asn Thr Lys Val Asp Lys Arg
465                 470                 475                 480
Val Glu Pro Lys Ser Cys Asp Lys Thr His Thr Cys Pro Pro Cys Pro
                485                 490                 495
Ala Pro Glu Phe Leu Gly Gly Pro Cys Val Phe Leu Phe Pro Pro Lys
                500                 505                 510
Pro Lys Asp Thr Leu Met Ile Ser Arg Thr Pro Glu Val Thr Cys Val
            515                 520                 525
Val Val Asp Val Ser His Glu Asp Pro Glu Val Lys Phe Asn Trp Tyr
            530                 535                 540
Val Asp Gly Val Glu Val His Asn Ala Lys Thr Lys Pro Arg Glu Glu
545                 550                 555                 560
Gln Tyr Asn Ser Thr Tyr Arg Val Val Ser Val Leu Thr Val Leu His
                565                 570                 575
Gln Asp Trp Leu Asn Gly Lys Glu Tyr Lys Cys Lys Val Ser Asn Lys
            580                 585                 590
Ala Leu Pro Ala Pro Ile Glu Lys Thr Ile Ser Lys Ala Lys Gly Gln
                595                 600                 605
Pro Arg Glu Pro Gln Val Tyr Thr Leu Pro Pro Ser Arg Glu Glu Met
        610                 615                 620
Thr Lys Asn Gln Val Ser Leu Thr Cys Leu Val Lys Gly Phe Tyr Pro
625                 630                 635                 640
Ser Asp Ile Ala Val Glu Trp Glu Ser Asn Gly Gln Pro Glu Asn Asn
                645                 650                 655
Tyr Lys Thr Thr Pro Pro Val Leu Asp Ser Asp Gly Ser Phe Phe Leu
                660                 665                 670
Tyr Ser Lys Leu Thr Val Asp Lys Ser Arg Trp Gln Gln Gly Asn Val
            675                 680                 685
Phe Ser Cys Ser Val Met His Glu Ala Leu His Asn His Tyr Thr Gln
        690                 695                 700
Lys Ser Leu Cys Leu Ser Pro Gly Lys
705                 710

<210> SEQ ID NO 53
```

<211> LENGTH: 220
<212> TYPE: PRT
<213> ORGANISM: Artificial Sequence
<220> FEATURE:
<223> OTHER INFORMATION: Synthetic

<400> SEQUENCE: 53

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Val Phe Phe Arg
            20                  25                  30

Ser Asn Asn Lys Asn Ile Leu Ala Trp Tyr Leu Gln Lys Pro Gly Gln
        35                  40                  45

Pro Pro Gln Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Tyr Phe Gly Ser Pro Phe Thr Phe Gly Pro Gly Thr Lys Val Asp Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 54
<211> LENGTH: 658
<212> TYPE: PRT
<213> ORGANISM: Artificial Sequence
<220> FEATURE:
<223> OTHER INFORMATION: Synthetic

<400> SEQUENCE: 54

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro

-continued

```
              100                 105                 110
Gly Gly Leu Arg Glu Leu Gln Leu Arg Ser Leu Thr Glu Ile Leu Lys
            115                 120                 125

Gly Gly Val Leu Ile Gln Arg Asn Pro Gln Leu Cys Tyr Gln Asp Thr
            130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
                180                 185                 190

Leu Thr Arg Thr Val Cys Ala Gly Gly Cys Ala Arg Cys Lys Gly Pro
                195                 200                 205

Leu Pro Thr Asp Cys Cys His Glu Gln Cys Ala Ala Gly Cys Thr Gly
                210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
                260                 265                 270

Cys Val Thr Ala Cys Pro Tyr Asn Tyr Leu Ser Thr Asp Val Gly Ser
                275                 280                 285

Cys Thr Leu Val Cys Pro Leu His Asn Gln Glu Val Thr Ala Glu Asp
                290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
                340                 345                 350

Ala Phe Leu Pro Glu Ser Phe Asp Gly Asp Pro Ala Ser Asn Thr Ala
                355                 360                 365

Pro Leu Gln Pro Glu Gln Leu Gln Val Phe Glu Thr Leu Glu Glu Ile
                370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
                420                 425                 430

Leu Arg Ser Leu Arg Glu Leu Gly Ser Gly Leu Ala Leu Ile His His
                435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
                500                 505                 510

Leu Arg Gly Gln Glu Cys Val Glu Cys Arg Val Leu Gln Gly Leu
                515                 520                 525
```

```
Pro Arg Glu Tyr Val Asn Ala Arg His Cys Leu Pro Cys His Pro Glu
        530                 535                 540
Cys Gln Pro Gln Asn Gly Ser Val Thr Cys Phe Gly Pro Glu Ala Asp
545                 550                 555                 560
Gln Cys Val Ala Cys Ala His Tyr Lys Asp Pro Pro Phe Cys Val Ala
                565                 570                 575
Arg Cys Pro Ser Gly Val Lys Pro Asp Leu Ser Tyr Met Pro Ile Trp
            580                 585                 590
Lys Phe Pro Asp Glu Glu Gly Ala Cys Gln Pro Cys Pro Ile Asn Cys
        595                 600                 605
Thr His Ser Cys Val Asp Leu Asp Asp Lys Gly Cys Pro Ala Glu Gln
        610                 615                 620
Arg Ala Ser Pro Leu Thr Glu Gln Lys Leu Ile Ser Glu Glu Asp Leu
625                 630                 635                 640
Gly Gly Glu Gln Lys Leu Ile Ser Glu Glu Asp Leu His His His His
                645                 650                 655
His His
```

```
<210> SEQ ID NO 55
<211> LENGTH: 5
<212> TYPE: PRT
<213> ORGANISM: Artificial Sequence
<220> FEATURE:
<223> OTHER INFORMATION: Synthetic

<400> SEQUENCE: 55

Tyr Gln Asp Thr Ile
1               5
```

```
<210> SEQ ID NO 56
<211> LENGTH: 17
<212> TYPE: PRT
<213> ORGANISM: Artificial Sequence
<220> FEATURE:
<223> OTHER INFORMATION: Synthetic

<400> SEQUENCE: 56

Arg Ser Arg Ala Cys His Pro Cys Ser Pro Met Cys Lys Gly Ser Arg
1               5                   10                  15
Cys
```

```
<210> SEQ ID NO 57
<211> LENGTH: 15
<212> TYPE: PRT
<213> ORGANISM: Artificial Sequence
<220> FEATURE:
<223> OTHER INFORMATION: Synthetic

<400> SEQUENCE: 57

Met Lys Leu Arg Leu Pro Ala Ser Pro Glu Thr His Leu Asp Met
1               5                   10                  15
```

```
<210> SEQ ID NO 58
<211> LENGTH: 11
<212> TYPE: PRT
<213> ORGANISM: Artificial Sequence
<220> FEATURE:
<223> OTHER INFORMATION: Synthetic

<400> SEQUENCE: 58

Thr Tyr Leu Pro Thr Asn Ala Ser Leu Ser Phe
```

<210> SEQ ID NO 59
<211> LENGTH: 14
<212> TYPE: PRT
<213> ORGANISM: Artificial Sequence
<220> FEATURE:
<223> OTHER INFORMATION: Synthetic

<400> SEQUENCE: 59

Ile Ala His Asn Gln Val Arg Gln Val Pro Leu Gln Arg Leu
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Synthetic

<400> SEQUENCE: 60

Ala Phe Leu Pro Glu Ser Phe
1               5

<210> SEQ ID NO 61
<211> LENGTH: 16
<212> TYPE: PRT
<213> ORGANISM: Artificial Sequence
<220> FEATURE:
<223> OTHER INFORMATION: Synthetic

<400> SEQUENCE: 61

Ile Gln Arg Asn Pro Gln Leu Cys Tyr Gln Asp Thr Ile Leu Trp Lys
1               5                   10                  15

<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Ser Pro Met Cys Lys Gly Ser Arg Cys
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic

<400> SEQUENCE: 63

Thr Arg Thr Val Cys Ala Gly
1               5

<210> SEQ ID NO 64
<211> LENGTH: 10
<212> TYPE: PRT
<213> ORGANISM: Artificial Sequence
<220> FEATURE:
<223> OTHER INFORMATION: Synthetic

<400> SEQUENCE: 64

His Lys Asn Asn Gln Leu Ala Leu Thr Leu
1               5                   10

```
<210> SEQ ID NO 65
<211> LENGTH: 16
<212> TYPE: PRT
<213> ORGANISM: Artificial Sequence
<220> FEATURE:
<223> OTHER INFORMATION: Synthetic

<400> SEQUENCE: 65

Glu Ser Met Pro Asn Pro Glu Gly Arg Tyr Thr Phe Gly Ala Ser Cys
1               5                   10                  15
```

BISPECIFIC ANTIGEN BINDING MOLECULES THAT BIND HER2, AND METHODS OF USE THEREOF

RELATED APPLICATIONS

This application claims priority under 35 U.S.C. § 119(e) of U.S. Provisional Application No. 62/982,989 filed Feb. 28, 2020; the disclosure of which is herein incorporated by reference in its entirety.

TECHNICAL FIELD

The present invention relates to bispecific antibodies and antigen-binding fragments thereof, as well as antibody-drug conjugates of such antibodies, which specifically bind human epidermal growth factor receptor 2 (HER2) and modulate HER2 signal transduction, and methods of use thereof.

SEQUENCE LISTING

An official copy of the sequence listing is submitted concurrently with the specification electronically via EFS-Web as an ASCII formatted sequence listing with a file name of 10719US01_Sequence_Listing_ST25.TXT, a creation date of Feb. 26, 2021, and a size of about 64 kilobytes. The sequence listing contained in this ASCII formatted document is part of the specification and is herein incorporated by reference in its entirety.

BACKGROUND

Human epidermal growth factor receptor 2 (HER2) is a tyrosine kinase receptor encoded by the ERBB2 gene located at the long arm of human chromosome 17 (17q12). The protein is involved in the signal transduction pathways leading to cell growth and differentiation. HER2 is a 1255 amino acid, 185 kD transmembrane glycoprotein, consisting of an extracellular ligand binding domain, though there are no known ligands for HER2, a transmembrane domain, and an intracellular domain. HER2 is thought to be the preferential dimerization partner of the other members of the ErbB family, including erbB-2, erbB-3, and erbB-4. HER2 can also be activated by complexing with other membrane receptors such as insulin-like growth factor receptor 1. Dimerization, including homodimerization, results in the autophosphorylation of tyrosine residues within the cytoplasmic domain of the receptors, initiating a variety of signaling pathways leading to cell proliferation and tumorigenesis.

HER2 overexpression results in induction of angiogenesis. The protein is overexpressed in about 30% of breast cancers and about 30% of gastric/esophageal cancers. HER2 overexpression is also found in other cancers, including ovary, uterine, cervical, endometrial, bladder, lung, colon, and head and neck cancers. Breast cancers can have up to 25-50 copies of the HER2 gene, and up to 40-100 fold increase in HER2 protein. HER2 amplification is an early event in breast and gastric tumorigenesis and associated with significantly shorter disease-free survival.

Both preclinical and clinical results indicate that tumors overexpressing HER2 respond to anti-HER2 therapies, validating HER2 as a cancer driver. Treatment of HER2 positive tumors with anti-HER2 therapies has led to dramatic improvements in early survival and advanced disease. Various monovalent HER2 blocking antibodies are in clinical development for the treatment of various cancers (U.S. Patent Application Publication Nos. 2019/0076438 and 2015/0343058). Those antibodies include trastuzumab, pertuzumab, and margetuximab. (Pernas and Tolaney, Therapeutic Advances in Medical Oncology, 11: doi 10.1177/1758835919833519, 2019). Other HER2 antibodies are bispecific, or multispecific, such as PRS (Pieris Pharmaceuticals, Inc., a monoclonal antibody-bispecific protein targeting HER2 and CD137), GBR1302 (Glenmark Pharmaceuticals, a HER2×CD3 bispecific antibody), ZW25 (Zymeworks, Inc., a bispecific antibody that binds two different epitopes on the extracellular domain of HER2-ECD2 and ECD4), and MCLA-128 (Merus, a bispecific antibody to HER2 and HER5). Some HER2 antibodies are conjugated to cytotoxic payloads, including MEDI4276 (Medimmune, a bispecific ADC binding two HER2 domains conjugated with tubulysin; see U.S. Pat. No. 10,160,812), SYD985 (Synthon Biopharmaceuticals BV, an ADC based on Trastuzumab and a cleavable linker), and Trastuzumab deruxtecan (Daiichi Sankyo, Inc., comprising Trastuzumab, a cleavable drug linker, and a topoisomerase I payload).

Nearly all patients with metastatic HER2 positive cancers eventually progress on anti-HER2 therapy due to de novo or acquired resistance. Tumors expressing intermediate levels of HER2 (IHC 2+) remain resistant to certain therapies including Trastuzumab-DM1 ado-trastuzumab emtansine (T-DM1), a microtubule disruptor maytansine, apparently due to inefficient internalization and processing of T-DM1 in lysosomes. Trastuzumab-DMl is effective in only about 25% of HER2 breast cancer patients. There remains a significant unmet medical need for improved anti-cancer drugs that potently are effective in HER2 expressing cancers, and especially in cancers expressing intermediate levels of HER2.

BRIEF SUMMARY

Provided herein are bispecific antibodies that bind human HER2 receptor protein (HER2×HER2). The antibodies are useful, inter alia, for targeting tumor cells that express HER2. The anti-HER2 antibodies, and antigen-binding portions thereof, may be used alone in unmodified form, or may be included as part of an antibody-drug conjugate.

Other embodiments will become apparent from a review of the ensuing detailed description.

BRIEF DESCRIPTION OF THE FIGURES

FIG. 14 provides deuterium uptake data for Her2 peptides with significant protection upon formation of Her2-Parental Ab1 complex compared to Her2 alone.

FIG. 15 provides deuterium uptake data for Her2 peptides with significant protection upon formation of Her2-Parental Ab2 complex compared to Her2 alone.

FIG. 16 provides deuterium uptake data for Her2 peptides with significant protection upon formation of Her2-Parental Ab3 complex compared to Her2 alone.

FIG. 17 provides deuterium uptake data for Her2 peptides with significant protection upon formation of Her2-Parental Ab4 complex compared to Her2 alone.

DETAILED DESCRIPTION

Figure 1A:
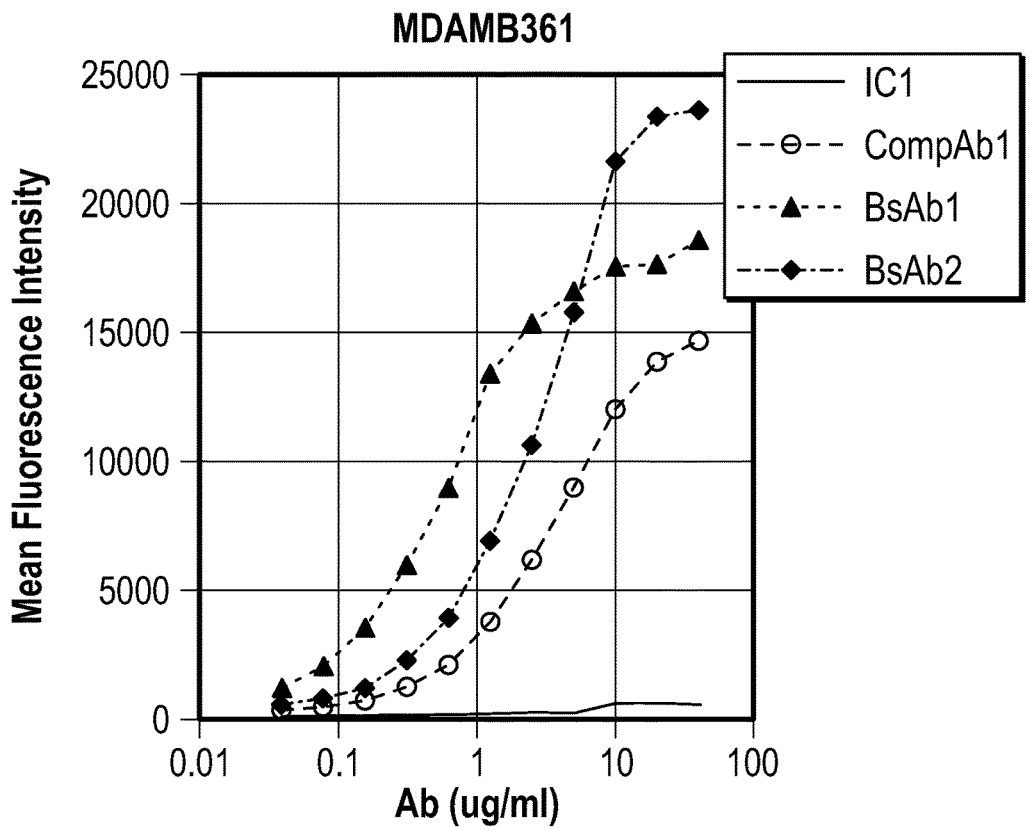
FIG. 1A, FIG. 1B, and FIG. 1C show cell surface binding of CompAb1 (open circles), BsAb1 (grey triangles), and BsAb2 (black triangles) to MDAMB361 cells, JIMT1 cells, and ZR751 cells. Both bispecific antibodies bound with greater affinity and avidity than trastuzumab in the three cell lines, while the isotype control antibody showed little or no binding.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

HER2 Protein

The expressions "HER2" and the like, as used herein, a member of the epidermal growth factor (EGF) receptor family of receptor tyrosine kinases. The protein is also known as NEU; NGL; HER2; TKR1; CD340; HER-2; MLN 19; HER-2/neu. HER2 can refer to the amino acid sequence as set forth in SEQ ID NO: 51, and/or having the amino acid sequence as set forth in NCBI accession No. NP_004439.2.

All references to proteins, polypeptides and protein fragments herein are intended to refer to the human version of the respective protein, polypeptide or protein fragment unless explicitly specified as being from a non-human species. Thus, the expression "HER2" means human HER2 unless specified as being from a non-human species, e.g., "mouse HER2" "monkey HER2," etc.

As used herein, the expression "cell surface-expressed HER2" means one or more HER2 protein(s), or the extracellular domain thereof, that is/are expressed on the surface of a cell in vitro or in vivo, such that at least a portion of a HER2 protein is exposed to the extracellular side of the cell membrane and is accessible to an antigen-binding portion of an antibody. A "cell surface-expressed HER2" can comprise or consist of a HER2 protein expressed on the surface of a cell which normally expresses HER2 protein. Alternatively, "cell surface-expressed HER2" can comprise or consist of HER2 protein expressed on the surface of a cell that normally does not express human HER2 on its surface but has been artificially engineered to express HER2 on its surface.

HER2×HER2 Bispecific Antigen-Binding Molecules

Provided herein are bispecific antigen binding molecules comprising a first antigen-binding domain (also referred to herein as "D1"), and a second antigen-binding domain (also referred to herein as "D2"). The simultaneous binding of the two separate HER2 epitopes by the bispecific antigen-binding molecule results in cluster formation of the antibodies on a HER2 expressing cell surface and results in internalization of the HER2 protein along with the bound antibody.

The bispecific antigen-binding molecules, which comprise a first antigen-binding domain (D1) which specifically binds a first epitope of human HER2 and a second antigen-binding domain (D2) which specifically binds a second epitope of human HER2, may be referred to herein as "HER2×HER2 bispecific antibodies," "HER2×HER2," or other related terminology.

In certain embodiments, D1 and D2 domains of a HER2× HER2 bispecific antibody are non-competitive with one another. Non-competition between D1 and D2 for binding to HER2 means that, the respective monospecific antigen binding proteins from which D1 and D2 were derived do not compete with one another for binding to human HER2. Exemplary antigen-binding protein competition assays are known in the art, non-limiting examples of which are described elsewhere herein.

In certain embodiments, D1 and D2 bind to different (e.g., non-overlapping, or partially overlapping) epitopes on HER2, as described elsewhere herein.

HER2×HER2 bispecific antigen-binding molecules may be constructed using the antigen-binding domains of two separate monospecific anti-HER2 antibodies. For example, a collection of monoclonal monospecific anti-HER2 antibodies may be produced using standard methods known in the art. The individual antibodies thus produced may be tested pairwise against one another for cross-competition to a HER2 protein. If two different anti-HER2 antibodies are able to bind to HER2 at the same time (i.e., do not compete with one another), then the antigen-binding domain from the first anti-HER2 antibody and the antigen-binding domain from the second, non-competitive anti-HER2 antibody can be engineered into a single HER2×HER2 bispecific antibody in accordance with the present disclosure.

In certain embodiments, the bispecific antigen-binding molecule has one or more of the following characteristics: (a) binds to ErbB2 with an equilibrium dissociation constant ($K_D$) of less than about 1 nM as measured in a surface plasmon resonance assay; (b) binds to ErbB2 with a dissociative half life (t½) of at least about 30 minutes as measured in a surface plasmon resonance assay; (c) binds to cell surface HER2 with greater affinity and/or avidity when compared to Trastuzumab; (d) binds to HER2 IHC2+ and IHC3+expressing cells with greater efficiency than Trastuzumab; (e) binds to HER2 IHC1+expressing cells with greater IC50 than CompAb2; (f) binds to cells expressing HER2 at levels of at least 6%, wherein the expression levels of HER2 are determined by Western Blot analysis; (g) forms antibody clusters on the surface of HER2 expressing cells; (h) is internalized by HER2 expressing cells more efficiently than Trastuzumab; and (i) wherein D1 and D2 do not compete with one another for binding to human HER2.

In certain embodiments, the bispecific antigen-binding molecule has one or more of the following characteristics: (a) demonstrates greater tumor killing with lower dosages relative to Trastuzumab conjugated to a cytotoxin; (b) demonstrates greater tumor killing with lower dosages relative to Trastuzumab conjugated to DM1; (c) demonstrates greater tumor killing with lower dosages relative to CompAb2 conjugated to a cytotoxin; (d) demonstrates greater tumor killing with lower dosages relative to CompAb2 conjugated to tubulysin; or (e) inhibits growth of cells expressing HER2 at levels of at least 6%, wherein the expression levels of HER2 are determined by Western Blot analysis.

According to the present disclosure, a bispecific antigen-binding molecule can be a single multifunctional polypeptide, or it can be a multimeric complex of two or more polypeptides that are covalently or non-covalently associated with one another. As will be made evident by the present disclosure, any antigen binding construct which has the ability to simultaneously bind two separate, non-identical epitopes of the HER2 molecule is regarded as a bispecific antigen-binding molecule. Any of the bispecific antigen-binding molecules described herein, or variants thereof, may be constructed using standard molecular biological techniques (e.g., recombinant DNA and protein expression technology) as will be known to a person of ordinary skill in the art.

Anti-HER2 Bispecific Antibody Sequences

The term "antibody", as used herein, means any antigen-binding molecule or molecular complex comprising at least one complementarity determining region (CDR) that specifically binds to or interacts with a particular antigen (e.g., HER2). The term "antibody" includes immunoglobulin molecules comprising four polypeptide chains, two heavy (H) chains and two light (L) chains inter-connected by disulfide bonds, as well as multimers thereof (e.g., IgM). The term "antibody" also includes immunoglobulin molecules consisting of four polypeptide chains, two heavy (H) chains and two light (L) chains inter-connected by disulfide bonds. Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order FR1, CDR1, FR2, CDR2, FR3, CDR3, FR4. In different embodiments of the invention, the FRs of the anti-HER2 antibody (or antigen-binding portion thereof) may be identical to the human germline sequences, or may be naturally or artificially modified. An amino acid consensus sequence may be defined based on a side-by-side analysis of two or more CDRs.

Likewise, the term "antibody" includes immunoglobulin molecules comprising eight polypeptide chains, four heavy (H) chains and four light (L) chains inter-connected by disulfide bonds, i.e. a bispecific antibody. The term "antibody" also includes immunoglobulin molecules consisting of eight polypeptide chains, four heavy (H) chains and four light (L) chains inter-connected by disulfide bonds.

Furthermore, the term "antibody" includes functionalized immunoglobulin molecules comprising at least one HC, wherein the HC comprises an azido-$PEG_3$-amine. In some aspects, the azido-$PEG_3$-amine is located at a Q295 site on the antibody HC. In some aspects, the azido-$PEG_3$-amine is located at a Q297 site on the antibody. In some aspects, the bispecific antibody has two HCs functionalized with azido-$PEG_3$-amines located at both Q295 sites in the HCs. In some aspects, the bispecific antibody has two HCs functionalized with azido-$PEG_3$-amines located at both Q297 sites in the HCs. In some aspects, the bispecific antibody has two HCs functionalized with azido-$PEG_3$-amines located at both Q295 sites and at both Q297 sites in the HCs. The Q297 sites in the HCs are obtained by modifying the N297 to a Q297, also referred to herein as an N297Q modification.

According to one aspect, HER2 bispecific antibodies are provided. Exemplary HER2 bispecific antibodies according to this aspect are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the bispecific antigen-binding molecules (used interchangeably herein with bispecific antigen-binding protein) disclosed herein. Table 2 sets forth the nucleic acid sequence identifiers of the HCVRs, LCVRs, HCDR1, HCDR2 HCDR3, LCDR1, LCDR2 and LCDR3 of the exemplary antibodies.

Provided herein are bispecific antibodies that specifically bind HER2, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

Provided herein are bispecific antibodies that specifically bind HER2, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

Provided herein are bispecific antibodies that specifically bind HER2, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the bispecific antibodies comprise two HCVR/LCVR amino acid sequence pairs contained within any of the exemplary HER2 bispecific antibodies listed in Table 1. In certain embodiments, an HCVR/LCVR amino acid sequence pair is selected from the group consisting of: SEQ ID NO: 2/18, 10/18, 32/18, and 40/18.

Also provided are bispecific antibodies that specifically bind HER2, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

Also provided are bispecific antibodies that specifically bind HER2, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

Also provided are bispecific antibodies that specifically bind HER2, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

Also provided are bispecific antibodies that specifically bind HER2, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

Also provided are bispecific antibodies that specifically bind HER2, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

Also provided are bispecific antibodies that specifically bind HER2, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

Also provided are bispecific antibodies that specifically bind HER2, comprising an HCDR1 and an LCDR1 amino acid sequence pair (HCDR1/LCDR1) comprising any of the HCDR1 amino acid sequences listed in Table 1 paired with any of the LCDR1 amino acid sequences listed in Table 1. According to certain embodiments, bispecific antibodies comprise at least one HCDR1/LCDR1 amino acid sequence pair contained within any of the exemplary anti-HER2 antibodies listed in Table 1. In certain embodiments, the HCDR1/LCDR1 amino acid sequence pair is selected from the group consisting of: SEQ ID NO: 4/20, 12/20, 34/20, and 42/20.

Also provided are bispecific antibodies that specifically bind HER2, comprising an HCDR2 and an LCDR2 amino acid sequence pair (HCDR2/LCDR2) comprising any of the HCDR2 amino acid sequences listed in Table 1 paired with any of the LCDR2 amino acid sequences listed in Table 1. According to certain embodiments, the bispecific antibodies comprise at least one HCDR2/LCDR2 amino acid sequence pair contained within any of the exemplary anti-HER2 antibodies listed in Table 1. In certain embodiments, the HCDR2/LCDR2 amino acid sequence pair is selected from the group consisting of: SEQ ID NO: 6/22, 14/22, 36/22, and 44/22.

Also provided herein are bispecific antibodies that specifically bind HER2, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments the bispecific antibodies comprise at least one HCDR3/LCDR3 amino acid sequence pair contained within any of the exemplary bispecific antibodies listed in Table 1. In certain embodiments, the HCDR3/LCDR3 amino acid sequence pair is selected from the group consisting of: SEQ ID NO: 8/24, 16/24, 38/24, and 46/24.

Also provided herein are bispecific antibodies that specifically bind HER2, comprising two sets of six CDRs (i.e., HCDR1-HCDR2-HCDR3-LCDR1-LCDR2-LCDR3) contained within any of the exemplary anti-HER2 antibodies listed in Table 1. In certain embodiments, the HCDR1-HCDR2-HCDR3-LCDR1-LCDR2-LCDR3 amino acid sequence sets are selected from the group consisting of: SEQ ID NO: 4-6-8-20-22-24, 12-14-16-20-22-24, 34-36-38-20-22-24, and 42-44-46-20-22-24.

In a related embodiment, bispecific antibodies that specifically bind HER2 comprise two sets of six CDRs (i.e., HCDR1-HCDR2-HCDR3-LCDR1-LCDR2-LCDR3) contained within two HCVR/LCVR amino acid sequence pairs as defined by any of the exemplary HER2 bispecific antibodies listed in Table 1. For example, HER2 bispecific antibodies comprise an HCDR1-HCDR2-HCDR3-LCDR1-LCDR2-LCDR3 amino acid sequence set contained within an HCVR/LCVR amino acid sequence pair selected from the group consisting of: SEQ ID NOs: 2/18, 10/18, 32/18, and 40/18.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Provided herein are bispecific antibodies that specifically bind HER2, comprising a heavy chain (HC) comprising an amino acid sequence selected from any of the HC amino acid sequences listed in Table 3, or a substantially similar sequence thereof having at least 90%, at least 95%, at least 98% or at least 99% sequence identity thereto. For example, provided herein are bispecific antibodies that specifically bind HER2, comprising a HC comprising an amino acid sequence selected from any of the HC amino acid sequences listed in Table 3, but comprising an N297Q modification, or an equivalent modification. Illustratively, provided herein is a bispecific antibody having a heavy chain comprising an N297Q modification within a HC amino acid sequence selected from the group consisting of SEQ ID NOs: 26, 28, 48, and 50. In some aspects, the bispecific antibody comprises a HC comprising an N297Q modification within the HC amino acid sequence of SEQ ID NO: 26. In some aspects, the bispecific antibody comprises a HC comprising an N297Q modification within the HC amino acid sequence of SEQ ID NO: 28. In some aspects, the bispecific antibody comprises a HC comprising an N297Q modification within the HC amino acid sequence of SEQ ID NO: 48. In some aspects, the bispecific antibody comprises a HC comprising an N297Q modification within the HC amino acid sequence of SEQ ID NO: 50. In some aspects, the bispecific antibody comprises a HC comprising an N297Q modification within the HC amino acid sequence of SEQ ID NO: 26 and a HC comprising an N297Q modification within the HC amino acid sequence of SEQ ID NO: 28. In some aspects, the bispecific antibody comprises a HC comprising an N297Q modification within the HC amino acid sequence of SEQ ID NO: 48 and a HC comprising an N297Q modification within the HC amino acid sequence of SEQ ID NO: 50.

Provided herein are bispecific antibodies that specifically bind HER2, comprising a light chain (LC) comprising an amino acid sequence selected from any of the LC amino acid sequences listed in Table 3, or a substantially similar sequence thereof having at least 90%, at least 95%, at least 98% or at least 99% sequence identity thereto.

Provided herein are bispecific antibodies that specifically bind HER2, comprising an HC and an LC amino acid sequence pair (HC/LC) comprising any of the HC amino acid sequences listed in Table 3 paired with any of the LC amino acid sequences listed in Table 3. According to certain embodiments, the bispecific antibodies comprise two HC/LC amino acid sequence pairs contained within any of the exemplary HER2 bispecific antibodies listed in Table 3. In certain embodiments, an HC/LC amino acid sequence pair is selected from the group consisting of: SEQ ID NO: 26/30, 28/30, 48/30, and 50/30. In some aspects, the HC comprises an N297Q modification as provided above.

Also provided herein are nucleic acid molecules encoding anti-HER2 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

Also provided are nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

Also provided are nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

Also provided are nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

Also provided are nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

Also provided are nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

Also provided are nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

Also provided are nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

Also provided are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary HER2 bispecific antibodies listed in Table 1.

Also provided are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary HER2 bispecific antibodies listed in Table 1.

Also provided are nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect, the nucleic acid molecule encodes an HCVR and LCVR, wherein the HCVR and LCVR are both derived from the same HER2 bispecific antibody listed in Table 1.

Also provided are nucleic acid molecules encoding any of the HC amino acid sequences listed in Table 3; or encoding a substantially similar sequence thereof having at least 90%, at least 95%, at least 98% or at least 99% sequence identity thereto. For example, the nucleic acid molecules can encode any of the HC amino acid sequences listed in Table 3, wherein the HC has an N297Q modification.

Also provided are nucleic acid molecules encoding any of the LC amino acid sequences listed in Table 3; or encoding a substantially similar sequence thereof having at least 90%, at least 95%, at least 98% or at least 99% sequence identity thereto.

Also provided herein are recombinant expression vectors capable of expressing a polypeptide comprising a heavy or light chain variable region of HER2 bispecific antibody. For example, recombinant expression vectors comprise any of the nucleic acid molecules mentioned above, i.e., nucleic acid molecules encoding any of the HCVR, LCVR, and/or CDR sequences as set forth in Table 1. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

Provided herein are HER2 bispecific antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Antigen-Binding Domains

The bispecific antigen-binding molecules of the present disclosure comprise two separate antigen-binding domains (D1 and D2). As used herein, the expression "antigen-binding domain" means any peptide, polypeptide, nucleic acid molecule, scaffold-type molecule, peptide display molecule, or polypeptide-containing construct that is capable of specifically binding a particular antigen of interest (e.g., human HER2). The term "specifically binds" or the like, as used herein, means that the antigen-binding domain forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another.

Exemplary categories of antigen-binding domains that can be used in the context of the present disclosure include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]), and aptamers or portions thereof.

Methods for determining whether two molecules specifically bind one another are well known in the art and include, for example, equilibrium dialysis, surface plasmon resonance, and the like. For example, an antigen-binding domain, as used in the context of the present disclosure, includes polypeptides that bind a particular antigen (e.g., a target molecule [T] or an internalizing effector protein [E]) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

As indicated above, an "antigen-binding domain" (D1 and/or D2) may comprise or consist of an antibody or antigen-binding fragment of an antibody. The term "antibody," as used herein, means any antigen-binding molecule or molecular complex comprising at least one complementarity determining region (CDR) that specifically binds to or interacts with a particular antigen (e.g., human HER2). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the antibodies provided herein (or antigen-binding portion thereof) may be identical to the human germline sequences, or may be naturally or artificially modified. An amino acid consensus sequence may be defined based on a side-by-side analysis of two or more CDRs.

The D1 and/or D2 components of the bispecific antigen-binding molecules provided herein may comprise or consist of antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The bispecific antigen-binding molecules provided herein may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The bispecific antigen-binding molecules of the present disclosure may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl.

Acids. Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Methods for making bispecific antibodies are known in the art and may be used to construct bispecific antigen-binding molecules disclosed herein. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats).

Exemplary antigen-binding domains (D1 and D2) that can be included in the HER2×HER2 bispecific antigen-binding molecules provided herein include antigen-binding domains derived from any of the anti-HER2 sequences disclosed herein. For example, the present disclosure includes HER2× HER2 bispecific antigen-binding molecules comprising a D1 or D2 antigen-binding domain comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

Also provided herein are HER2×HER2 bispecific antigen-binding molecules comprising a D1 or D2 antigen-binding domain comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

Provided herein are HER2×HER2 bispecific antigen-binding molecules comprising a D1 or D2 antigen-binding domain comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides HER2× HER2 bispecific antigen-binding molecules comprising a D1 or D2 antigen-binding domain comprising an HCVR/LCVR amino acid sequence pair contained within any of the exemplary anti-HER2 antibodies listed in Table 1.

Also provided herein are HER2×HER2 bispecific antigen-binding molecules comprising a D1 or D2 antigen-binding domain comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

Also provided are HER2×HER2 bispecific antigen-binding molecules comprising a D1 or D2 antigen-binding domain comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

Also provided are HER2×HER2 bispecific antigen-binding molecules comprising a D1 or D2 antigen-binding domain comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

Also provided are HER2×HER2 bispecific antigen-binding molecules comprising a D1 or D2 antigen-binding domain comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

Also provided are HER2×HER2 bispecific antigen-binding molecules comprising a D1 or D2 antigen-binding domain comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

Also provided are HER2×HER2 bispecific antigen-binding molecules comprising a D1 or D2 antigen-binding domain comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

Also provided are HER2×HER2 bispecific antigen-binding molecules comprising a D1 or D2 antigen-binding domain comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary anti-HER2 antibodies listed in Table 1.

Also provided are HER2×HER2 bispecific antigen-binding molecules comprising a D1 or D2 antigen-binding domain comprising a set of six CDRs (i.e., HCDR1-HCDR2-HCDR3-LCDR1-LCDR2-LCDR3) contained within any of the exemplary anti-HER2 antibodies listed in Table 1.

In a related embodiment, the present disclosure provides HER2×HER2 bispecific antigen-binding molecules comprising a D1 or D2 antigen-binding domain comprising a set of six CDRs (i.e., HCDR1-HCDR2-HCDR3-LCDR1-LCDR2-LCDR3) contained within an HCVR/LCVR amino acid sequence pair selected from the anti-HER2 sequences listed in Table 1.

The HER2×HER2 bispecific antigen-binding molecules provided herein may comprise a D1 antigen-binding domain derived from any of the anti-HER2 sequences of Table 1, and a D2 antigen-binding domain derived from any other anti-HER2 sequence of Table 1. Non-limiting examples of HER2×HER2 bispecific antibodies of the present disclosure are depicted in the Examples provided herein.

As a non-limiting illustrative example, the present disclosure includes HER2×HER2 bispecific antigen binding molecules comprising a D1 antigen-binding domain and a D2 antigen-binding domain, wherein the D1 antigen binding domain comprises an HCVR/LCVR amino acid sequence pair of SEQ ID NOs: 2/18, or a set of heavy and light chain CDRs (HCDR1-HCDR2-HCDR3-LCDR1-LCDR2-LCDR3) comprising SEQ ID NOs: 4-6-8-20-22-24, and wherein the D2 antigen-binding domain comprises an HCVR/LCVR amino acid sequence pair of SEQ ID NOs: 10/18, or a set of heavy and light chain CDRs (HCDR1-HCDR2-HCDR3-LCDR1-LCDR2-LCDR3) comprising SEQ ID NOs: 12-14-16-20-22-24. An exemplary HER2×HER2 bispecific antibody having these sequence characteristics is the bispecific antibody designated H4H17325D, also referred to as bispecific antibody 1 (bsAb1).

As a further non-limiting illustrative example, the present disclosure includes HER2×HER2 bispecific antigen binding molecules comprising a D1 antigen-binding domain and a D2 antigen-binding domain, wherein the D1 antigen binding domain comprises an HCVR/LCVR amino acid sequence pair of SEQ ID NOs: 32/18, or a set of heavy and light chain CDRs (HCDR1-HCDR2-HCDR3-LCDR1-LCDR2-LCDR3) comprising SEQ ID NOs: 34-36-38-20-22-24, and wherein the D2 antigen-binding domain comprises an HCVR/LCVR amino acid sequence pair of SEQ ID NOs: 40/18, or a set of heavy and light chain CDRs (HCDR1-HCDR2-HCDR3-LCDR1-LCDR2-LCDR3) comprising SEQ ID NOs: 42-44-46-20-22-24. An exemplary HER2×HER2 bispecific antibody having these sequence characteristics is the bispecific antibody designated H4H17087D, also referred to as bispecific antibody 2 (bsAb2).

Multimerizing Components

The bispecific antigen-binding molecules provided herein, in certain embodiments, may also comprise one or more multimerizing component(s). The multimerizing components can function to maintain the association between the antigen-binding domains (D1 and D2). As used herein, a "multimerizing component" is any macromolecule, protein, polypeptide, peptide, or amino acid that has the ability to associate with a second multimerizing component of the same or similar structure or constitution. For example, a multimerizing component may be a polypeptide comprising an immunoglobulin $C_H3$ domain. A non-limiting example of a multimerizing component is an Fc portion of an immunoglobulin, e.g., an Fc domain of an IgG selected from the isotypes IgG1, IgG2, IgG3, and IgG4, as well as any allotype within each isotype group. In certain embodiments, the multimerizing component is an Fc fragment or an amino acid sequence of 1 to about 200 amino acids in length containing at least one cysteine residues. In other embodiments, the multimerizing component is a cysteine residue, or a short cysteine-containing peptide. Other multimerizing domains include peptides or polypeptides comprising or consisting of a leucine zipper, a helix-loop motif, or a coiled-coil motif.

In certain embodiments, the bispecific antigen-binding molecules provided herein comprise two multimerizing domains, M1 and M2, wherein D1 is attached to M1 and D2 is attached to M2, and wherein the association of M1 with M2 facilitates the physical linkage of D1 and D2 to one another in a single bispecific antigen-binding molecule. In certain embodiments, M1 and M2 are identical to one another. For example, M1 can be an Fc domain having a particular amino acid sequence, and M2 is an Fc domain with the same amino acid sequence as M1. Alternatively, M1 and M2 may differ from one another at one or more amino acid position. For example, M1 may comprise a first immunoglobulin (Ig) $C_H3$ domain and M2 may comprise a second Ig $C_H3$ domain, wherein the first and second Ig $C_H3$ domains differ from one another by at least one amino acid, and wherein at least one amino acid difference reduces binding of the targeting construct to Protein A as compared to a reference construct having identical M1 and M2 sequences. In one embodiment, the Ig $C_H3$ domain of M1 binds Protein A and the Ig $C_H3$ domain of M2 contains a mutation that reduces or abolishes Protein A binding such as an H95R modification (by IMGT exon numbering; H435R by EU numbering). The $C_H3$ of M2 may further comprise a Y96F modification (by IMGT; Y436F by EU). Further modifications that may be found within the $C_H3$ of M2 include: D16E, L18M, N44S, K52N, V57M, and V82I (by IMGT; D356E, L358M, N384S, K392N, V397M, and V422I by EU) in the case of an IgG1 Fc domain; N44S, K52N, and V82I (IMGT; N384S, K392N, and V422I by EU) in the case of an IgG2 Fc domain; and Q15R, N44S, K52N, V57M, R69K, E79Q, and V82I (by IMGT; Q355R, N384S, K392N, V397M, R409K, E419Q, and V422I by EU) in the case of an IgG4 Fc domain.

The bispecific antigen-binding molecules of the disclosure may be "isolated." An "isolated bispecific antigen-binding molecule," as used herein, means a bispecific antigen-binding molecule that has been identified and separated and/or recovered from at least one component of its natural environment. For example, a bispecific antibody that has been separated or removed from at least one component of an organism, or from a tissue or cell in which the antibody is produced, is an "isolated bispecific antibody" for purposes of the present disclosure. An isolated bispecific antigen-binding molecule also includes molecules in situ within a recombinant cell. Isolated bispecific antigen-binding molecules are molecules that have been subjected to at least one purification or isolation step. According to certain embodiments, an isolated bispecific antigen-binding molecule may be substantially free of other cellular material and/or chemicals.

The bispecific antigen-binding molecules disclosed herein, or the antigen-binding domains thereof (D1 and/or D2) may comprise one or more amino acid substitutions, insertions and/or deletions in the framework and/or CDR regions of the heavy and light chain variable domains as compared to the corresponding germline sequences from which the antigen-binding proteins or antigen-binding domains were derived. Such mutations can be readily ascertained by comparing the amino acid sequences disclosed herein to germline sequences available from, for example, public antibody sequence databases. The present disclosure includes bispecific antigen-binding molecules disclosed herein, or the antigen-binding domains thereof (D1 and/or D2), which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations").

A person of ordinary skill in the art, starting with the heavy and light chain variable region sequences disclosed herein, can easily produce numerous bispecific antigen-binding molecules, or antigen-binding domains thereof (D1 and/or D2), which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

Furthermore, the bispecific antigen-binding molecules, or the antigen-binding domains thereof (D1 and/or D2), of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, bispecific antigen-binding molecules, or the antigen-binding domains thereof (D1 and/or D2), that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules, or the antigen-binding domains thereof (D1 and/or D2), obtained in this general manner are encompassed within the present disclosure.

Variants

The present disclosure also includes anti-HER2 antibodies and bispecific antigen-binding molecules comprising variants of any of the HCVR, LCVR, and/or CDR amino acid sequences disclosed herein. Exemplary variants included within this aspect include variants of any of the HCVR, LCVR, and/or CDR amino acid sequences disclosed herein having one or more substitutions, for example, conservative substitutions. In some aspects, the present disclosure includes anti-HER2 antibodies and HER2×HER2 bispecific antigen-binding molecules having HCVR, LCVR, and/or CDR amino acid sequences with, e.g., 10 or fewer, 8 or fewer, 6 or fewer, 4 or fewer, 3 or fewer, 2, or 1 amino acid substitutions relative to any of the HCVR, LCVR, and/or CDR amino acid sequences set forth in Table 1 herein, where the modified antibodies and bispecific antigen-binding molecules maintain the binding activity against HER2.

Exemplary variants included within this aspect of the disclosure also include variants having substantial sequence identity to any of the HCVR, LCVR, and/or CDR amino acid sequences disclosed herein. As used herein in the context of amino acid sequences, the term "substantial identity" or "substantially identical" means that two amino acid sequences, when optimally aligned, such as by the programs GAP or BESTFIT using default gap weights, share at least 95%, 98% or 99% sequence identity. In certain embodiments, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence identity between two different amino acid sequences is typically measured using sequence analysis software. Sequence analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence provided herein to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

HER2×HER2 Bispecific Antigen-Binding Molecules Comprising Fc Variants

According to certain embodiments provided herein, HER2×HER2 bispecific antigen binding proteins are provided comprising an Fc domain comprising one or more mutations which enhance or diminish antibody binding to the FcRn receptor, e.g., at acidic pH as compared to neutral pH. For example, the present disclosure includes HER2×HER2 bispecific antigen binding proteins comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present disclosure includes HER2×HER2 bispecific antigen binding proteins comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

Biological Characteristics of the Antigen-Binding Molecules Provided Herein

Provided herein are HER2×HER2 bispecific antigen-binding proteins that bind human HER2 (e.g., hErbB2 ecto-mFc) with high affinity. For example, the present disclosure includes anti-HER2×HER2 bispecific antigen-binding proteins that bind human HER2 with a $K_D$ of less than about 3 nM as measured by surface plasmon resonance at 25° C., e.g., using an assay format as defined in Example 8 herein, or a substantially similar assay. According to certain embodiments, anti-HER2 antibodies are provided that bind human HER2 at 25° C. with a $K_D$ of less than about 1 nM, less than about 0.9 nM, less than about 0.8 nM, less than about 0.7 nM, less than about 0.6 nM, less than about 0.5 nM, less than about 0.4 nM, less than about 0.3 nM, less than about 0.25 nM, less than about 200 pM, less than about 150 pM, less than about 100 nM, or less than 50 pM, as measured by surface plasmon resonance, e.g., using an assay format as defined in Example 8 herein, or a substantially similar assay.

Also provided herein are HER2×HER2 bispecific antigen-binding proteins that bind human HER2 (e.g., hErbB2 ecto-mFc) with a dissociative half-life (t1/2) of greater than about 20 minutes as measured by surface plasmon resonance at 25° C., e.g., using an assay format as defined in Example 8 herein, or a substantially similar assay. According to certain embodiments, HER2×HER2 bispecific antigen-binding proteins are provided that bind human HER2 at 25° C. with a t1/2 of greater than about 20 minutes, greater than about 25 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, greater than about 1100 minutes, or longer, as measured by surface plasmon resonance, e.g., using an assay format as defined in Example 8 herein, or a substantially similar assay.

Also provided herein are HER2×HER2 bispecific antigen-binding proteins that exhibit internalization in early endosomes and trafficking from early endosomes to lysosomes. Also provided herein are HER2×HER2 bispecific antigen-binding proteins that form surface clusters and induce internalization of HER2.

The antigen-binding proteins of the present disclosure may possess one or more of the aforementioned biological characteristics, or any combination thereof. The foregoing list of biological characteristics of the antibodies is not intended to be exhaustive. Other biological characteristics of the antibodies provided herein will be evident to a person of ordinary skill in the art from a review of the present disclosure including the working Examples herein.

Antibody-Drug Conjugates (ADCs)

Provided herein are antibody-drug conjugates (ADCs) comprising a HER2×HER2 bispecific antigen-binding protein conjugated to a therapeutic moiety such as a cytotoxic agent, a chemotherapeutic drug, or a radioisotope.

Cytotoxic agents include any agent that is detrimental to the growth, viability or propagation of cells, including, but not limited to, tubulin-interacting agents and DNA-damaging agents. In some embodiments, the cytotoxic agent is a tubulin inhibitor. In particular embodiments, the tubulin inhibitor inhibits tubulin polymerization. In some embodiments, the cytotoxic payload is a topoisomerase I inhibitor. In some embodiments, the cytotoxic agent is a maytansinoid, an auristatin, a hemiasterlin, a vinblastine, a vincristine, a pyrrolobenzodiazepine, a paclitaxel, a docetaxel, a cryptophycin, a tubulysin, or a camptothecin. Examples of suitable cytotoxic agents and chemotherapeutic agents that can be conjugated to anti-HER2 antibodies in accordance with this aspect of the disclosure also include, e.g., 1-(2chloroethyl)-1,2-dimethanesulfonyl hydrazide, 1,8-dihydroxybicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins (e.g., calicheamicin $\gamma_1$), camptothecin, carminomycins, carmustine, cemadotins, cisplatin, colchicin, combretastatins, cyclophosphamide, cytarabine, cytochalasin B, dactinomycin, daunorubicin, decarbazine, diacetoxypentyldoxorubicin, dibromomannitol, dihydroxy anthracin dione, disorazoles, dolastatin (e.g., dolastatin 10), doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, kinesin spindle protein (KSP) inhibitors, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, and derivatives of any of the foregoing. According to certain embodiments, the cytotoxic agent that is conjugated to an anti-HER2 antibody is a maytansinoid such as DM1 or DM4, a tomaymycin derivative, or a dolastatin derivative. According to certain embodiments, the cytotoxic agent that is conjugated to an anti-HER2 antibody is an auristatin such as MMAE, MMAF, or derivatives thereof. In some embodiments, the cytotoxic agent is Dxd or a derivative thereof. In some embodiments, the cytotoxic agent is AZ13599185 (see, e.g., Li et. al., 2016 Cancer Cell 29, 117-129). Other cytotoxic agents known in the art are contemplated within the scope of the present disclosure, including, e.g., protein toxins such ricin, *C. difficile* toxin, *pseudomonas* exotoxin, ricin, diphtheria toxin, botulinum toxin, bryodin, saporin, pokeweed toxins (i.e., phytolaccatoxin and phytolaccigenin), and others such as those set forth in Sapra et al., *Pharmacol. & Therapeutics*, 2013, 138:452-469. In some embodiments, the cytotoxic agent is a tubulysin, a maytansinoid, or a camptothecin.

In certain embodiments, the cytotoxic agent is a tubulysin. Suitable tubulysins include those described in U.S. patent application Ser. No. 16/724,164 filed Dec. 20, 2019. In some embodiments, the tubulysin is Compound IVa, IVa', IVb, IVc, IVd, IVe, IVf, IVg, IVh, IVj, IVk, IV-I, IVm, IVn, IVo, IVp, IVq, IVr, IVs, IVt, IVu, IVvA, IVvB, IVw, IVx, IVy, Va, Va', Vb, Vc, Vd, Ve, Vf, Vg, Vh, Vi, Vj, Vk, Via, VIb, VIc, VId, VIe, VIf, VIg, VIh, VI, VIi, VII, VIII, IX, X, D-5a, or D-5c from U.S. patent application Ser. No. 16/724,164 filed Dec. 20, 2019. In certain embodiments, the tubulysin is Compound Ve in U.S. patent application Ser. No. 16/724,164 filed Dec. 20, 2019. In some embodiments, the tubulysin has the following structure:

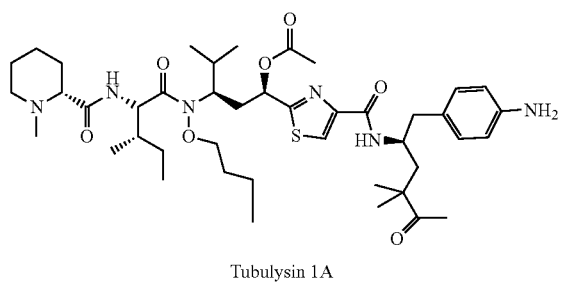

Tubulysin 1A

Tubulysin 1A can be prepared using the methods disclosed in U.S. Ser. No. 16/724,164 filed Dec. 20, 2019.

In certain embodiments, the cytotoxic agent is a maytansinoid, e.g., derivative of maytansine. Suitable maytansinoids include DM1, DM4, or derivatives, stereoisomers, or isotopologues thereof. Suitable maytansinoids also include, but are not limited to, those disclosed in WO 2014/145090A1, WO 2015/031396A1, US 2016/0375147A1, and US 2017/0209591A1, incorporated herein by reference in their entireties. In some embodiments, the maytansinoid is DM1.

In some embodiments, the maytansinoid has the following structure:

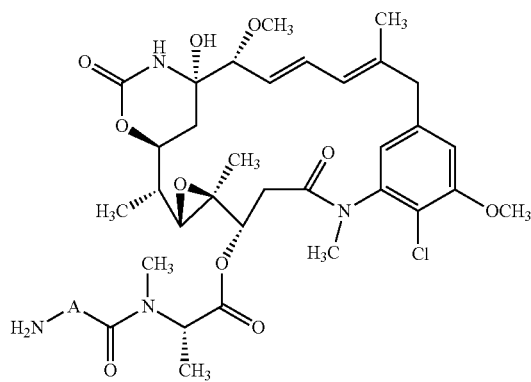

wherein A is an optionally substituted arylene or heteroarylene.

In some embodiments, the maytansinoid has the following structure:

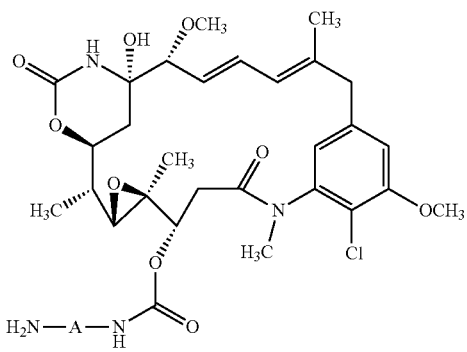

wherein A is an optionally substituted arylene or heteroarylene.

In some embodiments, the maytansinoid has the following structure:

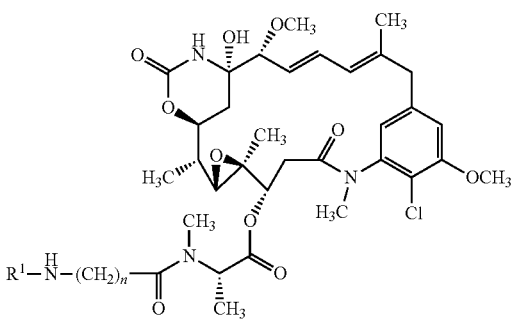

wherein n is an integer from 1-12 and $R^1$ is alkyl.

In some embodiments, the maytansinoid is:

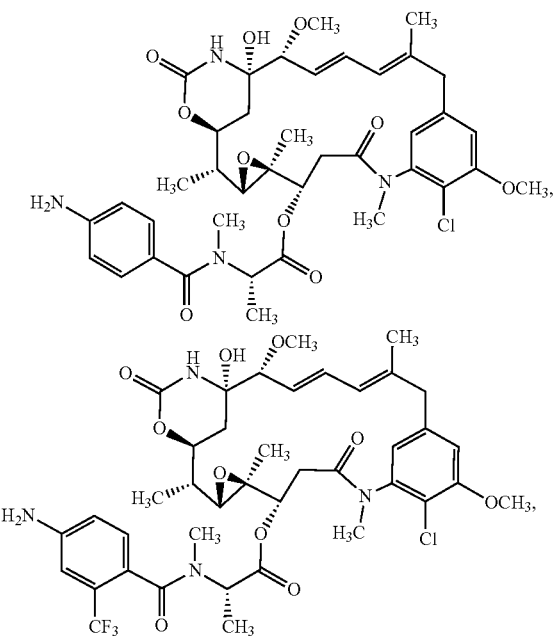

-continued
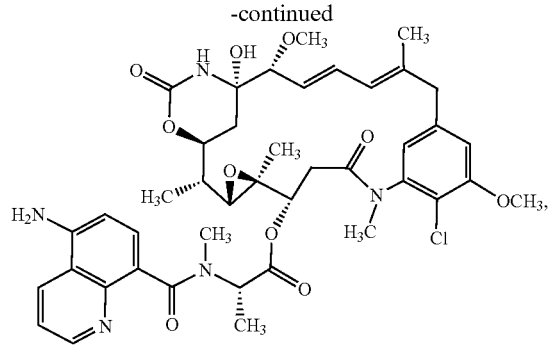
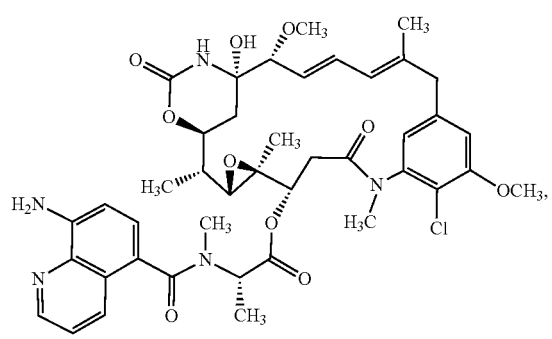
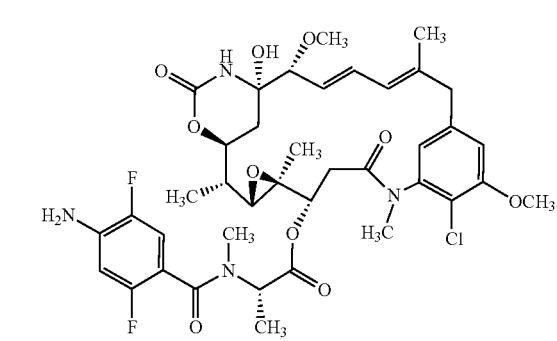
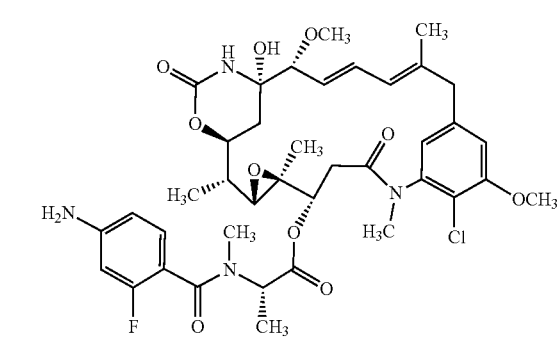
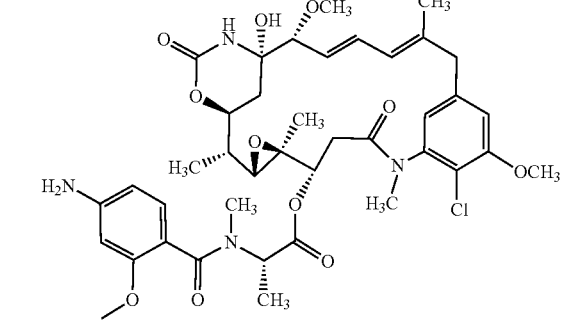
-continued
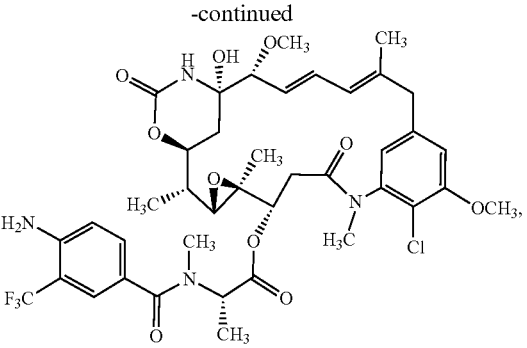
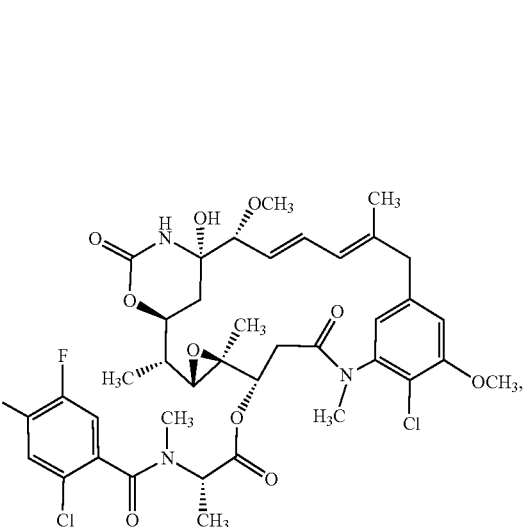
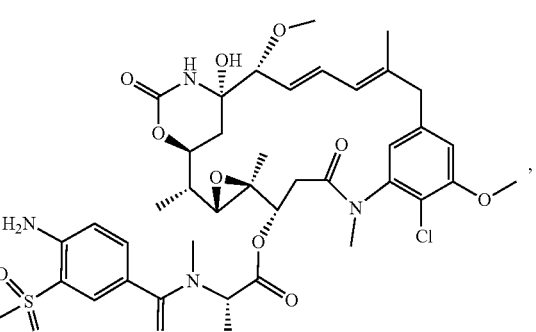
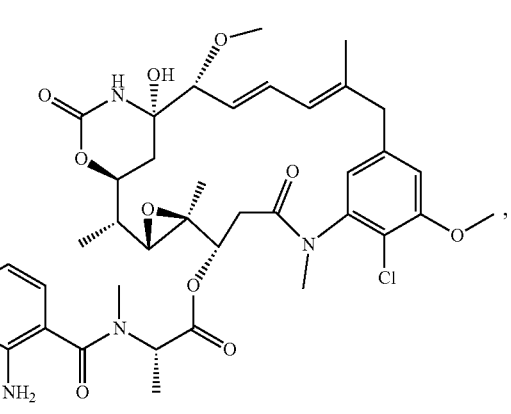

-continued
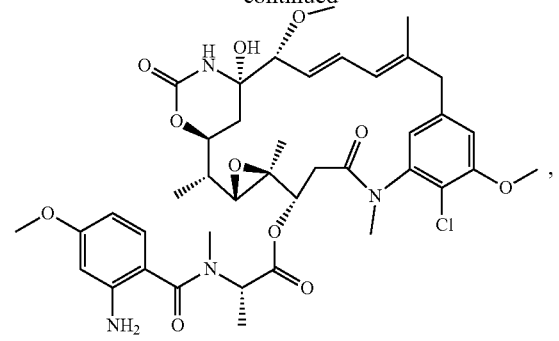
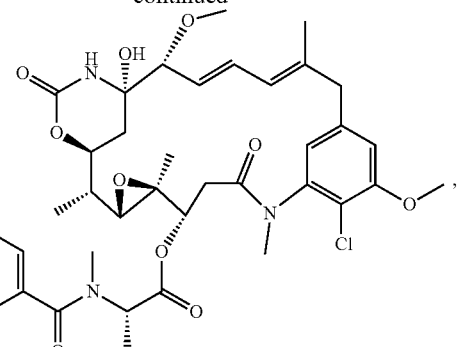
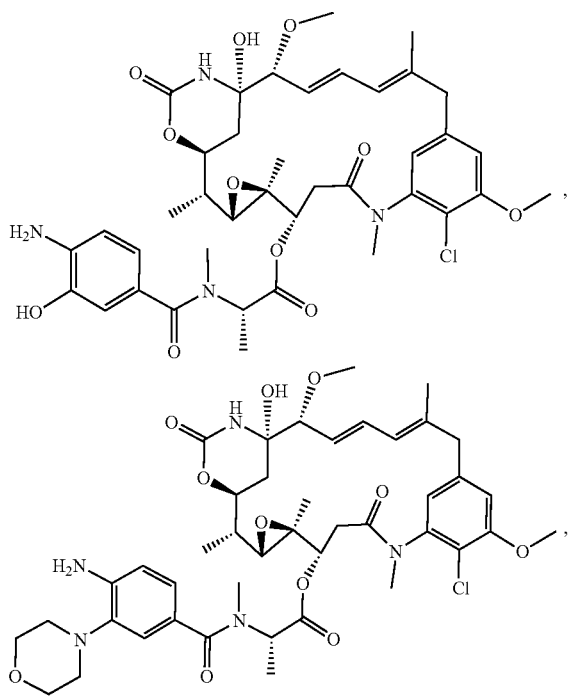
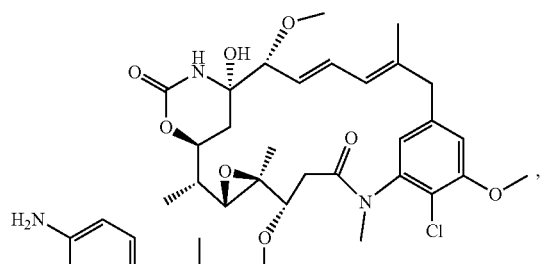
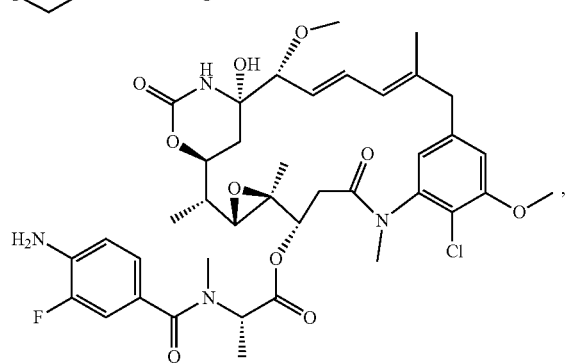
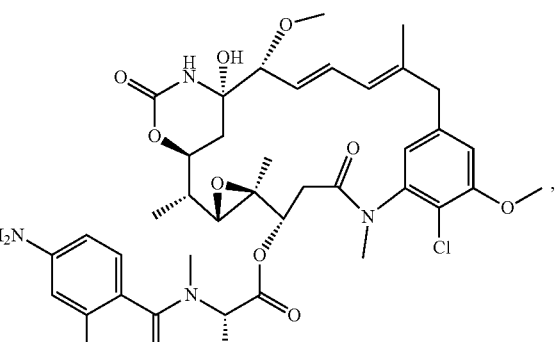
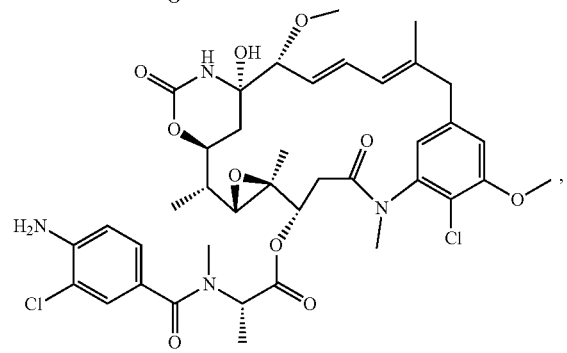
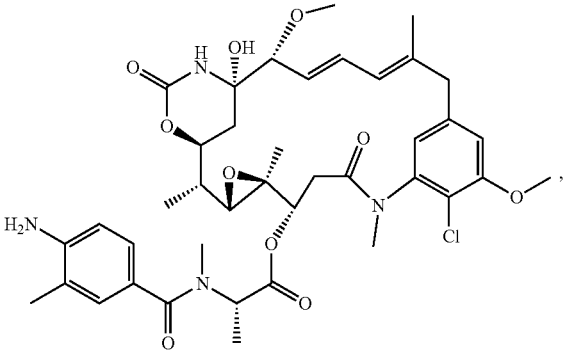

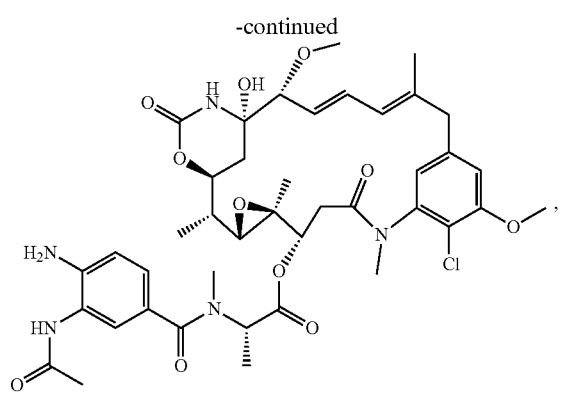
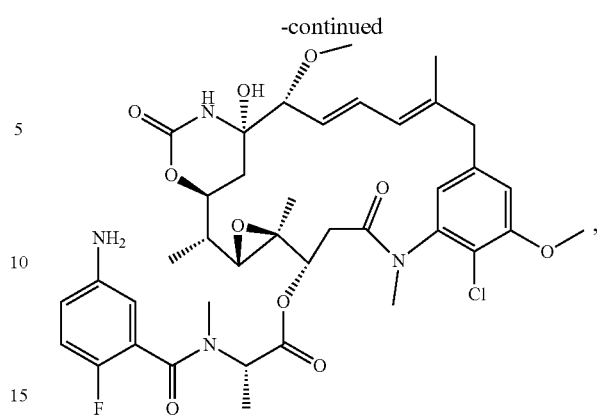
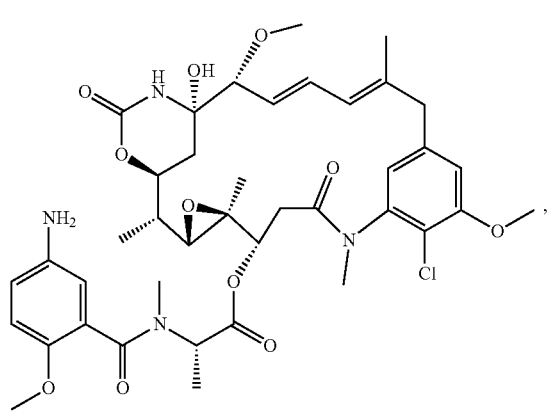
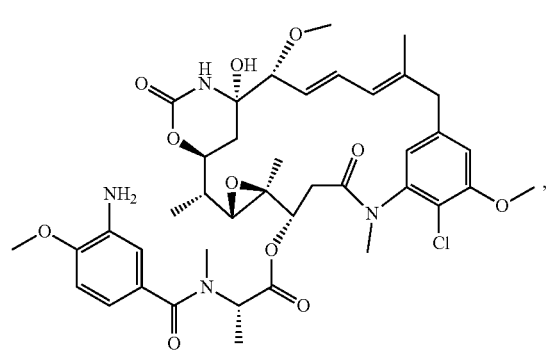
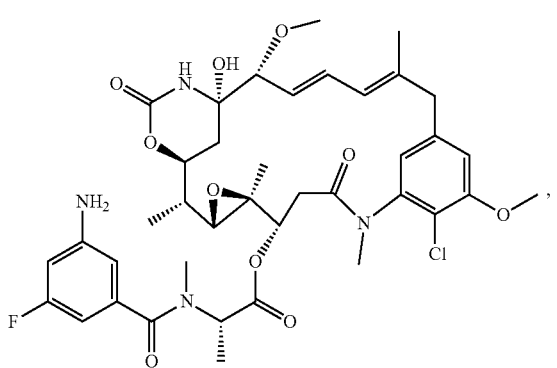
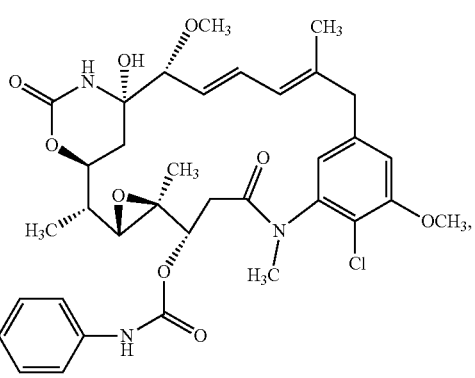

-continued
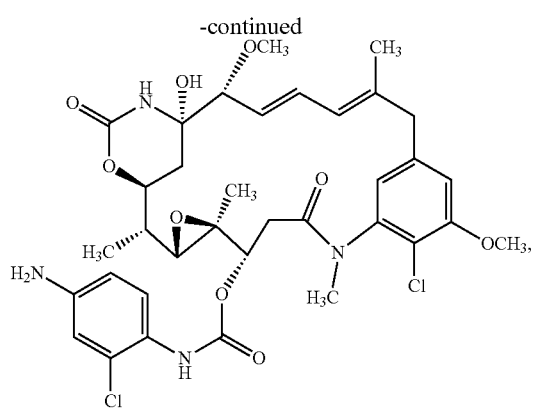
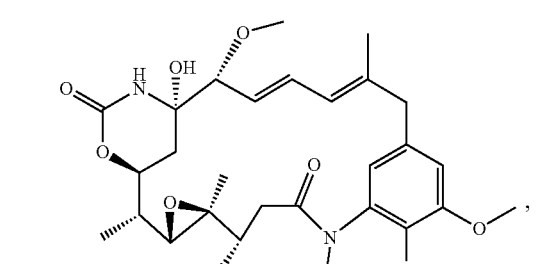
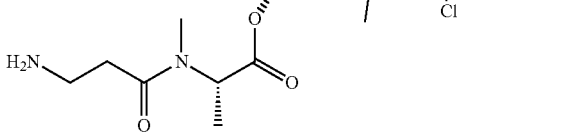
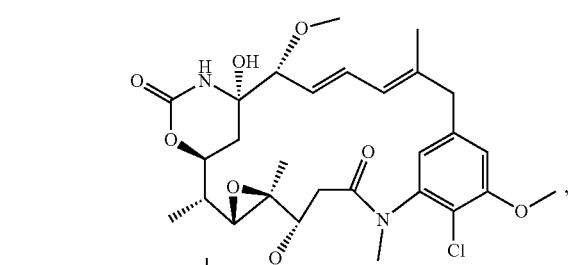
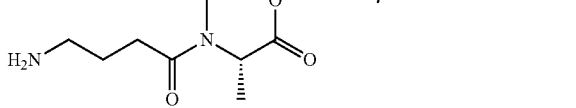
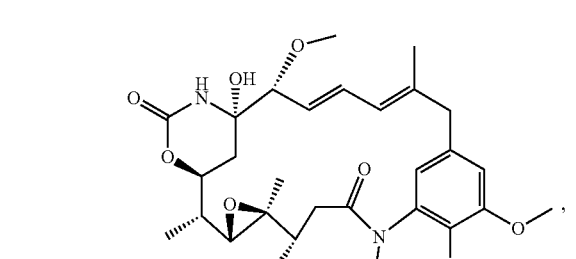
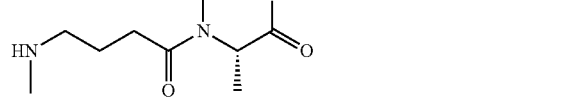
-continued
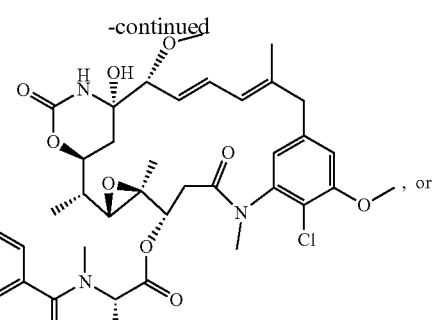, or
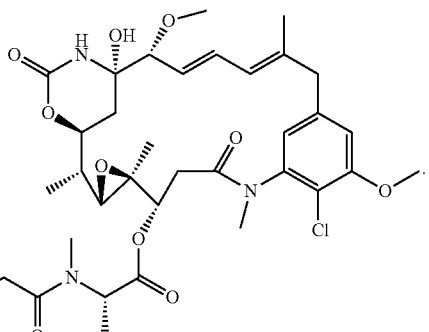
In some embodiments, the maytansinoid is:
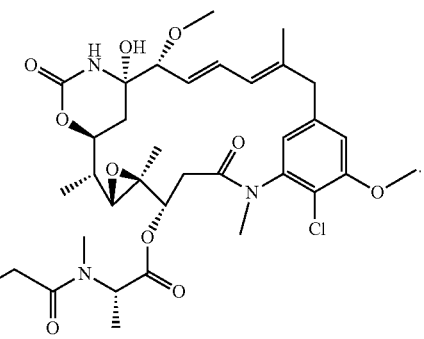
In some embodiments, the maytansinoid is:
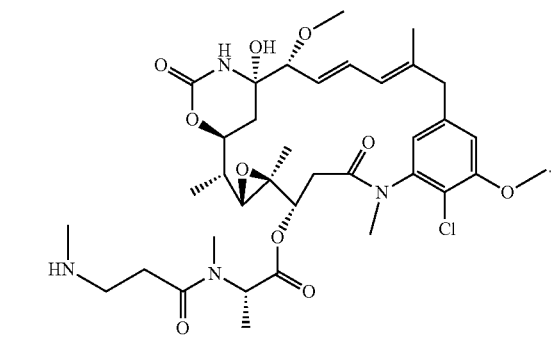 [SMILES: CNCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]
In some embodiments, the cytotoxic agent is a camptothecin, e.g., analog or derivative of camptothecin. In some embodiments, the HER2×HER2 bispecific antigen-binding protein e.g., antibody, is conjugated to exatecan, deruxtecan, DX-8951, DXd, camptothecin, or derivatives or analogs thereof. In particular embodiments, the cytotoxic agent is DXd. In particular embodiments, the cytotoxic agent is:

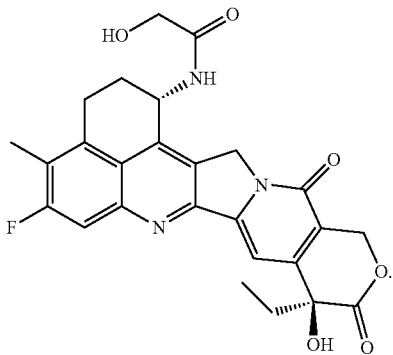 [SMILES: CC[C@@]1(O)C(=O)OCc2c1cc1n(c2=O)Cc2c-1nc1cc(F)c(C)c3c1c2[C@@H](NC(=O)CO)CC3]

Also provided herein are antibody-radionuclide conjugates (ARCs) comprising anti-HER2 antibodies conjugated to one or more radionuclides. Exemplary radionuclides that can be used in the context of this aspect of the disclosure include, but are not limited to, e.g., $^{225}$Ac, $^{212}$Bi, $^{213}$Bi, $^{131}$I, $^{186}$Re, $^{227}$Th, $^{222}$Rn, $^{223}$Ra, $^{224}$Ra, and $^{90}$Y.

In certain embodiments provided herein, ADCs are provided comprising a HER2×HER2 bispecific antigen-binding protein conjugated to a cytotoxic agent (e.g., any of the cytotoxic agents disclosed above) via a linker molecule. Linkers are any group or moiety that links, connects, or bonds the antibody or antigen-binding proteins described herein with a therapeutic moiety, e.g. cytotoxic agent. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers include linkers that are cleaved by intracellular metabolism following internalization, e.g., cleavage via hydrolysis, reduction, or enzymatic reaction. Non-cleavable linkers include linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyl (PAB) units.

Any linker molecule or linker technology known in the art can be used to create or construct an ADC of the present disclosure. In certain embodiments, the linker is a cleavable linker. According to other embodiments, the linker is a non-cleavable linker. Exemplary linkers that can be used in the context of the present disclosure include, linkers that comprise or consist of e.g., MC (6-maleimidocaproyl), MP (maleimidopropanoyl), val-cit (valine-citrulline), val-ala (valine-alanine), dipeptide site in protease-cleavable linker, ala-phe (alanine-phenylalanine), dipeptide site in protease-cleavable linker, PAB (p-aminobenzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present disclosure are provided, e.g., in U.S. Pat. No. 7,754,681 and in Ducry, Bioconjugate Chem., 2010, 21:5-13, and the references cited therein, the contents of which are incorporated by reference herein in their entireties.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. In some embodiments, the linker comprises two amino acids. In some embodiments, the linker comprises three amino acids. In some embodiments, the linker comprises four amino acids. Suitable amino acids include natural, non-natural, standard, non-standard, proteinogenic, non-proteinogenic, and L- or D-α-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine. In some embodiments, the linker comprises a dipeptide, tripeptide, or tetrapeptide. In some embodiments, the linker comprises a peptide, wherein the peptide is valine-citruline (val-cit or VC), glutamic acid-valine-citruline (EVC), or glycine-glycine-phenylalanine-glycine (GGFC).

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). In some embodiments, the linker comprises a moiety having the following structure:

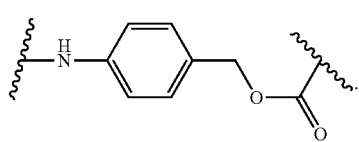 [SMILES: *Nc1ccc(COC(*)=O)cc1]

Those of skill will recognize that a self-immolative group is capable of carrying out a chemical reaction which releases the remaining atoms of a linker from a payload.

In some embodiments, the linker is:

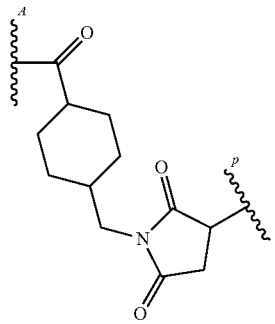

wherein

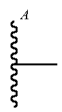

is a bond to the antibody or antigen-binding protein (e.g., via lysine residue) and

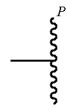

is a bond to the cytotoxic agent (e.g., DM1). In some embodiments, the linker is:

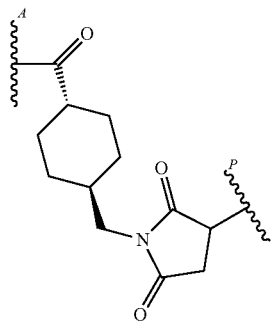

wherein

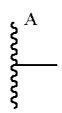

is a bond to the antibody or antigen-binding protein (e.g., via lysine residue) and

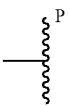

is a bond to the cytotoxic agent (e.g., DM1). In certain embodiments, the linker is:

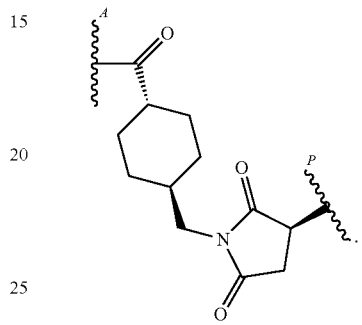

In certain embodiments, the linker is:

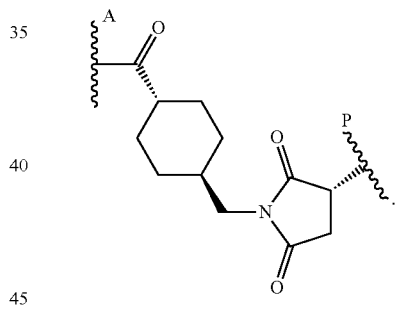

In some embodiments, the linker is derived from maleimidylmethyl-4-trans-cyclohexanecarboxysuccinate:

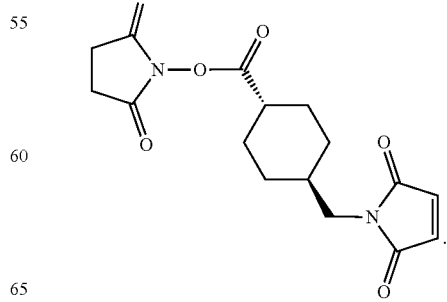

In some embodiments, the linker is:

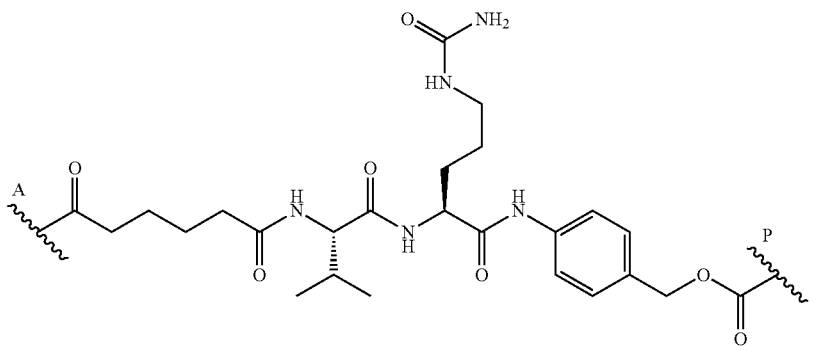

wherein

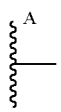

is a bond to the antibody or antigen-binding protein (e.g., via lysine residue) and

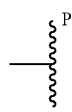

is a bond to the cytotoxic agent (e.g., a compound having the following formula:

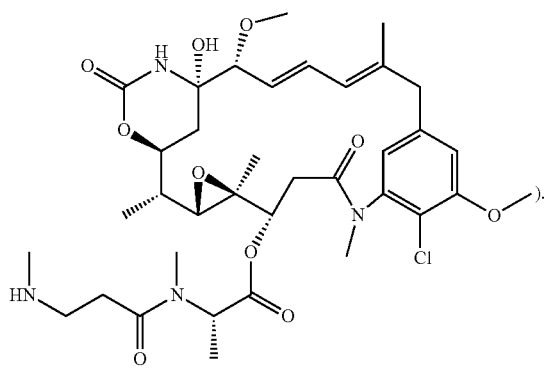 [SMILES: CNCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

Suitable linkers also include, but are not limited to, linkers that comprise one or more cyclic moieties. In some embodiments, the cyclic moiety is derived from a cycloaddition reaction. In certain embodiments, the cyclic moiety is derived from a 1-3-cycloaddition reaction between an azide and alkyne, e.g., cycloalkyne. In some embodiments, the cyclic moiety is

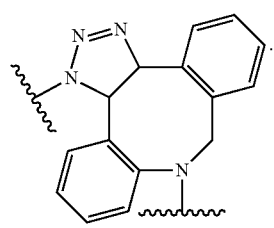 [SMILES: *N1Cc2ccccc2C2N=NN(*)C2c2ccccc21]

In some embodiments, the linker comprises one or more spacers. Suitable spacers include moieties that link, e.g. covalently or through ionic interaction, two linker portions, a linker portion with a payload, or a linker portion with an antibody. In certain embodiments, the spacer is a PEG group.

The present disclosure comprises ADCs in which a linker connects a HER2×HER2 bispecific antigen-binding protein to a drug or cytotoxin through an attachment at a particular amino acid within the antibody or antigen-binding molecule. Exemplary amino acid attachments that can be used in the context of this aspect, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA*, 2008, 105:12451-12456), formyl glycine (see, e.g., Carrico et al., *Nat. Chem. Biol.*, 2007, 3:321-322; Agarwal et al., *Proc. Natl. Acad. Sci., USA*, 2013, 110:46-51, and Rabuka et al., *Nat. Protocols*, 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.*, 2001, 13:127-130) and disulfide linkers (see, e.g., WO 2013/085925, WO 2010/010324, WO 2011/018611, and Shaunak et al., *Nat. Chem. Biol.*, 2006, 2:312-313). Site specific conjugation techniques can also be employed to direct conjugation to particular residues of the antibody or antigen binding protein (see, e.g., Schumacher et al. *J Clin Immunol* (2016) 36(Suppl 1): 100). Site specific conjugation techniques include, but are not limited to, glutamine conjugation via transglutaminase (see e.g., Schibli, Angew Chemie Inter Ed. 2010, 49, 9995).

According to certain embodiments, the present disclosure provides ADCs, wherein a HER2×HER2 bispecific antigen-binding protein as described herein is conjugated to a linker-drug composition as set forth in International Patent Publication WO2014/145090, (e.g., compound "7," also referred to herein as "M0026" and depicted below), the disclosure of which is hereby incorporated by reference herein in its entirety:

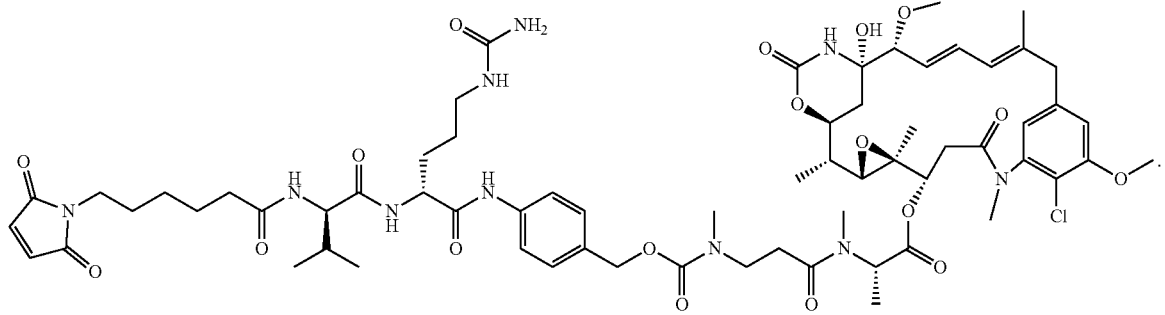

Provided herein are also antibody-drug conjugates comprising the monospecific anti-HER2 antibodies and HER2× HER2 bispecific antibodies disclosed herein, where said HER2×HER2 bispecific antibody is conjugated to a cytotoxic agent. In certain embodiments, the cytotoxic agent is a maytansinoid. In certain embodiments, the maytansinoid is a compound having the following formula:

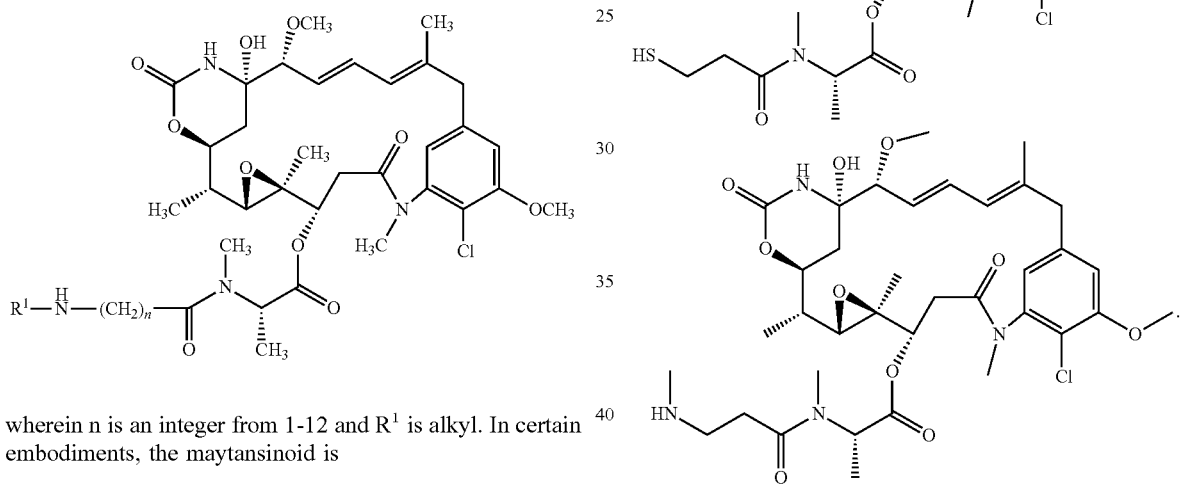

wherein n is an integer from 1-12 and $R^1$ is alkyl. In certain embodiments, the maytansinoid is In certain embodiments, the cytotoxic agent is a maytansinoid, and the maytansinoid is covalently attached to the antibody via non-cleavable linker. In certain embodiments, the cytotoxic agent is a maytansinoid, and the maytansinoid is covalently attached to the bispecific antibody via cleavable linker.

In one embodiment, the bispecific antibody is conjugated to:

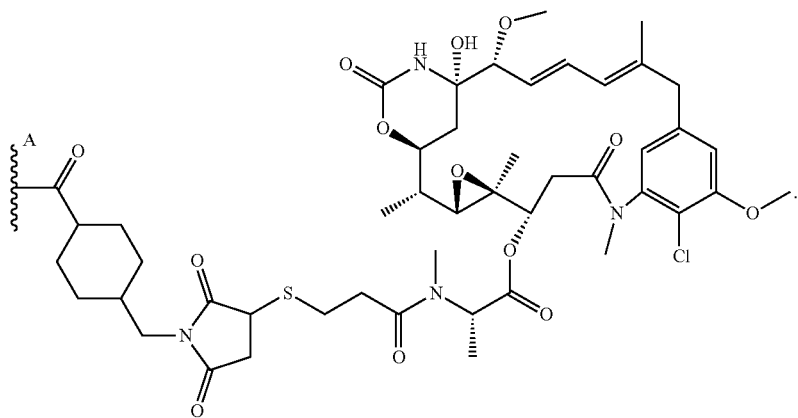
wherein
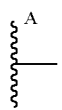
is a bond to the antibody.
In one embodiment, the bispecific antibody is conjugated to:
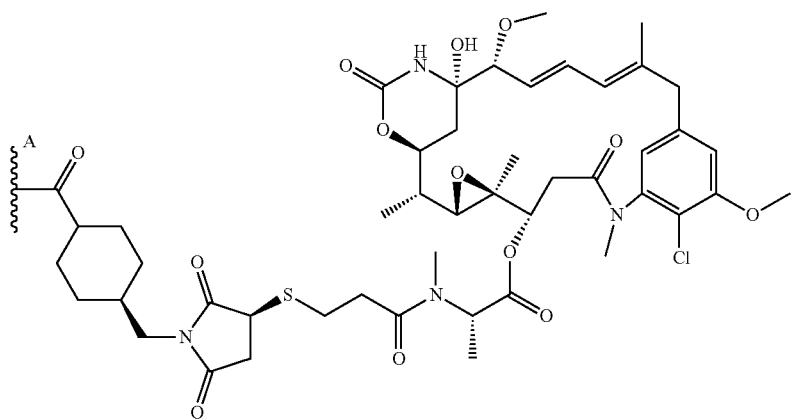
wherein
is a bond to the antibody.
In one embodiment, the bispecific antibody is conjugated to:

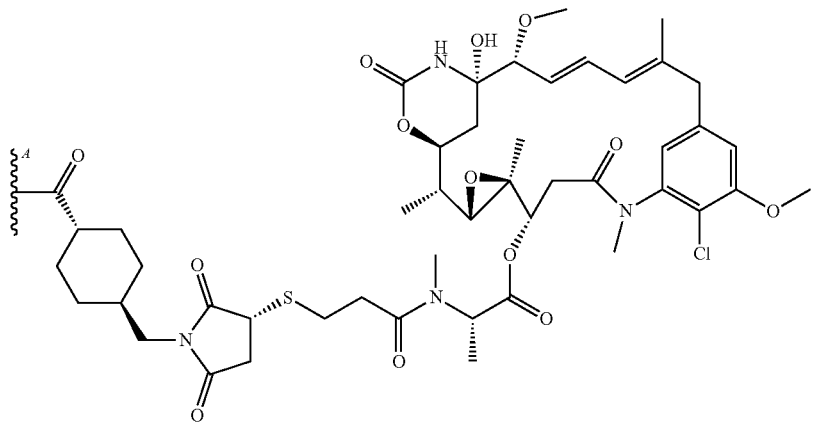
wherein
is a bond to the antibody.
In one embodiment, the bispecific antibody is conjugated to:
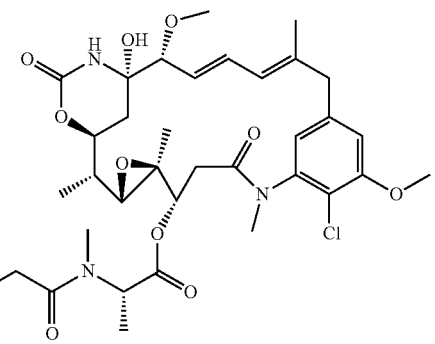
is a bond to the antibody.
In some embodiments, the bispecific antibody is conjugated to:
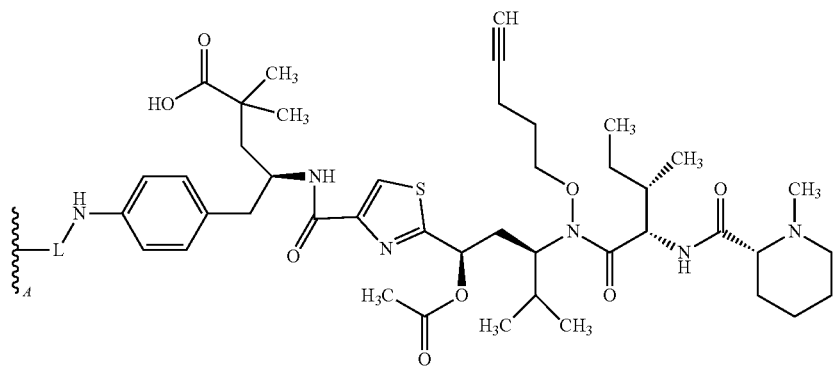
wherein wherein L is a linker and
is a bond to the antibody.
In some embodiments, the bispecific antibody is conjugated to:
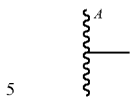
is a bond to the antibody.
In some embodiments, the bispecific antibody is conjugated to:
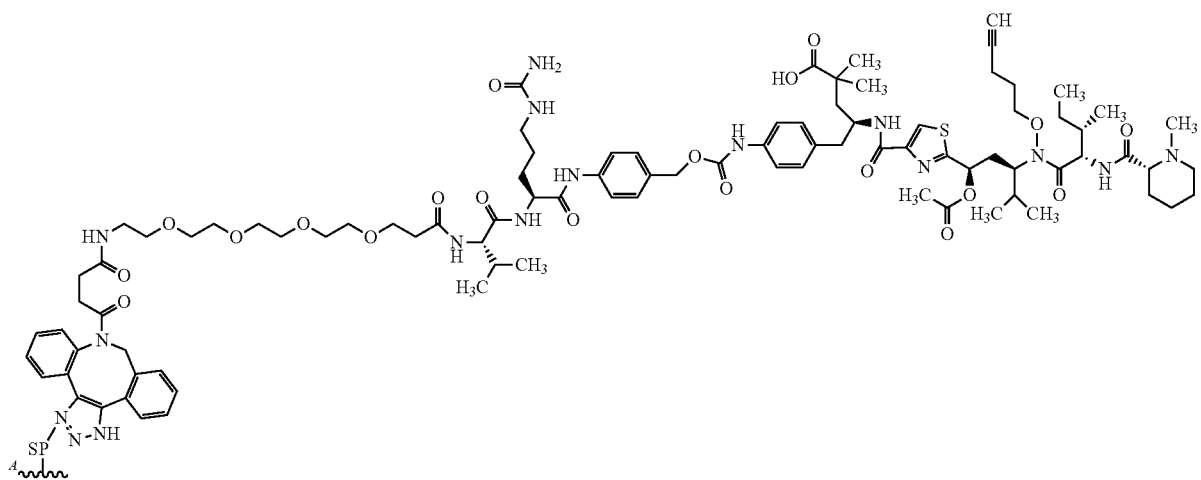
or a regioisomer thereof, wherein SP is a spacer and
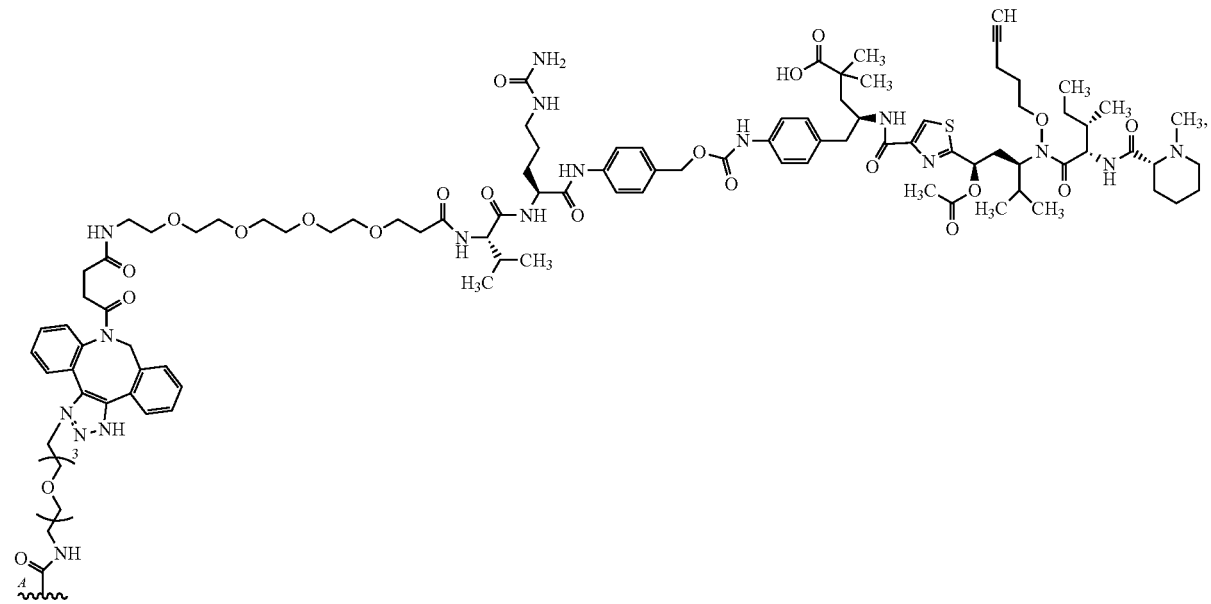
regioisomer thereof, wherein

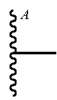
is a bond to a glutamine residue of the antibody. In certain embodiments, the glutamine is a heavy chain Q295 glutamine. In certain embodiments, the bispecific antibody is conjugated to a heavy chain Q295 and Q297, wherein said Q297 is derived from an N297Q mutation.
In some embodiment, the bispecific antibody is conjugated to:

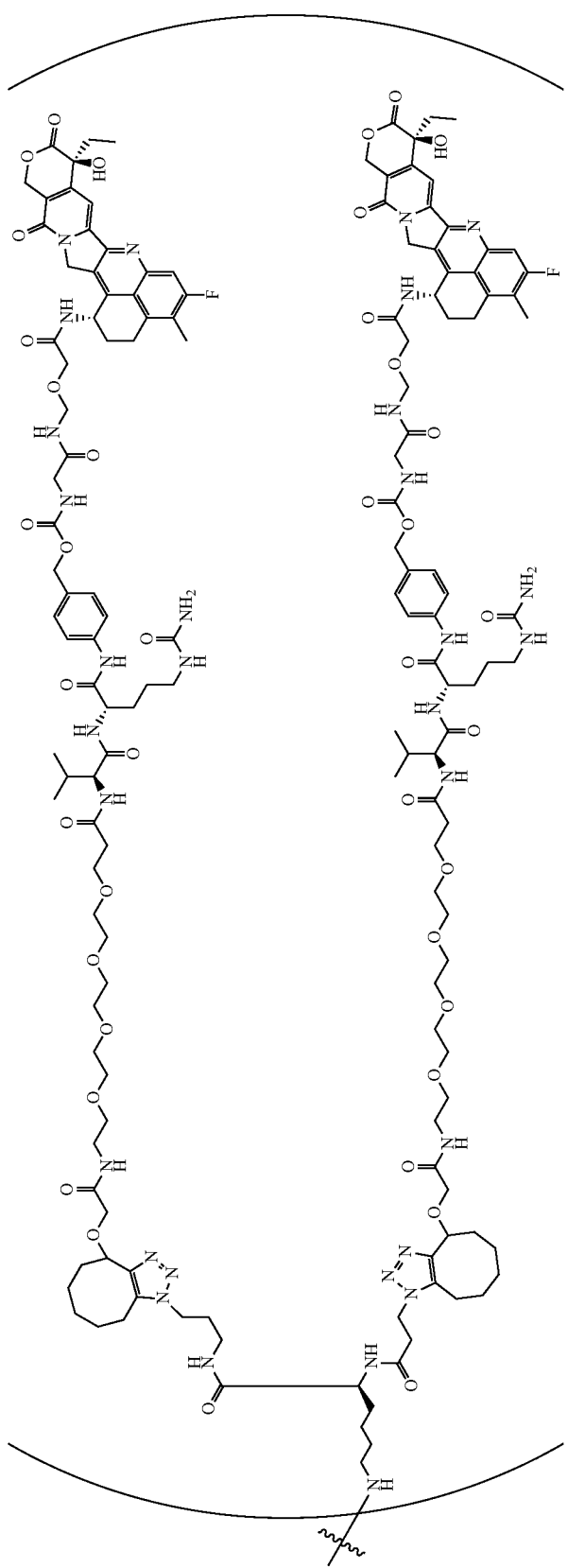

wherein

is a bond to a glutamine residue of the antibody. In certain embodiments, the glutamine is a heavy chain Q295 glutamine. In certain embodiments, the bispecific antibody is conjugated to a heavy chain Q295 and Q297, wherein said Q297 is derived from an N297Q mutation.

In some embodiments, the conjugates have the following structure:

Ab-[L-Pay]$_n$ wherein:
Ab is a HER2×HER2 bispecific antigen-binding protein as described herein;
L is a linker;
Pay is a cytotoxic agent; and
n is an integer from 1-12.

In some embodiments, n is 2. In some embodiments, n is 4. In some embodiments, Pay is:

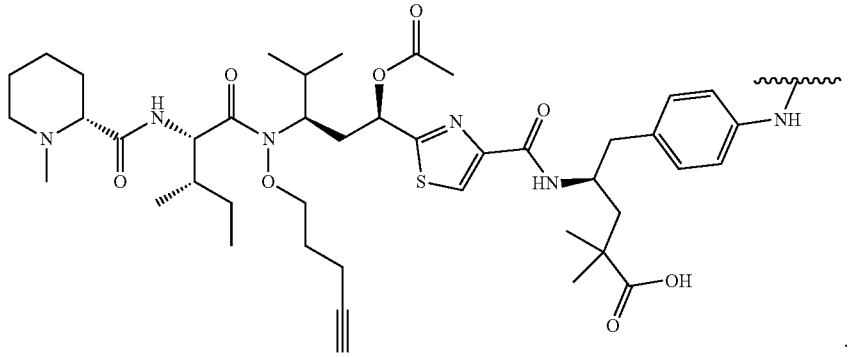
(Tubulysin 1a)

In some embodiments, L is a cleavable linker. In some embodiments, L comprises a peptide. In some embodiments, L comprises val-cit. In some embodiments, L comprises

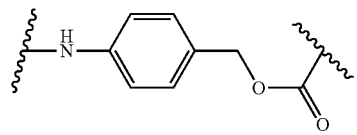

In some embodiments, L comprises a PEG group. In some embodiments, L comprises a cyclic moiety. In certain embodiments, the cyclic moiety is the product of a 1,3-cycloaddition between an azide and a cycloalkyne. In some embodiments, -L-Pay is

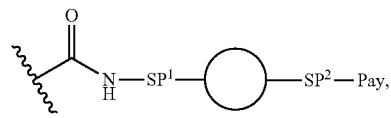

wherein SP$^1$ and SP$^2$ are each independently a spacer,

is a cyclic moiety, and

is a bond to a heavy chain glutamine. In some embodiments, the glutamine is a Q295 glutamine. In some embodiments, n is 2, wherein two L-Pay are conjugated to Q295. In some embodiments, n is 4, wherein two L-Pay are conjugated to Q295 and two L-Pay are conjugated to Q297. In some embodiments, the cyclic moiety is a product of a cycloaddition reaction. In certain embodiments, the cyclic moiety is a product of a cycloaddition reaction between an azide and cycloalkyne. In certain embodiments, the cyclic moiety is

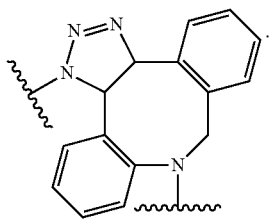 [SMILES: *N1Cc2ccccc2C2N=NN(*)C2c2ccccc21]

In certain embodiments, SP$^1$ comprises a PEG moiety. In certain embodiments, SP$^2$ comprise a dipeptide. In certain embodiments, SP2 comprises val-cit. In certain embodiments, SP$^2$ comprises

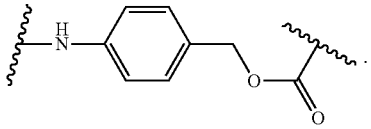 [SMILES: *Nc1ccc(COC(*)=O)cc1]

In certain embodiments, SP² comprises a PEG moiety. In some embodiments, SP2-Pay is:
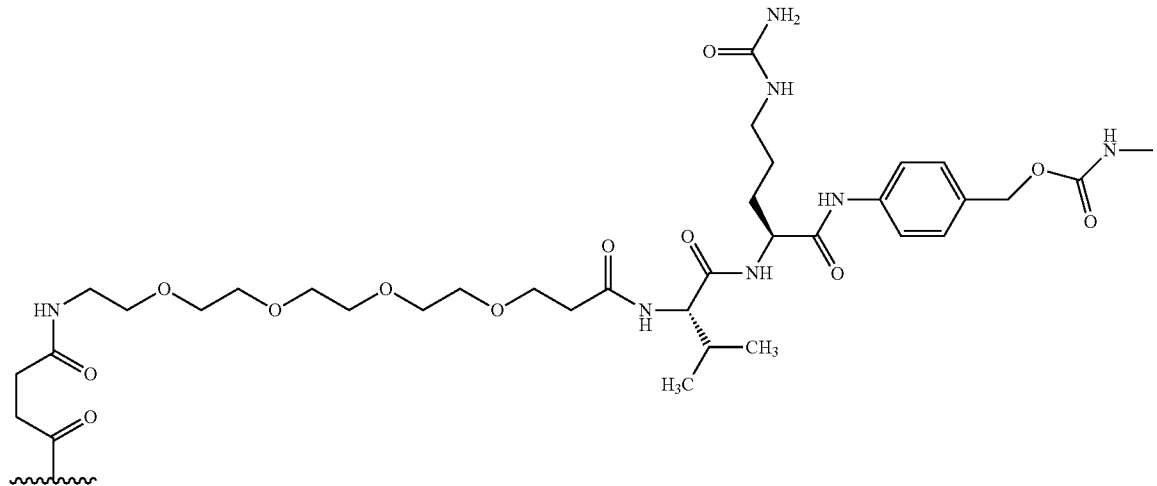
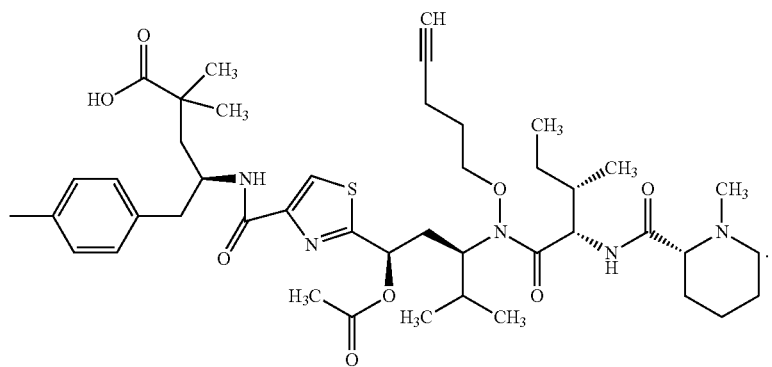

In certain embodiments,
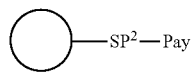
is
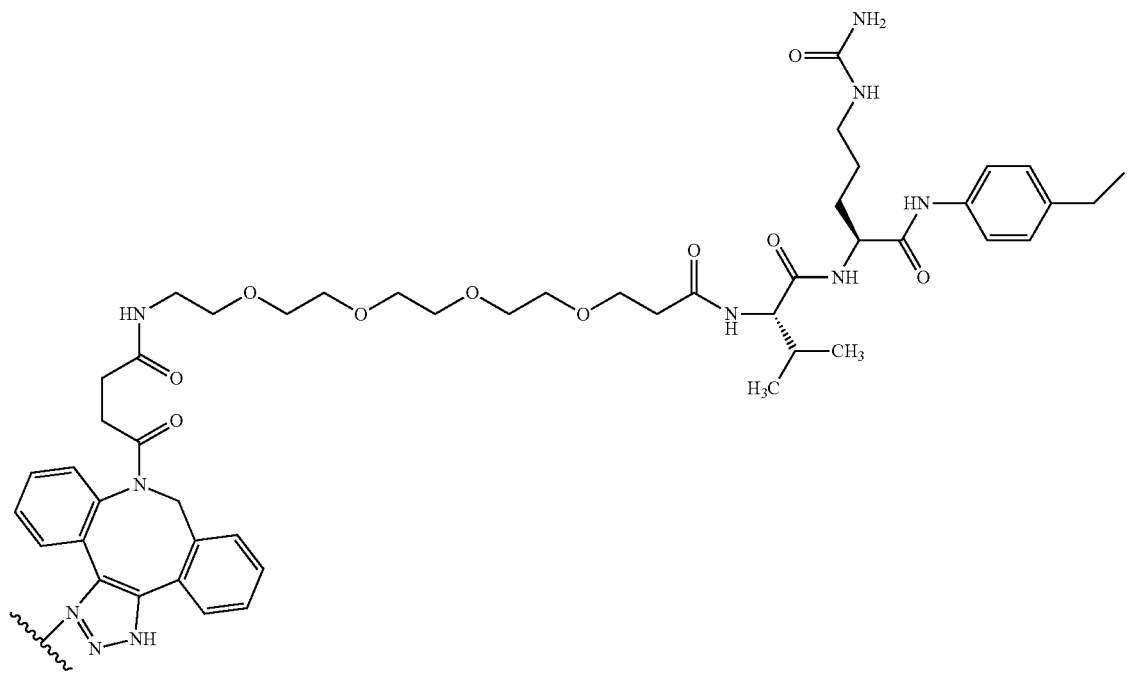
or a regioisomer thereof.
In certain embodiments,
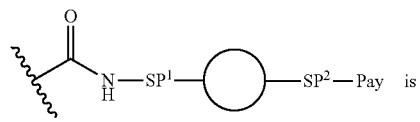

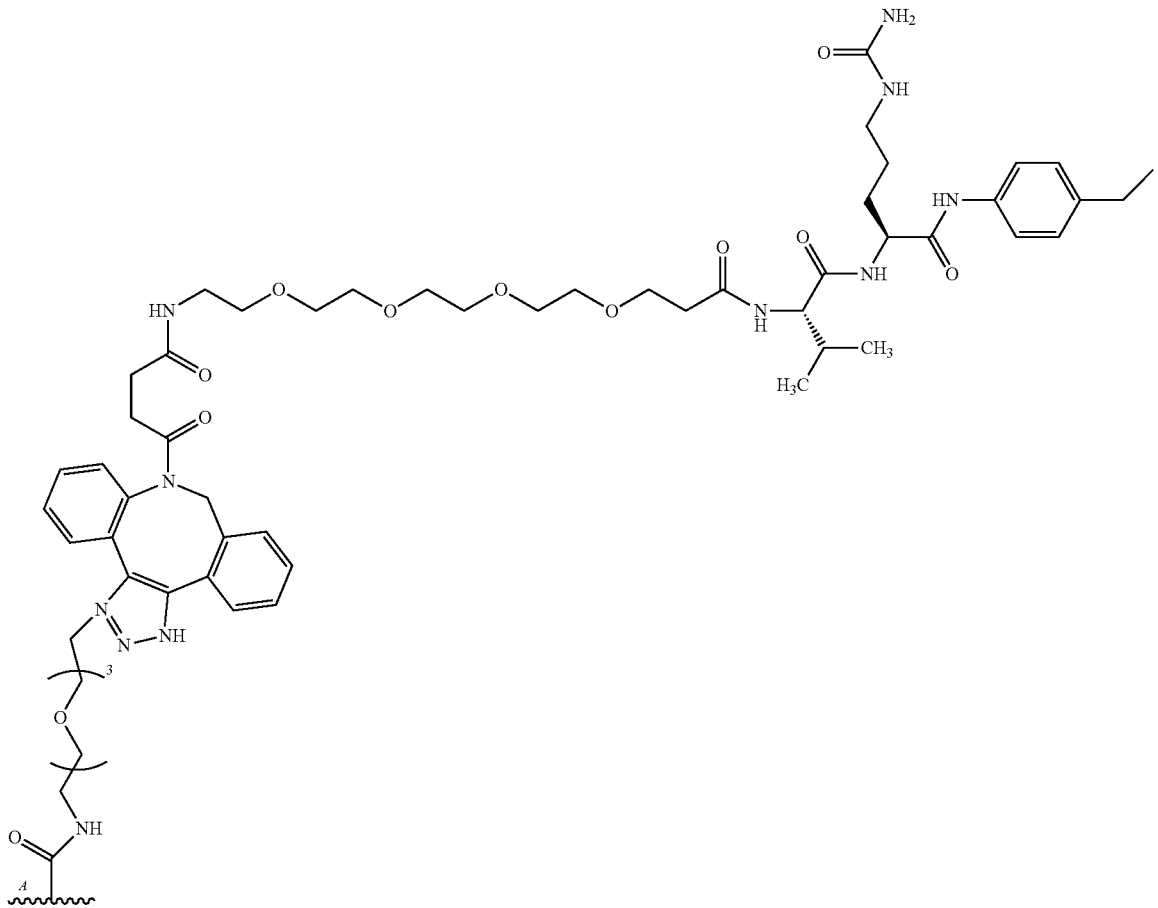
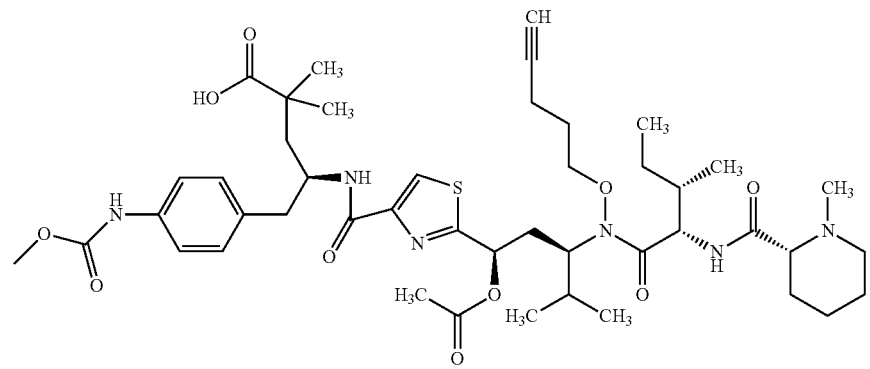

(tubulysin 1b) or a regioisomer thereof, wherein

is a bond to the antibody.

In some embodiments, the Ab is conjugated to a linker-payload or payload disclosed in WO2015/157592, e.g., compound T32 disclosed therein. In some embodiments, the Ab is conjugated to deruxtecan (DXd), optionally through a linker comprising GGFG.

In some embodiments, Ab is a HER2×HER2 bispecific antigen-binding protein comprising the CDRs within the D1-HCVR amino acid sequence of SEQ ID NO: 2 and the CDRs within the D2-HCVR amino acid sequence of SEQ ID NO: 10. In some aspects, the HER2×HER2 bispecific antigen-binding protein further comprises the CDRs within the LCVR amino acid sequence of SEQ ID NO: 18. In some embodiments, Ab is a HER2×HER2 bispecific antigen-binding protein comprising the D1-HCVR amino acid sequence of SEQ ID NO: 2 and the D2-HCVR amino acid sequence of SEQ ID NO: 10. In some aspects, the HER2×HER2 bispecific antigen-binding protein further comprises the LCVR amino acid sequence of SEQ ID NO: 18.

In some embodiments, Ab is a HER2×HER2 bispecific antigen-binding protein comprising the CDRs within the D1-HCVR amino acid sequence of SEQ ID NO: 32 and the CDRs within the D2-HCVR amino acid sequence of SEQ ID NO: 40. In some aspects, the HER2×HER2 bispecific antigen-binding protein further comprises the CDRs within the LCVR amino acid sequence of SEQ ID NO: 18. In some embodiments, Ab is a HER2×HER2 bispecific antigen-binding protein comprising the D1-HCVR amino acid sequence of SEQ ID NO: 32 and the D2-HCVR amino acid sequence of SEQ ID NO: 40. In some aspects, the HER2×HER2 bispecific antigen-binding protein further comprises the LCVR amino acid sequence of SEQ ID NO: 18.

In some embodiments, L is a cleavable linker. In some embodiments, L is a non-cleavable linker. In some embodiments, L comprises a dipeptide. In some embodiments, L comprises a PAB moiety.

In some embodiments, L comprises a moiety having the following structure:

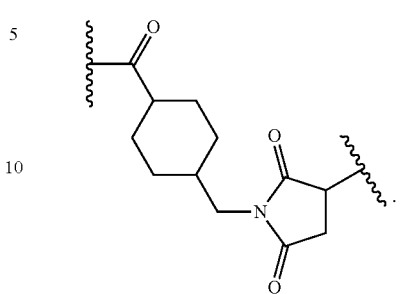

In some embodiments, L comprises a moiety having the following structure:

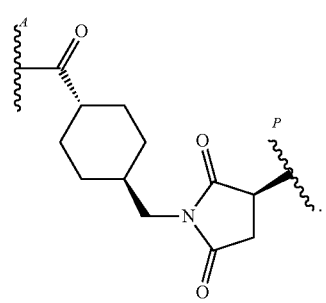

In some embodiments, L comprises a moiety having the following structure:

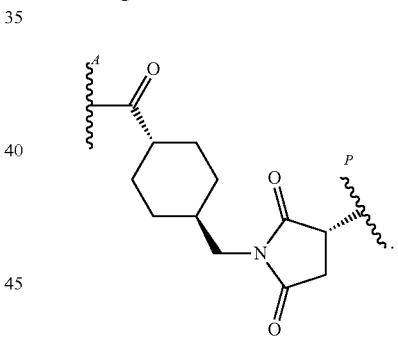

In some embodiments, L comprises a moiety having the following structure:

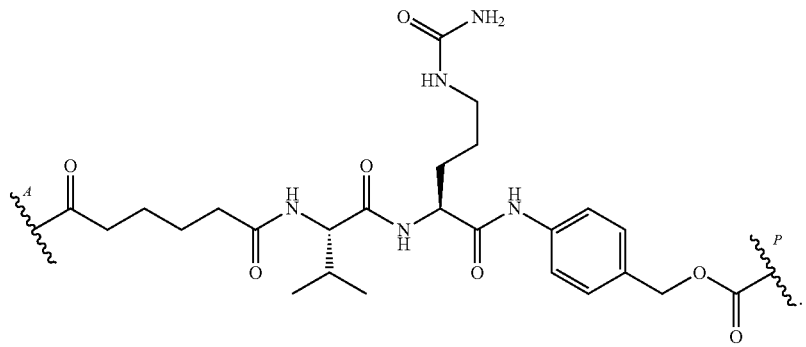

In some embodiments, Pay is a tubulysin.
In some embodiments, Pay is a maytansinoid.
In some embodiments, Pay is:
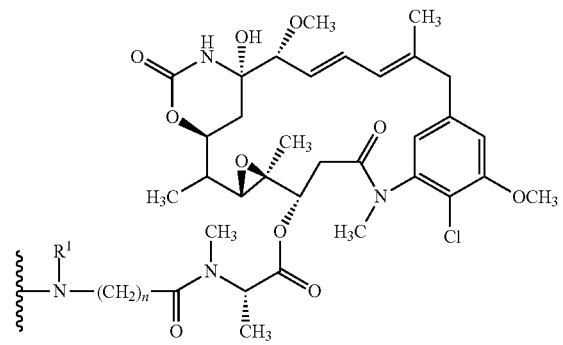
wherein R¹ is alkyl.
In some embodiments, Pay is:
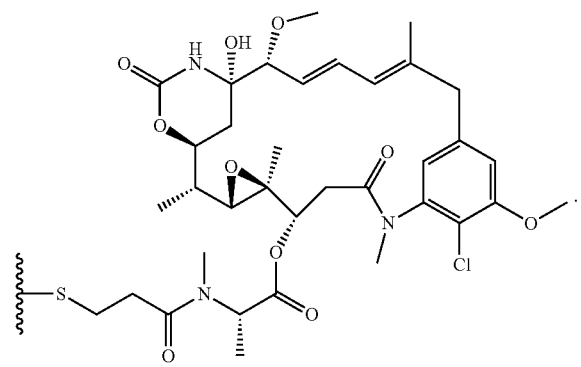 [SMILES: *SCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]
In some embodiments, Pay is:
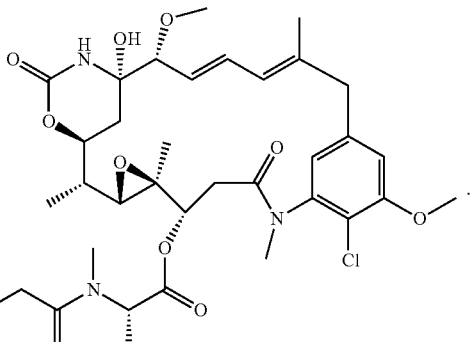
In some embodiments, n is an integer from 2 to 5.
In some embodiments, -L-Pay is:
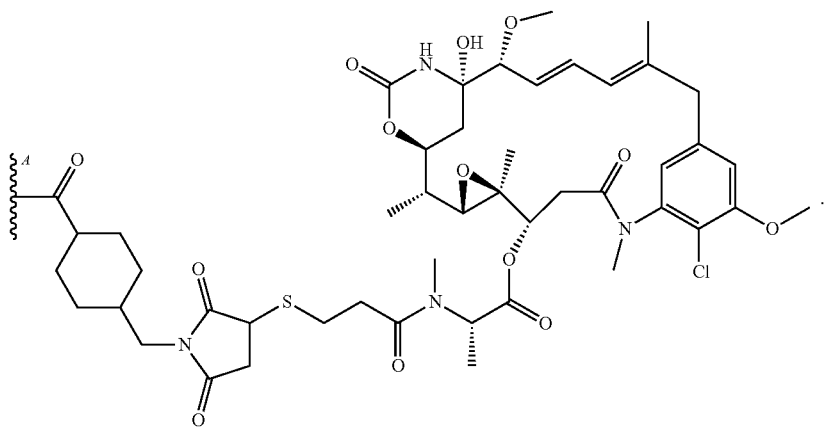
wherein
is a bond to the antibody.

In some embodiments, -L-Pay is:
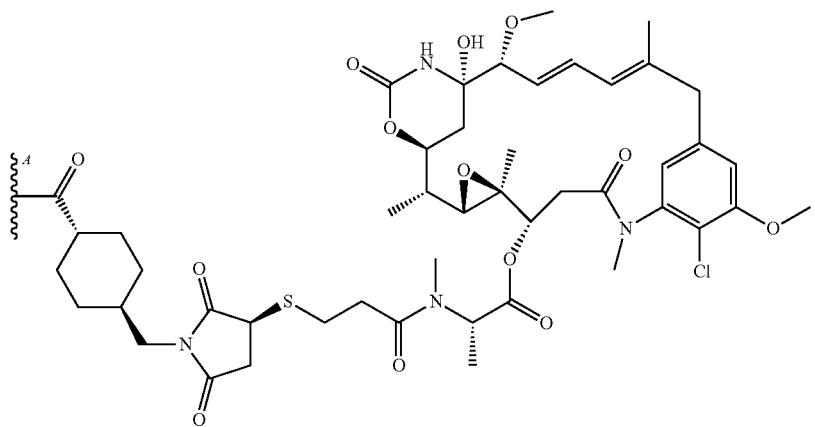
wherein
is a bond to the antibody.
In some embodiments, -L-Pay is
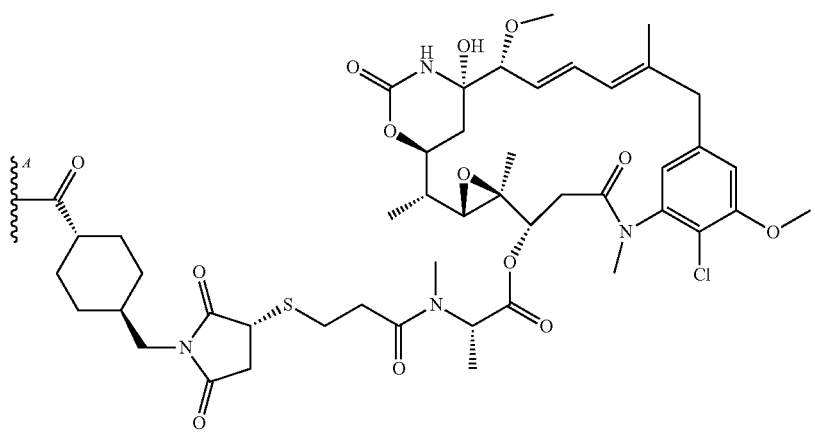
wherein
is a bond to the antibody.

In some embodiments, -L-Pay is:
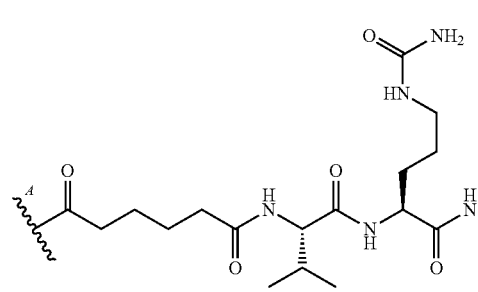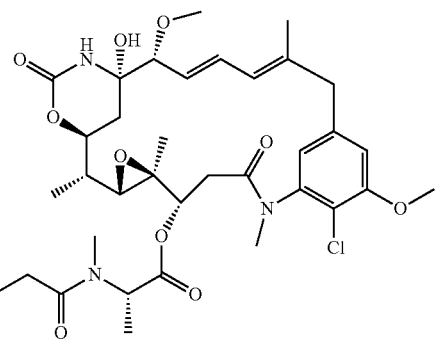
wherein
is a bond to the antibody.
In some embodiments -Pay is
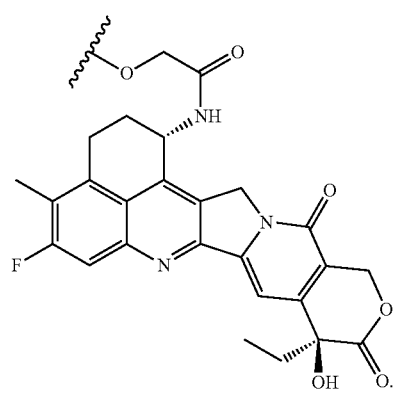 [SMILES: *OCC(=O)N[C@H]1CCc2c(C)c(F)cc3nc4c(c1c23)Cn1c-4cc2c(c1=O)COC(=O)[C@]2(O)CC]
In some embodiments, -L-Pay is:

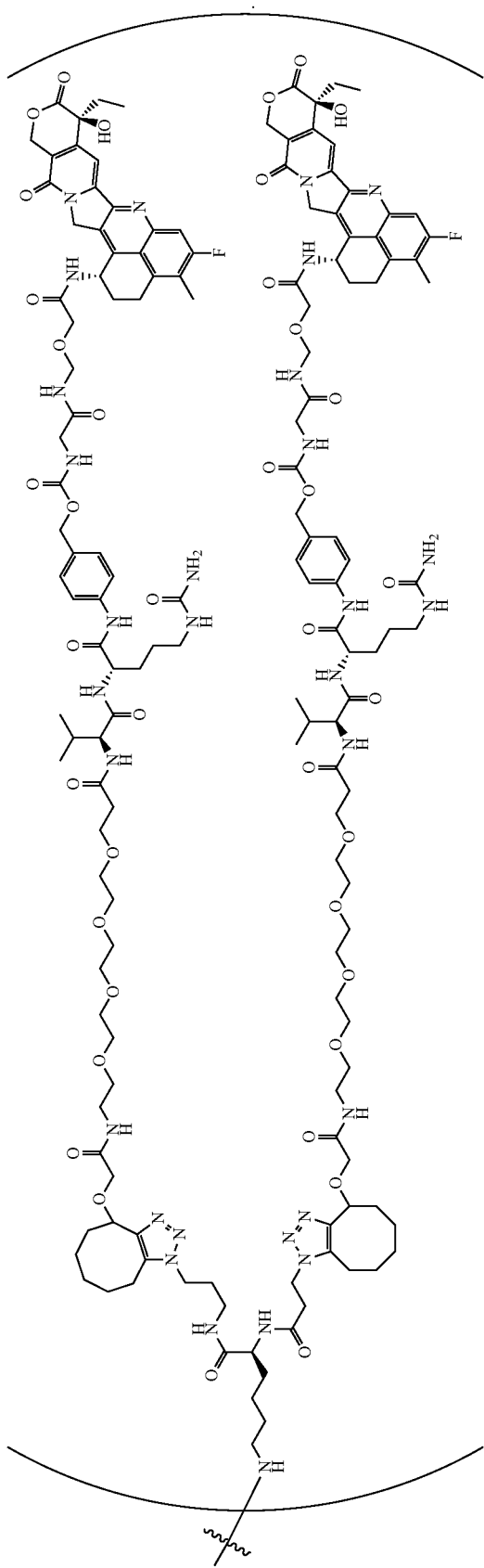

In particular embodiments, L-Pay is

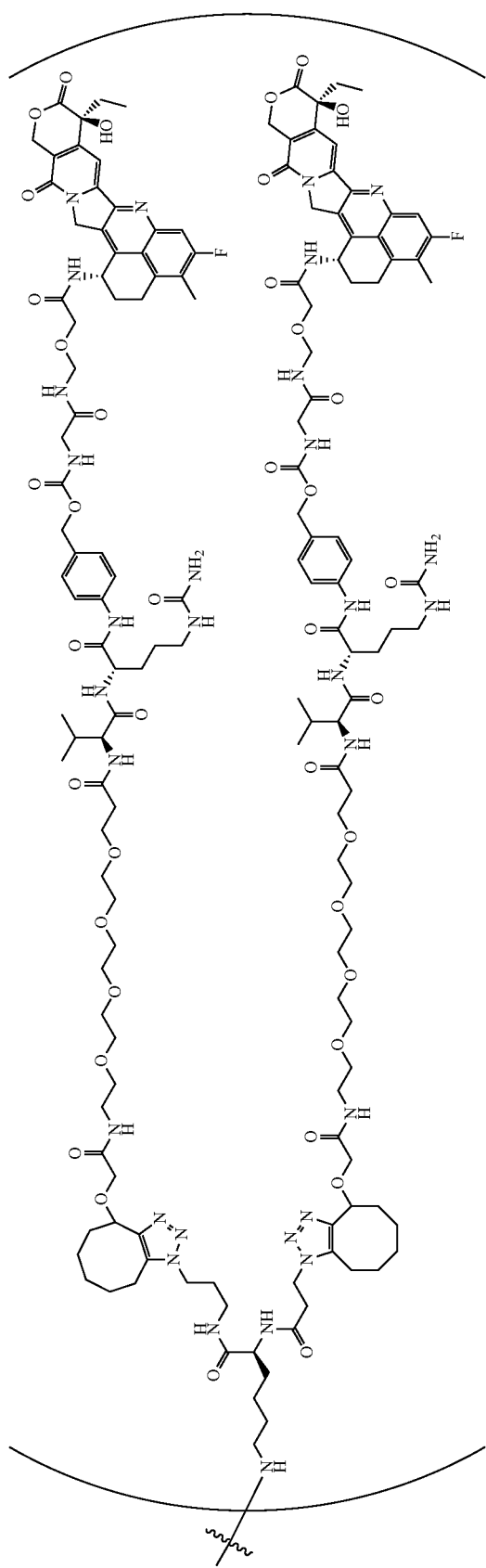

and n is 2.

In some embodiments, t he conjugates have the following structure:

Ab-[L-Pay]$_n$ wherein:
Ab is a HER2×HER2 bispecific antigen-binding protein comprising the D1-HCVR amino acid sequence of SEQ ID NO: 2 and the D2-HCVR amino acid sequence of SEQ ID NO: 10;
L-Pay is

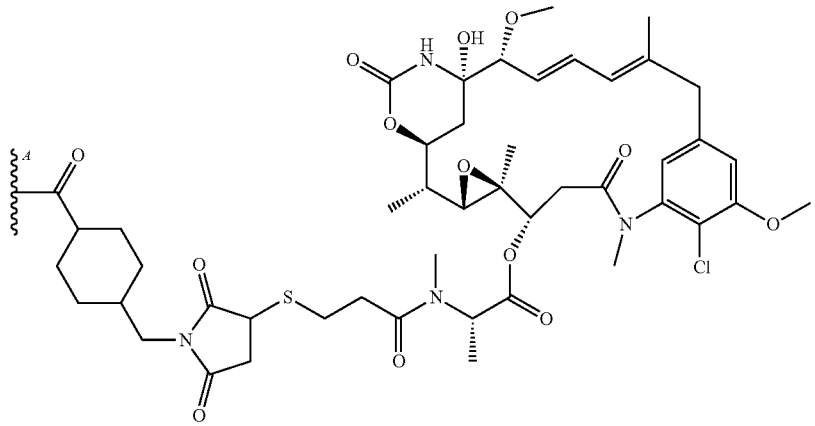

wherein

is a bond to the antigen binding protein; and n is an integer from 2-5.

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 2 and the D2-HCVR amino acid sequence of SEQ ID NO: 10;
L-Pay is

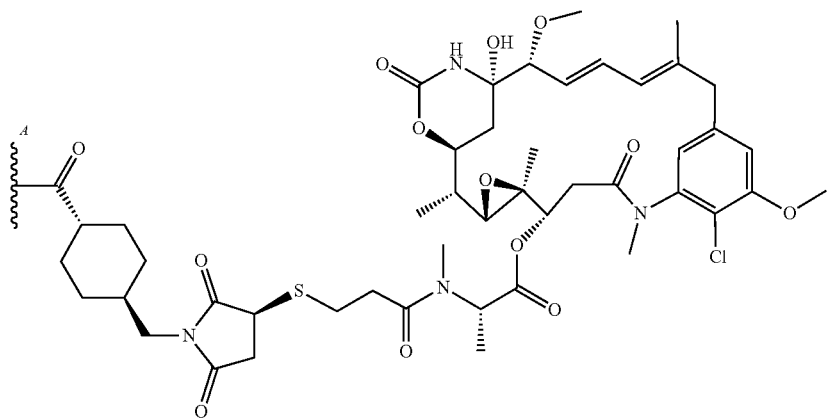

wherein

is a bond to the antigen-binding protein; and n is an integer from 2-5.

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 2 and the D2-HCVR amino acid sequence of SEQ ID NO: 10;
L-Pay is

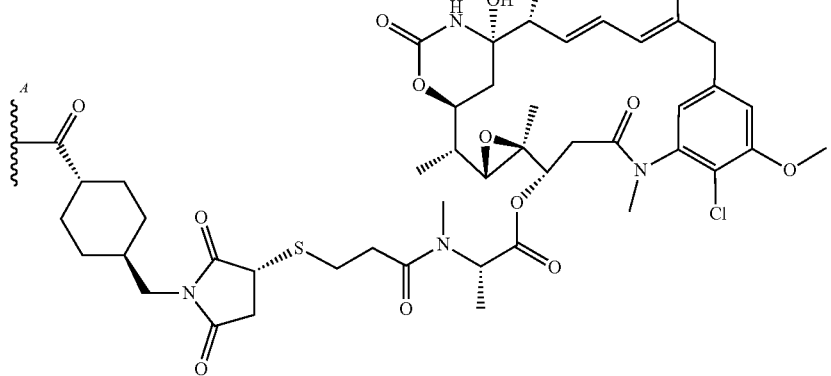

wherein

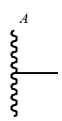

is a bond to the antigen-binding protein; and n is an integer from 2-5.

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 2 and the D2-HCVR amino acid sequence of SEQ ID NO: 10;
L-Pay is

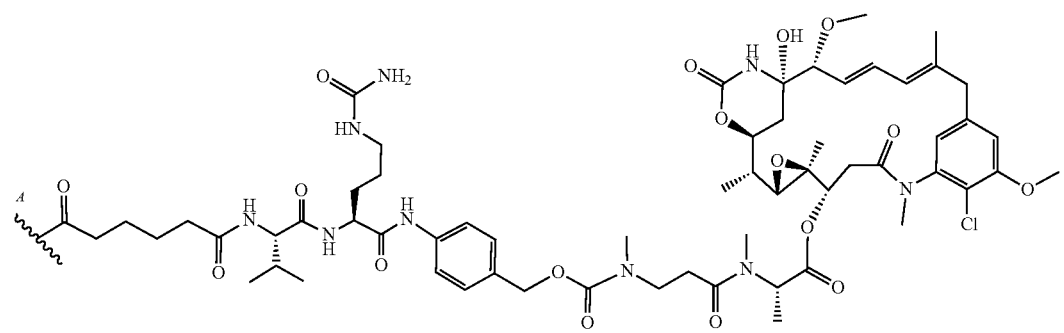

wherein

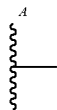

is a bond to the antigen-binding protein; and n is an integer from 2-5.

In some embodiments, the conjugates have the following structure:

wherein:
Ab is a HER2×HER2 bispecific antigen-binding protein comprising the D1-HCVR amino acid sequence of SEQ ID NO: 32 and the D2-HCVR amino acid sequence of SEQ ID NO: 40;
L-Pay is

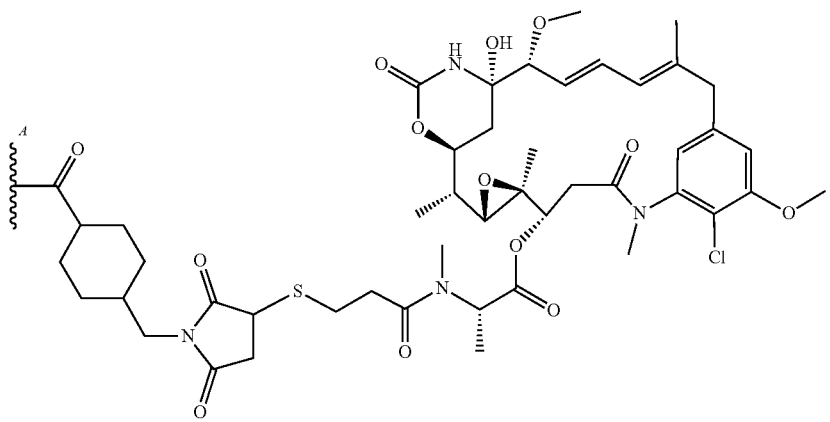

wherein

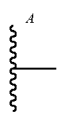

is a bond to the antigen-binding protein; and n is an integer from 2-5.

In some embodiments, the conjugates have the following structure:

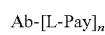

wherein:
Ab is a HER2×HER2 bispecific antigen-binding protein comprising the D1-HCVR amino acid sequence of SEQ ID NO: 32 and the D2-HCVR amino acid sequence of SEQ ID NO: 40;
L-Pay is

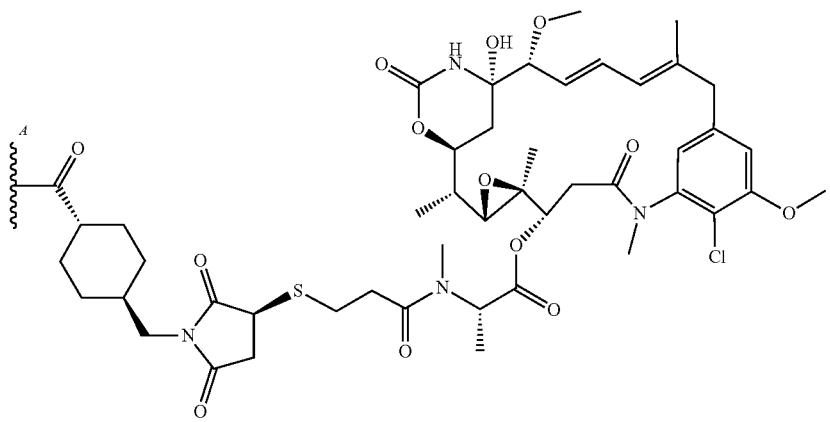

wherein

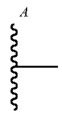

is a bond to the antigen-binding protein; and n is an integer from 2-5.

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 32 and the D2-HCVR amino acid sequence of SEQ ID NO: 40;
L-Pay is

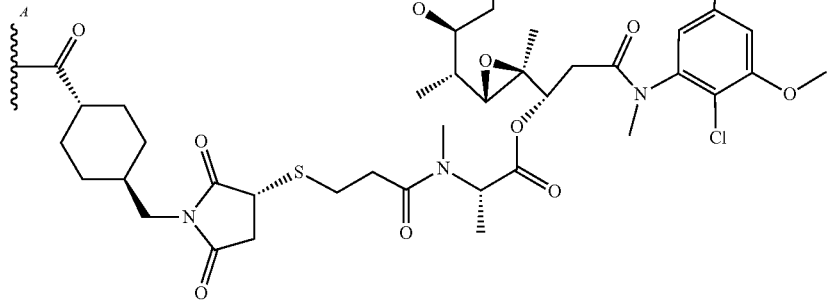

wherein

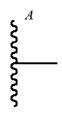

is a bond to the antigen-binding protein; and n is an integer from 2-5.

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 32 and the D2-HCVR amino acid sequence of SEQ ID NO: 40;
L-Pay is

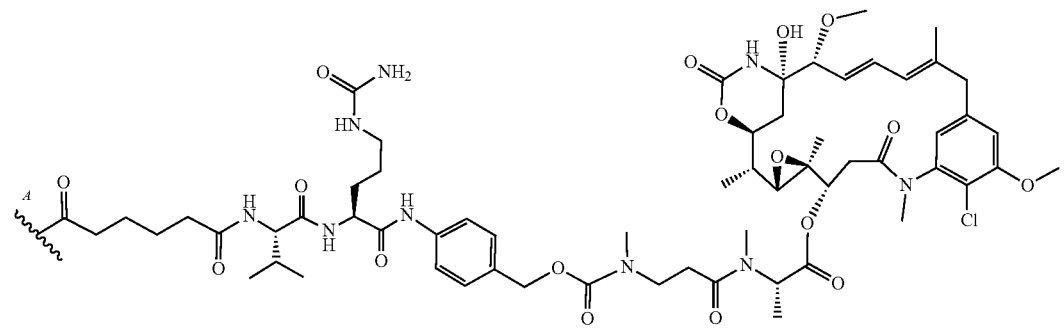

wherein

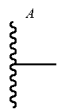

is a bond to the antigen-binding protein; and n is an integer from 2-5.

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 2 and the D2-HCVR amino acid sequence of SEQ ID NO: 10; Pay is

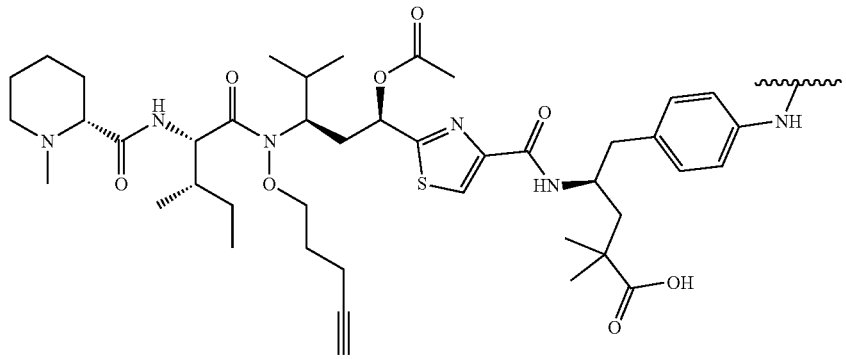

wherein

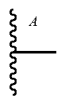

is a bond to the antigen-binding protein; and n is an integer from 2-5.

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 32 and the D2-HCVR amino acid sequence of SEQ ID NO: 40; Pay is

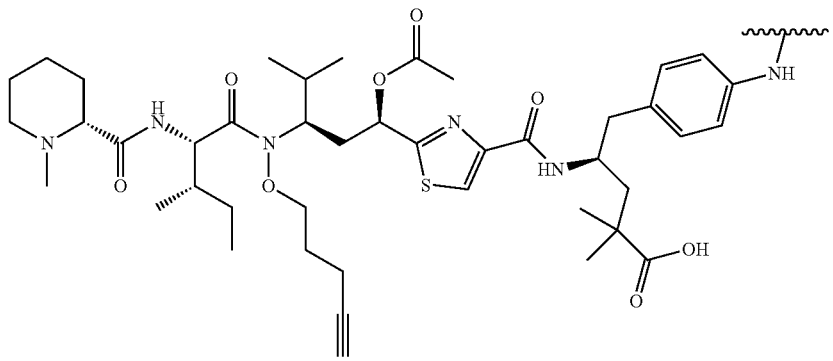 [SMILES: *Nc1ccc(C[C@@H](CC(C)(C)C(=O)O)NC(=O)c2csc([C@@H](C[C@H](C(C)C)N(OCCCC#C)C(=O)[C@@H](NC(=O)[C@H]3CCCCN3C)[C@@H](C)CC)OC(C)=O)n2)cc1]

wherein

is a bond to the antigen-binding protein; and n is an integer from 2-5.

In some embodiments, the conjugates have the following structure:

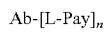

wherein:
Ab is a HER2×HER2 bispecific antigen-binding protein comprising the D1-HCVR amino acid sequence of SEQ ID NO: 2 and the D2-HCVR amino acid sequence of SEQ ID NO: 10;
L-Pay is

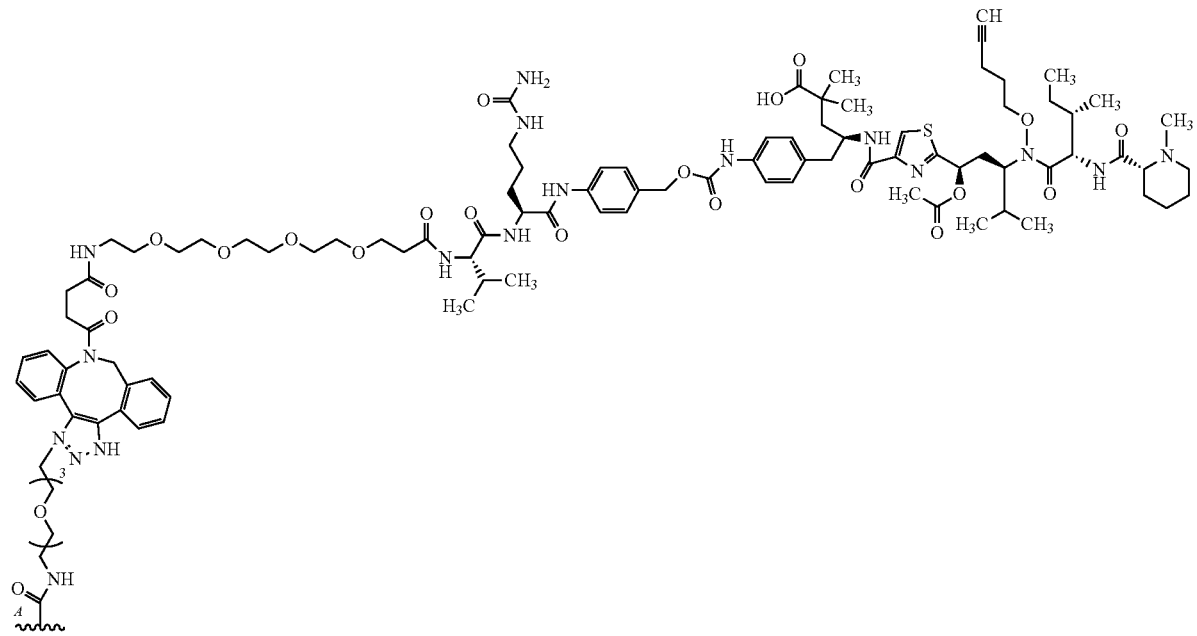

wherein

is a bond to a heavy chain glutamine. In some embodiments, n is 2. In certain embodiments, n is 2 and L-Pay is bonded to Q295 glutamines. In some embodiments, n is 4. In certain embodiments, n is 4 and L-Pay is bonded to Q295 and Q297 glutamines.

In some embodiments, the conjugates have the following structure:

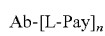

wherein:
Ab is a HER2×HER2 bispecific antigen-binding protein comprising the D1-HCVR amino acid sequence of SEQ ID NO: 32 and the D2-HCVR amino acid sequence of SEQ ID NO: 40;

L-Pay is

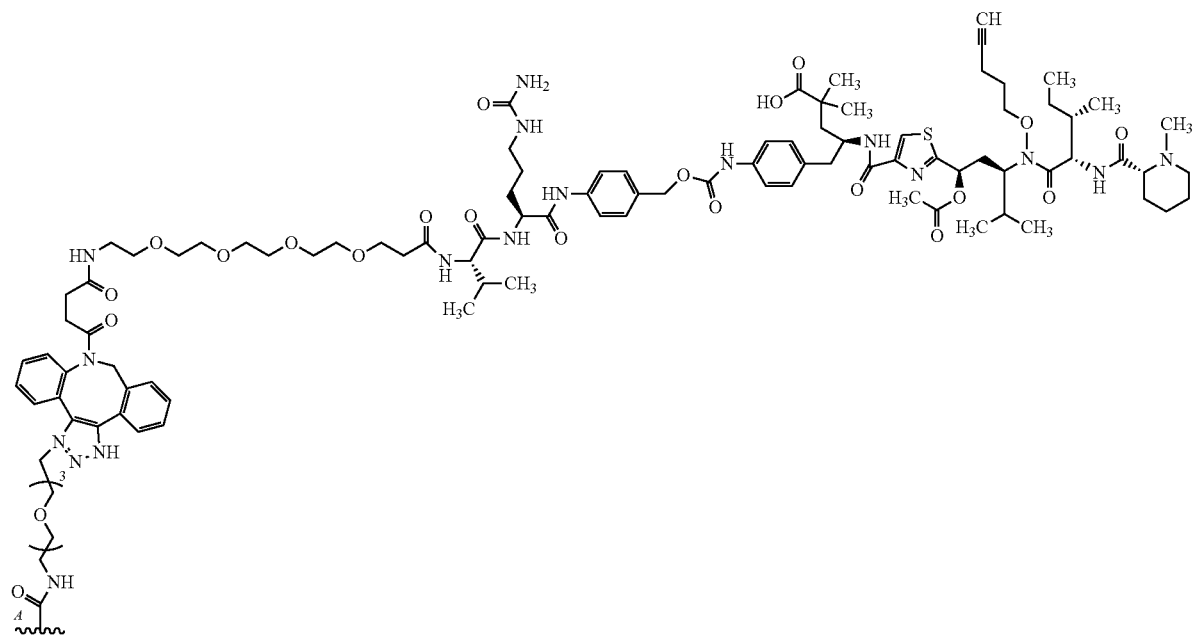

wherein

is a bond to a heavy chain glutamine. In some embodiments, n is 2. In certain embodiments, n is 2 and L-Pay is bonded to Q295 glutamines. In some embodiments, n is 4. In certain embodiments, n is 4 and L-Pay is bonded to Q295 and Q297 glutamines.

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 2 and the D2-HCVR amino acid sequence of SEQ ID NO: 10; Pay is

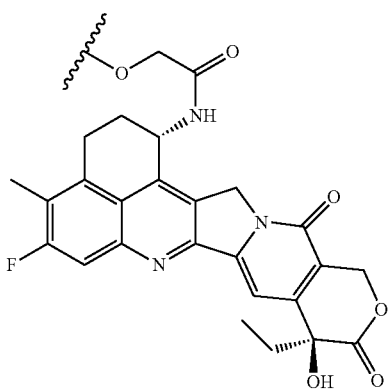 [SMILES: *OCC(=O)N[C@H]1CCc2c(C)c(F)cc3nc4c(c1c23)Cn1c-4cc2c(c1=O)COC(=O)[C@]2(O)CC]

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 32 and the D2-HCVR amino acid sequence of SEQ ID NO: 40; Pay is

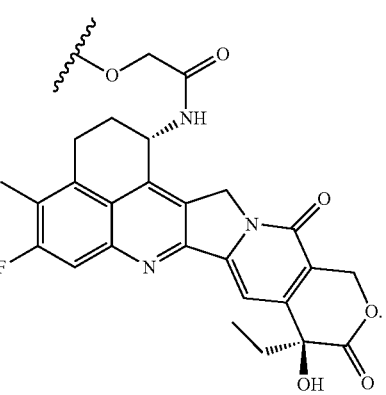

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 2 and the D2-HCVR amino acid sequence of SEQ ID NO: 10;
L-Pay is

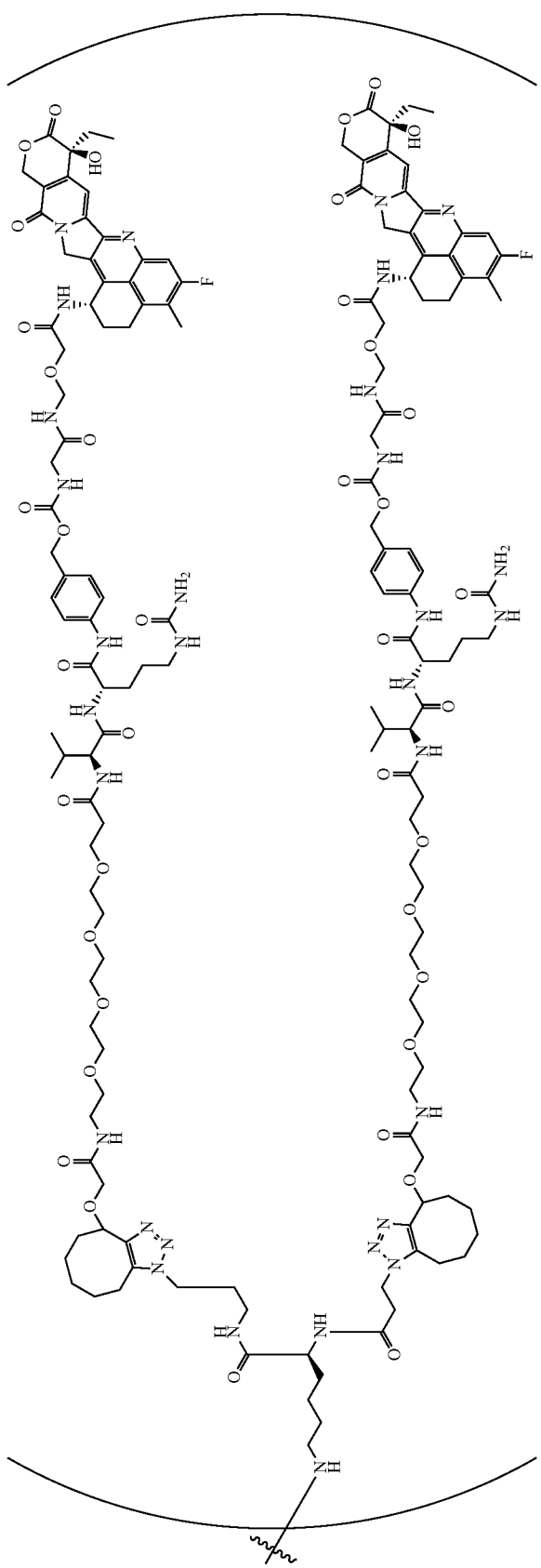

wherein

is a bond to a heavy chain glutamine of the binding protein. In some embodiments, n is 2. In certain embodiments, n is 2 and L-Pay is bonded to Q295 glutamines. In some embodiments, n is 4. In certain embodiments, n is 4 and L-Pay is bonded to Q295 and Q297 glutamines.

In some embodiments, the conjugates have the following structure:

Ab-[L-Pay]$_n$ wherein:
Ab is a HER2×HER2 bispecific antigen-binding protein comprising the D1-HCVR amino acid sequence of SEQ ID NO: 32 and the D2-HCVR amino acid sequence of SEQ ID NO: 40;
L-Pay is

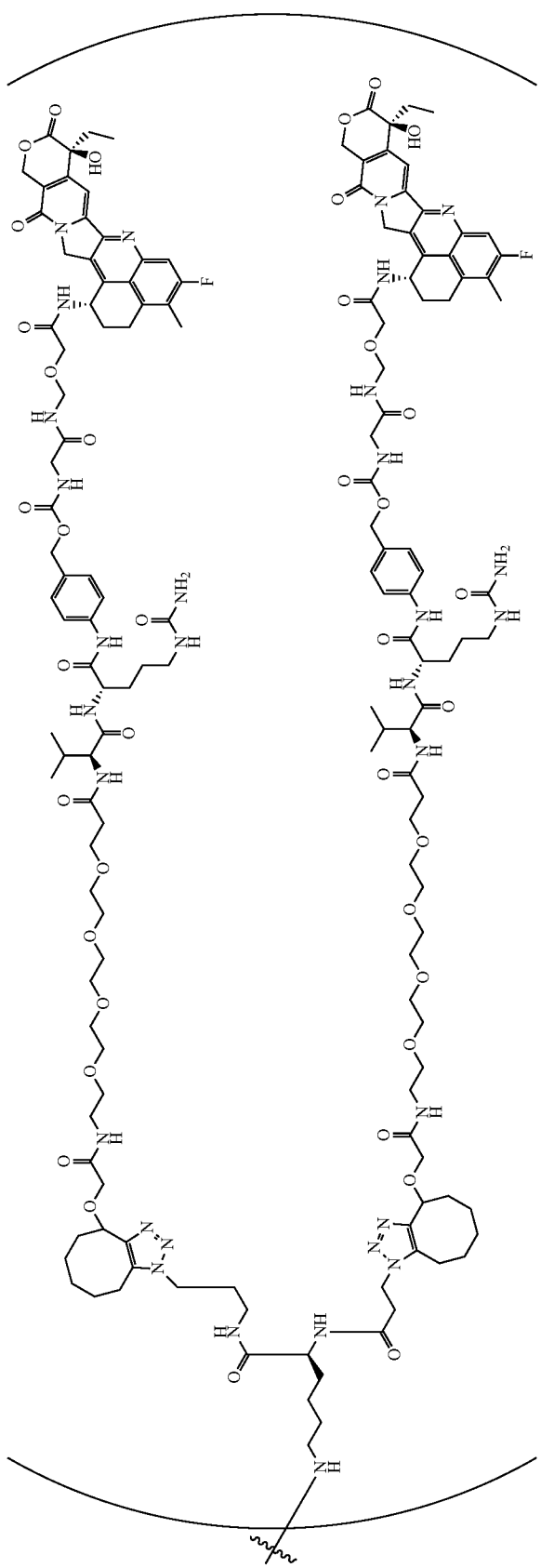

wherein

is a bond to a heavy chain glutamine of the binding protein. In some embodiments, n is 2. In certain embodiments, n is 2 and L-Pay is bonded to Q295 glutamines. In some embodiments, n is 4. In certain embodiments, n is 4 and L-Pay is bonded to Q295 and Q297 glutamines.

The antibody drug conjugates described herein can be prepared using conjugation conditions known to those of ordinary skill in the art, (see, e.g., Doronina et al. Nature Biotechnology 2003, 21, 7, 778, which is incorporated herein by reference in its entirety). In some embodiments a HER2×HER2 bispecific antigen-binding protein antibody drug conjugate is prepared by contacting a HER2×HER2 bispecific antigen-binding protein described herein with a compound comprising the desired linker and cytotoxic agent, wherein said linker possesses a moiety that is reactive with the antibody or antigen-binding protein, e.g., at the desired residue of the antibody or antigen-binding protein.

In some embodiments, the antibody drug conjugates provided herein are conjugated at heavy chain Q295 or Q297 glutamines. Antibodies comprising heavy chain Q297 glutamines can be prepared using techniques known in the art, e.g., through N297Q mutation. See, e.g., *Bioconjugate Chem.* 2014, 25, 3, 569 (2014). Such conjugation methods can provide antibody drug conjugates having a DAR of 2 or 4. In some embodiments, such methods comprise installing a first reactive moiety at the heavy chain glutamines by reacting the antibody with a primary amine compound comprising said first reactive moiety in the presence of transglutaminase to produce an antibody comprising the first reactive moiety at Q295, and optionally Q297. This product can be subsequently reacted with a payload having a linker and complementary second reactive moiety to provide antibody-drug conjugates provided herein. In some embodiments, the first reactive moiety is an azide. In some embodiments, the second reactive moiety is a cycloalkyne. In some embodiments, the payload having a linker and complementary second reactive moiety is:

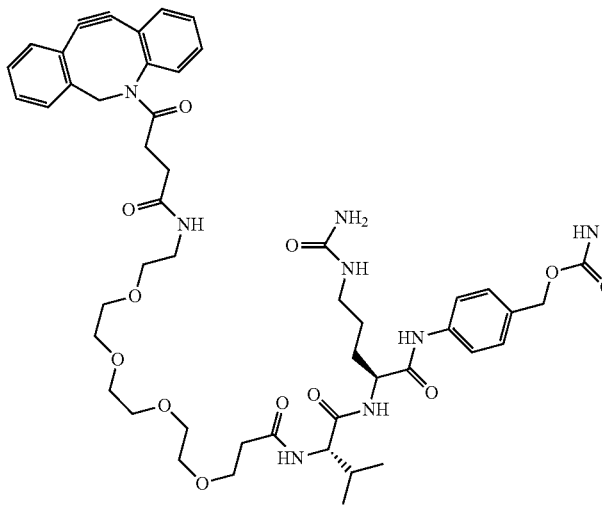
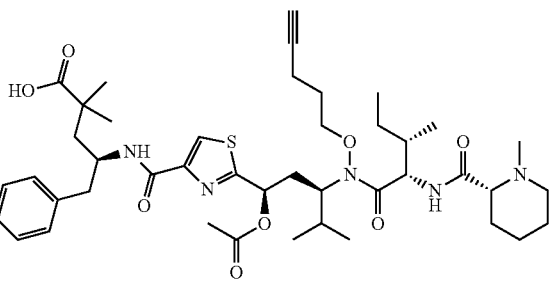

which can be prepared using methods described in U.S. patent application Ser. No. 16/724,164 filed Dec. 20, 2019 (e.g., compound LP4 described therein). In certain embodiments, the primary amine compound is

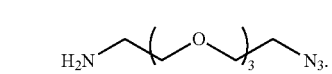

In some embodiments, the payload having a linker and complementary second reactive moiety is:

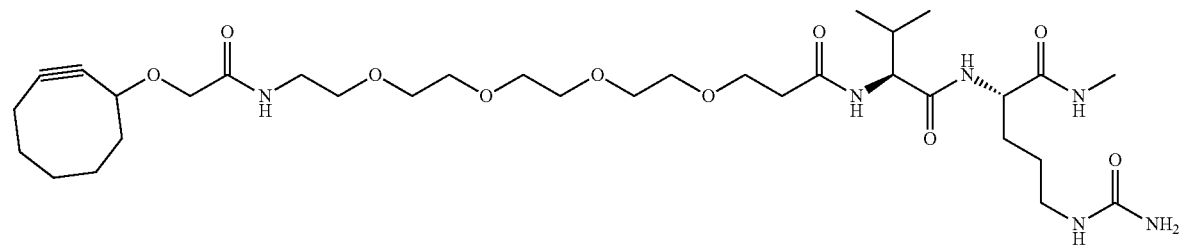

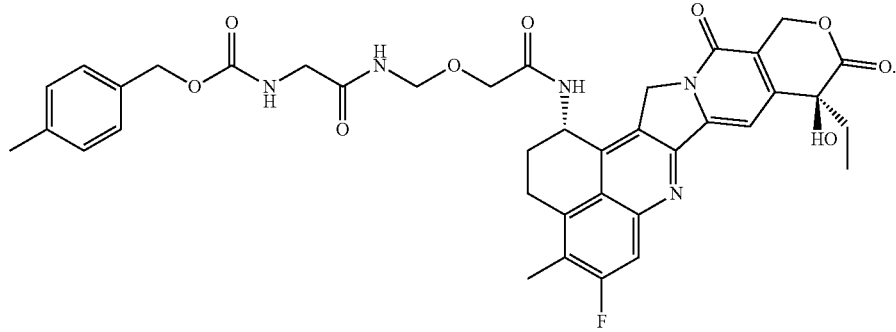

In certain embodiments, the primary amine compound is

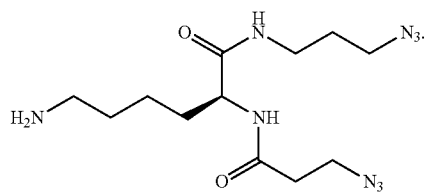 [SMILES: [N-]=[N+]=NCCCNC(=O)[C@H](CCCCN)NC(=O)CCN=[N+]=[N-]]

In some embodiments, provided herein are processes for preparing an antibody-drug conjugate comprising contacting a HER2×HER2 bispecific antigen-binding protein described herein with a compound having the following formula $A^1$:

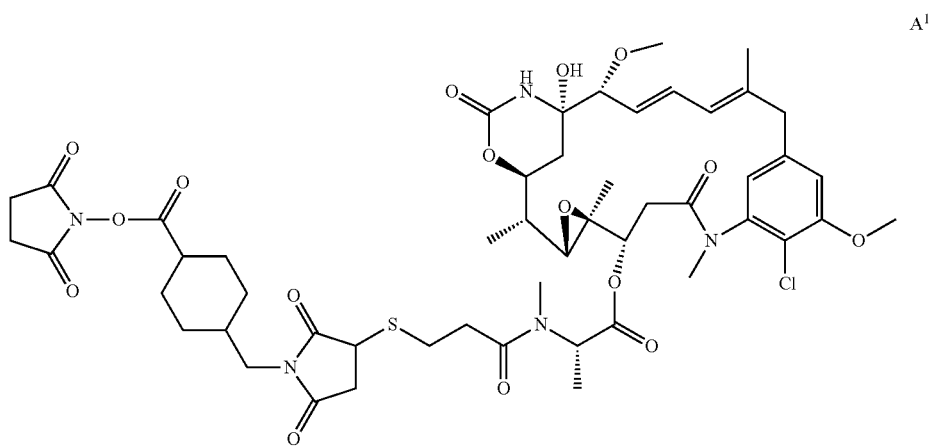 [SMILES: "A1" ; COc1cc2cc(c1Cl)N(C)C(=O)C[C@H](OC(=O)[C@H](C)N(C)C(=O)CCSC1CC(=O)N(CC3CCC(C(=O)ON4C(=O)CCC4=O)CC3)C1=O)[C@]1(C)O[C@H]1[C@H](C)[C@@H]1C[C@@](O)(NC(=O)O1)[C@H](OC)/C=C/C=C(\C)C2]

and aqueous diluent.

In some embodiments, the compound of formula $A^1$ is present in stoichiometric excess. In some embodiments, the compound of formula $A^1$ is present in 5-6 fold stoichiometric excess. In some embodiments, the aqueous diluent comprises HEPES. In some embodiments, the aqueous diluent comprises DMA.

In some embodiments, the compound of formula A¹ is a compound of formula A² or A³:

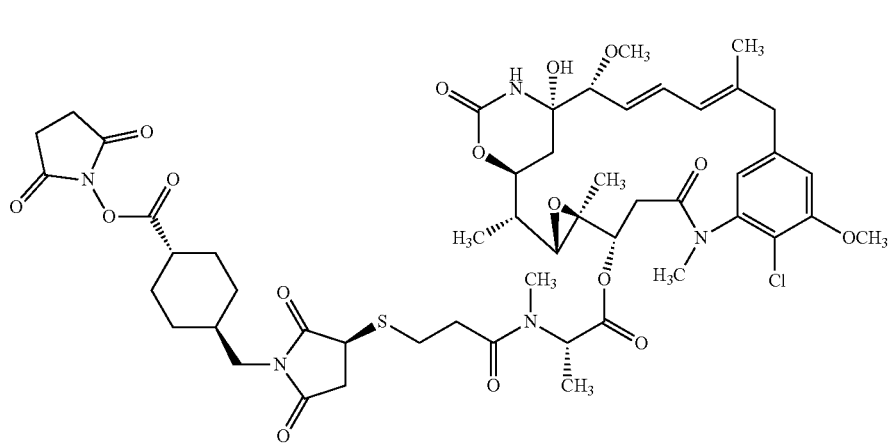

A²

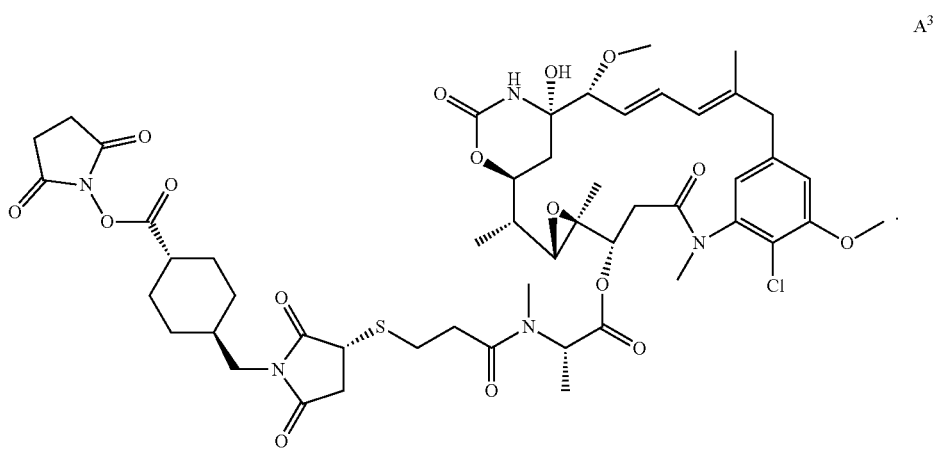

A³

In some embodiments, the compound of formula A² is A³ stereomerically pure. In some embodiments, the compound of formula A¹ comprises a compound of formula A¹ or A², wherein the compound of A¹ or A² is present in a diastereomeric excess of more than 50%. In certain embodiments, the diastereomeric excess is more than 70%. In certain embodiments, the diastereomeric excess is more than 90%. In certain embodiments, the diastereomeric excess is more than 95%.

The term "diastereomeric excess" refers to the difference between the mole fraction of the desired single diastereomer as compared to the remaining diastereomers in a composition. Diastereomeric excess is calculated as follows: (amount of single diastereomer)−(amount of other diastereomers)/1. For example, a composition that contains 90% of 1 and 10% of 2, 3, 4, or a mixture thereof has a diastereomeric excess of 80% [(90−10)/1]. A composition that contains 95% of 1 and 5% of 2, 3, 4, or a mixture thereof has a diastereomeric excess of 90% [(95−5)/1]. A composition that contains 99% of 1 and 1% of 2, 3, 4, or a mixture thereof has a diastereomeric excess of 98% [(99−1)/1]. The diastereomeric excess can similarly be calculated for any one of 1, 2, 3, or 4.

In some embodiments, the compound of formula A¹ is prepared by contacting a compound of formula (a):

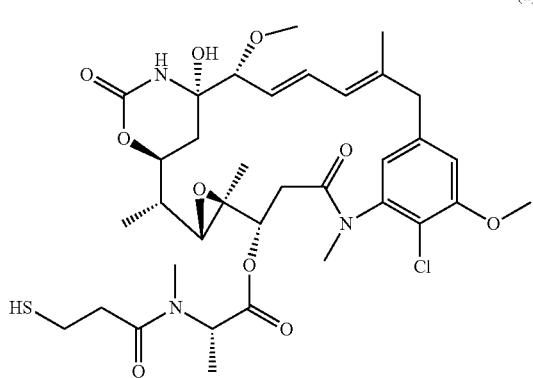

(a)

with a compound of formula (b)

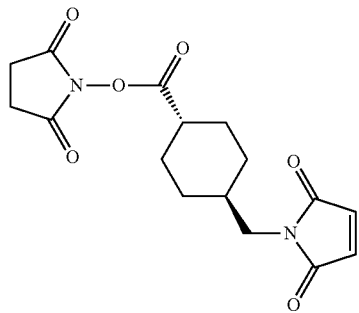
(b)

in the presence of silica gel and diluent. In some embodiments, the diluent comprises an organic solvent and water.

Provided herein is also the product prepared by the process of:

(i) contacting a compound of formula (a):

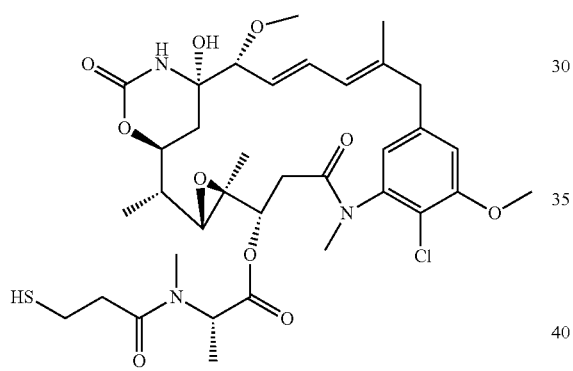
(a)

with a compound of formula (b):

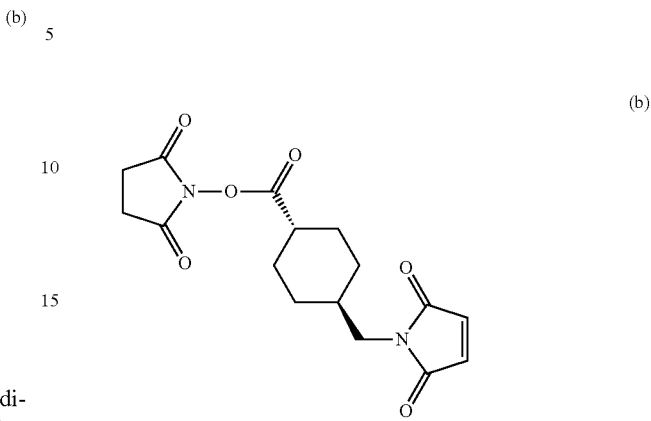
(b)

in the presence of silica gel and diluent to synthesize an intermediate; and (ii) contacting a HER2×HER2 bispecific antigen-binding protein described herein with the intermediate and aqueous diluent.

In some embodiments, provided herein are processes for preparing an antibody-drug conjugate comprising contacting a HER2×HER2 bispecific antigen-binding protein described herein with a compound having the following formula B:

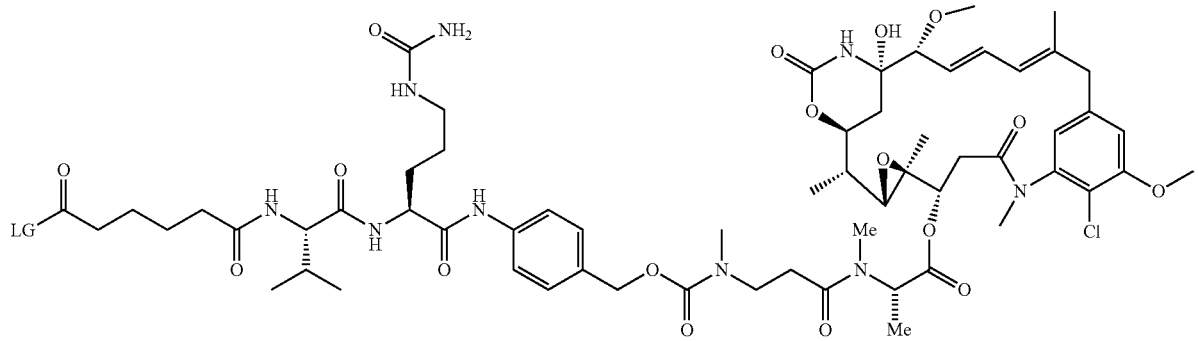

wherein LG is a leaving group, and aqueous diluent.

In some embodiments, the compound of formula B is present in stoichiometric excess. In some embodiments, the compound of formula B is present in 5-6 fold stoichiometric excess. In some embodiments, the aqueous diluent comprises HEPES. In some embodiments, the aqueous diluent comprises DMA. In some embodiments, the —C(O)-LG is an ester, e.g., NHS or trifluorophenyl ester.

In some embodiments, the compound of formula B is a compound of formula B¹:

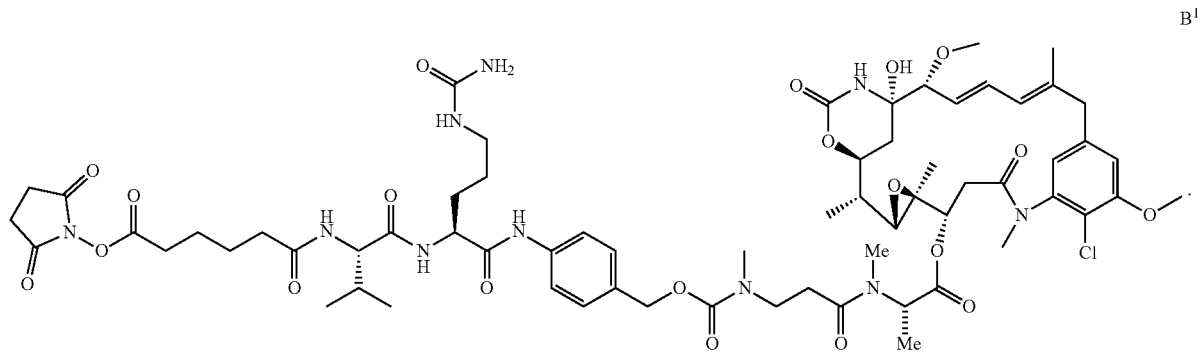 [SMILES: COc1cc2cc(c1Cl)N(C)C(=O)C[C@H](OC(=O)[C@H](C)N(C)C(=O)CCN(C)C(=O)OCc1ccc(NC(=O)[C@H](CCCNC(N)=O)NC(=O)[C@@H](NC(=O)CCCCC(=O)ON3C(=O)CCC3=O)C(C)C)cc1)[C@]1(C)O[C@H]1[C@H](C)[C@@H]1C[C@@](O)(NC(=O)O1)[C@H](OC)/C=C/C=C(\C)C2]

B¹

In some embodiments, the compound of formula B¹ is prepared by contacting a compound of formula C:

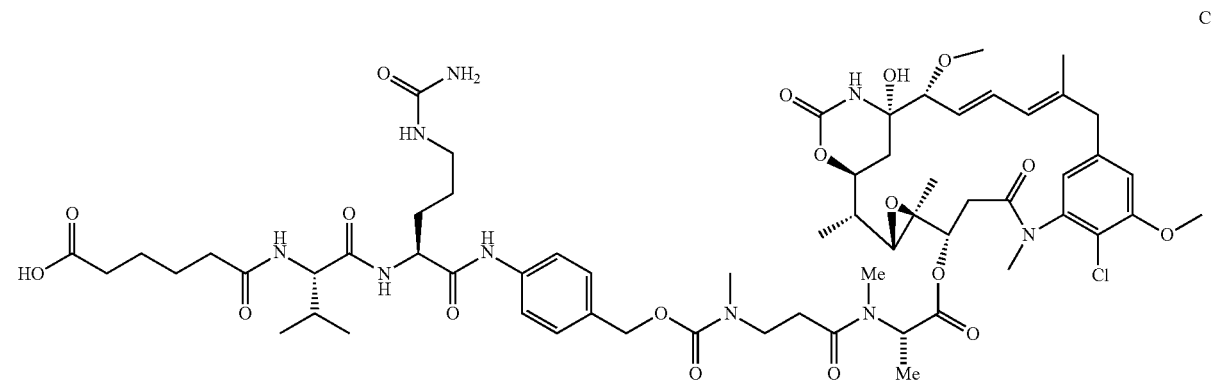 [SMILES: COc1cc2cc(c1Cl)N(C)C(=O)C[C@H](OC(=O)[C@H](C)N(C)C(=O)CCN(C)C(=O)OCc1ccc(NC(=O)[C@H](CCCNC(N)=O)NC(=O)[C@@H](NC(=O)CCCCC(=O)O)C(C)C)cc1)[C@]1(C)O[C@H]1[C@H](C)[C@@H]1C[C@@](O)(NC(=O)O1)[C@H](OC)/C=C/C=C(\C)C2]

C with N-hydroxysuccinimide (NHS), a peptide coupling reagent, and an organic diluent. Suitable peptide coupling reagents include those that activate, i.e., render reactive, carboxylic acid moieties for reaction with a nucleophile. In certain embodiments, the peptide coupling reagent is N-(3-dimethylaminopropyl)-N'-ethylcarbodiimide hydrochloride (EDC). In some embodiments, the organic solvent is dichloromethane.

In some embodiments, the compound of formula C is prepared by contacting a compound of formula D:

with adipic acid, a peptide coupling agent, and an organic solvent. In certain embodiments, the peptide coupling agent is 2-ethoxy-1-ethoxycarbonyl-1,2-dihydroquinoline (EEDQ). In certain embodiments, the organic solvent comprises dichloromethane. Compound D can be prepared as described in WO2014/145090.

Epitope Mapping and Related Technologies

The epitope to which the antibodies and antigen-binding domains bind may consist of a single contiguous sequence of 3 or more (e.g., 3, 4, 5, 6, 7, 8, 9, 10, 11, 12, 13, 14, 15,

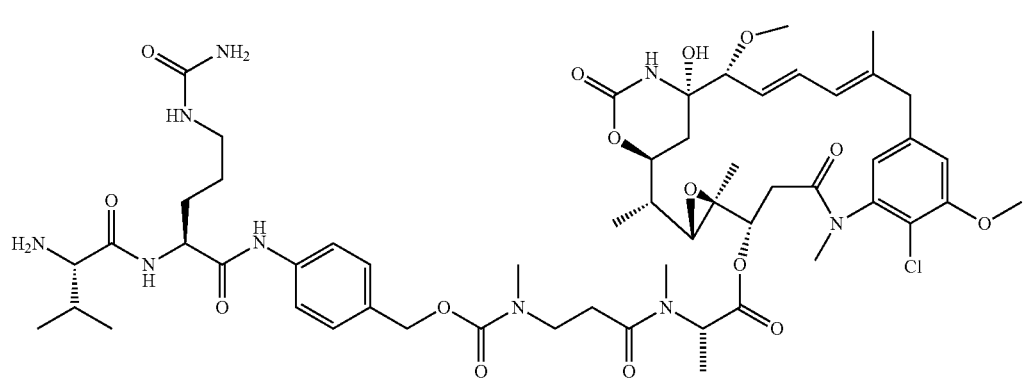

D 16, 17, 18, 19, 20 or more) amino acids of a HER2 protein. Alternatively, the relevant epitope may consist of a plurality of non-contiguous amino acids (or amino acid sequences) of HER2.

As described elsewhere herein, e.g. Examples 21 and 22, the individual antigen binding domains (D1 and D2) of the HER2×HER2 bispecific antigen-binding molecules may bind to distinct, or non-overlapping, or partially overlapping epitopes, relative to one another. As used herein, "partially overlapping epitopes" means that the first and second epitopes share less than 5, less than 4, less than 3, or only one common amino acid as determined by any epitope mapping methodology known in the art (e.g., X-ray crystallography, alanine-scan mutagenesis, hydrogen/deuterium exchange [HDX], domain swapping, etc.). The D1 and D2 domains may be non-competitive with one another. For example, in certain embodiments, the binding of a D1 domain of a particular HER2×HER2 bispecific antigen-binding molecule to its epitope on ErbB2 does not inhibit (or only minimally inhibits) the binding of the D2 domain of the HER2×HER2 bispecific antigen-binding molecule to its epitope on HER2. Due to the non-overlapping (or at most, partially overlapping) nature of the respective epitopes of the D1 and D2 components, the HER2×HER2 bispecific antigen-binding molecules are able to bind to a single HER2 molecule on a cell surface. In addition, the HER2×HER2 bispecific binding molecules are able to cluster at ErbB2 on the cell surface, and trigger HER2 internalization.

Various techniques known to persons of ordinary skill in the art can be used to determine the epitope on HER2 with which the antibodies and antigen-binding domains of the present disclosure interact. Exemplary techniques that can be used to determine an epitope or binding domain of a particular antibody or antigen-binding domain include, e.g., point mutagenesis (e.g., alanine scanning mutagenesis, arginine scanning mutagenesis, etc.), peptide blots analysis (Reineke, 2004, Methods Mol Biol 248:443-463), protease protection, and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) Anal. Chem. 73:256A-265A. X-ray crystal structure analysis can also be used to identify the amino acids within a polypeptide with which an antibody interacts.

Further provided herein are HER2 bispecific antibodies that bind to the same epitope as any of the specific exemplary antibodies or antigen-binding domains described herein (e.g. antibodies comprising any of the amino acid sequences as set forth in Table 1 herein). Likewise, also provided herein are HER2 bispecific antibodies that compete for binding to HER2 with any of the specific exemplary antibodies described herein (e.g. antibodies comprising any of the amino acid sequences as set forth in Table 1 herein).

One can easily determine whether an antibody binds to the same epitope as, or competes for binding with, a reference anti-HER2 antibody by using routine methods known in the art and exemplified herein. For example, to determine if a test antibody binds to the same epitope as a reference anti-HER2 antibody provided herein, the reference antibody is allowed to bind to a HER2 protein. Next, the ability of a test antibody to bind to the HER2 molecule is assessed. If the test antibody is able to bind to HER2 following saturation binding with the reference anti-HER2 antibody, it can be concluded that the test antibody binds to a different epitope than the reference anti-HER2 antibody. On the other hand, if the test antibody is not able to bind to the HER2 molecule following saturation binding with the reference anti-HER2 antibody, then the test antibody may bind to the same epitope as the epitope bound by the reference anti-HER2 antibody. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-HER2 antibody, the above-described binding methodology is performed in two orientations: In a first orientation, the reference antibody is allowed to bind to a HER2 protein under saturating conditions followed by assessment of binding of the test antibody to the HER2 molecule. In a second orientation, the test antibody is allowed to bind to a HER2 molecule under saturating conditions followed by assessment of binding of the reference antibody to the HER2 molecule. If, in both orientations, only the first (saturating) antibody is capable of binding to the HER2 molecule, then it is concluded that the test antibody and the reference antibody compete for binding to HER2. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The HER2×HER2 bispecific antibodies provided herein can be fully human antibodies. Methods for generating monoclonal antibodies, including fully human monoclonal antibodies are known in the art. Any such known methods can be used in the context of the present disclosure to make human antibodies that specifically bind to human HER2.

Using VELOCIMMUNE™ technology, for example, or any other similar known method for generating fully human monoclonal antibodies, high affinity chimeric antibodies to HER2 are initially isolated having a human variable region and a mouse constant region. As in the experimental section below, the antibodies are characterized and selected for desirable characteristics, including affinity, dimerization blocking activity, selectivity, epitope, etc. If necessary, mouse constant regions are replaced with a desired human constant region, for example wild-type or modified IgG1 or IgG4, to generate a fully human anti-HER2 antibody. While the constant region selected may vary according to specific use, high affinity antigen-binding and target specificity characteristics reside in the variable region. In certain instances, fully human anti-HER2 antibodies are isolated directly from antigen-positive B cells.

Bioequivalents

The HER2 bispecific antibodies and antibody fragments provided herein encompass proteins having amino acid sequences that vary from those of the described antibodies but that retain the ability to bind human HER2. Such variant antibodies and antibody fragments comprise one or more additions, deletions, or substitutions of amino acids when compared to parent sequence, but exhibit biological activity that is essentially equivalent to that of the described antibodies. Likewise, the anti-HER2 antibody-encoding DNA sequences of the present disclosure encompass sequences that comprise one or more additions, deletions, or substitutions of nucleotides when compared to the disclosed sequence, but that encode an anti-HER2 antibody or antibody fragment that is essentially bioequivalent to an anti-HER2 antibody or antibody fragment of the disclosure. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of HER2 bispecific antibodies provided herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include HER2 bispecific antibody variants comprising amino acid changes which modify the glycosylation characteristics of the antibodies, e.g., mutations which eliminate or remove glycosylation.

Species Selectivity and Species Cross-Reactivity

The present disclosure, according to certain embodiments, provides anti-HER2 antibodies (and antigen-binding molecules comprising anti-HER2 antigen-binding domains) that bind to human HER2 but not to HER2 from other species. The present disclosure also includes anti-HER2 antibodies (and antigen-binding molecules comprising anti-HER2 antigen-binding domains) that bind to human HER2 and to HER2 from one or more non-human species. For example, the anti-HER2 antibodies and antigen-binding molecules may bind to human HER2 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee HER2.

Multispecific Antibodies

As described elsewhere herein, the present disclosure provides bispecific antigen-binding molecules comprising two different antigen-binding domains, wherein the first antigen-binding domain (D1) binds a first epitope on HER2, and wherein the second antigen-binding domain (D2) binds a second epitope on HER2. In certain embodiments, the first and/or second epitopes are within the ectodomain of HER2, for example, within SEQ ID NO: 54. In certain embodiments, the first and second epitopes on HER2 to which the D1 and D2 domains bind are distinct, or non-overlapping, or partially overlapping. According to this aspect, the D1 domain can comprise any of the HCVR/LCVR or CDR amino acid sequences as set forth in Table 1 herein, and the D2 domain can comprise any other of the HCVR/LCVR or CDR amino acid sequences as set forth in Table 1 herein (so long as the binding specificity of the D1 domain is different from the binding specificity of the D2 domain, and/or the antigen-binding protein from which D1 was obtained does not compete for binding to HER2 with the antigen-binding protein from which D2 was obtained).

In some embodiments, the human HER2 epitope to which the anti-HER2×anti-HER2 bispecific antibodies bind comprise amino acids 9-23 (SEQ ID NO: 57), amino acids 41-51 (SEQ ID NO: 58), amino acids 64-77 (SEQ ID NO: 59), amino acids 133-148 (SEQ ID NO: 61), amino acids 141-145 (SEQ ID NO: 155), amino acids 152-161 (SEQ ID NO: 64), amino acids 166-182 (SEQ ID NO: 56), amino acids 174-182 (SEQ ID NO: 162), amino acids 194-200 (SEQ ID NO: 163), amino acids 258-273 (SEQ ID NO: 65), and/or amino acids 353-359 (SEQ ID NO: 60) of SEQ ID NO: 54.

In some embodiments, the first epitope of human HER2 comprises amino acids 141-145 and/or 166-182 of SEQ ID NO: 54; and the second epitope of human HER2 comprises amino acids 9-23, 41-51, 64-67, and/or 353-359 of SEQ ID NO: 54. In some embodiments, the first epitope of human HER2 comprises amino acids 133-148, 174-182, and/or 194-200 of SEQ ID NO: 54; and the second epitope of human HER2 comprises amino acids 152-161, 258-273, and/or 194-200 of SEQ ID NO: 54.

An exemplary bispecific antibody format that can be used in the context of the present disclosure involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^e$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

Provided herein are pharmaceutical compositions comprising the anti-HER2 antibodies or HER2×HER2 bispecific antigen-binding molecules, including HER2×HER2 ADCs, of the present invention. The pharmaceutical compositions may be formulated with suitable carriers, excipients, and other agents that provide improved transfer, delivery, tolerance, and the like.

Therapeutic Uses of the Antibodies

Provided herein are methods comprising administering to a subject in need thereof a therapeutic composition comprising a HER2×HER2 bispecific antigen-binding molecule, including HER2×HER2 ADCs, comprising any of the D1 and D2 components as set forth herein). The therapeutic composition can comprise any of the HER2×HER2 bispecific antigen-binding molecules, including HER2×HER2 ADCs, disclosed herein, and a pharmaceutically acceptable carrier or diluent.

The HER2×HER2 bispecific antigen-binding molecules, including HER2×HER2 ADCs, are useful, inter alia, for the treatment, prevention and/or amelioration of any disease or disorder associated with or mediated by HER2 expression, signaling or activity, or treatable by blocking HER2 dimerization, or otherwise inhibiting HER2 activity and/or signaling, and/or promoting receptor internalization and/or decreasing cell surface receptor number.

For example, HER2×HER2 bispecific antigen-binding molecules, including HER2×HER2 ADCs, of the present disclosure are useful for the treatment of tumors that express (or overexpress) HER2. In some embodiments, the HER2× HER2 bispecific antigen-binding molecules, including HER2×HER2 ADCs, bind cells expressing high levels of HER2, e.g. IHC3+. In some embodiments, the HER2×HER2 bispecific antigen-binding molecules, including HER2× HER2 ADCs, bind cells expressing intermediate levels of HER2, e.g. IHC2+. In some embodiments, the HER2×HER2 bispecific antigen-binding molecules, including HER2× HER2 ADCs, bind poorly to cells expressing low levels of HER2, e.g. IHC1+.

In some embodiments, HER2×HER2 bispecific antigen-binding molecules, including HER2×HER2 ADCs, exhibit cell killing of intermediate or high HER2 expressing cells but not low HER2 expressors. In some aspects, cell killing is less than about 5%, less than about 4%, less than about 3%, or less than about 2% of cells expressing low levels of HER2.

In certain embodiments, the HER2×HER2 bispecific antigen-binding molecules, including HER2×HER2 ADCs, are used to treat one or more of the following cancers: breast cancer, cervical cancer, gastric cancer (e.g., gastric cancer with HER2 amplification), esophageal cancer, colorectal cancer, endometrial cancer, glioblastomata, head and neck cancer (e.g., head and neck squamous cell carcinoma [HN-SCC]), ovarian cancer, lung cancer (e.g., non-small cell lung cancer [NSCLC]), small cell lung cancer, acute myelogenous leukemia, adult T-cell leukemia, astrocytomas, bladder cancer, cholangiocarcinoma, chronic myeloid leukemia, Kaposi's sarcoma, kidney cancer, leiomyosarcomas, liver cancer, lymphomas, malignant gliomas, malignant mesothelioma, melanoma, mesothelioma, MFH/fibrosarcoma, multiple myeloma, nasopharyngeal cancer, osteosarcoma, pancreatic carcinoma, prostate cancer, renal cell carcinoma, rhabdomyosarcoma, synovial sarcoma, thyroid cancer, and Wilms' tumor.

In some aspects, the HER2×HER2 bispecific antigen-binding molecules, including HER2×HER2 ADCs, may be used to treat primary and/or metastatic tumors expressing high or intermediate levels of HER2, i.e. tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye.

In the context of the methods of treatment described herein, the HER2×HER2 bispecific antigen-binding molecules, including HER2×HER2 ADCs, may be administered as a monotherapy (i.e., as the only therapeutic agent), in combination with one or more additional therapeutic agents (examples of which are described elsewhere herein), or as an ADC (examples of which are also described elsewhere herein).

Combination Therapies and Formulations

Provided herein are compositions and therapeutic formulations comprising any of the anti-HER2 antibodies and HER2×HER2 bispecific antigen-binding molecules, including HER2×HER2 ADCs, described herein in combination with one or more additional therapeutically active components, and methods of treatment comprising administering such combinations to subjects in need thereof.

The anti-HER2 antibodies and HER2×HER2 bispecific antigen-binding molecules, including HER2×HER2 ADCs, may be co-formulated with and/or administered in combination with one or more additional therapeutically active component(s) selected from the group consisting of: another antagonist of Her2/ErbB2 (e.g., anti-ErbB2 [e.g., Trastuzumab or T-DM1 {KADCYLA®}, or trastuzumab deruxtican {T-SXD; a DNA topoisomerase 1 inhibitor}], or small molecule inhibitor of ErbB2 activity), an antagonist of another EGFR family member such as ErbB3 or ErbB4 (e.g., anti-ErbB3 or anti-ErbB4 antibody or small molecule inhibitor of ErbB3 or ErbB4 activity), a MET antagonist (e.g., an anti-MET antibody [e.g., onartuzumab, emibetuzumab, and H4H14639D] or small molecule inhibitor of MET), an EGFR antagonist (e.g., an anti-EGFR antibody [e.g., cetuximab or panitumumab] or small molecule inhibitor of EGFR [e.g., gefitinib or erlotinib]), an antagonist of EGFRvIII (e.g., an anti-EGFRvIII antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFRβ inhibitor (e.g., an anti-PDGFRβ antibody or small molecule kinase inhibitor such as, e.g., imatinib mesylate or sunitinib malate), a PDGF ligand inhibitor (e.g., anti-PDGF-A, -B, -C, or -D antibody, aptamer, siRNA, etc.), a VEGF antagonist (e.g., a VEGF-Trap such as aflibercept, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGR5 antagonist (e.g., an anti-LGR5 antibody), a monovalent $CD_2O$ antagonist (e.g., a monovalent anti-$CD_2O$ antibody such as rituximab), a CD20×CD3 bispecific antibody, a PD-1 blocking agent (e.g., an anti-PD-1 antibody such as pembrolizumab or nivolumab), etc. Other agents that may be beneficially administered in combination with antibodies provided herein include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

Illustratively, a PD-1 inhibitor such as an anti-PD-1 antibody can be combined with a HER2×HER2 antibody-drug conjugate as described herein. The target patient population includes specifically those patients with tumors that overexpress the HER2 mutation (e.g. IHC2+ or IHC3+), such as a patient with a HER2-expressing breast cancer.

Provided herein are compositions and therapeutic formulations comprising any of the anti-HER2 antibodies and HER2×HER2 bispecific antigen-binding molecules, including HER2×HER2 ADCs, described herein in combination with one or more chemotherapeutic agents. Examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The HER2×HER2 bispecific antigen-binding molecules may also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

The additional therapeutically active component(s), e.g., any of the agents listed above or derivatives thereof, may be administered just prior to, concurrent with, or shortly after the administration of a HER2×HER2 bispecific antigen-binding molecule; (for purposes of the present disclosure, such administration regimens are considered the administration of an antibody "in combination with" an additional therapeutically active component). The present disclosure includes pharmaceutical compositions in which a HER2×HER2 bispecific antigen-binding molecule is co-formulated with one or more of the additional therapeutically active component(s) as described elsewhere herein.

Administration Regimens

According to certain embodiments, multiple doses of a HER2×HER2 bispecific antigen-binding molecule, including HER2×HER2 ADCs, (or a pharmaceutical composition comprising a combination of an anti-HER2 antibody, HER2×HER2 bispecific antigen-binding molecule, or HER2×HER2 ADC, and any of the additional therapeutically active agents mentioned herein) may be administered to a subject over a defined time course. The methods according to this aspect comprise sequentially administering to a subject multiple doses of a HER2×HER2 bispecific antigen-binding molecule provided herein. As used herein, "sequentially administering" means that each dose of antibody is administered to the subject at a different point in time, e.g., on different days separated by a predetermined interval (e.g., hours, days, weeks or months). The present disclosure includes methods which comprise sequentially administering to the patient a single initial dose of a HER2×HER2 bispecific antigen-binding molecule, followed by one or more secondary doses of the HER2×HER2 bispecific antigen-binding molecule, and optionally followed by one or more tertiary doses of the HER2×HER2 bispecific antigen-binding molecule.

The terms "initial dose," "secondary doses," and "tertiary doses," refer to the temporal sequence of administration of the HER2×HER2 bispecific antigen-binding molecule. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of HER2×HER2 bispecific antigen-binding molecule, but generally may differ from one another in terms of frequency of administration. In certain embodiments, however, the amount of antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Diagnostic Uses of the Antibodies

The HER2×HER2 bispecific antigen-binding molecule of the present disclosure may also be used to detect and/or measure HER2, or HER2-expressing cells in a sample, e.g., for diagnostic purposes. For example, an anti-HER2 antibody, or fragment thereof, may be used to diagnose a condition or disease characterized by aberrant expression (e.g., over-expression, under-expression, lack of expression, etc.) of HER2. Exemplary diagnostic assays for HER2 may comprise, e.g., contacting a sample, obtained from a patient, with a HER2×HER2 bispecific antigen-binding molecule, wherein the antibody is labeled with a detectable label or reporter molecule. Alternatively, an unlabeled HER2×HER2 bispecific antigen-binding molecule can be used in diagnostic applications in combination with a secondary antibody which is itself detectably labeled. The detectable label or reporter molecule can be a radioisotope, such as $^3$H, $^{14}$C, 32P, $^{35}$S, or $^{125}$I; a fluorescent or chemiluminescent moiety such as fluorescein, or rhodamine; or an enzyme such as alkaline phosphatase, beta-galactosidase, horseradish peroxidase, or luciferase. Specific exemplary assays that can be used to detect or measure HER2 in a sample include enzyme-linked immunosorbent assay (ELISA), radioimmunoassay (RIA), immuno-PET (e.g., $^{83}$Zr, $^{64}$Cu, etc.), and fluorescence-activated cell sorting (FACS). In some embodiments, the HER2×HER2 bispecific antigen-binding molecule is labeled as described in WO 2018/044540, the entirety of which is incorporated herein by reference in its entirety. In some embodiments, the HER2×HER2 bispecific antigen is labeled to:

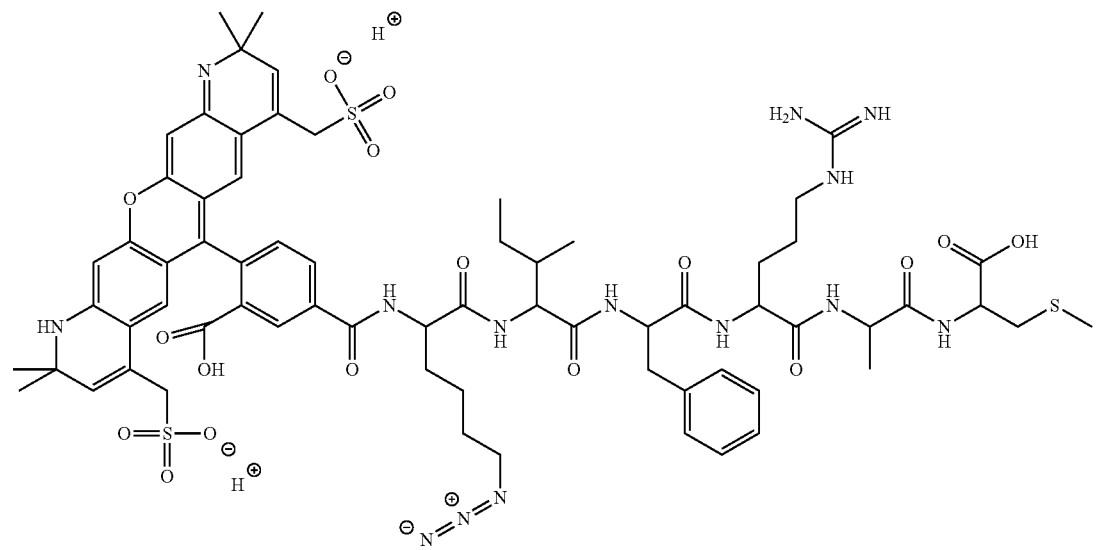

Biosensor 1

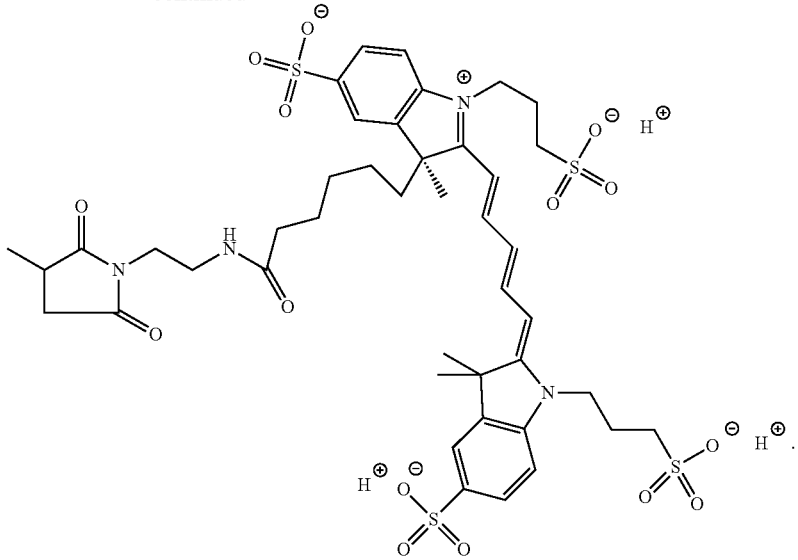

In some embodiments, a HER2×HER2 bispecific antigen-binding protein comprising the D1-HCVR amino acid sequence of SEQ ID NO: 2 and the D2-HCVR amino acid sequence of SEQ ID NO: 10 is labeled to Biosensor 1.

In some embodiments, a HER2×HER2 bispecific antigen-binding protein comprising the D1-HCVR amino acid sequence of SEQ ID NO: 32 and the D2-HCVR amino acid sequence of SEQ ID NO: 40 is labeled to Biosensor 1.

Samples that can be used in HER2 diagnostic assays according to the present disclosure include any tissue or fluid sample obtainable from a patient. Generally, levels of HER2 in a particular sample obtained from a healthy patient (e.g., a patient not afflicted with a disease or condition associated with abnormal HER2 levels or activity) will be measured to initially establish a baseline, or standard, level of HER2. This baseline level of HER2 can then be compared against the levels of HER2 measured in samples obtained from individuals suspected of having a HER2-related disease or condition.

EXAMPLES

The following examples are put forth so as to provide those of ordinary skill in the art with a complete disclosure and description of how to make and use the methods and compositions provided herein, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Comparator antibodies used in the Examples below include the following:

Trastuzumab-MCC-DM1, an anti-HER2 ADC comprising a DM1 payload. See, e.g., WO2015/031396A1. The ADC is referred to herein as CompAb1-MCC-Maytansinoid A. The parental anti-HER2 antibody, Herceptin, is referred to herein as CompAb1.

DS8201A, an anti-HER2 ADC comprising a DxD payload. See e.g., Ogitani et al. (Clinical Cancer Research, October 2016, 22(20): doi: 10.1158/1078-0432.ccr-15-2822) and Tamura (Lancet 2019). The ADC is referred to herein as CompAb1-Camptothecin-LP. The parental antibody is Herceptin, also referred to as CompAb1.

MEDI4276, a HER2×HER2 bispecific antibody ADC comprising the AZ13599185 payload. The antibody comprises SEQ ID NO: 52 (Domain IV_VL.(G4S)4 Linker_v3.DomainIV_VH.(G4S)3) and SEQ ID NO: 53 (Bs2AB_VK.hKappa). The linker payload is compound T32 shown below, in WO2015/157592, and Faria et al. (Antibodies, 2019, 8(11) doi: 10.3390/antib8010011). The parental bispecific antibody is referred to herein as CompAb2, and the ADC is referred to herein as CompAb2-Tubulysin 2A-LP.

Isotype control antibodies are referred to herein as IC1. The IC1 antibodies can be conjugated to Tubulysin 1A-LP, MCC-Maytansinoid A, Camptothecin, or Tubulysin 2A-LP.

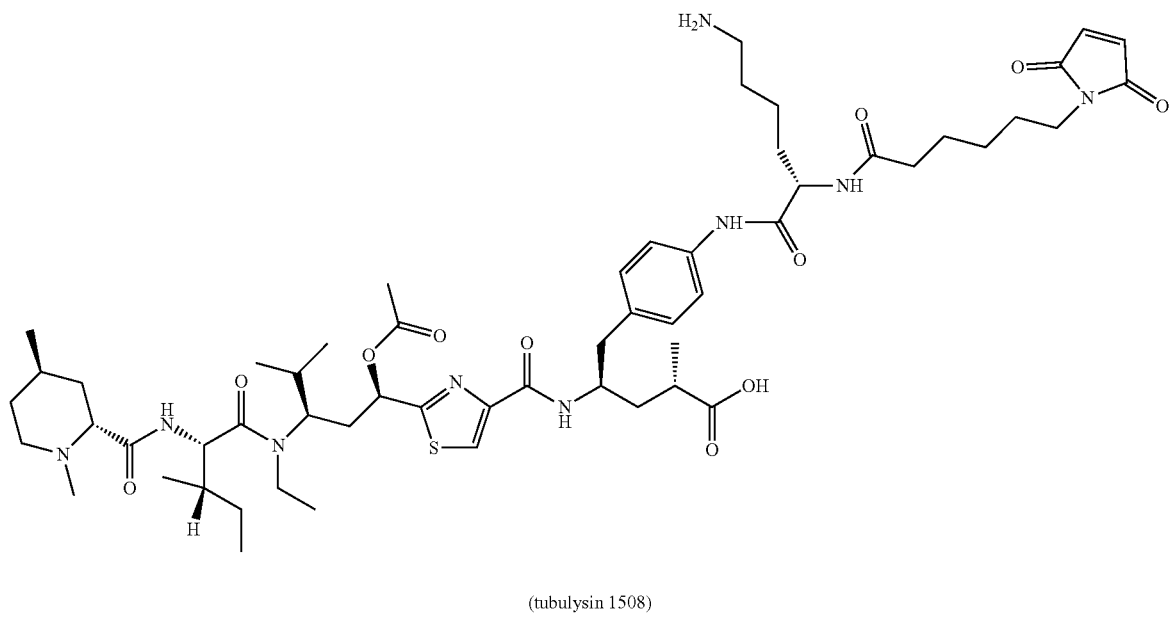

Compound T32

(tubulysin 1508)

Example 1. Generation of Anti-HER2 Antibodies

Anti-HER2 antibodies were obtained by immunizing a genetically engineered mouse comprising DNA encoding human immunoglobulin heavy and kappa light chain variable regions with an immunogen comprising recombinant human HER2 extracellular domain fused to mouse Fc, hErbB2 ecto-mFc (Company, Catalog #, Location). The mice used for the immunizations express a "universal light chain." That is, the antibodies produced in this mouse have different heavy chain variable regions but essentially identical light chain variable domains.

The antibody immune response was monitored by a HER2-specific immunoassay. When a desired immune response was achieved splenocytes were harvested and fused with mouse myeloma cells to preserve their viability and form hybridoma cell lines. The hybridoma cell lines were screened and selected to identify cell lines that produce HER2-specific antibodies. Using this technique several anti-HER2 chimeric antibodies (i.e., antibodies possessing human variable domains and mouse constant domains) were obtained. In addition, several fully human anti-HER2 antibodies were isolated directly from antigen-positive B cells without fusion to myeloma cells, as described in US 2007/0280945A1.

Certain biological properties of the exemplary anti-HER2 antibodies generated in accordance with the methods of this Example, and bispecific antibodies constructed therefrom, are described in detail in the Examples set forth below.

Example 2. Construction of Bispecific Antibodies Having Two Different Antigen-Binding Domains Specific for Different Epitopes of HER2

This example describes the construction of bispecific antibodies comprising two different antigen-binding domains (D1 and D2), wherein D1 and D2 are derived from different anti-HER2 antibodies and, consequently, bind to separate epitopes on the HER2 extracellular domain.

The individual anti-HER2 antigen-binding domains used to construct the bispecific antibodies of this Example were derived from various bivalent, monospecific anti-HER2 antibodies generated according to Example 1, herein. All HER2×HER2 bispecific antibodies described herein comprise the same ("common") light chain (comprising the light chain variable region [LCVR] amino acid sequence of SEQ ID NO:18, and light chain CDR [LCDR1, LCDR2 and LCDR3] amino acid sequences of SEQ ID NOs: 20, 22 and 24). Thus, both antigen-binding domains (D1 and D2) of all of the bispecific antibodies described in this example comprise this common light chain variable region; however, the bispecific antibodies differ from one another in terms of their D1 heavy chain variable regions (HCVRs) and heavy chain CDRs (HCDRs) and D2 heavy chain variable regions (HCVRs) and heavy chain CDRs (HCDRs). The components of the bispecific antibodies of this Example are summarized in Table 1.

In some aspects, the bispecific antibodies contain an N297Q modification in one or both heavy chains. The 297 residue within the heavy chain is identified according to the Kabat definition of numbering. As such, the HC chain sequences provided in Table 3 can comprise an N297Q modification.

TABLE 1

HER2 × HER2 Bispecific Antibody Amino Acid Sequences

SEQ ID NOs: (Amino Acid Sequences)

| | First Antigen-Binding Domain (D1) | | | | Second Antigen-Binding Domain (D2) | | | |
|---|---|---|---|---|---|---|---|---|
| Bispecific Antibody | D1-HCVR/ LCVR | D1-HCDR1/ LCDR1 | D1-HCDR2/ LCDR2 | D1-HCDR3/ LCDR3 | D2-HCVR/ LCVR | D2-HCDR1/ LCDR1 | D2-HCDR2/ LCDR2 | D2-HCDR3/ LCDR3 |
| H4H17325D (BsAb1) | 2 | 4 | 6 | 8 | 10 | 12 | 14 | 16 |
| | 18 | 20 | 22 | 24 | 18 | 20 | 22 | 24 |
| H4H17087D (BsAb2) | 32 | 34 | 36 | 38 | 40 | 42 | 44 | 46 |
| | 18 | 20 | 22 | 24 | 18 | 20 | 22 | 24 |

TABLE 2

HER2 × HER2 Bispecific Nucleic Acid Sequences

SEQ ID NOs: (Nucleic Acid Sequences)

| | First Antigen-Binding Domain (D1) | | | | Second Antigen-Binding Domain (D2) | | | |
|---|---|---|---|---|---|---|---|---|
| Bispecific Antibody | D1-HCVR/ LCVR | D1-HCDR1/ LCDR1 | D1-HCDR2/ LCDR2 | D1-HCDR3/ LCDR3 | D2-HCVR/ LCVR | D2-HCDR1/ LCDR1 | D2-HCDR2/ LCDR2 | D2-HCDR3/ LCDR3 |
| BsAb1 | 1 | 3 | 5 | 7 | 9 | 11 | 13 | 15 |
| | 17 | 19 | 21 | 23 | 17 | 19 | 21 | 23 |
| BsAb2 | 31 | 33 | 35 | 37 | 39 | 41 | 43 | 45 |
| | 17 | 19 | 21 | 23 | 17 | 19 | 21 | 23 |

TABLE 3

HER2 × HER2 Bispecific Full Length Heavy and Light Chain Amino Acid Sequences

SEQ ID NOs:

| Antibody Designation | D1 Full length Heavy Chain Amino Acid | D2 Full length Heavy Chain Amino Acid | Full length Light Chain Amino Acid |
|---|---|---|---|
| BsAb1 | 26 | 28 | 30 |
| BsAb2 | 48 | 50 | 30 |

Example 3. Surface Binding of HER2×HER2 Bispecific Antibodies

In this example, the ability of CompAb1 and HER2×HER2 bispecific antibodies to bind to the cell surface of ZR751 (ATCC Cat. #CRL-1500), JIMT1 (DSMZ Cat. #ACC589), and MDAMB361 (ATCC Cat. #HTB-27) cells was tested.

For the assay, cells were grown in cell culture treated 75 cm² flasks (Corning #430641 U) in the medium indicated above at 37° C. in 5% CO2. The day of the assay, cells were trypsinized and incubated with Violet viability marker (Biolegend #77477) in PBS (10 minutes, 4C, 1 ml). After, cells were centrifuged (1500 RPM, 5 minutes, 4° C.), resuspended in DMEM+10% FBS, plated in U-Bottom, 96-well plates at 200,000 cells/well and incubated with the indicated dilutions of Alexa 674-labeled (Thermo, Cat #A37573) antibody (20 minutes, DMEM+10% FBS, 4° C., 50 ul/well). Cells were then centrifuged and washed twice (5 minutes, DMEM+10% FBS, 4° C., 200 ul/well). After, cells were fixed with 1% paraformaldehyde (Electron Microcopy Sciences #15710) in PBS (10 minutes, 4° C., 50 ul/well), fixative was diluted with additional 150 ul PBS and cells were subjected to flow cytometry analysis using Fortessa X20 instrument (BD Biosciences).

Figure 1B:
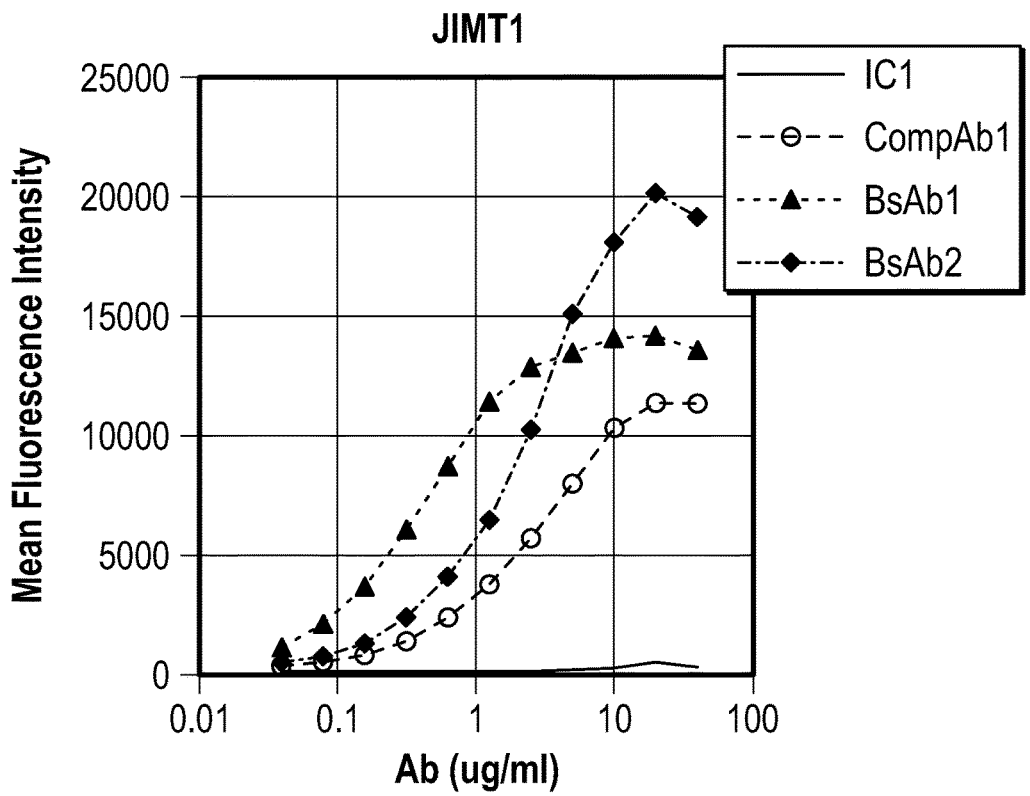
Figure 1C:
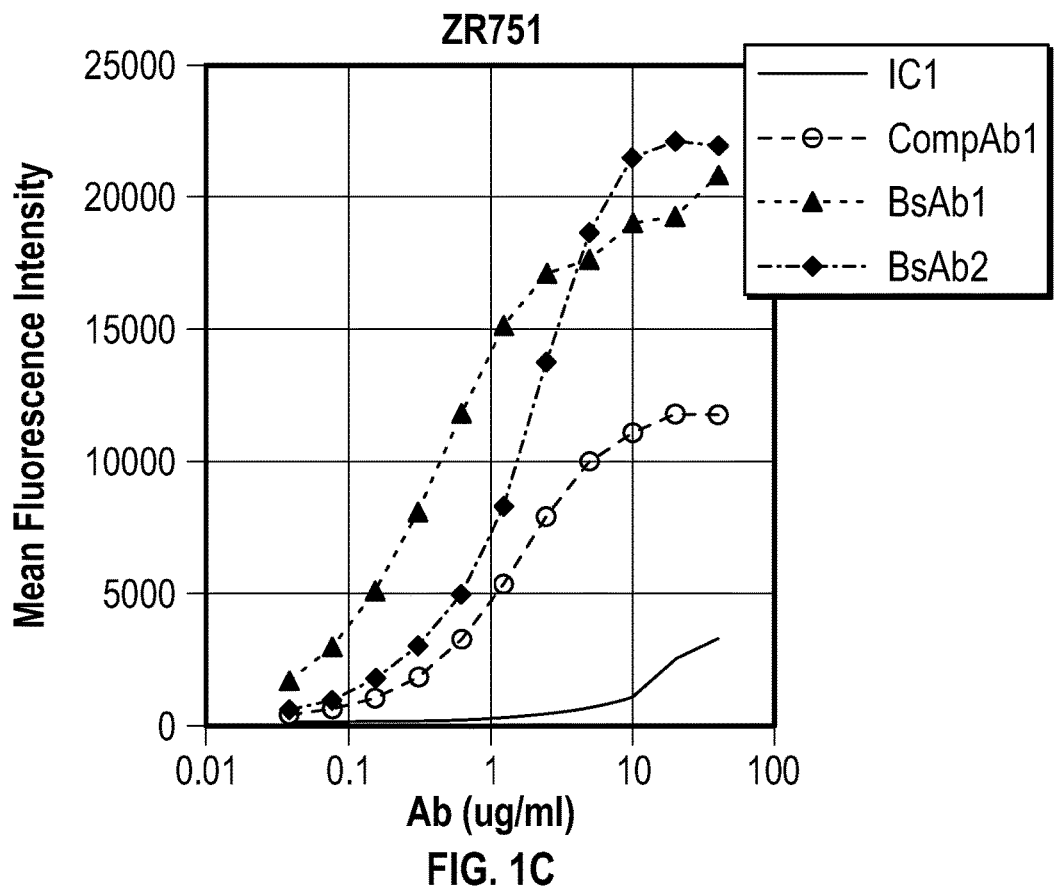

As shown in Tables 4-6, both HER2×HER2 bispecific antibodies bound with greater affinity and avidity than CompAb1 in the three cell lines tested, while the isotype control antibody (IC1) showed little or no binding. See also FIGS. 1A, 1B, and 1C.

TABLE 4

Cell Surface Binding of HER2 × HER2 Bispecific Antibodies to MDAMB361 Cells

| [Ab] ug/ml | IC1-MFI A.U. | CompAb1-MFI A.U. | BsAb1-MFI A.U. | BsAb2-MFI A.U. |
|---|---|---|---|---|
| 0 | 131 | 131 | 136 | 136 |
| 0.04 | 132 | 304 | 1236 | 474 |
| 0.08 | 133 | 465 | 2073 | 743 |
| 0.16 | 141 | 720 | 3536 | 1195 |
| 0.31 | 154 | 1259 | 5999 | 2271 |
| 0.63 | 155 | 2097 | 9007 | 3927 |
| 1.25 | 202 | 3780 | 13409 | 6908 |
| 2.5 | 273 | 6183 | 15403 | 10626 |
| 5 | 253 | 8988 | 16558 | 15771 |
| 10 | 605 | 12003 | 17556 | 21616 |
| 20 | 617 | 13863 | 17649 | 23357 |
| 40 | 558 | 14675 | 18599 | 23613 |

TABLE 5

Cell Surface Binding of HER2 × HER2 Bispecific Antibodies to JIMT1 Cells

| [Ab] ug/ml | IC1-MFI A.U. | CompAb1-MFI A.U. | BsAb1-MFI A.U. | BsAb2-MFI A.U. |
|---|---|---|---|---|
| 0 | 150 | 149 | 148 | 175 |
| 0.04 | 149 | 276 | 1165 | 472 |
| 0.08 | 151 | 481 | 2121 | 742 |
| 0.16 | 153 | 811 | 3679 | 1287 |
| 0.31 | 156 | 1377 | 6107 | 2388 |

TABLE 5-continued

Cell Surface Binding of HER2 × HER2
Bispecific Antibodies to JIMT1 Cells

| [Ab] ug/ml | IC1- MFI A.U. | CompAb1- MFI A.U. | BsAb1- MFI A.U. | BsAb2- MFI A.U. |
|---|---|---|---|---|
| 0.63 | 160 | 2396 | 8726 | 4100 |
| 1.25 | 183 | 3778 | 11468 | 6454 |
| 2.5 | 167 | 5713 | 12889 | 10250 |
| 5 | 190 | 7995 | 13523 | 15103 |
| 10 | 240 | 10320 | 14121 | 18069 |
| 20 | 516 | 11378 | 14231 | 20133 |
| 40 | 315 | 11349 | 13585 | 19164 |

TABLE 6

Binding of HER2 × HER2 Bispecific
Antibodies to ZR751 Cells

| [Ab] ug/ml | IC1- MFI A.U. | CompAb1- MFI A.U. | BsAb1- MFI A.U. | BsAb2- MFI A.U. |
|---|---|---|---|---|
| 0 | 165 | 168 | 192 | 172 |
| 0.04 | 171 | 435 | 1753 | 613 |
| 0.08 | 175 | 648 | 3024 | 1008 |
| 0.16 | 182 | 1073 | 5147 | 1800 |
| 0.31 | 199 | 1850 | 8106 | 3019 |
| 0.63 | 271 | 3283 | 11848 | 4966 |
| 1.25 | 312 | 5369 | 15167 | 8295 |
| 2.5 | 484 | 7901 | 17112 | 13761 |
| 5 | 696 | 9983 | 17650 | 18654 |
| 10 | 1081 | 11078 | 19027 | 21468 |
| 20 | 2538 | 11793 | 19250 | 22096 |
| 40 | 3316 | 11749 | 20804 | 21931 |

Example 4. HER2×HER2 Surface Binding in a Panel of Cell Lines

To test the ability of HER2×HER bispecific antibodies of the invention to bind to cells lines expressing various levels of HER2, a high content imaging assay was performed. For the assay, 16 cancer cell lines and 4 normal primary cultures were used (see Table 7). The cell lines were classified for relative expression of HER2 by Western Blot Analysis.

TABLE 7

Cell Lines and Relative HER2 Expression

| Cell Line | Source | Catalog # | Relative HER2 Expression |
|---|---|---|---|
| Primary Myocardial cells | Promo Cell | C12811 | 6% |
| Primary Prostate Epithelial cells | ATCC | PCS-440-010 | 1% |
| Primary Lung Epithelial cells | ATCC | PCS-300-010 | 1% |
| Primary Mammary Epithelial cells | ATCC | PCS-600-010 | 1% |
| MDA-MB468 | ATCC | HTB-132 | 0% |
| MDA-MB231 | ATCC | HTB-26 | 3% |
| HepG2 | ATCC | HB-8065 | 13% |
| EBC-1 (Lung Carcinoma) | | | 6% |
| MCF7 | ATCC | HTB-22 | 15% |
| T47D | ATCC | HTB-133 | 24% |
| BT483 | ATCC | HTB121 | 37% |
| ZR751 | ATCC | CRL-1500 | 39% |
| JIMT1 | DSMZ | ACC589 | 52% |
| MDA-MB361 | ATCC | HTB-27 | 82% |
| MDA-MB453 | ATCC | HTB-131 | 60% |
| SK-BR-3 | ATCC | HTB-30 | 100% |
| B1474 | ATCC | HTB-20 | 89% |

TABLE 7-continued

Cell Lines and Relative HER2 Expression

| Cell Line | Source | Catalog # | Relative HER2 Expression |
|---|---|---|---|
| N87 (NCI-N87) | ATCC | HTB-5822 | 93% |
| Calu-3 | ATCC | HTB-55 | 84% |
| SKOV-3 | ATCC | HTB-77 | 93% |

Cells were plated on collagen-coated, black wall, 96-well, optical plates (Greiner, Cat #655936) at $2.5 \times 10^5$ cells per well in their appropriate culture media and incubated overnight at 37° C. in 5% CO2. The following day, cell were incubated for 30 minutes with 10 ug/mL of Alexa647 labeled (Thermo, Cat #A37573) antibodies in 50 uL of DMEM at 4° C. After, cells were washed twice with cold DMEM+10% FBS and incubated with 4% paraformaldehyde (Electron Microcopy Sciences, Cat #15710)+0.075% Saponin (Sigma, Cat #S4521)+10 ug/ml Hoechst (Lifetech, #H3569) in PBS for 10 minutes at room temperature. After, the solution was replaced with PBS.

Images were obtained with Image Xpress$^{Micro}$ high content microscope (Molecular Devices) and quantified by dividing the mean intensity fluorescence of AF647 by the nuclear signal using ImageJ.

Figure 2:
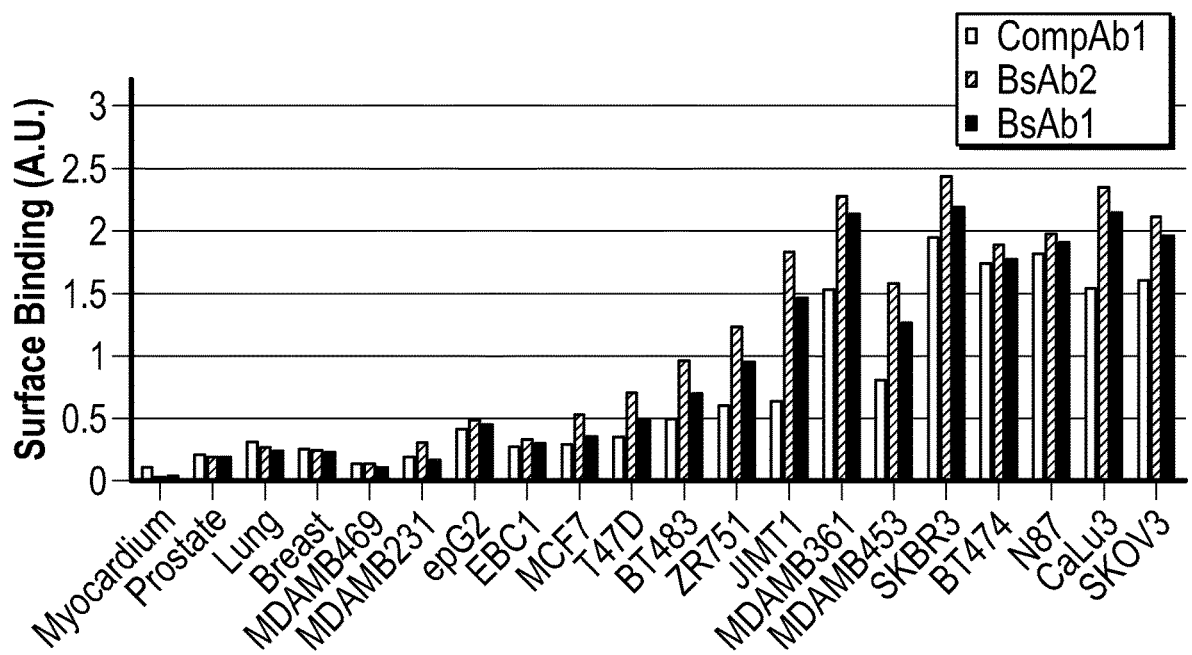
FIG. 2 is a bar graph depicting binding efficiency of the HER2 bispecific antibodies to cell types with increasing levels of HER2 expression. Both bispecific antibodies bound more efficiently than trastuzumab to cell lines expressing intermediate HER2 levels.

Table 8 shows that CompAb1 and HER2×HER2 bispecific antibodies (BsAb1 and BsAb2) efficiently bound to cancer cell lines expressing intermediate and high levels of HER2, but bound poorly to normal cells expressing low HER2 levels. In agreement with experiment from Example 3, HER2×HER2 bispecific antibodies bound more efficiently than CompAb1 to cell lines expressing intermediate HER2 levels. See also FIG. 2.

TABLE 8

Binding of HER2 × HER2 Bispecific Antibodies to
Cancer Cell Lines Expressing Various Levels of HER2

| Cancer Cell Line | CompAb1- MFI A.U. | BsAb2-MFI A.U. | BsAb1-MFI A.U. |
|---|---|---|---|
| Myocardium | 0.095432 | 0.02757 | 0.029776 |
| Prostate | 0.204242 | 0.19399 | 0.187972 |
| Lung | 0.303172 | 0.279337 | 0.239779 |
| Breast | 0.241461 | 0.254625 | 0.222378 |
| MDAMB469 | 0.130358 | 0.136112 | 0.106277 |
| MDAMB231 | 0.179825 | 0.300987 | 0.163362 |
| epG2 | 0.400157 | 0.469533 | 0.44311 |
| EBC1 | 0.2684 | 0.32991 | 0.295594 |
| MCF7 | 0.283129 | 0.544385 | 0.348432 |
| T47D | 0.341463 | 0.690112 | 0.480429 |
| B1483 | 0.494924 | 0.961112 | 0.69367 |
| ZR751 | 0.601427 | 1.208203 | 0.932819 |
| JIMT1 | 0.621217 | 1.834957 | 1.468691 |
| MDAMB361 | 1.521691 | 2.260846 | 2.125254 |
| MDAMB453 | 0.80355 | 1.57078 | 1.263122 |
| SKBR3 | 1.93848 | 2.4215 | 2.196925 |
| BT474 | 1.73622 | 1.892457 | 1.770925 |
| N87 | 1.8087 | 1.963576 | 1.905515 |
| CaLu3 | 1.530369 | 2.345307 | 2.145096 |
| SKOV3 | 1.603426 | 2.107737 | 1.955882 |

Example 5: HER2×HER2 Internalization and Cluster Formation

This example tested the ability of HER2×HER2 bispecific antibodies to form clusters and internalize on T47D cells (ATCC Catalog #HTB-133). For 2D monolayer assays, T47D cells were plated on collagen-coated 96-well optical plates (Greiner, Cat #655936) at 25,000 cells/well in complete media and incubated overnight at 37° C. in 5% CO2.

For 3D spheroids, cells were plated in low adhesion 96-well plates (Corning #4515) at 10,000 cells/well and incubated for 72 hours. The day of the assay, cells were incubated for 30 minutes with cold (4° C.) media containing 10 ug/mL of Alexa647 (Thermo, Cat #A37573) labeled antibodies. After, cells were washed twice (5 minutes, 100 ul, 4° C., complete medium) and incubated in complete media at 37° C. for 60 minutes. Cells were incubated for 30 minutes with cold (4° C.) media containing 4 ug/mL of Alexa488 anti-Human Fab (Jackson #109-547-003). After, cells were washed twice (5 minutes, 100 ul, 4° C., complete medium) and incubated with 4% paraformaldehyde (Electron Microcopy Sciences, Cat #15710)+0.075% Saponin (Sigma, Cat #S4521)+10 ug/ml Hoechst (Lifetech, #H3569) in PBS for 10 minutes at room temperature. After, the solution was replaced with PBS. Images were acquired with a Zeiss Spinning Disc Confocal Microscope and analyzed using Zeiss Zen Blue software. Quantification of the number of intracellular vesicles and surface clusters was performed in single confocal sections of representative images.

As can be seen in Tables 9 and 10, HER2×HER2 biparatopic antibody forms surface clusters and internalizes more efficiently than CompAb1.

TABLE 9

3D Spheroids (SD55)

| Ab ID | Internalized Vesicles % | Cluster % |
|---|---|---|
| CompAb1 | 4% | 24% |
| BsAb1 | 83% | 100% |
| BsAb2 | 42% | 24% |
| CompAb2 | 100% | 41% |

TABLE 10

2D monolayers (SD53)

| Ab ID | Internalized Vesicles % | Cluster % |
|---|---|---|
| CompAb1 | 11% | 6% |
| BsAb1 | 29% | 100% |
| BsAb2 | 43% | 12% |
| CompAb2 | 100% | 28% |

Example 6. DM1-Antibody Conjugation and Characterization of Conjugates

The antibodies (BsAb1, BsAb2 and 101; 10-20 mg/ml) in 50 mM HEPES, 150 mM NaCl, pH 8.0, and 10-15% (v/v) DMA were conjugated with a 5-6 fold excess of M1 (SMCC-DM1) for 2 hours at ambient temperature. The conjugates were purified by size exclusion chromatography or extensive ultrafiltration and sterile filtered. Protein concentrations were determined by UV spectral analysis. Size-exclusion HPLC established that all conjugates used were >90% monomeric, and RP-HPLC established that there was <1% unconjugated linker payload. All conjugated antibodies were analyzed by UV for linker payload loading values according to Hamblett et al. (American Association for Cancer Research. 2004 Oct. 15; 10(20):7063-70). Payload to antibody ratios are reported in Table 11.

TABLE 11

Percent Yield and Payload to Antibody Ratios for Each of the Antibody Drug Conjugates

| Antibody | Yield (%) | DAR (UV) |
|---|---|---|
| BsAb1-MCC-Maytansinoid A | 80 | 3.4 |
| BsAb2-MCC-Maytansinoid A | 80 | 3.6 |

Example 6A: Maytansinoid B Antibody Conjugation

In this example, the antibodies (BsAb1, BsAb2) were conjugated to Maytansinoid B:

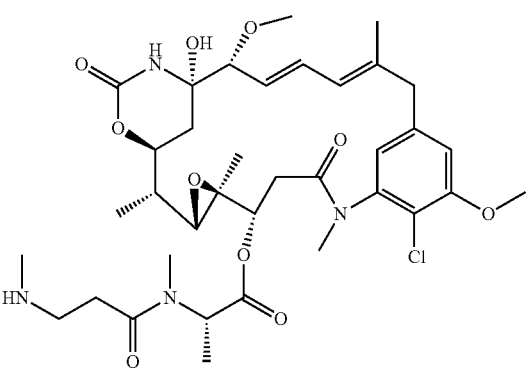

Maytansinoid B to form

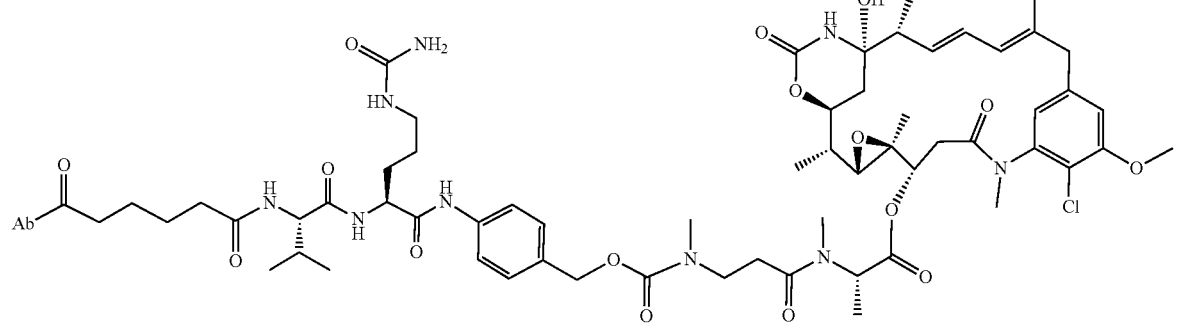

wherein Ab is BsAb1 or BsAB2.

The antibodies BsAb1 and BsAb2 10-20 mg/ml were conjugated with excess of maytansin-3-N-methyl-L-alanine-N-Me-beta-alanine-carbamyl-(p-amino)benzyl-citrulline-valine-adipoyl-succinate (Compound B¹). The conjugates were purified by size exclusion chromatography or extensive ultrafiltration and sterile filtered. Protein concentrations were determined by UV spectral analysis. All conjugated antibodies were analyzed by UV for linker payload loading values according to Hamblett et al. (American Association for Cancer Research. 2004 Oct. 15; 10(20): 7063-70) and/or by mass difference, native versus conjugated.

Compound B1 was synthesized following the methods described for "Compound 1" in US 2018-0134794 A1 (U.S. Ser. No. 15/814,095), incorporated herein by reference in its entirety.

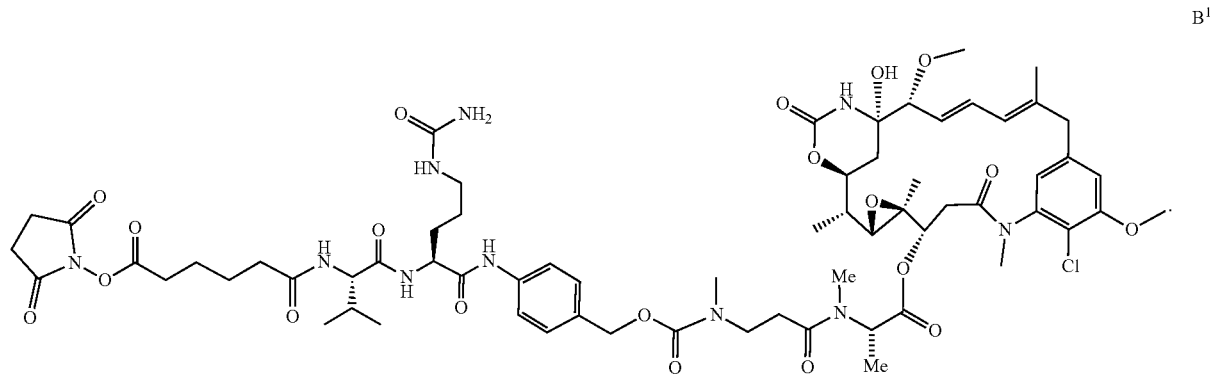 [SMILES: COc1cc2cc(c1Cl)N(C)C(=O)C[C@H](OC(=O)[C@H](C)N(C)C(=O)CCN(C)C(=O)OCc1ccc(NC(=O)[C@H](CCCNC(N)=O)NC(=O)[C@@H](NC(=O)CCCCC(=O)ON3C(=O)CCC3=O)C(C)C)cc1)[C@]1(C)O[C@H]1[C@H](C)[C@@H]1C[C@@](O)(NC(=O)O1)[C@H](OC)/C=C/C=C(\C)C2]

B¹

Example 7. Site Specific Conjugation of HER2×HER2 Bispecific Antibodies with Tubulysin 1A and Campt-1

In this example, the bispecific antibodies BsAb1 and BsAb2 were site specifically conjugated to 2 or more LP of the following structure:

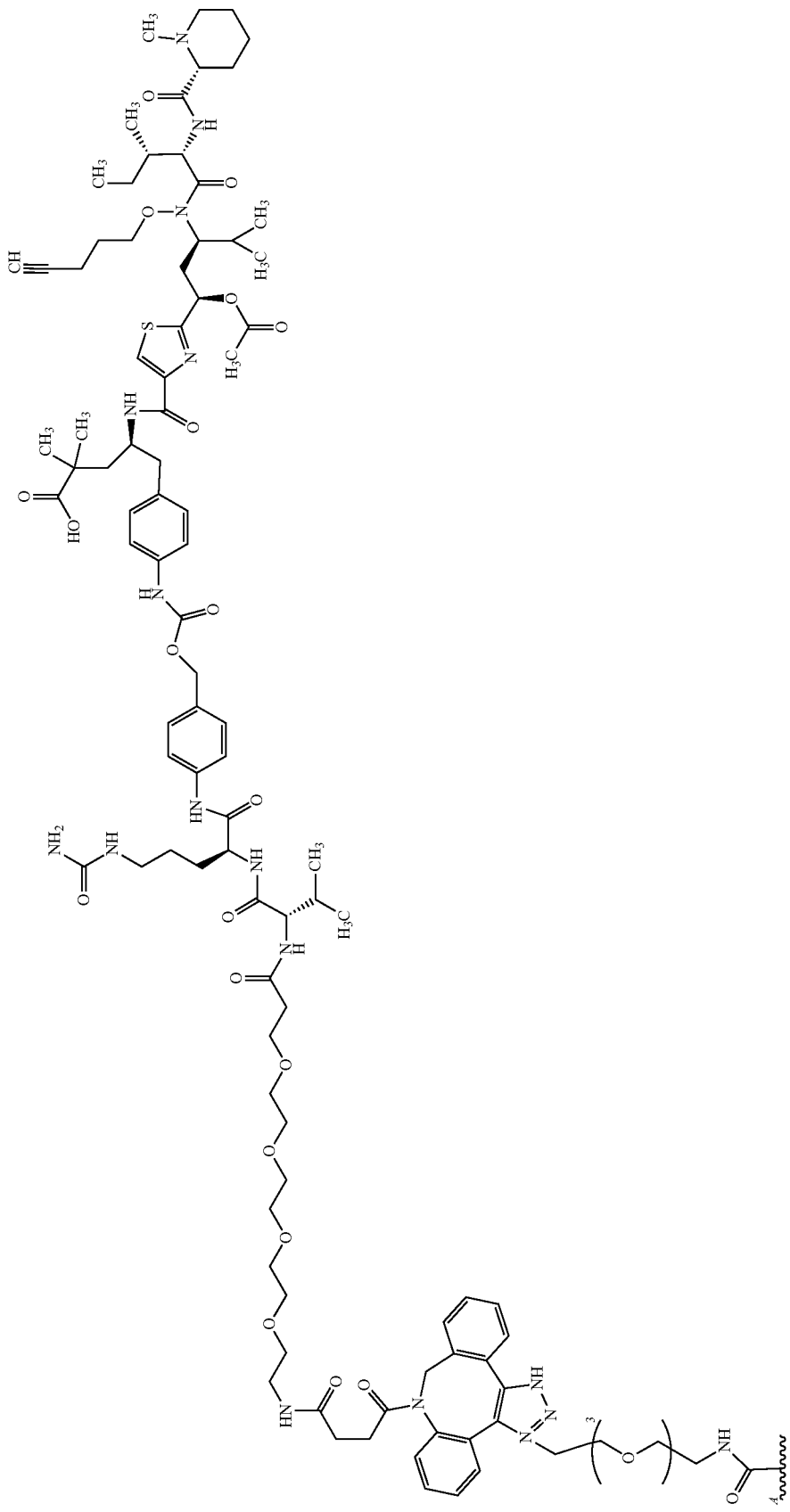

which comprises the payload tubulysin 1A. Furthermore, the bispecific antibodies BsAb1 and BsAb2 were site specifically conjugated to the following:

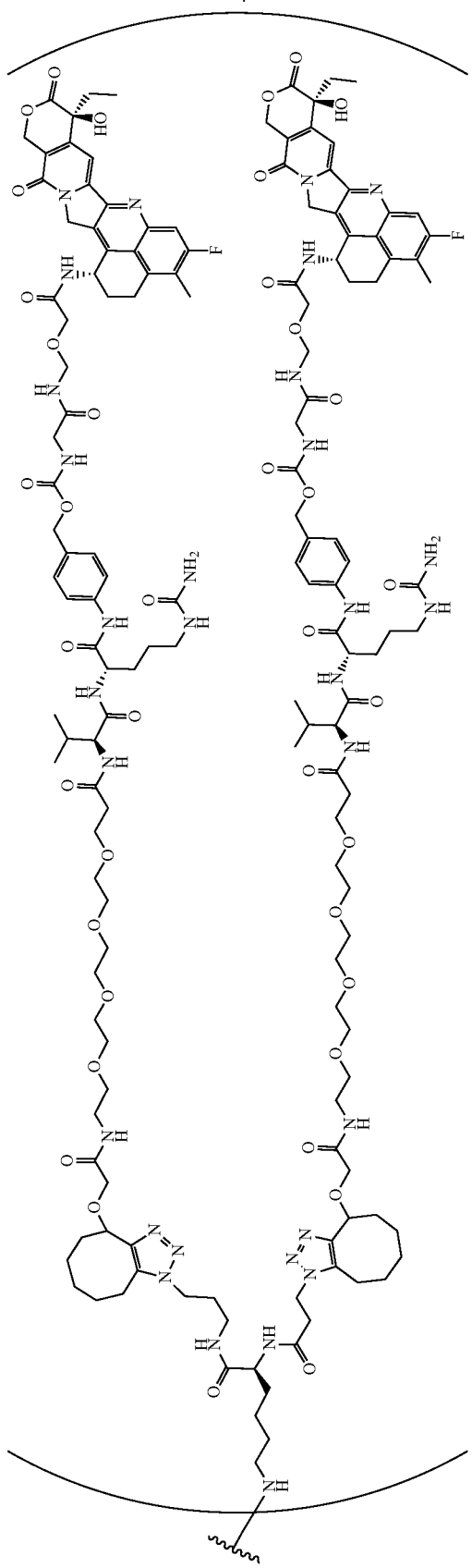

Figure 3A:
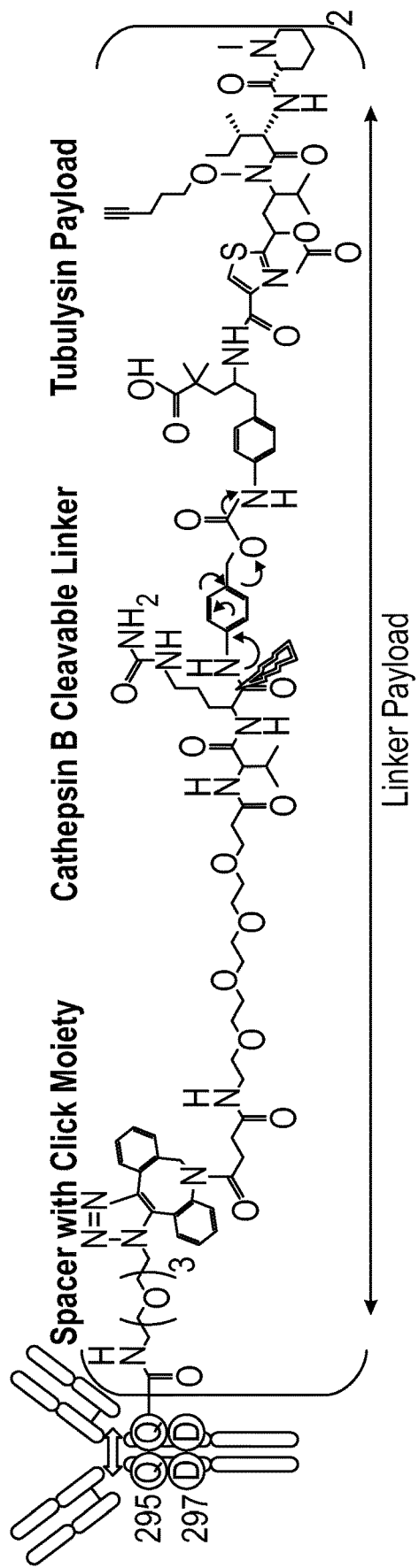
FIG. 3A depicts a monoclonal antibody with a click moiety spacer, a cathepsin B cleavable linker, and a tubulysin payload.
Figure 3B:
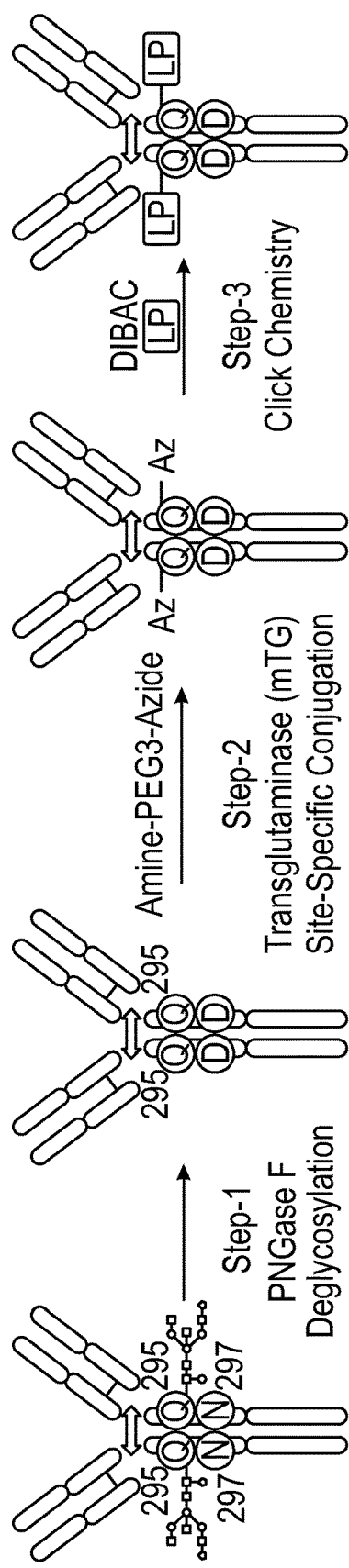
FIG. 3B depicts a process for site specific conjugation on the antibody.

Site-specific conjugates of a cyclooctyne-spacer-payload to a wild-type antibody or antigen-binding fragment thereof were produced in three steps. The first step was deglycosylation of a wild-type antibody. The second step was microbial transglutaminase (MTG) based enzymatic attachment of a small molecule, such as an azido-PEG$_3$-amine, to the Q295 site of the deglycosylated antibody (hereinafter "MTG-based" conjugation). The third step employed the attachment of a cyclooctyne-spacer-payload to the azido-functionalized antibody via a [2+3] cycloaddition, for example, the 1,3-dipolar cycloaddition between an azide and a cyclooctyne (aka copper-free click chemistry). See, Baskin, J. M.; Prescher, J. A.; Laughlin, S. T.; Agard, N. J.; Chang, P. V.; Miller, I. A.; Lo, A.; CodeHi, J. A.; Bertozzi, C. R. PNAS 2007, 104 (43), 16793-7. FIG. 3A is an example of a linker-spacer-payload having a DIBAC moiety conjugated with an azido-functionalized antibody via a [2+3] cycloaddition. This process provided site-specific and stoichiometric conjugates in about 50-80% isolated yield. FIG. 3B is an example of 3-step site specific conjugation carried out as follows:

PEG$_3$-amine added to two Q295 sites on the antibody resulting in a 404 Da increase for the 2DAR antibody-PEG$_3$-azide conjugate.

This process can also be carried out on antibodies having an N297Q modification in one or both heavy chains. In this instance, the azido-PEG$_3$-amine would be added to two Q295 sites and at least one 297Q site on the antibody resulting in a 3DAR or 4DAR antibody-PEG$_3$-azide conjugate.

Step 3: Preparation of Site-Specific Conjugates by a [2+3] Click Reaction Between the Azido-Functionalized Glutaminyl-Modified Antibodies and Cyclooctyne Containing Linker-Payload (LPs).

In general, an azido-functionalized antibody-LP conjugate was prepared by incubating the azido-functionalized glutaminyl-modified antibody with molar equivalents of LP, e.g., the compound of the following structure:

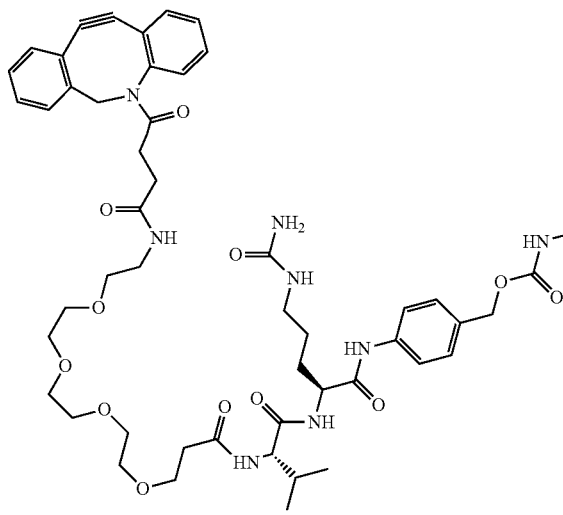
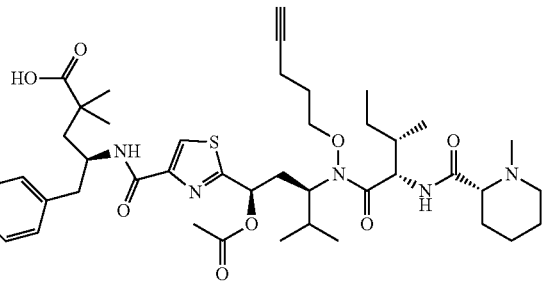

Step 1: Preparation of an Deglycosylated Antibody.

Deglycosylation was performed to expose the conjugation site. An anti-HER2 human IgG4 bispecific antibody (40 mg, 27 mg/mL in PBS; pH5.5-8.0) was mixed with PNGase F enzyme (New England BioLabs, 500,000 U/mL, 2 uL enzyme per 1 mg antibody, so 80 uL total). The reaction mixture was incubated at 37° C. overnight while gently shaking. The deglycosylation was monitored by ESI-MS. Upon reaction completion, the reaction mixture was used directly in next step.

Step 2: Preparation of an Azido-Functionalized Antibody.

The deglycosylated HER2×HER2 bispecific antibody (40 mg) in 1.5 mL PBS (pH 7.2) was incubated with 200 molar equivalents of the azido-PEG$_3$-amine (MW=218.26 g/mol) in the presence of MTG (ACTIVA TI, Ajinomoto, Japan) (0.06 mg MTG per mg antibody). The reaction was incubated at 37° C. for 4 h then 25° C. overnight while gently mixing. The reaction was monitored by ESI-MS. Upon reaction completion, excess azido-PEG$_3$-amine and MTG were removed by SEC (Superdex 200 PG, GE Healthcare), to generate the azido-functionalized antibody. The azidodissolved in a suitable organic solvent (e.g., DMSO, DMF or DMA; reaction mixture contains 10-20% organic solvent, v/v) at 25° C. to 37° C. for 3-24 h. The progress of the reaction was monitored by ESI-MS. Absence of azido-functionalized antibody (mAb-PEG$_3$-N$_3$) indicated completion of the conjugation. The excess linker-payload (LP) and organic solvent were removed by desalting column or size exclusion chromatography (SEC). The purified conjugate was analyzed by SEC-HPLC and ESI-MS. Conjugates' monomer purity was >99% by SEC-HPLC analysis.

Figure 4:
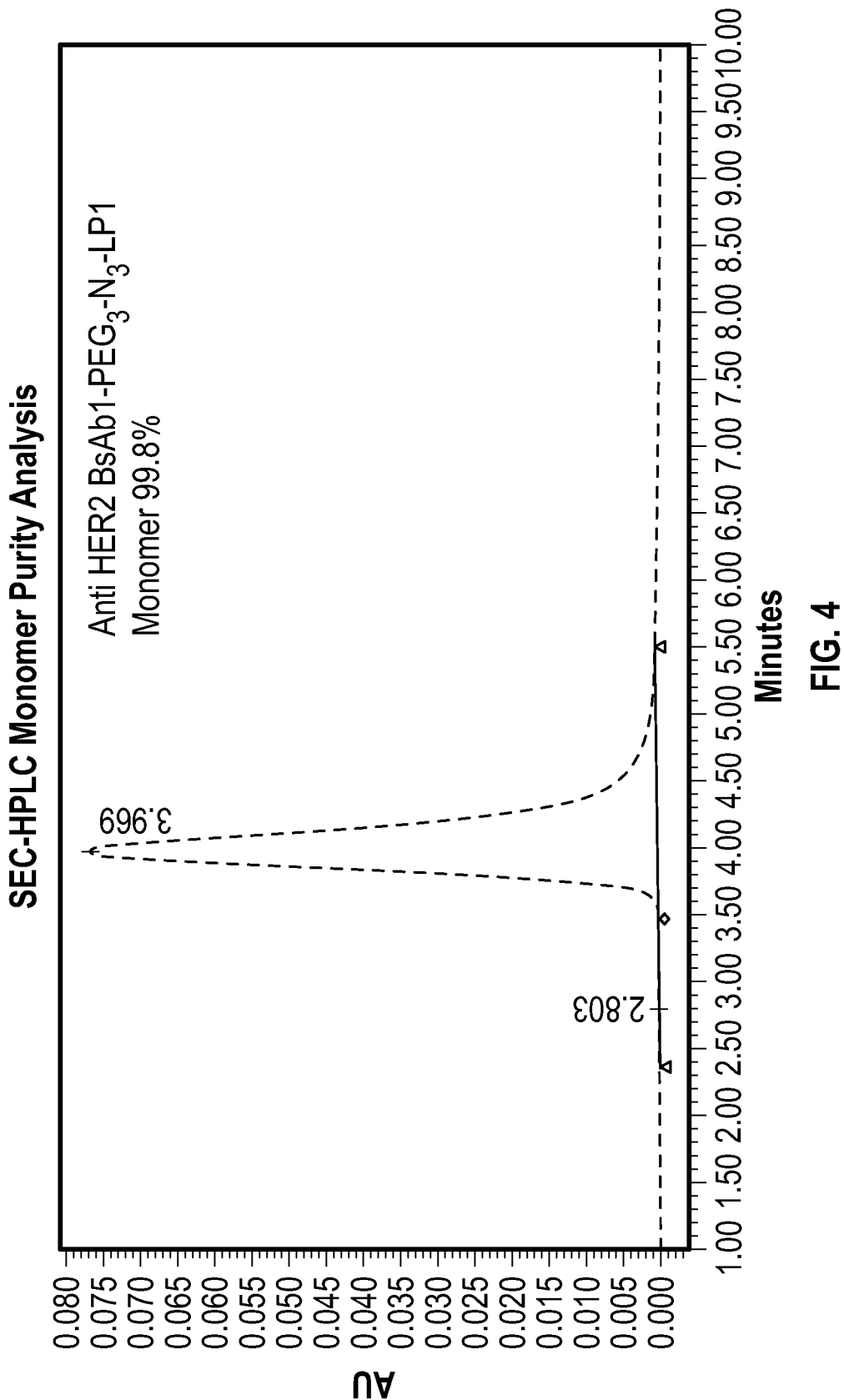
FIG. 4 provides SEC-HPLC analyses of the HER2 bispecific antibody-drug conjugates.

In a specific example, the azido-functionalized HER2× HER2 antibody, e.g. BsAb1 BsAb2, (31 mg) in 2.4 mL PBS was treated with six equivalents of Tubulysin 1A-LP (conc. 10 mg/mL in DMA) at 30° C. overnight. The excess linker payload (LP) was removed by SEC (Superdex 200 PG, GE Healthcare). The final product was characterized by UV, SEC-HPLC (see FIG. 4), and ESI-MS.

In a similar fashion, BsAb1 and BsAb2, both azido functionalized with a bis azido-alkyl substituted amine (bisSP1) as described at Q295, were treated with CAMPT-1-LP, which has the structure below, to provide BsAb1-Campt1 and BsAb2-Campt1, shown below.

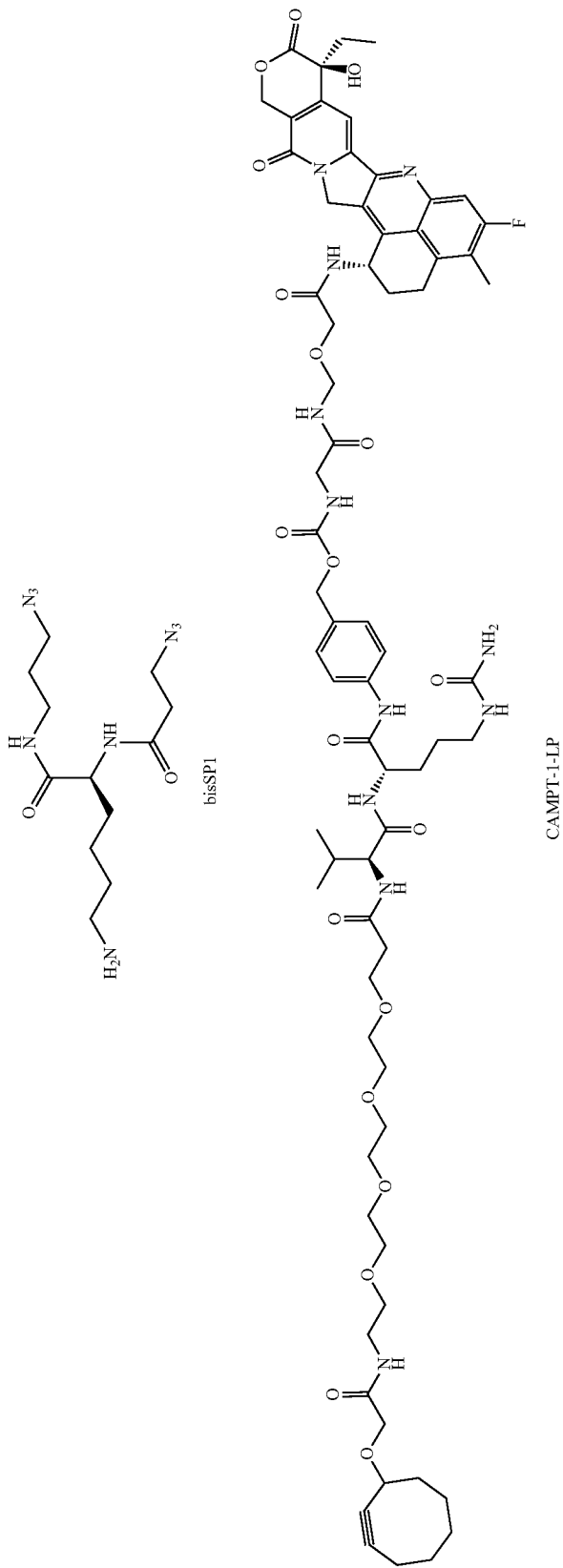

-continued
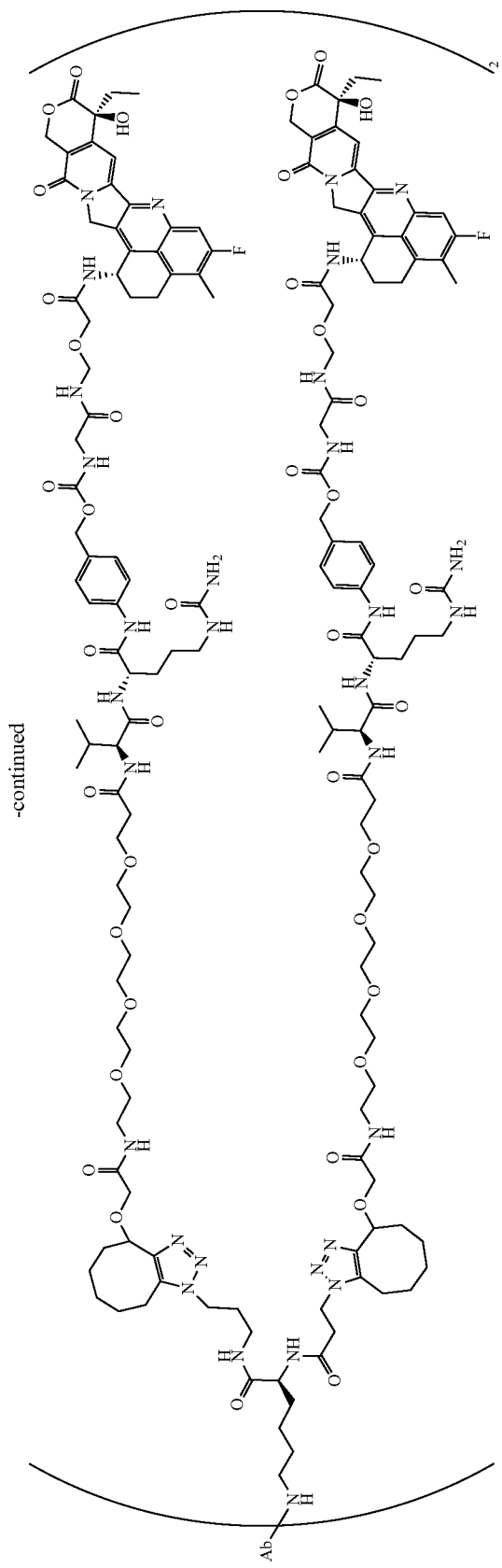
Ab = BsAb1: BsAb1-Campt1; Ab-BsAb2: BsAb2-Campt1

CAMPT-1-LP (i.e., LP1) is synthesized as described in Scheme 1 and in Examples i-iii, below. Starting material L1-1 (CAS 2226472-26-8) was synthesized according to WO2018089373A2, incorporated by reference herein in its entirety.
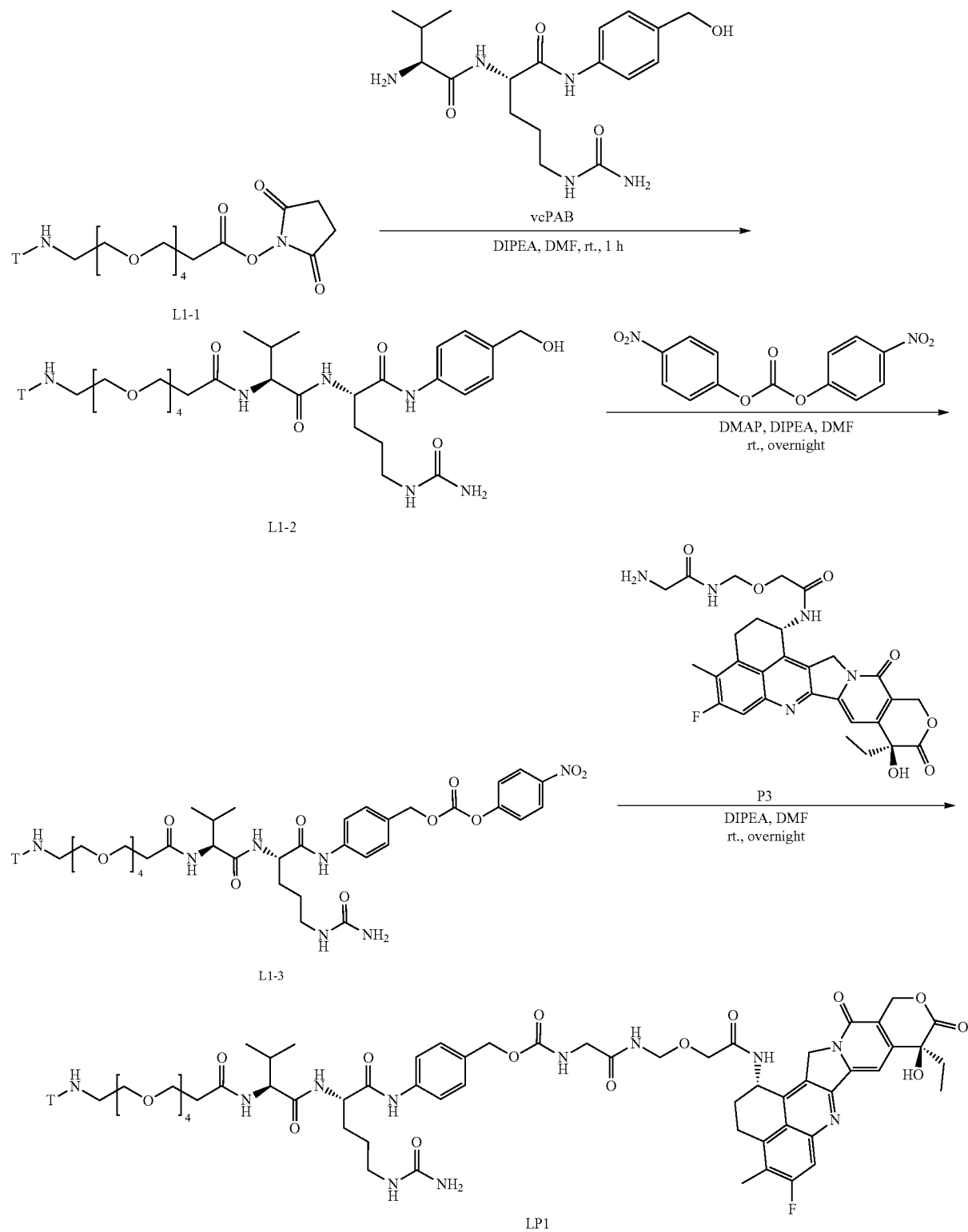
Scheme 1. Synthesis of vcPAB-carbamate linker-payload CAMPT-1-LP L1, LP1, T = 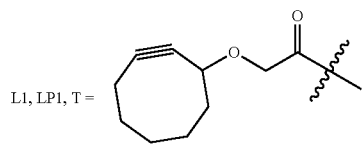

Example i: N-[(1S)-1-{[(1S)-4-(Carbamoylamino)-1-{[4-(hydroxymethyl)phenyl] carbamoyl}butyl] carbamoyl}-2-methylpropyl]-1-[2-(cyclooct-2-yn-1-yloxy)acetamido]-3,6,9,12-tetraoxapentadecan-15-amide (L1-2)

(L1-2)

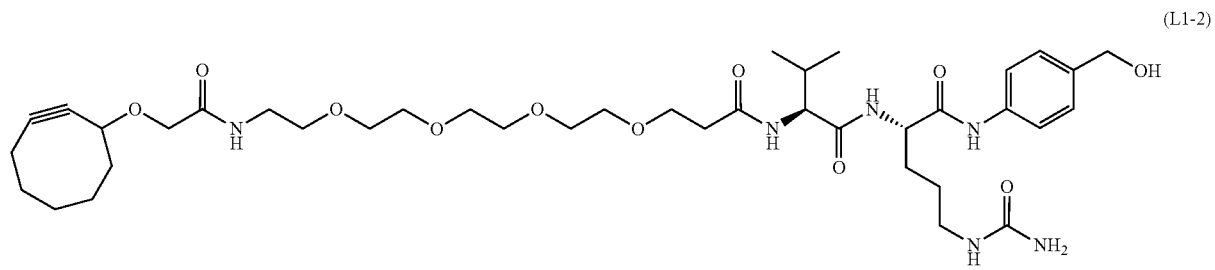 [SMILES: CC(C)[C@H](NC(=O)CCOCCOCCOCCOCCNC(=O)COC1C#CCCCCC1)C(=O)N[C@@H](CCCNC(N)=O)C(=O)Nc1ccc(CO)cc1]

To a solution of compound L1-1 (0.17 g, 0.33 mmol) in DMF (10 mL) were added DIPEA (0.13 g, 1.0 mmol) and vcPAB (0.13 g, 0.34 mmol) successively, and the reaction mixture was stirred at RT for an hour. Reaction completion was monitored by LCMS. The resulting mixture was directly purified by reversed phase flash chromatography (0-80% acetonitrile in water) to give compound L1-2 (0.18 g, 70% yield) as a colorless oil. ESI m/z: 791.3 (M+H)+. $^1$H NMR (400 MHz, DMSO$_{d6}$) δ 9.91 (s, 1H), 8.11 (d, J=8.4 Hz, 1H), 7.89 (d, J=8.8 Hz, 1H), 7.61 (t, J=5.6 Hz, 1H), 7.55 (d, J=8.4 Hz, 2H), 7.23 (d, J=8.4 Hz, 2H), 5.98 (t, J=5.6 Hz, 1H), 5.42 (s, 2H), 5.10 (br s, 1H),), 4.43 (s, 2H), 4.39-4.37 (m, 1H), 4.30-4.21 (m, 2H), 3.87 (d, J=14.8 Hz, 1H), 3.75 (d, J=14.8 Hz, 1H), 3.62-3.58 (m, 2H), 3.50-3.46 (m, 12H), 3.43 (t, J=6.0 Hz, 2H), 3.27-3.22 (m, 2H), 3.06-2.92 (m, 2H), 2.41-2.32 (m, 2H), 2.26-2.05 (m, 3H), 1.99-1.66 (m, 6H), 1.62-1.55 (m, 3H), 1.44-1.35 (m, 3H), 0.89 (d, J=6.8 Hz, 3H), 0.83 (d, J=6.8 Hz, 3H) ppm.

Example ii: {4-[(2S)-5-(Carbamoylamino)-2-[(2S)-2-{1-[2-(cyclooct-2-yn-1-yloxy) acetamido]-3,6,9,12-tetraoxapentadecan-15-amido}-3-methylbutanamido]pentanamido]phenyl} methyl 4-nitrophenyl carbonate (L1-3)

(L1-3)

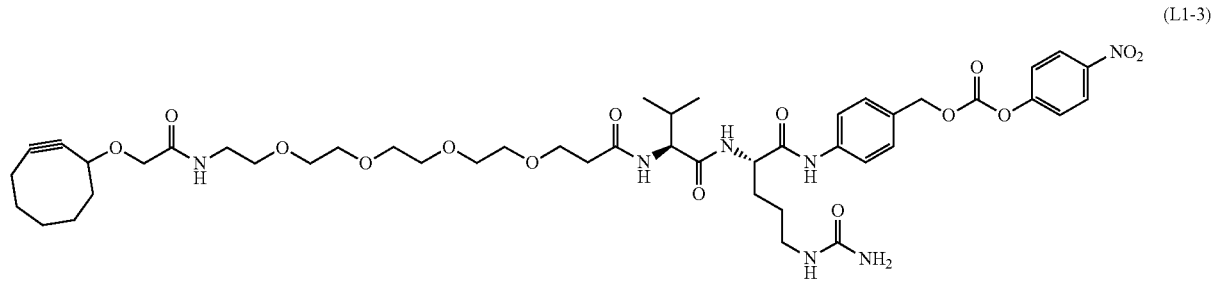 [SMILES: CC(C)[C@H](NC(=O)CCOCCOCCOCCOCCNC(=O)COC1C#CCCCCC1)C(=O)N[C@@H](CCCNC(N)=O)C(=O)Nc1ccc(COC(=O)Oc2ccc([N+](=O)[O-])cc2)cc1]

A suspension of compound L1-2 (80 mg, 0.10 mmol), DMAP (12 mg, 0.10 mmol) and DIPEA (26 mg, 0.20 mmol) in dry DMF (5 mL) was stirred at RT for 10 minutes before the addition of bis(4-nitrophenyl) carbonate (61 mg, 0.20 mmol). The reaction mixture was stirred at RT for 2 hours. Reaction completion was monitored by LCMS. The resulting mixture was directly purified by reversed phase flash chromatography (0-80% acetonitrile in water) to give compound L1-3 (53 mg, 55% yield) as a white solid. ESI m/z: 956.3 (M+H)+.

Example iii: {4-[(2S)-5-(Carbamoylamino)-2-[(2S)-2-{1-[2-(cyclooct-2-yn-1-yloxy)acetamido]-3,6,9,12-tetraoxapentadecan-15-amido}-3-methylbutanamido]pentanamido] phenyl}methyl N-({[({[(10S,23S)-10-ethyl-18-fluoro-10-hydroxy-19-methyl-5,9-dioxo-8-oxa-4,15-diazahexacyclo[14.7.1.0$^{2,14}$.0$^{4,13}$.0$^{6,11}$.0$^{20,24}$]tetracosa-1,6(11),12,14,16,18,20(24)-heptaen-23-yl]carbamoyl}methoxy)methyl]carbamoyl}methyl)carbamate (LP1/CAMPT-1-LP)

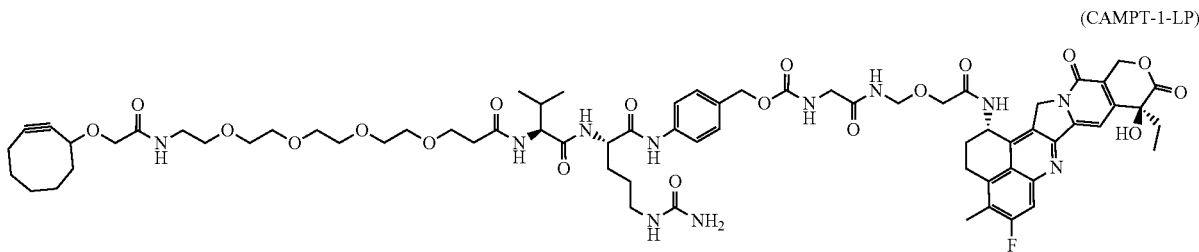 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)OCc1ccc(NC(=O)[C@H](CCCNC(N)=O)NC(=O)[C@@H](NC(=O)CCOCCOCCOCCOCCNC(=O)COC2C#CCCCCC2)C(C)C)cc1)CC3]

(CAMPT-1-LP)

To a yellow solution of compound L1-3 (16 mg, 17 μmol) and Exatecan mesylate (12 mg, 17 μmol) in dry DMF (2 mL) was added DIPEA (6.5 mg, 51 μmol), and the clear reaction solution was stirred at RT for 2 hours. Reaction completion was monitored by LCMS. The resulting mixture was directly purified by reversed phase flash chromatography (0-60% acetonitrile in aq. TFA (0.01%)) to give linker-payload LP1 (15 mg, 63% yield as TFA salt) as a white solid. ESI m/z: 698.8 (M/2+H)$^+$. $^1$H NMR (400 MHz, DMSO$_{d6}$) δ 9.99 (s, 1H), 8.80 (t, J=6.8 Hz, 1H), 8.50 (d, J=9.2 Hz, 1H), 8.12 (d, J=7.2 Hz, 1H), 7.87 (d, J=8.8 Hz, 1H), 7.79 (d, J=10.8 Hz, 1H), 7.62-7.58 (m, 3H), 7.42 (t, J=6.0 Hz, 1H), 7.31 (s, 1H), 7.28 (d, J=8.4 Hz, 2H), 6.53 (br s, 1H), 5.98 (t, J=5.2 Hz, 1H), 5.63-5.57 (m, 1H), 5.46-5.37 (m, 3H), 5.21 (s, 2H), 4.93 (s, 2H), 4.63 (d, J=6.4 Hz, 2H), 4.41-4.35 (m, 1H), 4.29-4.21 (m, 2H), 4.02 (s, 2H), 3.87 (d, J=14.4 Hz, 1H), 3.75 (d, J=14.8 Hz, 1H), 3.63-3.58 (m, 4H), 3.50-3.48 (m, 12H), 3.46-3.41 (m, 2H), 3.27-3.24 (m, 2H), 3.23-3.12 (m, 2H), 3.07-2.91 (m, 2H), 2.47-2.45 (m, 0.5H), 2.41-2.33 (m, 4.5H), 2.25-2.04 (m, 5H), 1.99-1.69 (m, 9H), 1.63-1.54 (m, 3H), 1.44-1.33 (m, 3H), 0.88-0.82 (m, 9H) ppm. (The proton of TFA was not observed). $^{19}$F NMR (376 MHz, DMSO$_{d6}$) δ -74 (TFA), -111 (Ar—F) ppm.

Shown in Table 12 is a list of DAR (ESI-MS) values for the synthesized antibody tubulysin and camptothecin conjugates (ADCs).

Characterization of Antibody and ADCs by SEC-HPLC and LC-ESI-MS

The purified conjugates were analyzed by SEC-HPLC and ESI-MS, with representative SEC and ESI-MS.

Analytical SEC experiments were run using a Waters 1515 instrument, on a Superdex™ 200 Increase (1.0×30 cm) column, at flow rate of 0.80 mL/min using PBS pH 7.2 and monitored at λ=280 nm using a Waters 2998 PDA. An analytic sample was composed of 30-80 μL of test sample. The SEC results in FIG. 4 indicate typical retention times for monomeric mAb and conjugates thereof, with minimal aggregation or degradation.

Measurement of intact mass for the ADC samples by LC-ESI-MS was performed to determine drug-payload distribution profiles and to calculate the average DAR. Each testing sample (20-50 ng, 5 μL) was reduced by DTT then loaded onto an Acquity UPLC Protein BEH C$_4$ column (10K psi, 300 Å, 1.7 μm, 75 μm×100 mm; Cat No. 186003810). After desalting for 3 min, the protein was eluted, and mass spectra were acquired by a Waters Synapt G2-Si mass spectrometer. As summarized in Table 12, most site-specific ADCs have near 2DAR.

TABLE 12

Antibody Drug Conjugate DARs

| ADC | | DAR (by ESI-MS) |
|---|---|---|
| BsAb1-Tubulysin 1A-LP | Anti HER2 BsAb1-PEG$_3$-N$_3$-Tubulysin 1A-LP | 2.1 |
| BsAb2-Tubulysin 1A-LP | Anti HER2 BsAb2-PEG$_3$-N$_3$-Tubulysin 1A-LP | 2.1 |
| BsAb1-CAMPT1 | Anti-HER2 BsAb1-subsituted alkyl amine-(N$_3$)$_2$-CAMPT-1-LP | 5.2 |
| BsAb2-CAMPT1 | Anti-HER2 BsAb1-subsituted alkyl amine-(N$_3$)$_2$-CAMPT-1-LP | 3.8 |
| IC1-Tubulysin 1A-LP | Isotype mAb-PEG$_3$-N$_3$-Tubulysin 1A-LP | 2.0 |
| IC1-CAMP1 | Isotype-substituted alkyl amine-(N$_3$)$_2$-CAMP-1-LP | 3.8 |

The ADCs generated in this experiment were used in the following Examples.

Example 8. Surface Plasmon Resonance Derived Binding Affinities and Kinetic Constants of HER2×HER2 Human Bispecific Monoclonal Antibodies and Conjugated HER2×HER2 Human Bispecific Monoclonal Antibodies Equilibrium dissociation constants ($K_D$) values) for hErbB2.mmh binding to anti-HER2×HER2 antibodies conjugated with either M830 or M1 were determined using a real-time surface plasmon resonance biosensor assay on a MASS-2 instrument. The MASS-2 sensor surface was derivatized by amine coupling with a monoclonal mouse anti-human Fc antibody (REGN2567) to capture anti-HER2×HER2 ADC and parent unmodified antibodies expressed with human constant regions. Biacore binding studies were performed in HBS-EP running buffer (0.01M HEPES pH 7.4, 0.15M NaCl, 3 mM EDTA, 0.05% v/v Surfactant P20). Human hErbB2 was prepared in-house expressing a C-terminal myc-myc-hexahistidine tag (hErbB2-MMH). Different concentrations (3-fold dilutions)

of hErbB2-MMH (ranging from 90 nM to 1.1 nM) prepared in HBS-EP running buffer were injected over the anti-HER2×HER2 ADC or antibody captured surface at a flow rate of 30 μL/min. Association of hErbB2-MMH to each of the captured ADCs and monoclonal antibodies was monitored for 3 minutes. Subsequently, hErbB2-MMH dissociation was monitored for 10 minutes in HBS-EP running buffer. Anti-human Fc surface was regenerated by a brief injection of 20 mM $H_3PO_4$. All binding kinetic experiments were performed at 25° C.

Kinetic association ($k_a$) and dissociation ($k_d$) rate constants were determined by fitting the real-time sensorgrams to a 1:1 binding model using Scrubber 2.0c curve fitting software. All sensorgrams were double referenced by subtracting buffer injection sensorgram signal from the corresponding analyte sensorgram, thereby removing artifacts caused by dissociation of the antibody from the capture surface. Binding dissociation equilibrium constants ($K_D$) and dissociative half-lives (t1/2) were calculated from the kinetic rate constants as:

$$K_D(M) = k_d/k_a, \text{ and } t1/2(\min) = \ln 2/(60 \times k_d)$$

After, cells were washed twice (5 minutes, 100 ul, 4 C, complete medium), recording medium was added (DPBS+2% FBS+10 mM HEPES) and confocal live imaging was started immediately afterwards. Images were acquired with a Zeiss Spinning Disc Confocal Microscope and analyzed using Zeiss Zen Blue software. Quantification of the integrated fluorescence of Alexa 568 (cleaved biosensor) was performed in single confocal sections of 36 different fields.

Figure 5:
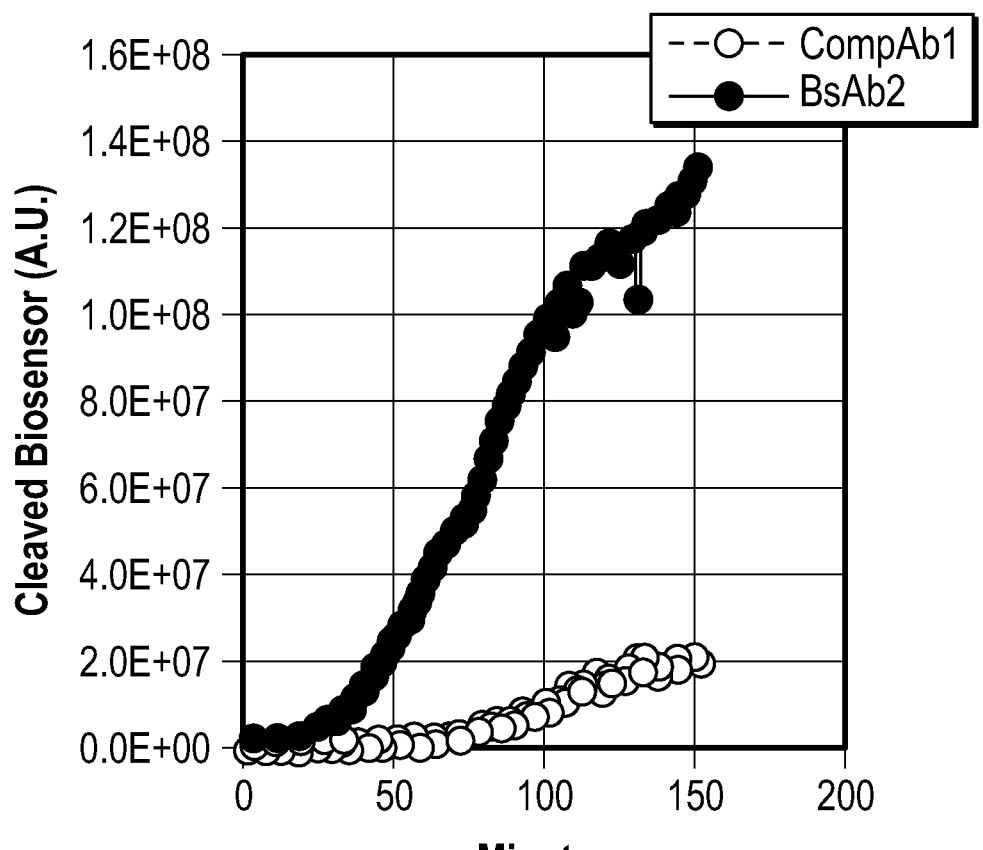
FIG. 5 depicts fluorescence of the cleaved biosensor over time, indicating that the HER2×HER2 antibody, BsAb2 (closed circle), induced processing of the cathepsin B cleavable linker more quickly relative to CompAb1 (open circle).

When the biosensor is intact it emits AF647 signal; upon internalization of biosensor-conjugated antibodies into endo/lysosomes and cleavage of the cathepsin B linker, both AF647 and AF568 signals are emitted. Table 14 shows that HER2×HER2 bispecific antibodies induce processing of the cathepsin B cleavable biosensor more efficiently than CompAb1. See also FIG. 5.

TABLE 13

Biacore Binding Affinities of Bispecific Anti-HER2 mAbs and ADCs at 25° C.

| ADC | mAb Captured (RU) | Antigen Bound (RU) | ka (1/Ms) | kd (1/s) | KD (M) | t1/2 (min) |
|---|---|---|---|---|---|---|
| BsAb1 | 155.4 ± 11.6 | 99.9 | 5.53E+05 | 3.99E−04 | 7.21E−10 | 29.0 |
| BsAb2 | 387.1 ± 0.7 | 122.1 | 2.10E+05 | ≤1.00E−05 | 4.76E−11 | ≥1155.2 |
| BsAb1-MCC-Maytansinoid A | 169.1 ± 1.4 | 93.6 | 6.90E+05 | 3.53E−04 | 5.12E−10 | 32.7 |
| BsAb2-MCC-Maytansinoid A | 207.8 ± 1.2 | 82.8 | 2.18E+05 | 1.02E−05 | 4.69E−11 | 1131.5 |
| BsAb1-Tubulysin 1A-LP | 202.3 ± 1 | 114.1 | 5.51E+05 | 3.45E−04 | 6.26E−10 | 33.5 |
| BsAb2-Tubulysin 1A-LP | 214.2 ± 0.7 | 72.7 | 2.32E+05 | ≤1.00E−05 | 4.31E−11 | ≥1155.2 |
| CompAb1 | 263 ± 0.7 | 149.4 | 2.73E+05 | 1.22E−04 | 4.47E−10 | 94.5 |
| CompAb1-MCC-Maytansinoid A | 102 ± 0.6 | 29.4 | 7.44E+04 | 1.40E−04 | 1.88E−09 | 82.4 |
| CompAb1-MCC-Maytansinoid A | 212.8 ± 0.6 | 111.6 | 2.89E+05 | 2.11E−04 | 7.28E−10 | 54.9 |
| CompAb1-L-Camptothecin | 232.2 ± 0.8 | 119.9 | 1.70E+05 | 1.54E−04 | 9.10E−10 | 74.8 |
| CompAb2 | 305.8 ± 1.3 | 177.8 | 2.90E+05 | ≤1.00E−05 | 3.45E−11 | ≥1155.2 |
| CompAb2-Tubulysin 2A-LP | 103.4 ± 1.2 | 60.6 | 4.09E+05 | 2.08E−05 | 5.09E−11 | 554.3 |
| BsAb1-CAMPT1 | 215.1 ± 1.5 | 117.1 | 5.97E+05 | 2.82E−04 | 4.72E−10 | 41.0 |
| BsAb2-CAMPT1 | 212.3 ± 1 | 77.0 | 2.58E+05 | 1.00E−05 | 3.88E−11 | 1155.2 |

As shown in Table 13, the bispecific HER2×HER2 antibodies described herein exhibited T 1/2 values of up to greater than 1155 minutes.

Example 9: Processing of Cathepsin B Cleavable Linker

The ability of CompAb1 and BsAb2 to induce cleavage of the cathepsin B cleavable linker on T47D cells (ATCC Cat. #HTB-133) was studied. T47D cells were plated on collagen-coated 96-well optical plates (Greiner, Cat #655936) at 25,000 cells/well in complete media (RPMI 1640+10% FBS+5 ml Pen/Strep/Glutamine+1 mM NaPyr+10 mM Hepes+10 ug/ml Insulin) and incubated overnight at 37° C. in 5% $CO_2$. The next day, cells were incubated for 30 minutes with cold (4° C.) media containing 10 ug/mL of fluorescent antibodies (antibodies labeled with Biosensor 1, see WO 2018/044540, incorporated by reference herein).

TABLE 14

Florescence of Cleaved Biosensor in CompAb1 Compared to BsAb2

| Time in | M378 Labeled Antibodies | |
|---|---|---|
| Mins | CompAb1 | BsAb1 |
| 3 | 1.8E+05 | 2.7E+05 |
| 5 | 3.2E+05 | 1.1E+06 |
| 7 | 1.3E+05 | 1.8E+06 |
| 9 | 2.0E+05 | 2.1E+06 |
| 11 | 2.3E+05 | 1.9E+06 |
| 13 | 1.9E+05 | 2.2E+06 |
| 15 | 2.2E+05 | 2.4E+06 |
| 17 | 2.2E+05 | 2.5E+06 |
| 19 | 3.6E+05 | 3.0E+06 |
| 21 | 6.0E+05 | 3.2E+06 |
| 23 | 7.4E+05 | 3.7E+06 |

TABLE 14-continued

Florescence of Cleaved Biosensor in CompAb1 Compared to BsAb2

| Time in Mins | M378 Labeled Antibodies | |
|---|---|---|
| | CompAb1 | BsAb1 |
| 25 | 9.7E+05 | 5.1E+06 |
| 27 | 8.7E+05 | 5.6E+06 |
| 29 | 9.1E+05 | 6.2E+06 |
| 31 | 7.1E+05 | 6.7E+06 |
| 33 | 7.9E+05 | 8.5E+06 |
| 35 | 7.7E+05 | 9.9E+06 |
| 37 | 8.7E+05 | 1.1E+07 |
| 39 | 9.8E+05 | 1.3E+07 |
| 41 | 1.0E+06 | 1.5E+07 |
| 43 | 1.1E+06 | 1.7E+07 |
| 45 | 1.5E+06 | 1.9E+07 |
| 47 | 1.4E+06 | 2.1E+07 |
| 49 | 1.5E+06 | 2.4E+07 |
| 51 | 1.6E+06 | 2.6E+07 |
| 53 | 1.7E+06 | 2.8E+07 |
| 55 | 2.0E+06 | 3.0E+07 |
| 57 | 2.1E+06 | 3.3E+07 |
| 59 | 2.2E+06 | 3.6E+07 |
| 61 | 2.3E+06 | 3.9E+07 |
| 63 | 2.1E+06 | 4.2E+07 |
| 65 | 2.2E+06 | 4.5E+07 |
| 67 | 2.6E+06 | 4.7E+07 |
| 69 | 3.0E+06 | 4.9E+07 |
| 71 | 3.2E+06 | 5.0E+07 |
| 73 | 3.3E+06 | 5.3E+07 |
| 75 | 3.7E+06 | 5.5E+07 |
| 77 | 4.0E+06 | 5.9E+07 |
| 79 | 4.5E+06 | 6.3E+07 |
| 81 | 4.8E+06 | 6.7E+07 |
| 83 | 5.4E+06 | 7.1E+07 |
| 85 | 5.4E+06 | 7.5E+07 |
| 87 | 5.6E+06 | 7.9E+07 |
| 89 | 5.9E+06 | 8.2E+07 |
| 91 | 7.1E+06 | 8.5E+07 |
| 93 | 8.2E+06 | 8.8E+07 |
| 95 | 7.9E+06 | 9.1E+07 |
| 97 | 8.5E+06 | 9.5E+07 |
| 99 | 8.8E+06 | 9.7E+07 |
| 101 | 1.0E+07 | 1.0E+08 |
| 103 | 1.0E+07 | 9.5E+07 |
| 105 | 1.2E+07 | 1.0E+08 |
| 107 | 1.2E+07 | 1.1E+08 |
| 109 | 1.4E+07 | 1.0E+08 |
| 111 | 1.4E+07 | 1.0E+08 |
| 113 | 1.4E+07 | 1.1E+08 |
| 115 | 1.5E+07 | 1.1E+08 |
| 117 | 1.7E+07 | 1.1E+08 |
| 119 | 1.4E+07 | 1.1E+08 |
| 121 | 1.5E+07 | 1.2E+08 |
| 123 | 1.6E+07 | 1.1E+08 |
| 125 | 1.7E+07 | 1.1E+08 |
| 127 | 1.8E+07 | 1.2E+08 |
| 129 | 1.7E+07 | 1.2E+08 |
| 131 | 2.0E+07 | 1.0E+08 |
| 133 | 2.0E+07 | 1.2E+08 |
| 135 | 1.8E+07 | 1.2E+08 |
| 137 | 1.8E+07 | 1.2E+08 |
| 139 | 1.8E+07 | 1.2E+08 |
| 141 | 1.8E+07 | 1.3E+08 |
| 143 | 2.0E+07 | 1.2E+08 |
| 145 | 2.1E+07 | 1.3E+08 |
| 147 | 2.0E+07 | 1.3E+08 |
| 149 | 2.1E+07 | 1.3E+08 |
| 151 | 2.0E+07 | 1.3E+08 |

Example 10. In Vitro Cell Killing by HER2×HER2 Conjugates in HER2+ Cell Lines To test the ability of CompAb1 and BsAb1 conjugated with either Maytansinoid A or Tubulysin A1-LP payloads to kill bioassay cells, in vitro cytotoxicity assays were performed. The assays were conducted on cells with varying levels of HER2 expression treated with decreasing ADC concentrations for 6 days. Cell viability was measured after treatment using Cell Titer Glow (Promega #G7571). For the assay, cells were grown in their respective media overnight at 37° C. in 5% $CO_2$. The following day either CompAb1, HER2×HER2 bispecific antibody, or control antibodies, conjugated with either MCC-Maytansinoid A or Tubulysin A1-LP payload, were added to cells at final concentrations ranging from 66.67 nM to 0.01 nM in DMEM and 10% FBS and incubated for 6 days. After the incubation, 100 uL of cell titer glow were added to each well and incubated for 5 minutes at room temperature and shaking at 500 RPM. Luminescence signal, which is proportional to the amount of APT in each well was measured with Envision 2105 multinode plate reader (Perkin Elmer). The $IC_{50}$ values were determined from a two-phase decay equation over a 10-point response curve (GraphPad Prism). All $IC_{50}$ values are expressed in nM concentration.

Table 15 shows that, in cells that express intermediate HER2 levels (ZR751 and JIMT1), the effect of CompAb1-MCC-Maytansinoid A was not different than control ADCs ($IC_{50}$ value of 30-40 nM), BsAb1-MCC-Maytansinoid A showed modest efficacy ($IC_{50}$ value of 6-7 nM), CompAb1-Tubulysin 1A-LP showed better efficacy ($IC_{50}$ value of 0.15-0.2 nM) and BsAb1-Tubulysin 1A-LP showed the most efficient cell killing of all ADCs tested ($IC_{50}$ value of 0.06-0.07 nM). In cells that express higher HER2 levels (MDAMB361, MDAMB453 and SKBR3), CompAb1-MCC-Maytansinoid A induced efficient cell killing ($IC_{50}$ value of 0.04-0.5 nM), BsAb1-MCC-Maytansinoid A showed better efficacy ($IC_{50}$ value of 0.02-0.1 nM), CompAb1-Tubulysin 1A-LP showed even better efficacy ($IC_{50}$ value of 0.006-0.008 nM) and BsAb1-Tubulysin 1A-LP again showed the most efficient cell killing of all ADCs tested ($IC_{50}$ value of 0.002-0.004 nM).

TABLE 15

Efficacy of ADCs Against Cells that Express Different HER2 Levels

| Antibody - Payload | DAR | ZR751 IC50 (nm) | JIMT1 IC50 (nm) | MDAMB453 IC50 (nm) | MDAMB361 IC50 (nm) | SKBR3 IC50 (nm) |
|---|---|---|---|---|---|---|
| IC1-MCC-Maytansinoid A | 2.9 | 40 | 40 | 20 | 9 | 9 |
| CompAb1-MCC-Maytansinoid A | 2.48 | 40 | 30 | 0.5 | 0.1 | 0.04 |

TABLE 15-continued

Efficacy of ADCs Against Cells that Express Different HER2 Levels

| Antibody - Payload | DAR | ZR751 IC50 (nm) | JIMT1 IC50 (nm) | MDAMB453 IC50 (nm) | MDAMB361 IC50 (nm) | SKBR3 IC50 (nm) |
|---|---|---|---|---|---|---|
| BsAb1 - MCC-Maytansinoid A | 2.4 | 6 | 7 | 0.1 | 0.05 | 0.02 |
| IC1-Tubulysin 1A-LP | 1.9 | 40 | 67 | 67 | 20 | 10 |
| CompAb1-Tubulysin 1A-LP | 1.9 | 0.15 | 0.2 | 0.06 | 0.008 | 0.007 |
| BsAb1-Tubulysin 1A-LP | 2.10 | 0.06 | 0.07 | 0.02 | 0.003 | 0.004 |

Example 11. In Vitro Cell Killing in Low HER2 Expressing Cell Lines

To test the killing effect of BsAb1 Tubulysin 1A-LP, BsAb2 Tubulysin 1A-LP, and Medimmune comparator HER2×HER2-Tubulysin (CompAb2-Tubulysin 2A-LP) on bioassay cells, in vitro cytotoxicity assays were performed. The assays were conducted on normal primary cultures and breast cancer cells expressing low HER2 levels. Cells were treated with decreasing ADC concentrations for 6 days and cell viability was measured after treatment using Cell Titer Glow (Promega #G7571).

For the assay, cells were grown in their respective media overnight at 37° C. in 5% CO2. The following day either BsAb1-Tubulysin 1A-LP, BsAb2-Tubulysin 1A-LP, CompAb2-Tubulysin 2A-LP, or their respective non-binding control antibodies, were added to cells at final concentrations ranging from 66.67 nM to 0.01 nM in DMEM and 10% FBS and incubated for 6 days. After the incubation, 100 uL of cell titer glow was added to each well and incubated for 5 minutes at room temperature with shaking at 500 RPM. Luminescence signal, which is proportional to the amount of APT in each well, was measured with Envision 2105 multinode plate reader (Perkin Elmer). The $IC_{50}$ values were determined from a two-phase decay equation over a 10-point response curve (GraphPad Prism). All $IC_{50}$ values are expressed in nM concentration.

Table 16 shows that BsAb1-Tubulysin 1A-LP and BsAb2-Tubulysin 1A-LP had little or no killing effect in cells expressing low HER2 levels ($IC_{50}$ value of 8->67 nM). This surprising benefit illustrates the usefulness of the ADC in killing tumor cells while not targeting normal tissues. In contrast, CompAb2-Tubulysin 2A-LP, an ADC reported to have anti-tumor effect in HER2 IHC 0+ xenografts and toxicity in humans, induced cell killing at $IC_{50}$ as low as 0.3 nM.

Example 12. Dose Dependency of HER2×HER2 Bispecific Antibodies ADCs in JIMT1 Xenografts To test the efficacy of BsAb1-Tubulysin 1A-LP in HER2 IHC2+ JIMT1 xenograft model, an in vivo tumor study was performed. For the assay, 6 week old female SCID mice (C.B-Igh-1b/IcrTac-Prkdcscid, Taconic Biosciences, n=50) were used. For implantation, JIMT1 (DSMZ Cat. #ACC589) cells were mixed with Matrigel (Corning, Cat #354234) and 150 uL of the cell and matrigel suspension containing 4×10$^6$ cells was injected to SCID mice. 11 days later, indicated ADCs were injected subcutaneously at the indicated doses to SCID mice that were randomized based on tumor size. The xenograft size for each mouse was measured using a Caliper (Roboz, Cat #RS6466).

Figure 6A:
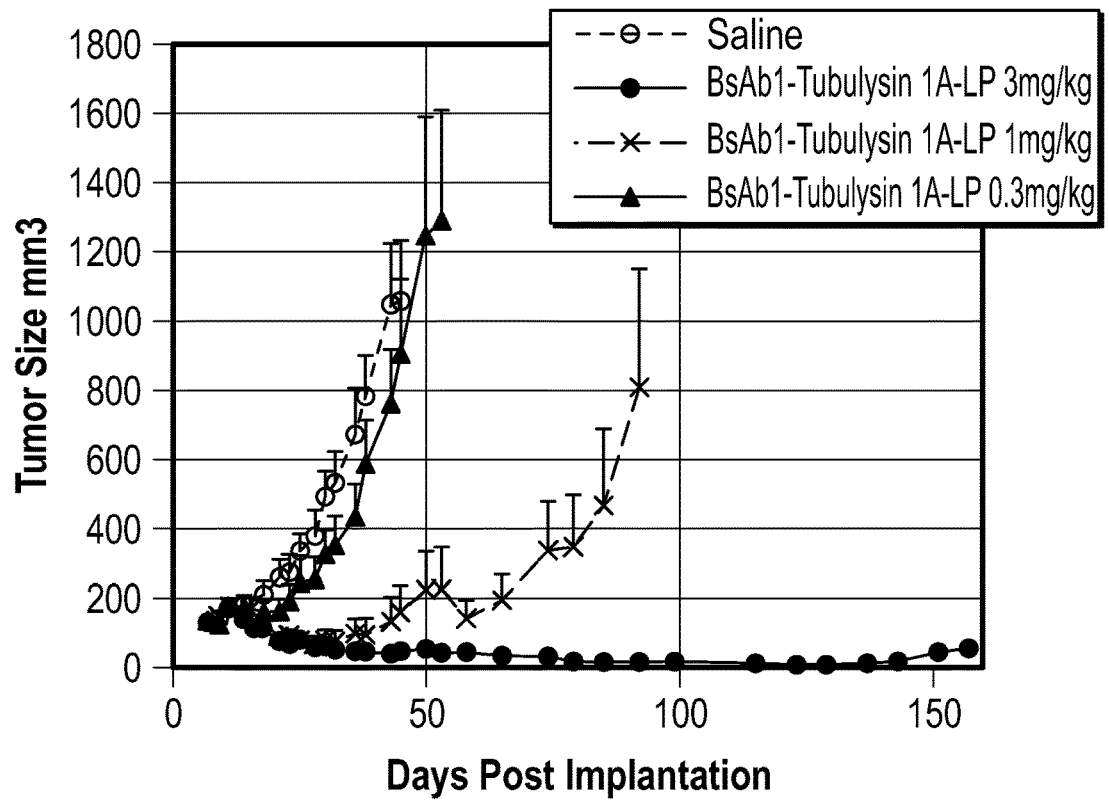
FIG. 6A and FIG. 6B depicts the efficacy of the ADCs in a HER2 IHC2+ JIMT1 xenograft model. The BsAb1-Tubulysin 1A-LP demonstrated cytotoxicity in a dose dependent fashion (3 mg/kg, black circles; 1 mg/kg, -x-; 0.3 mg/kg black triangles).
Figure 6B:
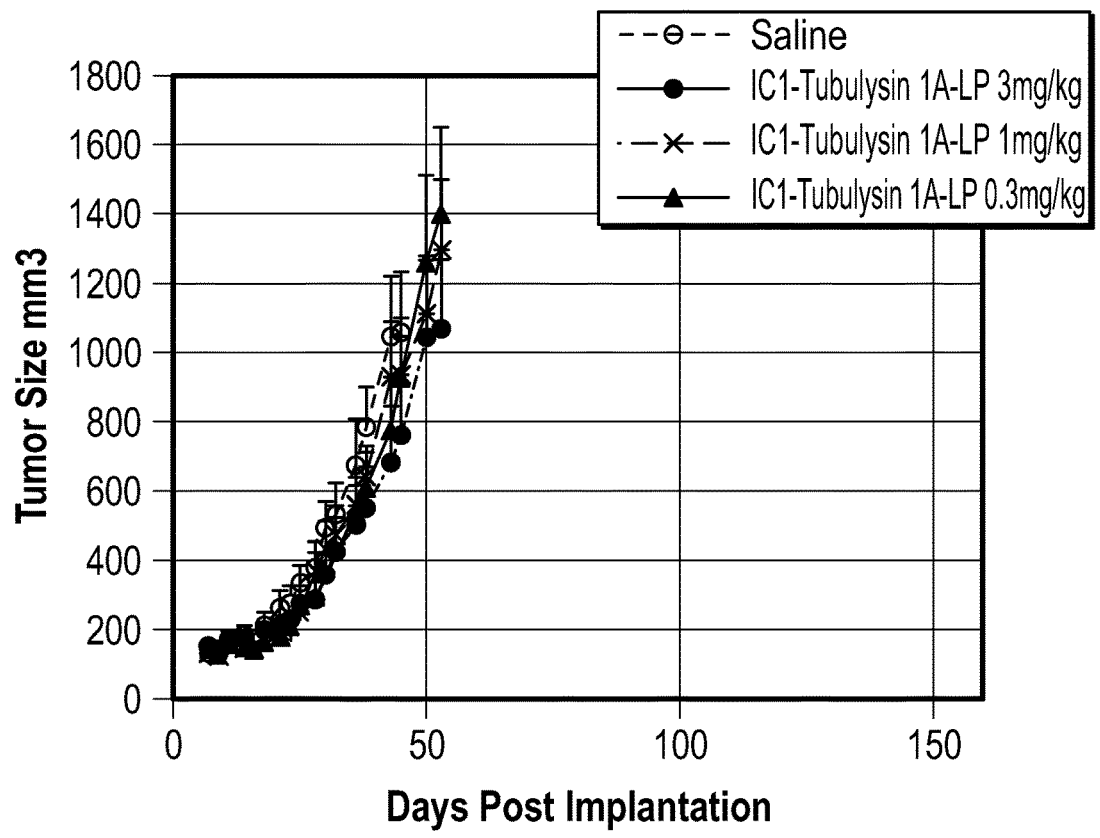

The average tumor size per treatment group for each time point measured is shown in Table 17. HER2×HER2 bispecific ADC, BsAb1-Tubulysin 1A-LP (DAR 2.1), showed tumor cell killing in a dose dependent fashion. Mice that received a single dose of 3 mg/kg HER2×HER2 bispecific ADC, BsAb1-Tubulysin 1A-LP, saw a significant and sustained reduction in JIMT1 xenograft size to an average size of 10 mm$^3$ (at 123 days). Mice that received a single dose of 1 mg/kg HER2×HER2 bispecific ADC, BsAb1-Tubulysin 1A-LP, saw a reduction in JIMT1 xenograft size to an average size of 74 mm$^3$ (at 28 days). In contrast, mice that received 3, 1, or 0.3 mg/kg isotype control ADC (IC1-Tubulysin 1A-LP; DAR 2) or saline saw little or no anti-tumor effect. See also FIG. 6A and FIG. 6B.

TABLE 16

Cytotoxicity of ADCs Against Low HER2 Expressing Cell Lines

| Ab - Payload | DAR IC50 (nm) | Myocard IC50 (nm) | Breast IC50 (nm) | Lung IC50 (nm) | Prostate IC50 (nm) | MDAMB231 IC50 (nm) | MDAMB468 IC50 (nm) | T47D IC50 (nm) |
|---|---|---|---|---|---|---|---|---|
| IC1-Tubulysin 1A-LP | 2.00 | 30.0 | 66.7 | >67 | >67 | >67 | >67 | >67 |
| IC1-Tubulysin 2A-LP | 4.00 | 1.5 | 3.0 | 9.0 | 4.0 | 2 | 5 | 4.000 |
| CompAb2-Tubulysin 2A-LP | 3.00 | 6.0 | 20.0 | >67 | >67 | 0.3 | 20 | 4.000 |
| BsAb2-Tubulysin 1A-LP | 2.10 | 30.0 | 20.0 | >67 | >67 | 50 | 67 | 8.000 |
| BsAb1-Tubulysin 1A-LP | 2.10 | 9.0 | 25.0 | >67 | 30.0 | 40 | 50 | 8.000 |

TABLE 17

JIMT1 Xenograft Tumor Size (mm³) After HER2 × HER2 Bispecific ADC and Control ADC treatment

| Day | Saline Av Average | St Error | IC1-Tubulysin 1A-LP 3 mg/kg Average | St Error | IC1-Tubulysin 1A-LP 1 mg/kg Average | St Error | IC1-Tubulysin 1A-LP 0.3 mg/kg Average | St Error | BsAb1-Tubulysin 1A-LP 3 mg/kg Average | St Error | BsAb1-Tubulysin 1A-LP 1 mg/kg Average | St Error | BsAb1-Tubulysin 1A-LP 0.3 mg/kg Average | St Error |
|---|---|---|---|---|---|---|---|---|---|---|---|---|---|---|
| 7 | 131 | 8 | 152 | 14 | 132 | 9 | 145 | 19 | 135 | 4 | 131 | 19 | 137 | 13 |
| 9 | 143 | 9 | 135 | 15 | 123 | 7 | 129 | 17 | 139 | 14 | 151 | 7 | 130 | 14 |
| 11 | 173 | 19 | 174 | 15 | 158 | 13 | 157 | 36 | 174 | 15 | 182 | 19 | 174 | 20 |
| 14 | 186 | 24 | 176 | 23 | 145 | 21 | 147 | 35 | 140 | 19 | 182 | 20 | 170 | 26 |
| 16 | 178 | 30 | 163 | 24 | 149 | 32 | 143 | 34 | 115 | 11 | 144 | 22 | 152 | 23 |
| 18 | 214 | 38 | 201 | 30 | 168 | 35 | 163 | 30 | 119 | 14 | 126 | 10 | 166 | 31 |
| 21 | 263 | 51 | 212 | 33 | 195 | 32 | 178 | 31 | 79 | 13 | 95 | 9 | 165 | 35 |
| 23 | 276 | 51 | 233 | 40 | 239 | 49 | 210 | 41 | 71 | 6 | 95 | 15 | 197 | 45 |
| 25 | 337 | 51 | 278 | 52 | 250 | 38 | 272 | 50 | 83 | 10 | 81 | 14 | 252 | 73 |
| 28 | 380 | 75 | 289 | 49 | 372 | 54 | 294 | 46 | 60 | 7 | 74 | 19 | 260 | 60 |
| 30 | 494 | 74 | 360 | 71 | 434 | 80 | 386 | 63 | 64 | 5 | 83 | 29 | 331 | 67 |
| 32 | 534 | 90 | 425 | 100 | 473 | 85 | 436 | 58 | 53 | 7 | 78 | 31 | 357 | 83 |
| 36 | 675 | 135 | 503 | 112 | 560 | 80 | 543 | 74 | 49 | 6 | 101 | 43 | 439 | 94 |
| 38 | 785 | 117 | 551 | 119 | 642 | 90 | 609 | 105 | 49 | 6 | 96 | 49 | 591 | 125 |
| 43 | 1049 | 174 | 684 | 163 | 930 | 163 | 775 | 142 | 41 | 2 | 135 | 70 | 766 | 155 |
| 45 | 1060 | 175 | 761 | 162 | 937 | 166 | 927 | 121 | 50 | 6 | 161 | 79 | 909 | 213 |
| 50 | | | 1047 | 234 | 1113 | 152 | 1264 | 250 | 56 | 6 | 226 | 113 | 1251 | 342 |
| 53 | | | 1072 | 199 | 1298 | 204 | 1402 | 250 | 45 | 4 | 228 | 122 | 1293 | 319 |
| 58 | | | | | | | | | 47 | 7 | 143 | 53 | | |
| 65 | | | | | | | | | 36 | 2 | 196 | 75 | | |
| 74 | | | | | | | | | 34 | 3 | 338 | 142 | | |
| 79 | | | | | | | | | 20 | 2 | 350 | 151 | | |
| 85 | | | | | | | | | 19 | 1 | 468 | 225 | | |
| 92 | | | | | | | | | 18 | 0 | 810 | 341 | | |
| 99 | | | | | | | | | 20 | 3 | | | | |
| 115 | | | | | | | | | 14 | 2 | | | | |
| 123 | | | | | | | | | 10 | 3 | | | | |
| 129 | | | | | | | | | 11 | 4 | | | | |
| 137 | | | | | | | | | 15 | 7 | | | | |
| 143 | | | | | | | | | 20 | 8 | | | | |
| 151 | | | | | | | | | 47 | 21 | | | | |
| 157 | | | | | | | | | 58 | 26 | | | | |

Example 13. In Vivo Efficacy of HER2×HER2 Bispecific ADCs Compared to CompAb1-MCC-Maytansinoid A To compare the efficacy of BsAb1-Tubulysin 1A-LP, BsAb2-Tubulysin 1A-LP, and CompAb1-MCC-Maytansinoid A in HER2 IHC2+ JIMT1 xenograft model, an in vivo tumor study was performed. For the assay, 6 week old female SCID mice (C.B-Igh-1b/IcrTac-Prkdcscid, Taconic Biosciences, n=50) were used. For implantation, JIMT1 (DSMZ, ACC589) cells were mixed with Matrigel (Corning, Cat #354234) and 150 uL of the cell and matrigel suspension containing 4×10⁶ cells was injected to SCID mice. 14 and 28 days later, indicated ADCs were injected subcutaneously to SCID mice that were randomized based on tumor size. The xenograft size for each mouse was measured using a Caliper (Roboz, Cat #RS6466).

Figure 7A:
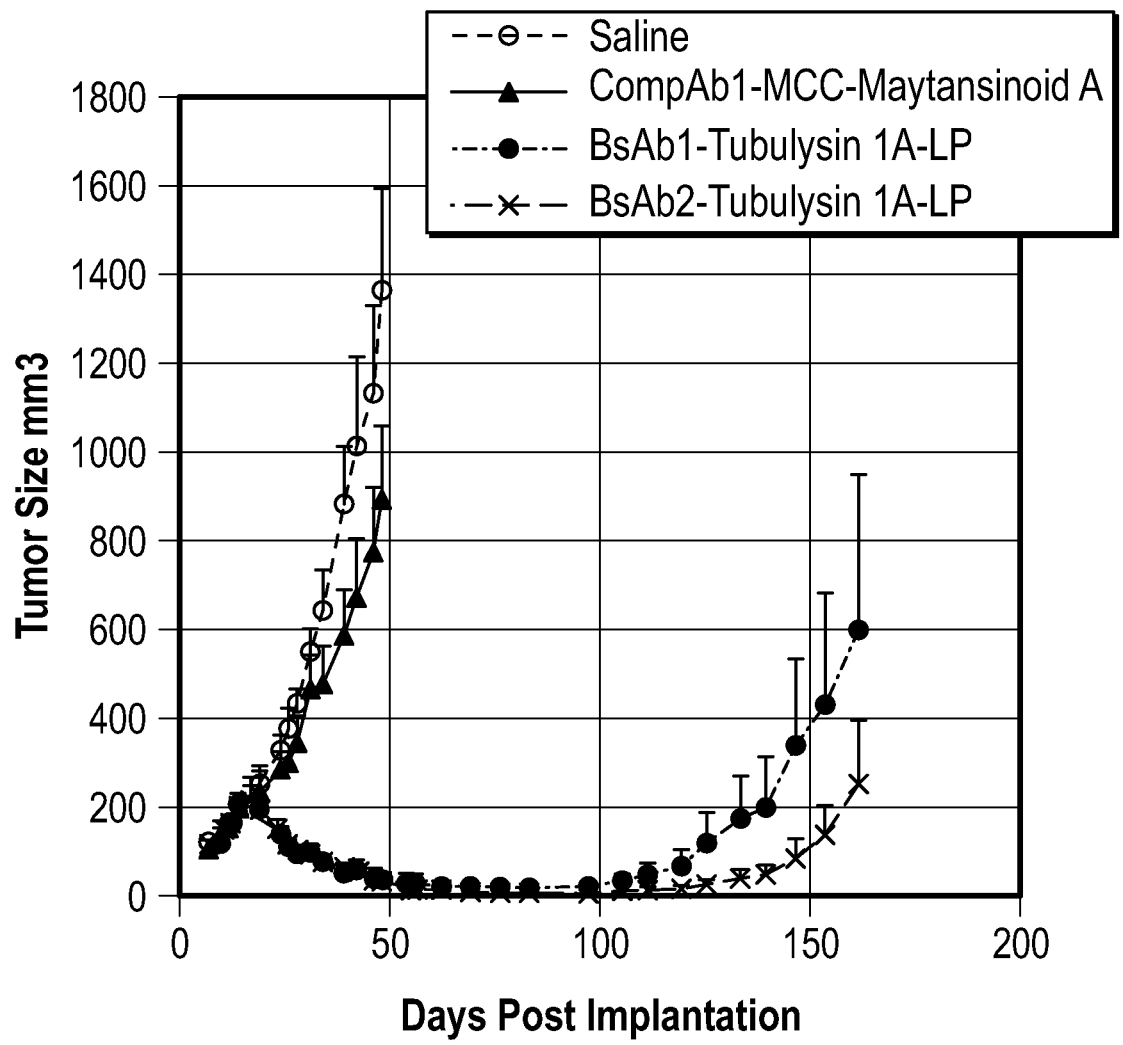
FIG. 7A and FIG. 7B depict average tumor size in a HER2 IHC2+ JIMT1 mouse xenograph model after treatment with the HER2×HER2-M830 ADCs. The mice that received a single dose of 3 mg/kg HER2×HER2 bispecific ADC, BsAb1-Tubulysin 1A-LP (black circles) or BsAb2-Tubulysin 1A-LP (-x-), saw a significant and sustained reduction in JIMT1 xenograft size, while mice that received two doses of 10 mg/kg CompAb1-MCC-Maytansinoid A (black triangles) saw little or no anti-tumor effect.
Figure 7B:
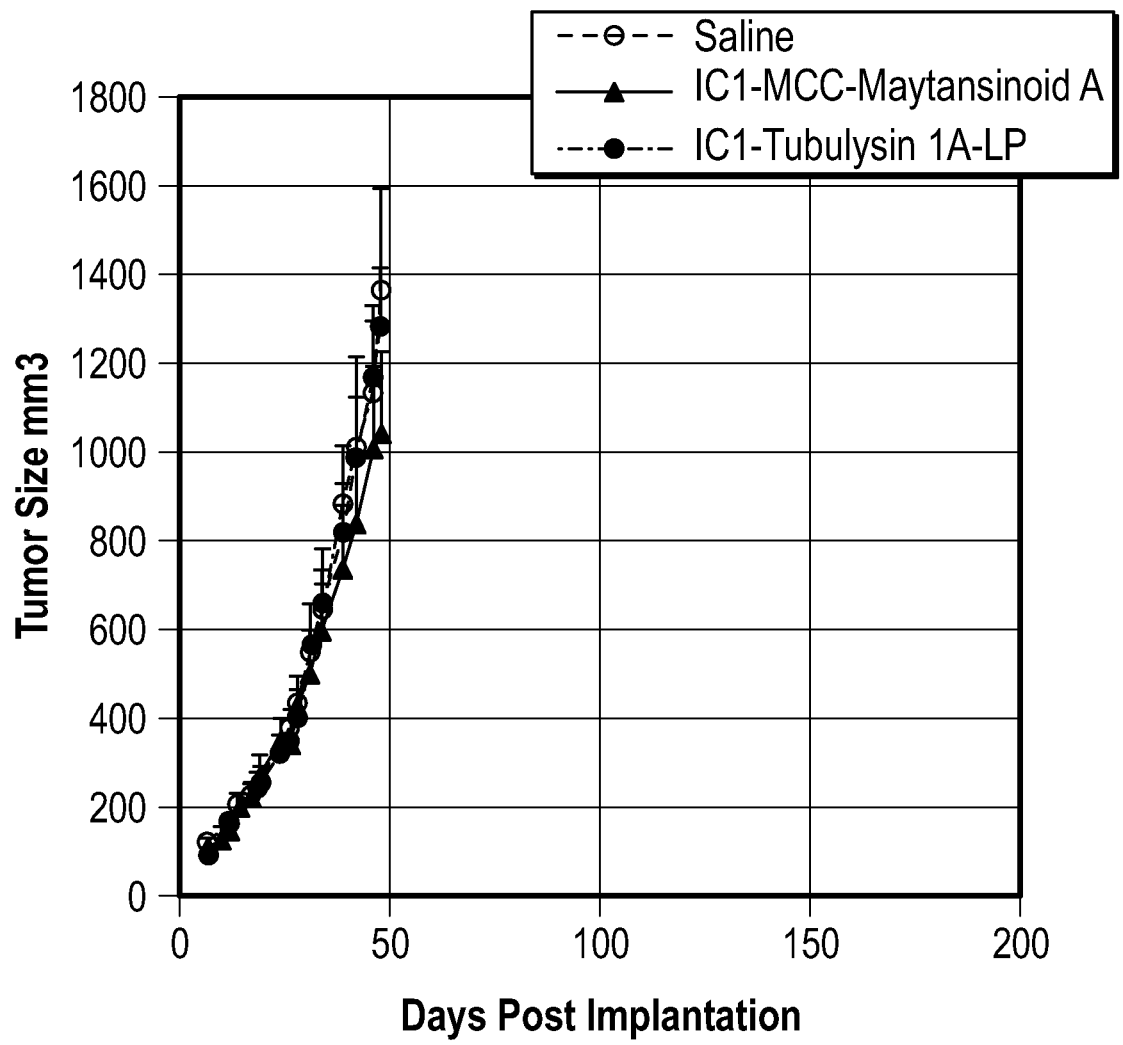

The average tumor size per treatment group for each time point measured is shown in Table 18. Mice that received a single dose of 3 mg/kg BsAb1-Tubulysin 1A-LP or BsAb2-Tubulysin 1A-LP, saw a significant and sustained reduction in JIMT1 xenograft size to an average size of 18 and 6 mm³, respectively (83 and 97 days, respectively). In contrast, mice that received two doses of 10 mg/kg CompAb1-MCC-Maytansinoid A saw little or no anti-tumor effect, similar to mice that received a single 3 mg/kg dose of IC1-Tubulysin 1A-LP or two 10 mg/kg doses of IC1-MCC-Maytansinoid A. See also FIG. 7A and FIG. 7B.

TABLE 18

JIMT1 Xenograft Tumor Size (mm³) After Indicated ADC Treatment

| Day | Saline Average | St Error | IC1-MCC-Maytansinoid A 10 mg/kg Average | St Error | IC1-Tubulysin 1A-LP 3 mg/kg Average | St Error | CompAb1-MCC-Maytansinoid A 10 mg/kg Average | St Error | BsAb1-Tubulysin 1A-LP 3 mg/kg Average | St Error | BsAb2-Tubulysin 1A-LP 3 mg/kg Average | St Error |
|---|---|---|---|---|---|---|---|---|---|---|---|---|
| 7 | 121 | 3 | 118 | 10 | 94 | 6 | 108 | 8 | 99 | 6 | 118 | 8 |
| 10 | 129 | 15 | 131 | 8 | 138 | 11 | 141 | 15 | 119 | 14 | 154 | 16 |
| 12 | 164 | 14 | 150 | 12 | 162 | 13 | 154 | 12 | 169 | 10 | 167 | 16 |
| 14 (Dose 1) | 208 | 23 | 205 | 26 | 202 | 25 | 199 | 26 | 199 | 19 | 202 | 19 |

TABLE 18-continued

JIMT1 Xenograft Tumor Size (mm³) After Indicated ADC Treatment

| Day | Saline Average | Saline St Error | IC1-MCC-Maytansinoid A 10 mg/kg Average | IC1-MCC-Maytansinoid A 10 mg/kg St Error | IC1-Tubulysin 1A-LP 3 mg/kg Average | IC1-Tubulysin 1A-LP 3 mg/kg St Error | CompAb1-MCC-Maytansinoid A 10 mg/kg Average | CompAb1-MCC-Maytansinoid A 10 mg/kg St Error | BsAb1-Tubulysin 1A-LP 3 mg/kg Average | BsAb1-Tubulysin 1A-LP 3 mg/kg St Error | BsAb2-Tubulysin 1A-LP 3 mg/kg Average | BsAb2-Tubulysin 1A-LP 3 mg/kg St Error |
|---|---|---|---|---|---|---|---|---|---|---|---|---|
| 17 | 225 | 24 | 226 | 32 | 219 | 26 | 235 | 33 | 208 | 23 | 213 | 25 |
| 19 | 254 | 38 | 276 | 41 | 245 | 35 | 238 | 43 | 195 | 24 | 190 | 20 |
| 24 | 327 | 35 | 356 | 44 | 323 | 42 | 288 | 38 | 138 | 18 | 160 | 13 |
| 26 | 377 | 44 | 345 | 52 | 347 | 51 | 303 | 36 | 110 | 19 | 120 | 6 |
| 28 (Dose 2) | 435 | 30 | 431 | 64 | 403 | 63 | 347 | 54 | 96 | 15 | 105 | 10 |
| 31 | 550 | 51 | 504 | 91 | 563 | 93 | 468 | 75 | 98 | 14 | 94 | 11 |
| 34 | 642 | 92 | 599 | 104 | 655 | 127 | 480 | 84 | 77 | 12 | 77 | 11 |
| 39 | 883 | 131 | 740 | 140 | 819 | 110 | 588 | 101 | 51 | 6 | 67 | 6 |
| 42 | 1013 | 201 | 841 | 164 | 987 | 136 | 675 | 129 | 60 | 15 | 51 | 7 |
| 46 | 1132 | 197 | 1009 | 183 | 1168 | 127 | 775 | 144 | 40 | 6 | 33 | 7 |
| 48 | 1364 | 229 | 1043 | 181 | 1282 | 130 | 894 | 164 | 36 | 9 | 33 | 7 |
| 54 | | | | | | | 972 | 216 | 28 | 5 | 19 | 4 |
| 56 | | | | | | | 1143 | 239 | 28 | 5 | 20 | 4 |
| 62 | | | | | | | 1320 | 229 | 20 | 4 | 15 | 1 |
| 69 | | | | | | | 1946 | 320 | 20 | 3 | 10 | 3 |
| 76 | | | | | | | 2345 | 363 | 18 | 5 | 8 | 3 |
| 83 | | | | | | | | | 18 | 2 | 8 | 3 |
| 97 | | | | | | | | | 22 | 9 | 6 | 3 |
| 105 | | | | | | | | | 34 | 14 | 12 | 5 |
| 111 | | | | | | | | | 48 | 27 | 15 | 4 |
| 119 | | | | | | | | | 68 | 37 | 16 | 7 |
| 125 | | | | | | | | | 119 | 70 | 26 | 11 |
| 133 | | | | | | | | | 174 | 96 | 40 | 18 |
| 139 | | | | | | | | | 200 | 113 | 49 | 21 |
| 146 | | | | | | | | | 340 | 195 | 84 | 44 |
| 153 | | | | | | | | | 431 | 251 | 138 | 67 |
| 161 | | | | | | | | | 599 | 348 | 252 | 142 |

Example 14. Efficacy of BsAb1-Tubulysin 1A-LP Compared to CompAb1-MCC-Maytansinoid A in MDAMB361 Xenografts To compare the efficacy of BsAb1-Tubulysin 1A-LP and CompAb1-MCC-Maytansinoid A in HER2 IHC2+ MDAMB361 xenograft model, an in vivo tumor study was performed. For the assay, 6 week old female SCID mice (C.B-Igh-1b/IcrTac-Prkdcscid, Taconic Biosciences, n=50) were used. One day before cell implantation, mice were subcutaneously implanted with 17b-Estradiol pellets (0.72 mg, 60 days release. Innovative research of America #SE-121). The next day, MDAMB361 (DSMZ, ACC589) cells were mixed with Matrigel (Corning, Cat #354234) and 150 uL of the cell and matrigel suspension containing 6×10⁶ cells was injected to SCID mice. 19 days later, indicated ADCs were injected subcutaneously at the indicated doses to SCID mice that were randomized based on tumor size. A second dose was administered at day 52 to the BsAb1-Tubulysin 1A-LP-treated cohort to assess development of drug resistance. The xenograft size for each mouse was measured using a Caliper (Roboz, Cat #RS6466).

Figure 8A:
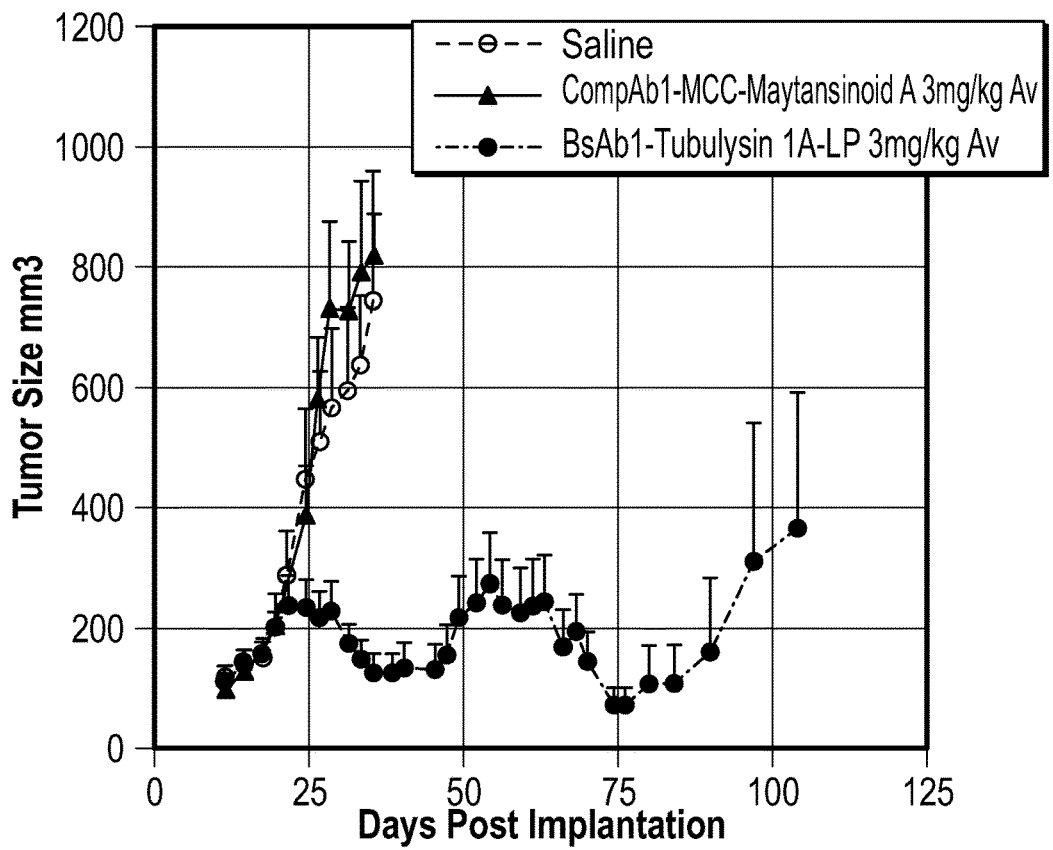
FIG. 8A and FIG. 8B depict average tumor size in a HER2 IHC2+ MDAMB361 mouse xenograph model after treatment with the BsAb1-Tubulysin 1A-LP. Mice that received two doses of the BsAb1-Tubulysin 1A-LP saw reduction in tumor size compared to CompAb1-MCC-Maytansinoid A which resulted in little or no anti-tumor effect.
Figure 8B:
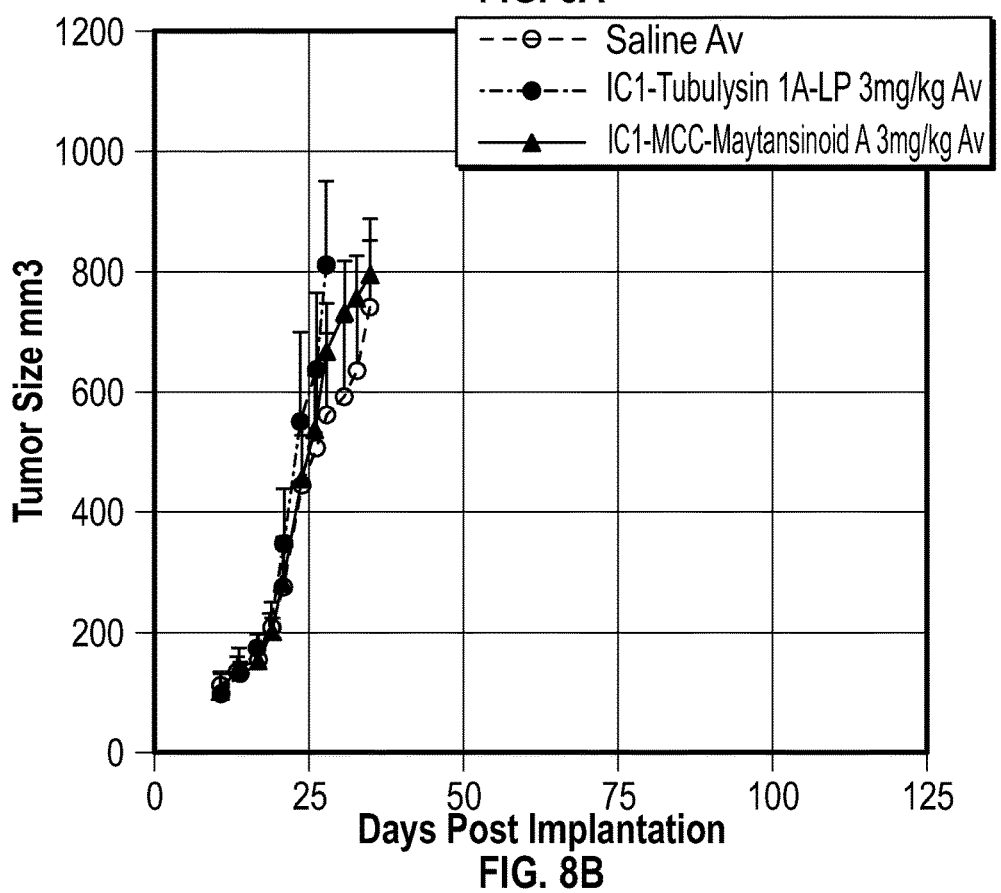

The average tumor size per treatment group for each time point measured is shown in Table 19. Mice that received a single dose of 3 mg/kg BsAb1-Tubulysin 1A-LP (DAR 2.1) saw a partial reduction in MDAMB361 xenograft size from an average size of 202 mm³ to an average size of 122 mm³ by day 38. A second dose administered at day 52 caused further regression of xenograft tumor size to 70 mm³ by day 76. In contrast, mice that received a single 3 mg/kg dose of CompAb1-MCC-Maytansinoid A (DAR 3.1) or control ADCs (IC1-MCC-Maytansinoid A, DAR 3.6, or IC1-Tubulysin 1A-LP, DAR 2) or saline, saw little or no anti-tumor effect. See also FIG. 8A and FIG. 8B.

TABLE 19

MDAMB361 Xenograft Tumor Size (mm³) After Indicated ADC Treatment.

| Day | Saline Average | Saline St Error | IC1-MCC-Maytansinoid A 1 1 × 3 mg/kg Average | IC1-MCC-Maytansinoid A 1 1 × 3 mg/kg St Error | IC1-Tubulysin 1A-LP 1 × 3 mg/kg Average | IC1-Tubulysin 1A-LP 1 × 3 mg/kg St Error | CompAb1-MCC-Maytansinoid A 1 × 3 mg/kg Average | CompAb1-MCC-Maytansinoid A 1 × 3 mg/kg St Error | BsAb1-Tubulysin 1A-LP 2 × 3 mg/kg Average | BsAb1-Tubulysin 1A-LP 2 × 3 mg/kg St Error |
|---|---|---|---|---|---|---|---|---|---|---|
| 11 | 113 | 22 | 101 | 17 | 97 | 8 | 97 | 14 | 105 | 11 |
| 14 | 141 | 19 | 146 | 30 | 134 | 18 | 127 | 20 | 134 | 13 |
| 17 | 150 | 20 | 152 | 15 | 176 | 20 | 162 | 10 | 155 | 17 |
| 19 (Dose 1) | 203 | 49 | 203 | 21 | 208 | 26 | 204 | 20 | 202 | 20 |
| 21 | 278 | 76 | 283 | 55 | 346 | 92 | 249 | 36 | 233 | 36 |
| 24 | 444 | 116 | 456 | 70 | 550 | 148 | 385 | 78 | 230 | 45 |

TABLE 19-continued

MDAMB361 Xenograft Tumor Size (mm³) After Indicated ADC Treatment.

| Day | Saline Average | Saline St Error | IC1-MCC-Maytansinoid A 1 1 × 3 mg/kg Average | IC1-MCC-Maytansinoid A 1 1 × 3 mg/kg St Error | IC1-Tubulysin 1A-LP 1 × 3 mg/kg Average | IC1-Tubulysin 1A-LP 1 × 3 mg/kg St Error | CompAb1-MCC-Maytansinoid A 1 × 3 mg/kg Average | CompAb1-MCC-Maytansinoid A 1 × 3 mg/kg St Error | BsAb1-Tubulysin 1A-LP 2 × 3 mg/kg Average | BsAb1-Tubulysin 1A-LP 2 × 3 mg/kg St Error |
|---|---|---|---|---|---|---|---|---|---|---|
| 26 | 507 | 115 | 540 | 85 | 635 | 129 | 580 | 99 | 213 | 44 |
| 28 | 560 | 135 | 666 | 80 | 810 | 138 | 729 | 144 | 225 | 48 |
| 31 | 590 | 124 | 734 | 81 | | | 726 | 113 | 171 | 34 |
| 33 | 633 | 116 | 757 | 67 | | | 789 | 150 | 146 | 32 |
| 35 | 739 | 145 | 795 | 55 | | | 816 | 141 | 123 | 33 |
| 38 | | | | | | | | | 122 | 32 |
| 40 | | | | | | | | | 133 | 39 |
| 45 | | | | | | | | | 128 | 42 |
| 47 | | | | | | | | | 153 | 51 |
| 49 | | | | | | | | | 214 | 68 |
| 52 (Dose 2) | | | | | | | | | 238 | 73 |
| 54 | | | | | | | | | 269 | 87 |
| 56 | | | | | | | | | 235 | 75 |
| 59 | | | | | | | | | 224 | 72 |
| 61 | | | | | | | | | 235 | 76 |
| 63 | | | | | | | | | 240 | 79 |
| 66 | | | | | | | | | 166 | 59 |
| 68 | | | | | | | | | 190 | 63 |
| 70 | | | | | | | | | 141 | 49 |
| 74 | | | | | | | | | 70 | 27 |
| 76 | | | | | | | | | 70 | 27 |
| 80 | | | | | | | | | 104 | 65 |
| 84 | | | | | | | | | 105 | 65 |
| 90 | | | | | | | | | 157 | 120 |
| 97 | | | | | | | | | 306 | 230 |

Example 15. Efficacy of BsAb1-Tubulysin 1A-LP Compared to CompAb1-MCC-Maytansinoid A in N87 Xenografts To compare the efficacy of BsAb1-Tubulysin 1A-LP and CompAb1-MCC-Maytansinoid A in HER2 IHC3+N87 xenograft model, an in vivo tumor study was performed. For the assay, 6 week old female SCID mice (CBySmn.CB17-Prkdcscid/J, Jackson Labs #001803, n=50) were used. For implantation, N87 (ATCC, HTB-5822) cells were mixed with Matrigel (Corning, Cat #354234) and 150 uL of the cell and matrigel suspension containing $3.6 \times 10^6$ cells was injected to SCID mice. 12 days later, indicated ADCs were injected subcutaneously at the indicated doses to SCID mice that were randomized based on tumor size. Two additional doses were administered at days 25 and 39 to the cohort treated with 1 mg/kg BsAb1-Tubulysin 1A-LP. The xenograft size for each mouse was measured using a Caliper (Roboz, Cat #RS6466).

Figure 9:
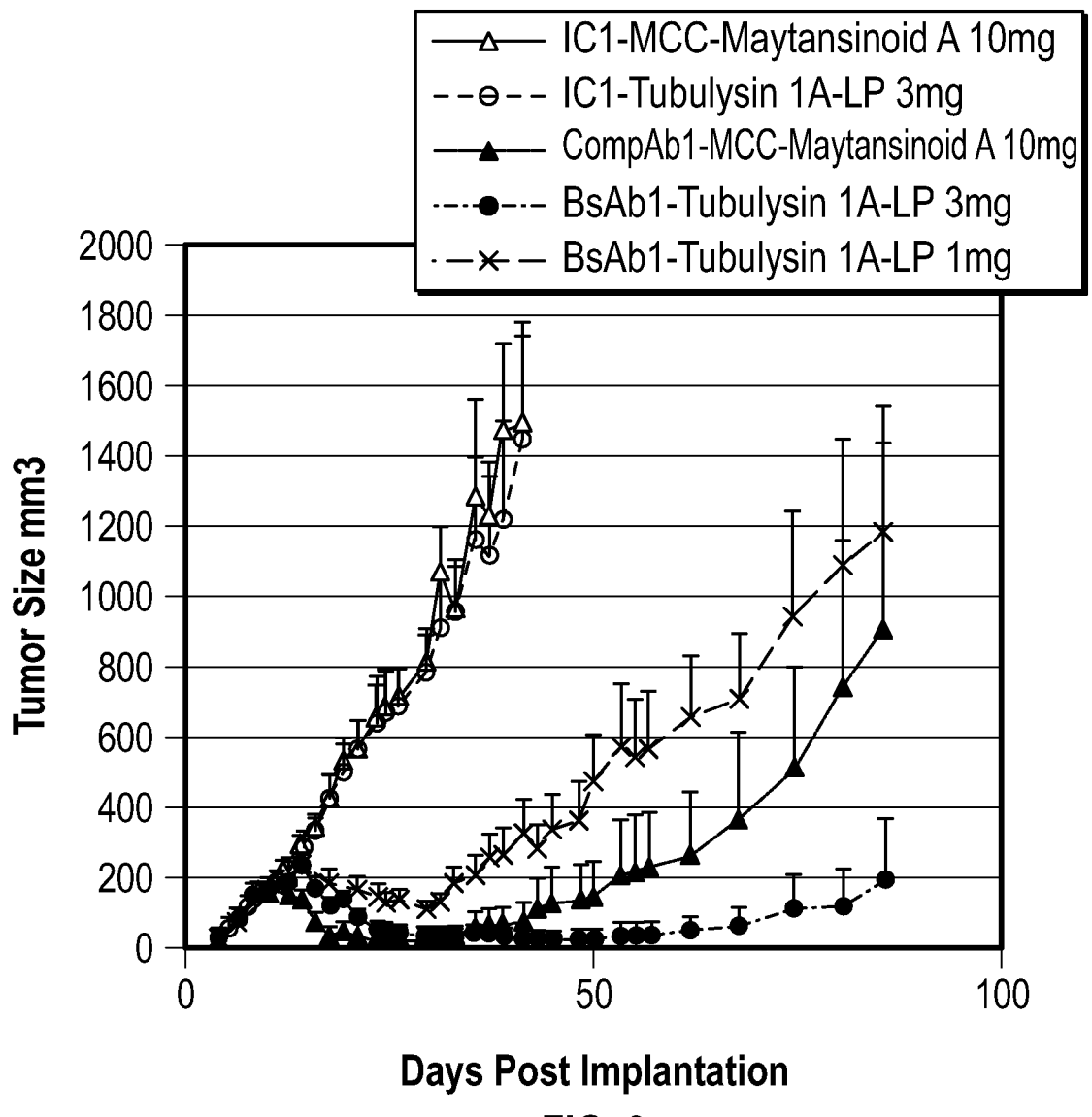
FIG. 9 depicts average tumor size in a HER2 IHC3+N87 mouse xenograph model after treatment with the HER2×HER2-M830 ADCs. Mice that received a single dose of 3 mg/kg HER2×HER2 bispecific ADC, BsAb1-Tubulysin 1A-LP (black circles) saw a significant and durable reduction in N87 xenograft size. Mice that received a single dose of 10 mg/kg CompAb1-MCC-Maytansinoid A (open triangles) saw a significant reduction in N87 xenograft size, however, tumor escaped earlier than those treated with BsAb1-Tubulysin 1A-LP.

The average tumor size per treatment group for each time point measured is shown in Table 20. Mice that received a single dose of 3 mg/kg BsAb1-Tubulysin 1A-LP (DAR 2.1), saw a significant and durable reduction in N87 xenograft size to an average size of 25 mm³ (day 57). Mice that received a single dose of 10 mg/kg CompAb1-MCC-Maytansinoid A (DAR 3.1) saw a significant reduction in N87 xenograft size to an average size of 15 mm³ however (day 29), tumor escaped earlier (i.e. became resistant to the treatment) than those treated with BsAb1-Tubulysin 1A-LP (day 51 versus day 88). Mice that received three doses of 1 mg/kg BsAb1-Tubulysin 1A-LP saw a partial reduction in N87 xenograft size to an average size of 109 mm³ (day 35). In contrast, mice that received a single dose of control ADCs (3 mg/kg IC1-Tubulysin 1A-LP, DAR 2, or 10 mg/kg IC1-MCC-Maytansinoid A, DAR 3.6) did not see anti-tumor effect. See also FIG. 9.

TABLE 20

N87 Xenograft Tumor Size (mm³) After Indicated ADC Treatment

| Day | IC1-MCC-Maytansinoid A 1 × 10 mg/kg Average | IC1-MCC-Maytansinoid A 1 × 10 mg/kg St Error | IC1-Tubulysin 1A-LP 1 × 3 mg/kg Average | IC1-Tubulysin 1A-LP 1 × 3 mg/kg St Error | CompAb1-MCC-Maytansinoid A 1 × 10 mg/kg Average | CompAb1-MCC-Maytansinoid A 1 × 10 mg/kg St Error | BsAb1-Tubulysin 1A-LP 1 × 3 mg/kg Average | BsAb1-Tubulysin 1A-LP 1 × 3 mg/kg St Error | BsAb1-Tubulysin 1A-LP 3 × 1 mg/kg Average | BsAb1-Tubulysin 1A-LP 3 × 1 mg/kg St Error |
|---|---|---|---|---|---|---|---|---|---|---|
| 5 | 25 | 5 | 31 | 8 | 26 | 5 | 31 | 7 | 33 | 6 |
| 8 | 88 | 13 | 84 | 14 | 89 | 17 | 88 | 13 | 80 | 11 |
| 10 | 162 | 22 | 165 | 21 | 147 | 23 | 157 | 10 | 133 | 10 |
| 12 (Dose 1) | 161 | 13 | 161 | 13 | 173 | 26 | 164 | 20 | 157 | 14 |

TABLE 20-continued

N87 Xenograft Tumor Size (mm³) After Indicated ADC Treatment

| | IC1-MCC-Maytansinoid A 1 × 10 mg/kg | | IC1-Tubulysin 1A-LP 1 × 3 mg/kg | | CompAb1-MCC-Maytansinoid A 1 × 10 mg/kg | | BsAb1-Tubulysin 1A-LP 1 × 3 mg/kg | | BsAb1-Tubulysin 1A-LP 3 × 1 mg/kg | |
|---|---|---|---|---|---|---|---|---|---|---|
| Day | Average | St Error | Average | St Error | Average | St Error | Average | St Error | Average | St Error |
| 15 | 221 | 30 | 208 | 37 | 152 | 34 | 186 | 37 | 202 | 23 |
| 17 | 304 | 29 | 269 | 30 | 138 | 26 | 238 | 34 | 213 | 25 |
| 19 | 348 | 16 | 338 | 42 | 71 | 13 | 169 | 24 | 185 | 20 |
| 21 | 427 | 20 | 425 | 68 | 33 | 9 | 124 | 16 | 185 | 40 |
| 23 | 541 | 53 | 501 | 97 | 44 | 26 | 137 | 24 | 149 | 19 |
| 25 (Dose 2) | 569 | 23 | 566 | 81 | 34 | 18 | 90 | 12 | 168 | 31 |
| 28 | 672 | 104 | 642 | 107 | 17 | 5 | 58 | 10 | 149 | 33 |
| 29 | 688 | 102 | 668 | 115 | 15 | 5 | 52 | 9 | 129 | 24 |
| 31 | 720 | 76 | 689 | 102 | 22 | 11 | 42 | 8 | 136 | 31 |
| 35 | 824 | 83 | 786 | 104 | 16 | 12 | 39 | 8 | 109 | 21 |
| 37 | 1066 | 134 | 909 | 147 | 24 | 20 | 37 | 10 | 131 | 24 |
| 39 (Dose 3) | 975 | 113 | 955 | 150 | 34 | 28 | 31 | 8 | 186 | 47 |
| 42 | 1284 | 275 | 1165 | 233 | 52 | 47 | 44 | 11 | 206 | 58 |
| 44 | 1225 | 158 | 1118 | 224 | 64 | 46 | 44 | 11 | 256 | 67 |
| 46 | 1472 | 250 | 1220 | 278 | 64 | 51 | 33 | 12 | 265 | 77 |
| 49 | 1492 | 289 | 1446 | 281 | 72 | 59 | 29 | 12 | 326 | 98 |
| 51 | | | | | 112 | 89 | 30 | 12 | 285 | 68 |
| 53 | | | | | 127 | 105 | 28 | 12 | 333 | 105 |
| 57 | | | | | 134 | 104 | 25 | 13 | 363 | 113 |
| 59 | | | | | 144 | 103 | 26 | 15 | 472 | 134 |
| 63 | | | | | 204 | 162 | 36 | 25 | 572 | 183 |
| 65 | | | | | 218 | 161 | 34 | 26 | 543 | 165 |
| 67 | | | | | 227 | 160 | 39 | 25 | 559 | 172 |
| 73 | | | | | 257 | 188 | 51 | 39 | 653 | 179 |
| 80 | | | | | 367 | 247 | 64 | 51 | 701 | 196 |
| 88 | | | | | 504 | 295 | 113 | 97 | 938 | 305 |
| 95 | | | | | 737 | 424 | 119 | 106 | 1084 | 364 |
| 101 | | | | | 912 | 525 | 193 | 177 | 1182 | 360 |

Example 16. In Vivo Comparison of Three ADCs in JIMT1 Xenografts

To compare the efficacy of BsAb1-Tubulysin 1A-LP with CompAb1-MCC-Maytansinoid A (DAR 3.1) and CompAb1-L-Camptothecin (DAR 8) in HER2 IHC2+ JIMT1 xenograft model, an in vivo tumor study was performed. For the assay, 6 week old female SCID mice (CBySmn.CB17-Prkdcscid/J, Jackson Labs #001803, n=50) were used. For implantation, JIMT1 (DSMZ, ACC589) cells were mixed with Matrigel (Corning, Cat #354234) and 150 uL of the cell and matrigel suspension containing 4×10⁶ cells was injected to SCID mice. 13, 20 and 27 days later, indicated ADCs were injected subcutaneously at the indicated doses to SCID mice that were randomized based on tumor size. One cohort received a single 3 mg/kg dose of BsAb1-Tubulysin 1A-LP at day 13. The xenograft size for each mouse was measured using a Caliper (Roboz, Cat #RS6466). The average tumor size per treatment group for each time point measured is shown in Table 21.

Figure 10A:
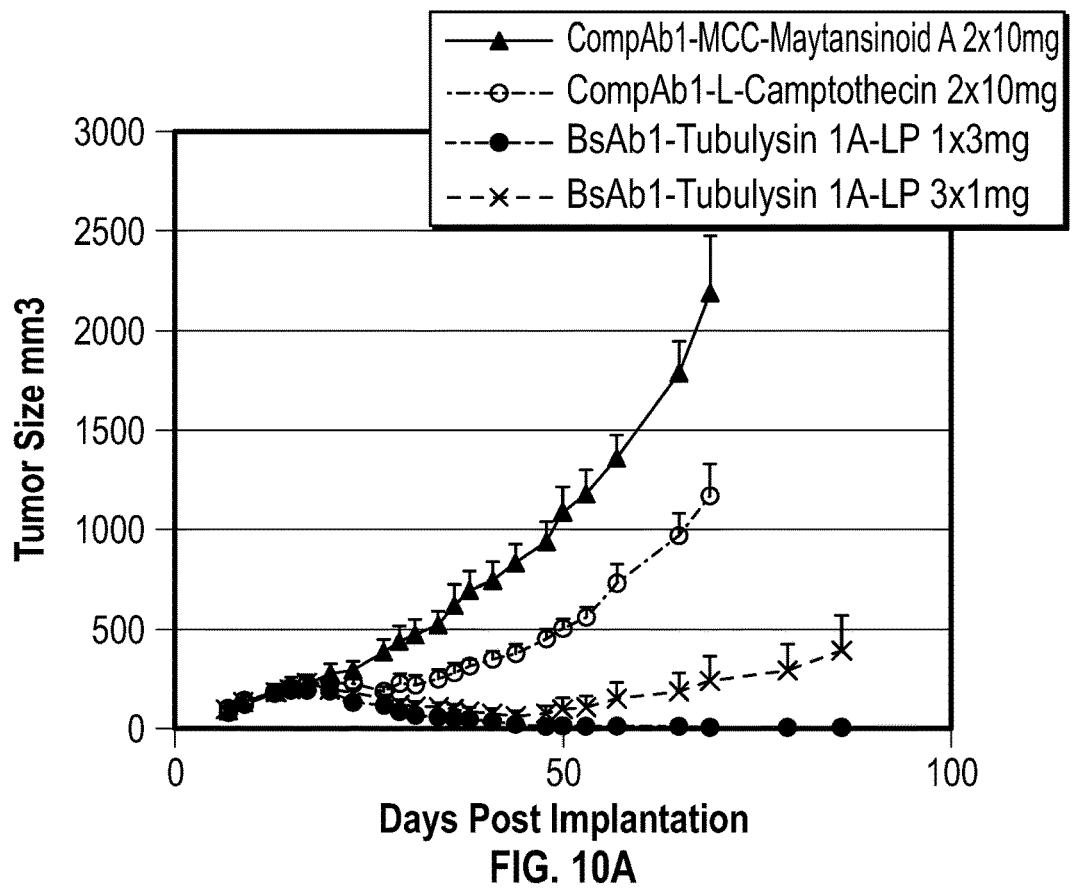
FIG. 10A and FIG. 10B depict average tumor size in a HER2 IHC2+ MDAMB361 mouse xenograph model after treatment with the HER2×HER2-M830 ADCs compared to treatment with CompAb1-MCC-Maytansinoid A and CompAb1-L-Camptothecin. Mice that received a single dose of 3 mg/kg HER2×HER2 bispecific ADC, BsAb1-Tubulysin 1A-LP (black circles) saw a significant and durable reduction in JIMT1 xenograft size, and mice that received three weekly doses of 1 mg/kg BsAb1-Tubulysin 1A-LP (-x-) saw a partial reduction in JIMT1 xenograft. In contrast mice that received three weekly doses of 10 mg/kg CompAb1-L-Camptothecin (open circles) saw only slow-down in tumor progression.
Figure 10B:
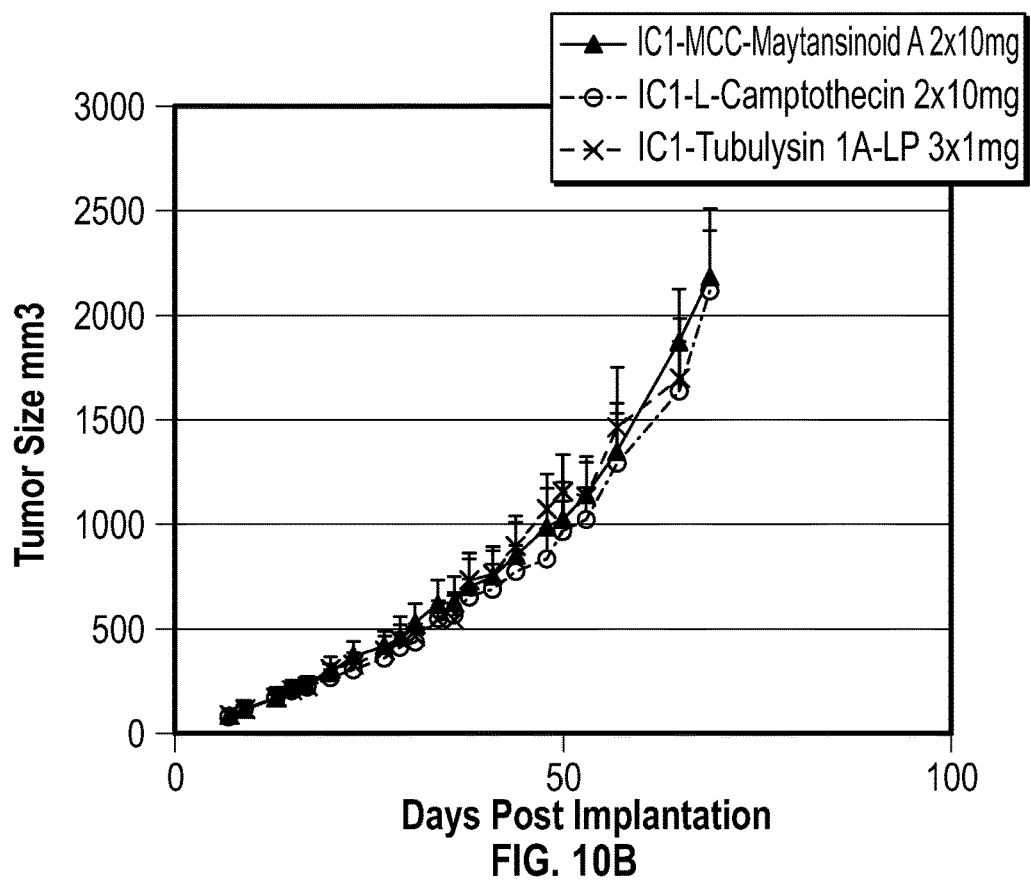

Mice that received a single dose of 3 mg/kg BsAb1-Tubulysin 1A-LP (DAR 2.1) saw a significant and durable reduction in JIMT1 xenograft size to an average size of 3 mm³ (day 79) Mice that received three weekly doses of 1 mg/kg BsAb1-Tubulysin 1A-LP saw a partial reduction in JIMT1 xenograft from an average size of 179 mm³ to an average size of 63 mm³ by day 44. In contrast, mice that received three weekly doses of 10 mg/kg CompAb1-L-Camptothecin saw only a slow-down in tumor progression that reached an average size of 374 mm³ by day 44. In contrast, mice that received weekly doses of 10 mg/kg CompAb1-MCC-Maytansinoid A or control ADCs (3 mg/kg IC1-Tubulysin 1A-LP, 10 mg/kg IC1-L-Camptothecin or 10 mg/kg IC1-MCC-Maytansinoid A) did not see anti-tumor effect. See also FIG. 10A and FIG. 10B.

TABLE 21

JIMT1 Xenograft Tumor Size (mm³) After Indicated ADC Treatment

| | IC1-MCC-Maytansinoid A 3 × 10 mg | | IC1-L-Camptothecin 3 × 10 mg | | IC1-Tubulysin 1A-LP 3 × 1 mg | | CompAb1-MCC-Maytansinoid A 3 × 10 mg | | CompAb1-L-Camptothecin 3 × 10 mg | | BsAb1-Tubulysin 1A-LP 3 × 1 mg | | BsAb1-Tubulysin 1A-LP 1 × 3 mg | |
|---|---|---|---|---|---|---|---|---|---|---|---|---|---|---|
| Day | Average | St Error | Average | St Error | Average | St Error | Average | St Error | Average | St Error | Average | St Error | Average | St Error |
| 7 | 92 | 8 | 88 | 13 | 101 | 12 | 85 | 6 | 84 | 10 | 91 | 5 | 102 | 11 |
| 9 | 128 | 12 | 128 | 12 | 126 | 12 | 127 | 11 | 121 | 19 | 121 | 9 | 147 | 16 |
| 13 | 180 | 18 | 178 | 13 | 182 | 11 | 180 | 13 | 182 | 11 | 179 | 9 | 180 | 13 |
| 15 | 226 | 23 | 211 | 22 | 217 | 35 | 215 | 38 | 204 | 31 | 203 | 31 | 190 | 17 |

TABLE 21-continued

JIMT1 Xenograft Tumor Size (mm³) After Indicated ADC Treatment

| | IC1-MCC-Maytansinoid A 3 × 10 mg | | IC1-L-Camptothecin 3 × 10 mg | | IC1-Tubulysin 1A-LP 3 × 1 mg | | CompAb1-MCC-Maytansinoid A 3 × 10 mg | | CompAb1-L-Camptothecin 3 × 10 mg | | BsAb1-Tubulysin 1A-LP 3 × 1 mg | | BsAb1-Tubulysin 1A-LP 1 × 3 mg | |
|---|---|---|---|---|---|---|---|---|---|---|---|---|---|---|
| Day | Average | St Error | Average | St Error | Average | St Error | Average | St Error | Average | St Error | Average | St Error | Average | St Error |
| 17 | 234 | 30 | 228 | 22 | 236 | 44 | 231 | 39 | 225 | 37 | 195 | 29 | 184 | 14 |
| 20 | 293 | 49 | 276 | 36 | 318 | 50 | 276 | 49 | 225 | 37 | 195 | 29 | 186 | 10 |
| 23 | 379 | 69 | 314 | 42 | 335 | 57 | 294 | 43 | 224 | 32 | 178 | 30 | 128 | 12 |
| 27 | 421 | 75 | 370 | 52 | 407 | 64 | 381 | 62 | 184 | 26 | 150 | 18 | 111 | 8 |
| 29 | 468 | 96 | 420 | 70 | 459 | 68 | 433 | 78 | 227 | 44 | 124 | 29 | 82 | 12 |
| 31 | 537 | 91 | 446 | 68 | 471 | 66 | 468 | 79 | 219 | 49 | 113 | 23 | 67 | 11 |
| 34 | 624 | 117 | 559 | 83 | 547 | 71 | 516 | 70 | 249 | 44 | 109 | 22 | 53 | 9 |
| 36 | 634 | 121 | 575 | 92 | 547 | 71 | 615 | 103 | 281 | 44 | 98 | 18 | 46 | 8 |
| 38 | 707 | 131 | 660 | 86 | 739 | 109 | 690 | 94 | 315 | 34 | 85 | 20 | 46 | 6 |
| 41 | 756 | 142 | 694 | 120 | 771 | 111 | 735 | 99 | 345 | 41 | 75 | 24 | 34 | 4 |
| 44 | 858 | 157 | 782 | 124 | 902 | 144 | 828 | 92 | 374 | 49 | 63 | 22 | 19 | 5 |
| 48 | 991 | 186 | 842 | 116 | 1076 | 169 | 932 | 100 | 446 | 53 | 74 | 36 | 10 | 3 |
| 50 | 1023 | 180 | 970 | 144 | 1161 | 175 | 1078 | 130 | 500 | 44 | 96 | 59 | 10 | 3 |
| 53 | 1143 | 186 | 1027 | 152 | 1139 | 165 | 1170 | 123 | 557 | 54 | 106 | 58 | 8 | 3 |
| 57 | 1348 | 234 | 1296 | 236 | 1465 | 192 | 1348 | 119 | 727 | 94 | 149 | 81 | 10 | 5 |
| 65 | 1874 | 257 | 1641 | 237 | 1705 | 284 | 1776 | 161 | 963 | 112 | 187 | 91 | 10 | 3 |
| 69 | 2188 | 323 | 2120 | 284 | | | 2178 | 285 | 1161 | 159 | 239 | 122 | 6 | 2 |
| 79 | | | | | | | | | | | 291 | 132 | 3 | 1 |
| 86 | | | | | | | | | | | 389 | 178 | 4 | 3 |

Example 17. Efficacy of HER2×HER2-M830 Bispecific Antibody Drug Conjugate Compared to CompAb1-MCC-Maytansinoid A in JIMT1 Xenografts To compare the efficacy of BsAb1-Tubulysin 1A-LP and CompAb1-MCC-Maytansinoid A (DAR 3.1) in HER2 IHC2+ CTG0807, an in vivo tumor study was performed. For the assay, 6-8 week old female Athymic Nude-Fox1 nu mice (Envifo, Indianapolis, Ind.) were used.

Pre-study Animals: When sufficient stock animals reached 1.0-1.5 cm³, tumors were harvested for re-implantation into pre-study animals. Pre-study animals were implanted unilaterally on the left flank with tumor fragments harvested from stock animals. Study Animals: Pre-study tumor volumes were recorded for each experiment beginning seven to ten days after implantation. When tumors reached an average tumor volume of 150-300 mm³ animals were matched by tumor volume into treatment or control groups to be used for dosing and dosing initiated on Day 0. Tumor volumes were measured twice weekly.

Matched study animals were injected intravenously at the indicated doses. The average tumor size per treatment group for each time point measured is shown in Table 22.

Figure 11A:
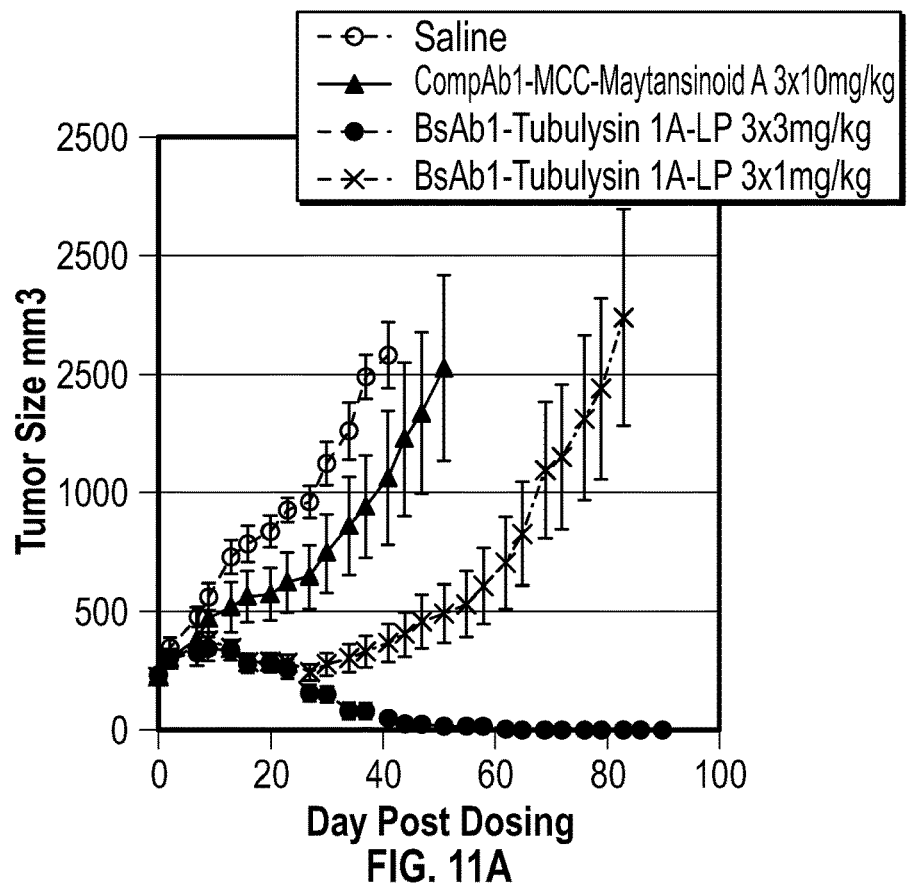
FIG. 11A and FIG. 11B depict average tumor size in a HER2 IHC2+ CTG0807 mouse xenograph model after treatment with the HER2×HER2-M830 ADCs compared to treatment with CompAb1-MCC-Maytansinoid A. Mice that received three weekly doses of 3 mg/kg HER2×HER2 bispecific ADC, BsAb1-Tubulysin 1A-LP (black circles), saw a complete and durable reduction in CTG0807 PDX tumor size. Mice that received three weekly doses of 1 mg/kg BsAb1-Tubulysin 1A-LP (-x-) saw a delay in tumor growth, as tumor size remained below 300 mm$^3$ for 30 days. Tumors in mice that received three weekly doses of 10 mg/kg CompAb1-MCC-Maytansinoid A (black triangles) continued to grow during and after treatment.
Figure 11B:
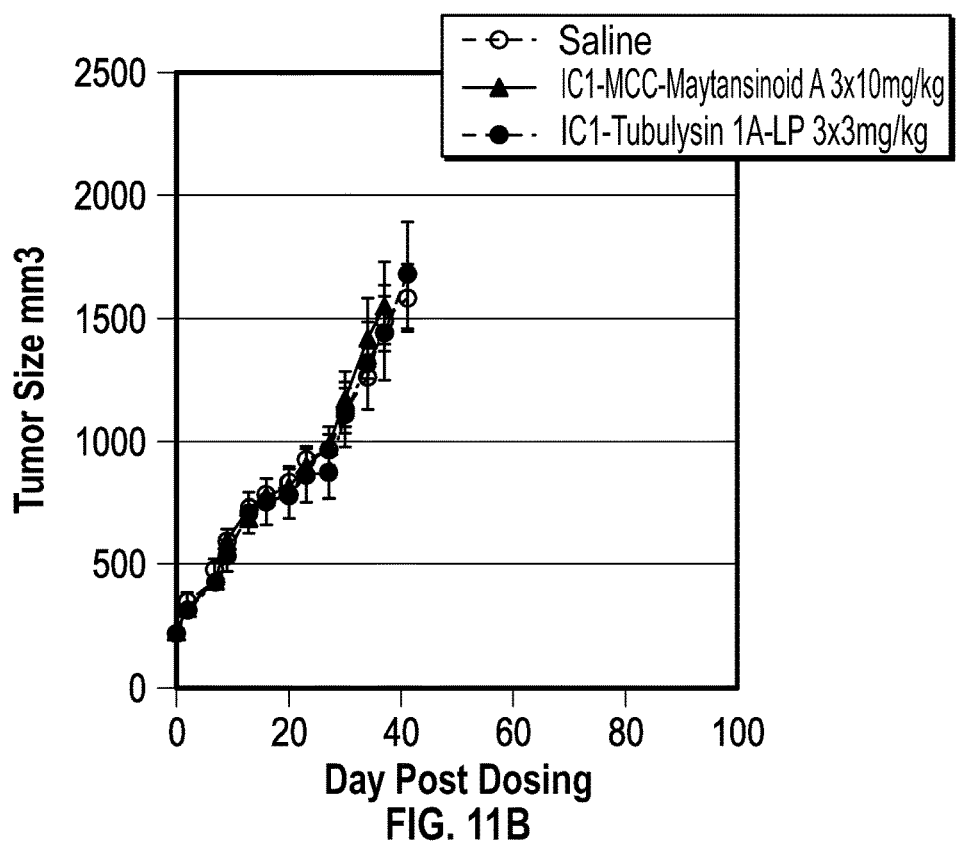

Mice that received three weekly doses of 3 mg/kg BsAb1-Tubulysin 1A-LP (DAR 2.1) saw a complete (0 mm³) and durable reduction in CTG0807 PDX tumor size. Mice that received three weekly doses of 1 mg/kg BsAb1-Tubulysin 1A-LP saw a delay in tumor growth, as tumor size remained below 300 mm³ for 30 days. Mice that received three weekly doses of 10 mg/kg CompAb1-MCC-Maytansinoid A (DAR 3.1) continued to grow during and after treatment, although at a slightly slower rate than tumors treated with three weekly doses of PBS or ADC control (10 mg/kg IC1-MCC-Maytansinoid A or 3 mg/kg IC1-Tubulysin 1A-LP). See also FIG. 11A and FIG. 11B.

TABLE 22

CTG0807 PDX Tumor Size (mm³) After Indicated ADC Treatment

| Day | Saline | IC1-MCC-Maytansinoid A 3 × 10 mg/kg | CompAb1-MCC-Maytansinoid A 3 × 10 mg/kg | IC1-Tubulysin 1A-LP 3 × 3 mg/kg | BsAb1-Tubulysin 1A-LP 3 × 3 mg/kg | BsAb1-Tubulysin 1A-LP 3 × 1 mg/kg |
|---|---|---|---|---|---|---|
| | | | Tumor Volume - Mean | | | |
| 0 | 220 | 222 | 233 | 220 | 231 | 221 |
| 2 | 349 | 341 | 296 | 315 | 310 | 287 |
| 7 | 478 | 463 | 386 | 429 | 317 | 342 |
| 9 | 561 | 594 | 471 | 537 | 341 | 380 |
| 13 | 728 | 683 | 518 | 707 | 337 | 349 |
| 16 | 783 | 752 | 565 | 756 | 278 | 284 |
| 20 | 834 | 801 | 574 | 786 | 278 | 289 |
| 23 | 925 | 897 | 623 | 859 | 253 | 285 |
| 27 | 962 | 971 | 645 | 871 | 156 | 245 |
| 30 | 1123 | 1169 | 744 | 1105 | 151 | 278 |
| 34 | 1260 | 1418 | 858 | 1309 | 80 | 304 |
| 37 | 1488 | 1549 | 941 | 1439 | 79 | 331 |
| 41 | 1579 | | 1064 | 1677 | 50 | 368 |
| 44 | | | 1225 | | 26 | 405 |
| 47 | | | 1330 | | 21 | 458 |

TABLE 22-continued

CTG0807 PDX Tumor Size (mm³) After Indicated ADC Treatment

| Day | Saline | IC1-MCC-Maytansinoid A 3 × 10 mg/kg | CompAb1-MCC-Maytansinoid A 3 × 10 mg/kg | IC1-Tubulysin 1A-LP 3 × 3 mg/kg | BsAb1-Tubulysin 1A-LP 3 × 3 mg/kg | BsAb1-Tubulysin 1A-LP 3 × 1 mg/kg |
|---|---|---|---|---|---|---|
| 51 | | | 1522 | | 15 | 490 |
| 55 | | | | | 14 | 530 |
| 58 | | | | | 15 | 608 |
| 62 | | | | | 7 | 705 |
| 65 | | | | | 0 | 828 |
| 69 | | | | | 0 | 1095 |
| 72 | | | | | 0 | 1149 |
| 76 | | | | | 0 | 1316 |
| 79 | | | | | 0 | 1436 |
| 83 | | | | | 0 | 1739 |
| 86 | | | | | 0 | |
| 90 | | | | | 0 | |
| Tumor Volume - SEM | | | | | | |
| 0 | 7 | 7 | 6 | 7 | 6 | 8 |
| 2 | 37 | 19 | 30 | 31 | 31 | 19 |
| 7 | 44 | 45 | 51 | 26 | 41 | 17 |
| 9 | 57 | 51 | 86 | 66 | 48 | 17 |
| 13 | 69 | 50 | 104 | 85 | 40 | 32 |
| 16 | 72 | 33 | 107 | 95 | 33 | 34 |
| 20 | 64 | 34 | 108 | 100 | 34 | 35 |
| 23 | 52 | 64 | 123 | 104 | 33 | 30 |
| 27 | 68 | 88 | 131 | 102 | 25 | 33 |
| 30 | 92 | 112 | 163 | 131 | 30 | 47 |
| 34 | 120 | 163 | 206 | 175 | 27 | 60 |
| 37 | 92 | 182 | 217 | 190 | 25 | 66 |
| 41 | 138 | | 282 | 215 | 16 | 80 |
| 44 | | | 324 | | 11 | 92 |
| 47 | | | 333 | | 13 | 113 |
| 51 | | | 388 | | 9 | 124 |
| 55 | | | | | 8 | 138 |
| 58 | | | | | 9 | 158 |
| 62 | | | | | 7 | 191 |
| 65 | | | | | 0 | 217 |
| 69 | | | | | 0 | 288 |
| 72 | | | | | 0 | 303 |
| 76 | | | | | 0 | 347 |
| 79 | | | | | 0 | 380 |
| 83 | | | | | 0 | 455 |
| 86 | | | | | 0 | |
| 90 | | | | | 0 | |

Example 18. Efficacy of BsAb1-Tubulysin 1A-LP Compared to CompAb1-MCC-Maytansinoid A in JIMT1 Xenografts To compare the efficacy of BsAb1-Tubulysin 1A-LP and CompAb1-MCC-Maytansinoid A in HER2 IHC2+ CTG1184, an in vivo tumor study was performed. For the assay, 6-8 week old female Athymic Nude-Fox1nu mice (Envifo, Indianapolis, Ind.) were used.

Pre-study Animals: When sufficient stock animals reached 1.0-1.5 cm³, tumors were harvested for re-implantation into pre-study animals. Pre-study animals were implanted unilaterally on the left flank with tumor fragments harvested from stock animals. Study Animals: Pre-study tumor volumes were recorded for each experiment beginning seven to ten days after implantation. When tumors reached an average tumor volume of 150-300 mm³ animals were matched by tumor volume into treatment or control groups to be used for dosing and dosing initiated on Day 0. Tumor volumes were measured twice weekly.

Matched study animals were injected intravenously at the indicated doses. The average tumor size per treatment group for each time point measured is shown in Table 23.

Figure 12A:
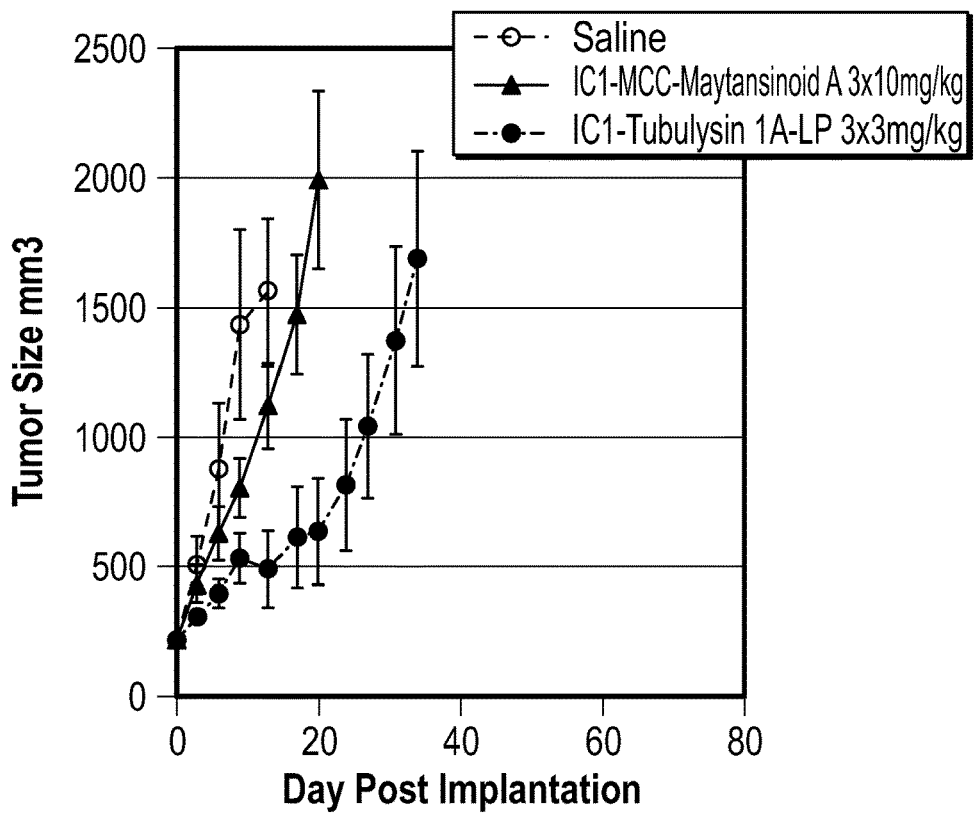
FIG. 12A and FIG. 12B depict average tumor size in a HER2 IHC2+ CTG1184 mouse xenograph model after treatment with the HER2×HER2-M830 ADCs compared to treatment with CompAb1-MCC-Maytansinoid A. Mice that received three weekly doses of 3 mg/kg (black circles) and 1 mg/kg (-x-) HER2×HER2 bispecific ADC, BsAb1-Tubulysin 1A-LP, saw a significant and durable reduction in CTG1184 PDX tumor size. Tumors in mice that received three weekly doses of 3 mg/kg IC1-Tubulysin 1A-LP (isotype control ADC) or 10 mg/kg CompAb1-MCC-Maytansinoid A (black triangles) continued to grow during and after treatment.
Figure 12B:
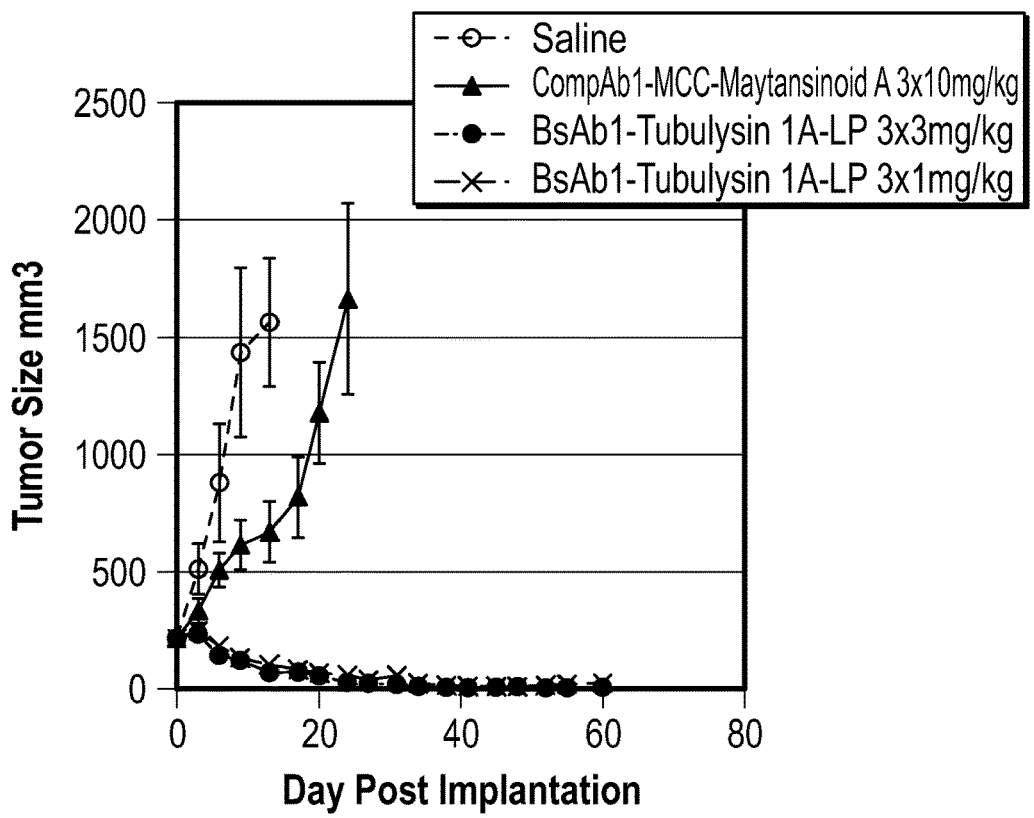

Mice that received three weekly doses of 3 mg/kg and 1 mg/kg BsAb1-Tubulysin 1A-LP (DAR 2.1) saw a significant and durable reduction in CTG1184 PDX tumor size to an average value of 6 (day 52) and 13 mm³ (day 45), respectively. Mice that received three weekly doses of 3 mg/kg IC1-Tubulysin 1A-LP (control ADC) or 10 mg/kg CompAb1-MCC-Maytansinoid A (DAR 3.1) continued to grow during and after treatment, although at a slower rate than tumors treated with three weekly doses of PBS or 10 mg/kg IC1-MCC-Maytansinoid A (control ADC). See also FIGS. 12A and 12B.

TABLE 23

CTG1184 PDX tumor size after indicated ADC treatment.

| Day | Saline | IC1-MCC-Maytansinoid A 3 × 10 mg/kg | CompAb1-MCC-Maytansinoid A 3 × 10 mg/kg | IC1-Tubulysin 1A-LP 3 × 3 mg/kg | BsAb1-Tubulysin 1A-LP 3 × 3 mg/kg | BsAb1-Tubulysin 1A-LP 3 × 1 mg/kg |
|---|---|---|---|---|---|---|
| Tumor Volume - Mean | | | | | | |
| 0  | 218  | 220  | 222  | 223  | 224 | 220 |
| 3  | 513  | 437  | 334  | 312  | 238 | 250 |
| 6  | 879  | 627  | 509  | 399  | 144 | 186 |
| 9  | 1435 | 805  | 616  | 535  | 123 | 134 |
| 13 | 1565 | 1124 | 665  | 492  | 72  | 104 |
| 17 |      | 1477 | 815  | 614  | 74  | 84  |
| 20 |      | 1994 | 1176 | 636  | 56  | 70  |
| 24 |      |      | 1660 | 818  | 28  | 60  |
| 27 |      |      |      | 1044 | 27  | 41  |
| 31 |      |      |      | 1372 | 19  | 57  |
| 34 |      |      |      | 1687 | 13  | 26  |
| 38 |      |      |      |      | 10  | 17  |
| 41 |      |      |      |      | 7   | 14  |
| 45 |      |      |      |      | 10  | 13  |
| 48 |      |      |      |      | 12  | 14  |
| 52 |      |      |      |      | 6   | 15  |
| 55 |      |      |      |      | 8   | 22  |
| 60 |      |      |      |      | 8   | 27  |
| Tumor Volume - SEM | | | | | | |
| 0  | 17  | 13  | 14  | 11  | 14 | 14 |
| 3  | 109 | 73  | 53  | 22  | 29 | 14 |
| 6  | 255 | 106 | 73  | 54  | 26 | 23 |
| 9  | 364 | 113 | 105 | 96  | 23 | 15 |
| 13 | 276 | 162 | 137 | 146 | 4  | 10 |
| 17 |     | 232 | 176 | 193 | 5  | 11 |
| 20 |     | 341 | 219 | 203 | 3  | 6  |
| 24 |     |     | 411 | 254 | 10 | 8  |
| 27 |     |     |     | 278 | 11 | 5  |
| 31 |     |     |     | 359 | 13 | 7  |
| 34 |     |     |     | 411 | 7  | 12 |
| 38 |     |     |     |     | 6  | 8  |
| 41 |     |     |     |     | 4  | 8  |
| 45 |     |     |     |     | 6  | 7  |
| 48 |     |     |     |     | 8  | 7  |
| 52 |     |     |     |     | 4  | 9  |
| 55 |     |     |     |     | 5  | 8  |
| 60 |     |     |     |     | 5  | 9  |

Example 19. Immunohistochemistry (IHC) Staining to Assess the Level of HER2 in Tumor Cell Lines and Patient-Derived Xenografts The PDX models used in Examples 17 and 1 were confirmed to be HER IHC 2+/3+ for CTG1184 according to the following method. Tissue samples were fixed in 10% neutral buffer formalin for 12 hours at 4° C. in the dark, washed 3× with PBS, dehydrated in a graded ethanol series (1×70%, 80%, 90% and 4×100%, 30 min each), processed in xylene and paraffin (3×, 30 min each) using Tissue-Tek® followed by embedding to generate 4 µm tissue sections. IHC staining was performed using the protocol provided with HercepTest™ Kit. HER2 IHC score was determined by visual comparison of tissue and control sections.

TABLE 24

IHC Score of Cell Lines and Patient Derived Xenografts

| Samples | Sample type | HER2 IHC Score |
|---|---|---|
| MDAMB468 | Cell line | 0+ |
| MDAMB231 | Cell line | 0+ |
| T47D | Cell line | 1+ |
| JIMT-1 | Xenograft | 2+ |
| MDAMB361 | Xenograft | 2+ |
| N-87 | Xenograft | 3+ |
| CTG0807 | PDX | 2+/3+ |
| CTG1184 | PDX | 2+ |

In summary, the present inventors have observed that efficient internalization of HER2×HER2 antibodies dramatically increased processing of cathepsin B-cleavable linker in intracellular vesicles. In accordance with that, HER2×HER2-Tubulysin killed cell lines expressing not only high, but also intermediate HER2 levels with sub-nanomolar $IC_{50}$. Moreover, HER2×HER2-Tubulysin induced complete and durable tumor regression in a number of HER2 IHC 3+ and 2+ tumor xenograft and PDX models.

Example 20. Efficacy of BsAb1-Campt1 and BsAb2-Campt2 Compared to Comp ADCs in N87 Xenografts To compare the efficacy of BsAb1-Camp1 and BsAb2-Camp1 ADCs to CompAb1-MCC-Maytansinoid A, COMPAb1-GGFG-Dxd and BsAb2-Tubulysin 1A-LP in HER2

IHC3+N87 xenograft model, an in vivo tumor study was performed. For the assay, 6 week old female SCID mice (CBySmn.CB17-Prkdcscid/J, Jackson Labs #001803, n=50) were used. For implantation, N87 (ATCC, HTB-5822) cells were mixed with Matrigel (Corning, Cat #354234) and 150 uL of the cell and matrigel suspension containing $4 \times 10^6$ cells was injected to SCID mice. 7 days later, indicated ADCs were injected subcutaneously at the indicated doses to SCID mice that were randomized based on tumor size. Two additional doses were administered at days 14 and 21 to the cohort treated with 1 mg/kg H4H17087D-Tubulysin 1A-LP. The xenograft size for each mouse was measured using a Caliper (Roboz, Cat #RS6466).

Figures 13A, 13B:
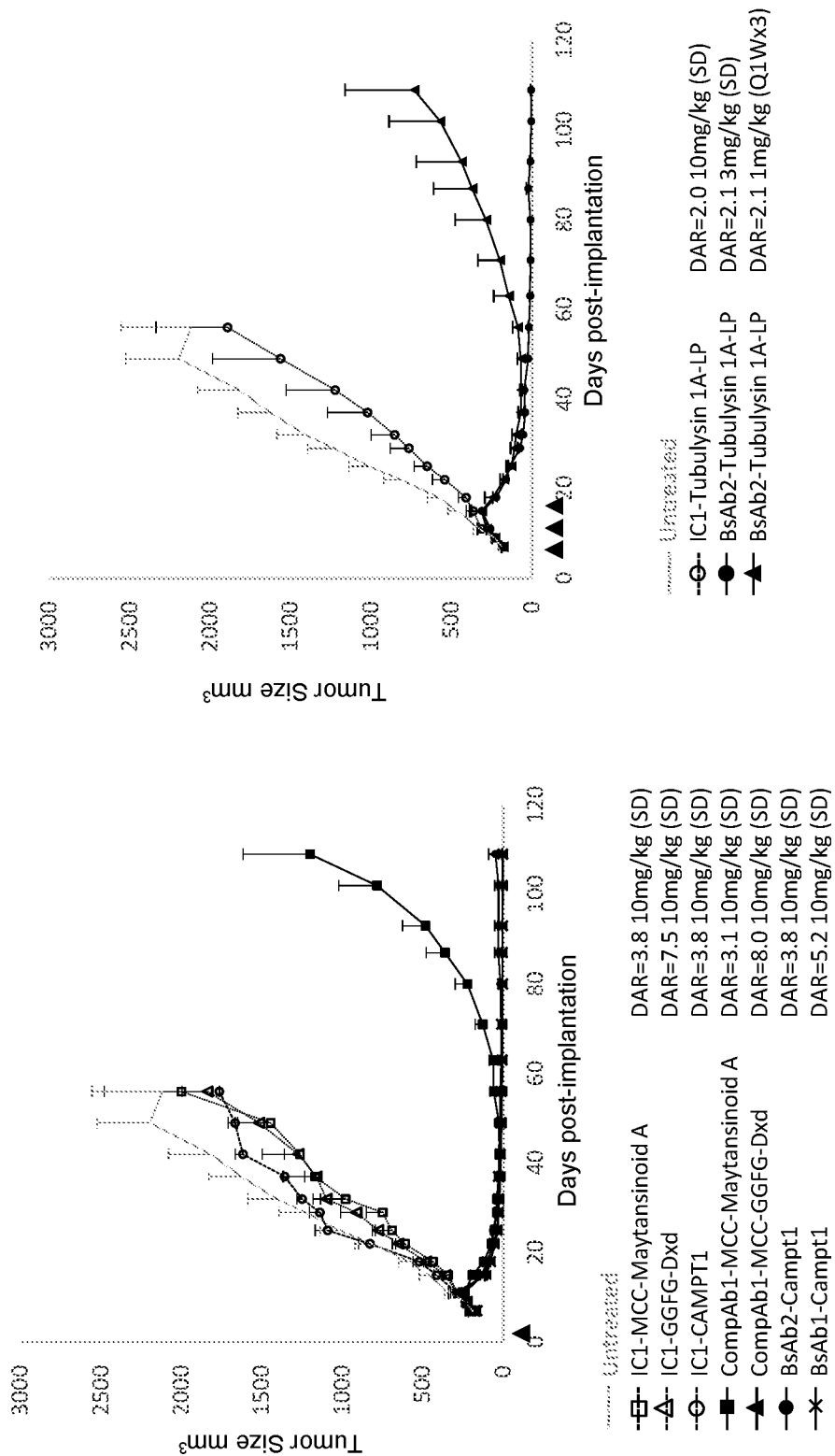
FIG. 13A and FIG. 13B depicts the average tumor size in a HER2 IHC3+N87 mouse xenograph model after treatment with the HER2×HER2 Campt1 ADCs. Panel A: Mice that received a single dose of 10 mg/kg BsAb1-Campt1 (panel A, x) or BsAb2-Campt1 (panel A, filled circle) saw a significant and durable reduction in N87 xenograft size. The anti-tumor response was comparable to CompAb1-GGFG-Dxd (panel A, filled triangle) but significantly greater than the response to CompAb1-MCC-Maytansinoid A (panel A, filled square). The anti-tumor response after treatment with BsAb1-Campt1 or BsAb2-Camp1 was comparable to the anti-tumor response of a single dose of 3 mg/kg BsAb2-Tubulysin 1A-LP (panel B, filled circle), but greater than 3 weekly doses of 1 mg/kg BsAb2-Tubulysin 1A-LP (panel B, filled triangle). The data is broken up into two panels for illustrative purposes, but all data are from the same experiment.

Mice that received a single dose of 10 mg/kg BsAb1-Campt1 or BsAb2-Camp1 saw complete regression of N87 tumors out to 110 days. The anti-tumor activity was comparable to that of 10 mg/kg CompAb1-GGFG-Dxd and 3 mg/kg BsAb2-Tubulysin 1A-LP. Mice that received a single dose of 10 mg/kg CompAb1-MCC-Maytansinoid A initially saw a significant reduction in N87 xenograft size but 5 of 5 tumors escaped treatment by day 50. A similar average anti-tumor response was observed for mice that received three doses of 1 mg/kg BsAb2-Tubulysin 1A-LP, however only 2 of 5 tumors escaped treatment. In contrast, mice that received a single dose of control ADCs did not see anti-tumor effect. See FIGS. 13A and 13B.

Example 21. Epitope Mapping Data for Binding of BsAb2 to Erbb2.mmH

Hydrogen-Deuterium Exchange Mass Spectrometry (HDX-MS) was performed to determine the amino acid residues of human epidermal growth factor receptor 2 that interact with the bivalent parental antibodies that comprise the binding arms of BsAb2 (Parental Ab1 and Parental Ab2). In this experiment a recombinantly produced version of the ecto domain (ECD) region of HER2 with a 6 histidine tag was used (SEQ ID NO: 54). A general description of the HDX-MS method is set forth in e.g., Ehring (1999) *Analytical Biochemistry* 267(2):252-259; and Engen and Smith (2001) *Anal. Chem.* 73:256A-265A.

The HDX-MS experiments were performed on a customized platform, consisting of a custom HDX automation system for deuterium labeling and quenching, a Waters Acquity Binary Solvent Manager for sample digestion and trapping, another Waters Acquity Binary Solvent Manager for analytical gradient, and a Thermo Q Exactive HF mass spectrometer for peptide identification and mass measurement.

The $D_2O$ labeling solution was prepared in $D_2O$ based buffer (50 mM phosphate, 100 mM sodium chloride, at pD 7.0). For deuterium labeling, 10 μL of 0.93 mg/mL Her2 protein or Her2 protein premixed with either bivalent parental (antigen to antibody molar ratio 1:0.7) were incubated at 20° C. with 90 μL of $D_2O$ labeling solution for various time-points in duplicates (non-deuterated control as 0 min; deuterium-labeling for 15 s, 60 s, 600 s, 3600 s and 6000 s). The deuteration reaction was quenched by adding 100 μL of 4 M guanidine hydrochloride, 0.85 M TCEP buffer (acidified by HCl to pH 2.3) to each sample for a 180-second incubation at 15° C. The quenched samples were then injected into the LC system for online pepsin digestion at 15° C. The digested peptides were trapped by a C8 column (1 mm×50 mm, Novabioassays) at −6° C. with a 12.5 min gradient from 2-32% for solvent B. (mobile phase A: 0.2% formic acid in water, mobile phase B: 0.2% formic acid in acetonitrile). The eluted peptides were analyzed by a Thermo Q Exactive HF mass spectrometry in LC-MS/MS or LC-MS mode.

The LC-MS/MS data from the undeuterated Her2 samples were searched against a database including amino acid sequences of Her2 protein and their reversed sequences using the Byonic search engine (Protein Metrics). The search parameters were set as default using non-specific enzymatic digestion and human glycosylation as common variable modification. The list of identified peptides was then imported into HDX WorkBench software (version 3.3) to calculate the deuterium uptake (D-uptake) and percentage of deuterium uptake (% D) for all deuterated samples. The residue number for the peptides is derived from the actual protein sequence (N-term residue T as $1^{st}$ AA) including the tag.

$$\text{Percentage of deuterium uptake } (\%D) = \frac{\text{Average } D\text{-uptake for peptide at each time point} \times 100\%}{\text{Maximum } D\text{-uptake of the peptide}}$$

A total of 351 peptides from Her2 were identified from both Her2 alone and Her2 in complex with Parental Ab1 samples, representing 100% sequence coverage of Her2. Any peptide that exhibited greater than 5% decrease in percentage of deuterium uptake was defined as significantly protected (Δ% D<−5%). Her2 ECD showed significant reduction in deuterium uptakes upon binding to mAb Parental Ab1 at sequences AA141-145, YQDTI (SEQ ID NO: 55), and AA166-182, RSRACHPCSPMCKGSRC (SEQ ID NO: 56), which were assigned as the epitope on human Her2 ECD targeted by Parental Ab1. The deuterium uptake data for peptides covering epitope regions I (AA141-145, YQDTI, SEQ ID NO: 55) and II (AA166-182, RSRACHPCSPMCKGSRC, SEQ ID NO: 56) are shown in FIG. 14.

A total of 366 peptides from Her2 were identified from both Her2 alone and Her2 in complex with Parental Ab2 samples, representing 100% sequence coverage of Her2. Any peptide that exhibited greater than 5% decrease in percentage of deuterium uptake was defined as significantly protected (Δ% D<−5%). Her2 ECD showed significant reduction in deuterium uptakes upon binding to Parental Ab2 at sequences AA9-23, MKLRLPASPETHLDM (SEQ ID NO: 57), AA41-51, TYLPTNASLSF (SEQ ID NO: 58), AA64-77, IAHNQVRQVPLQRL (SEQ ID NO: 59). In addition, there was significant reduction in deuterium uptakes at sequence AA353-359, AFLPESF (SEQ ID NO: 60), which could be due to allosteric effects. The deuterium uptake data for peptides covering epitope regions I (AA9-23, MKLRLPASPETHLDM, SEQ ID NO: 57), II (AA41-51, TYLPTNASLSF, SEQ ID NO: 58 and III (AA64-77, IAHNQVRQVPLQRL, SEQ ID NO: 59), and the peripheral epitope region IV (AA353-359, AFLPESF, SEQ ID NO: 60) are shown in FIG. 15.

Example 22. Epitope Mapping Data for Binding of BsAb1 to Erbb2.mmH

Hydrogen-Deuterium Exchange Mass Spectrometry (HDX-MS) was performed to determine the amino acid residues of HER2 that interact with the bivalent parental antibodies that comprise the binding arms of BsAb1 (Parental Ab3 and Parental Ab4). The same recombinant HER2 protein as described in Example 21 was used (SEQ ID NO: 54).

The HDX-MS experiments were performed on a customized platform, consisting of a custom HDX automation system for deuterium labeling and quenching, a Waters Acquity Binary Solvent Manager for sample digestion and trapping, another Waters Acquity Binary Solvent Manager for analytical gradient, and a Thermo Q Exactive HF mass spectrometer for peptide identification and mass measurement.

The $D_2O$ labeling solution was prepared in $D_2O$ based buffer (50 mM phosphate, 100 mM sodium chloride, at pD 7.0). For deuterium labeling, 10 µL of 0.93 mg/mL Her2 protein or Her2 protein premixed with either Parental Ab3 or Parental Ab4 (antigen to antibody molar ratio 1:0.7) were incubated at 20° C. with 90 µL of $D_2O$ labeling solution for various time-points in duplicates (non-deuterated control as 0 min; deuterium-labeling for 15 s, 60 s, 600 s and 3600 s). The deuteration reaction was quenched by adding 100 µL of 4 M guanidine hydrochloride, 0.85 M TCEP buffer (acidified by HCl to pH 2.3) to each sample for a 180-second incubation at 15° C. The quenched samples were then injected into the LC system for online pepsin digestion at 15° C. The digested peptides were trapped by a C8 column (1 mm×50 mm, Novabioassays) at −6° C. with a 12.5 min gradient from 2-32% for solvent B. (mobile phase A: 0.2% formic acid in water, mobile phase B: 0.2% formic acid in acetonitrile). The eluted peptides were analyzed by a Thermo Q Exactive HF mass spectrometry in LC-MS/MS or LC-MS mode.

The LC-MS/MS data from the undeuterated Her2 samples were searched against a database including amino acid sequences of Her2 protein and their reversed sequences using the Byonic search engine (Protein Metrics). The search parameters were set as default using non-specific enzymatic digestion and human glycosylation as common variable modification. The list of identified peptides was then imported into HDX WorkBench software (version 3.3) to calculate the deuterium uptake (D-uptake) and percentage of deuterium uptake (% D) for all deuterated samples. The residue number for the peptides is derived from the actual protein sequence (N-term residue T as $1^{st}$ AA) including the tag.

$$\text{Percentage of deuterium uptake } (\%D) = \frac{\text{Average } D\text{-uptake for peptide at each time point} \times 100\%}{\text{Maximum } D\text{-uptake of the peptide}}$$

A total of 386 peptides from Her2 were identified from both Her2 alone and Her2 in complex with Parental Ab3 samples, representing 99.8% sequence coverage of Her2. Any peptide that exhibited greater than 5% decrease in percentage of deuterium uptake was defined as significantly protected (Δ% D<−5%). Her2 ECD showed significant reduction in deuterium uptakes upon binding to Parental Ab3 at sequences AA133-148, IQRNPQLCYQDTILWK (SEQ ID NO: 61), and AA174-182, SPMCKGSRC (SEQ ID NO: 62), which were assigned as the epitope on human Her2 ECD targeted by Parental Ab3. In addition, human Her2 ECD showed a modest reduction in deuterium uptakes upon binding to Parental Ab3 at sequence AA194-200, TRTVCAG (SEQ ID NO: 63). The deuterium uptake data for peptides covering epitope regions I (AA133-148, IQRNPQLCYQDTILWK, SEQ ID NO: 61) and II (AA174-182, SPMCKGSRC, SEQ ID NO: 62), and the peripheral epitope region III (AA194-200, TRTVCAG, SEQ ID NO: 63) are shown in FIG. 16.

A total of 385 peptides from Her2 were identified from both Her2 alone and Her2 in complex with Parental Ab4 samples, representing 99.7% sequence coverage of Her2. Any peptide that exhibited greater than 5% decrease in percentage of deuterium uptake was defined as significantly protected (Δ% D<−5%). Her2 ECD showed significant reduction in deuterium uptakes upon binding to Parental Ab4 at sequences AA152-161, HKNNQLALTL (SEQ ID NO: 64), which was the assigned as the main epitope on human Her2 ECD targeted by Parental Ab4. In addition, human Her2 ECD showed modest reduction in deuterium uptakes upon binding to Parental Ab4 at sequences AA194-200, TRTVCAG (SEQ ID NO: 63), and AA258-273, ESMPNPEGRYTFGASC (SEQ ID NO: 65). The deuterium uptake data for peptides covering epitope region I (AA152-161, HKNNQLALTL, SEQ ID NO: 64), the peripheral epitope region II (AA194-200, TRTVCAG, SEQ ID NO: 63), as well as the region III (AA258-273, ESMPNPEGRYTFGASC, SEQ ID NO: 65) with detected deuterium reduction are shown in FIG. 17.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A bispecific antigen-binding molecule comprising:
a first antigen-binding domain (D1); and
a second antigen-binding domain (D2);
wherein D1 specifically binds a first epitope of human HER2; and
wherein D2 specifically binds a second epitope of human HER2; and
wherein D1 comprises three heavy chain complementarity determining regions (HCDR1, HCDR2 and HCDR3) within a heavy chain variable region (HCVR) comprising the amino acid sequence of SEQ ID NO: 2 and three light chain complementarity determining regions (LCDR1, LCDR2 and LCDR3) within a light chain variable region (LCVR) comprising the amino acid sequence of SEQ ID NO: 18, wherein the HCDR1 comprises the amino acid sequence of SEQ ID NO: 4; the HCDR2 comprises the amino acid sequence of SEQ ID NO: 6; the HCDR3 comprises the amino acid sequence of SEQ ID NO: 8; the LCDR1 comprises the amino acid sequence of SEQ ID NO: 20; the LCDR2 comprises the amino acid sequence of SEQ ID NO: 22; and the LCDR3 comprises the amino acid sequence of SEQ ID NO: 24; and
wherein D2 comprises three heavy chain complementarity determining regions (HCDR1, HCDR2 and HCDR3) within a heavy chain variable region (HCVR) comprising the amino acid sequence of SEQ ID NO: 10 and three light chain complementarity determining regions (LCDR1, LCDR2 and LCDR3) within a light chain variable region (LCVR) comprising the amino acid sequence of SEQ ID NO: 18, wherein the HCDR1 comprises the amino acid sequence of SEQ ID NO: 12; the HCDR2 comprises the amino acid sequence of SEQ ID NO: 14; the HCDR3 comprises the amino acid sequence of SEQ ID NO: 16; the LCDR1 comprises the amino acid sequence of SEQ ID NO: 20; the LCDR2 comprises the amino acid sequence of SEQ ID NO: 22; and the LCDR3 comprises the amino acid sequence of SEQ ID NO: 24.

2. The bispecific antigen-binding molecule of claim 1, wherein the bispecific antigen-binding molecule is conjugated to a cytotoxin.

3. The bispecific antigen-binding molecule of claim 2, wherein the cytotoxin is a tubulysin, a camptothecin, or a maytansinoid.

4. The bispecific antigen-binding molecule of claim 1, wherein the bispecific antigen-binding molecule is conjugated to a cytotoxin through a linker.

5. The bispecific antigen-binding molecule of claim 4, wherein the cytotoxin is a tubulysin.

6. The bispecific antigen-binding molecule of claim 5, wherein the tubulysin is:

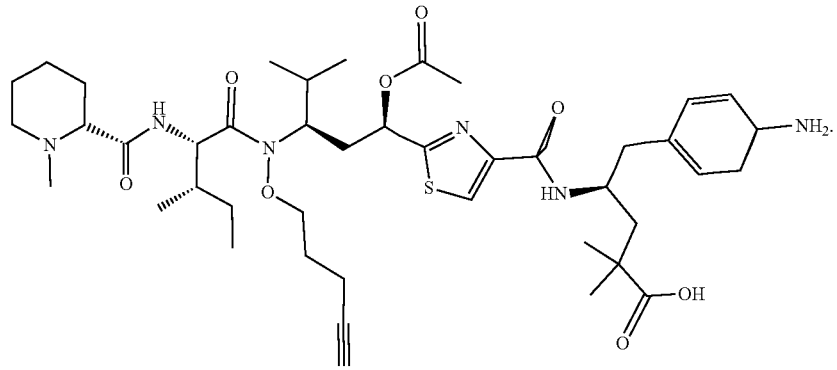

7. The bispecific antigen-binding molecule of claim 4, wherein the bispecific antigen-binding molecule is conjugated to

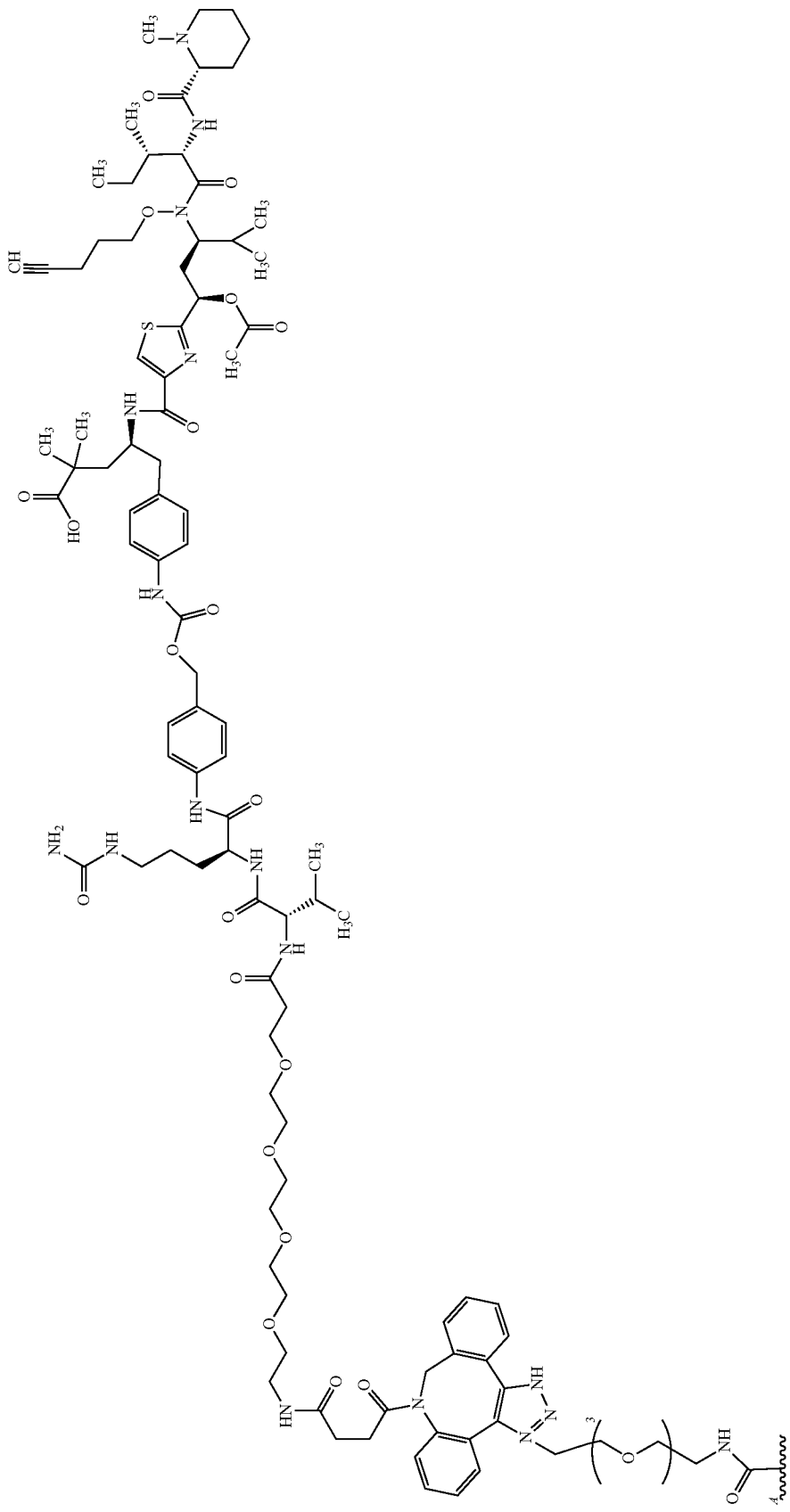

221 or a regioisomer thereof, wherein

is a bond to a heavy chain glutamine.

8. The bispecific antigen-binding molecule of claim 5, wherein the bispecific antigen-binding molecule comprises a heavy chain conjugated to tubulysin through Q295.

9. The bispecific antigen-binding molecule of claim 5, wherein the bispecific antigen-binding molecule comprises a heavy chain comprising an N297Q mutation (EU index numbering), and wherein the bispecific antigen-binding molecule is (1) conjugated to a tubulysin through the glutamine residue of the heavy chain Q295, and (2) conjugated to a tubulysin through the glutamine residue of the N297Q mutation.

10. The bispecific antigen-binding molecule of claim 4, wherein the cytotoxin is a maytansinoid.

11. The bispecific antigen-binding molecule of claim 10 wherein the maytansinoid is:

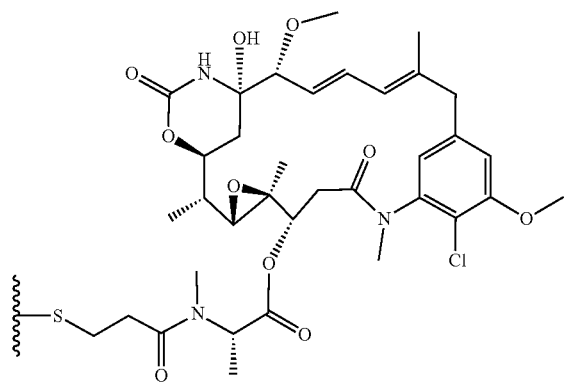 [SMILES: *SCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

wherein the

is the bond to the linker.

12. The bispecific antigen-binding molecule of claim 11, wherein the linker is:

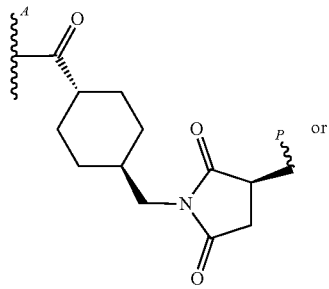

222

-continued

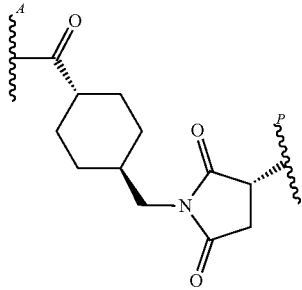

wherein the bond noted with

represents the bond to the bispecific antigen-binding molecule and the bond noted with

represents the bond to the maytansinoid.

13. The bispecific antigen-binding molecule of claim 10, wherein the maytansinoid is

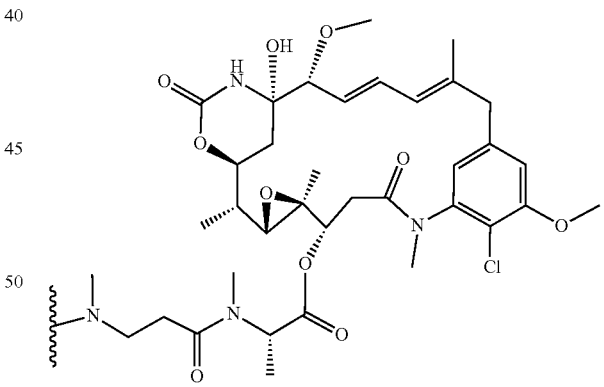

wherein the

is the bond to the linker.

14. The bispecific antigen-binding molecule of claim 13, wherein the linker is:

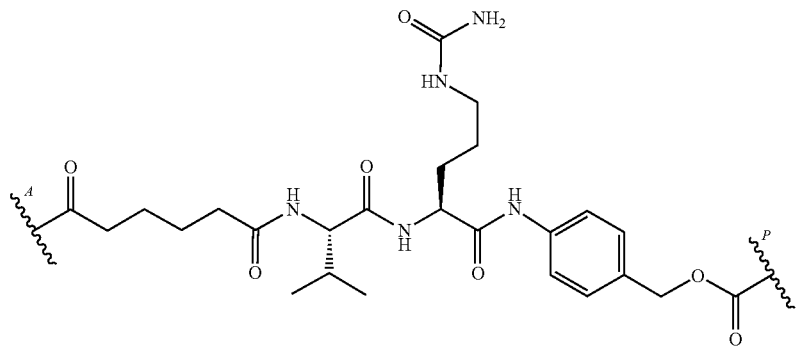

wherein the bond noted with

represents the bond to the bispecific antigen-binding molecule and the bond noted with

represents the bond to the maytansinoid.

15. A pharmaceutical composition comprising the bispecific antigen-binding molecule of claim 1, and a pharmaceutically acceptable carrier.

16. A method of treating a cancer in a subject suffering from a tumor overexpressing HER2, the method comprising administering to the subject the bispecific antigen-binding molecule of claim 2.

17. The method of claim 16, wherein the cancer is selected from the group consisting of a breast cancer, lung cancer, gastric cancer, cervical cancer, gastric cancer, endometrial cancer, and ovarian cancer.

18. The bispecific antigen-binding molecule of claim 4, wherein the cytotoxin is a camptothecin.

19. The bispecific antigen-binding molecule of claim 1, wherein the bispecific antigen-binding molecule comprises a heavy chain comprising an N297Q mutation (EU index numbering).

20. A bispecific antigen-binding molecule comprising:
a first antigen-binding domain (D1); and
a second antigen-binding domain (D2);
wherein D1 specifically binds a first epitope of human HER2; and
wherein D2 specifically binds a second epitope of human HER2; and
wherein D1 comprises three heavy chain complementarity determining regions (HCDR1, HCDR2 and HCDR3) within a heavy chain variable region (HCVR) comprising the amino acid sequence of SEQ ID NO: 2 and three light chain complementarity determining regions (LCDR1, LCDR2 and LCDR3) within a light chain variable region (LCVR) comprising the amino acid sequence of SEQ ID NO: 18; and
wherein D2 comprises three heavy chain complementarity determining regions (HCDR1, HCDR2 and HCDR3) within a heavy chain variable region (HCVR) comprising the amino acid sequence of SEQ ID NO: 10 and three light chain complementarity determining regions (LCDR1, LCDR2 and LCDR3) within a light chain variable region (LCVR) comprising the amino acid sequence of SEQ ID NO: 18.

21. The bispecific antigen-binding molecule of claim 20, wherein D1 comprises an HCDR1 amino acid sequence as set forth in SEQ ID NO: 4; an HCDR2 amino acid sequence as set forth in SEQ ID NO: 6; an HCDR3 amino acid sequence as set forth in SEQ ID NO: 8; an LCDR1 amino acid sequence as set forth in SEQ ID NO: 20; an LCDR2 amino acid sequence as set forth in SEQ ID NO: 22; and an LCDR3 amino acid sequence as set forth in SEQ ID NO: 24.

22. The bispecific antigen-binding molecule of claim 20, wherein D2 comprises an HCDR1 amino acid sequence as set forth in SEQ ID NO: 12; an HCDR2 amino acid sequence as set forth in SEQ ID NO: 14; an HCDR3 amino acid sequence as set forth in SEQ ID NO: 16; an LCDR1 amino acid sequence as set forth in SEQ ID NO: 20; an LCDR2 amino acid sequence as set forth in SEQ ID NO: 22; and an LCDR3 amino acid sequence as set forth in SEQ ID NO: 24.

* * * * *

UNITED STATES PATENT AND TRADEMARK OFFICE
CERTIFICATE OF CORRECTION

PATENT NO. : 11,958,910 B2
APPLICATION NO. : 17/187511
DATED : April 16, 2024
INVENTOR(S) : Julian Andreev et al.

Page 1 of 1

It is certified that error appears in the above-identified patent and that said Letters Patent is hereby corrected as shown below:

In the Claims

Column 218, between Line 41 and Line 60, Claim 6, The chemical structure is missing one of the double bonds on the benzene ring and the double bond to one of the Oxygen:

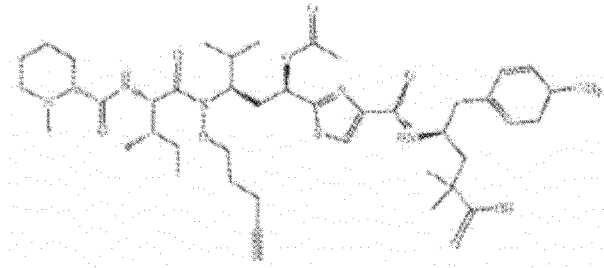

The chemical structure should be:

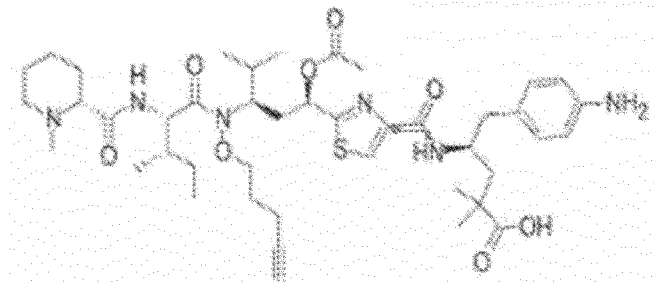

Signed and Sealed this
Twenty-first Day of May, 2024

Katherine Kelly Vidal
*Director of the United States Patent and Trademark Office*